United States Patent
Abdiche et al.

(10) Patent No.: US 10,155,037 B2
(45) Date of Patent: Dec. 18, 2018

(54) ANTI-PD-1 ANTIBODIES AND METHODS OF USE THEREOF

(71) Applicant: RINAT NEUROSCIENCE CORP., South San Francisco, CA (US)

(72) Inventors: Yasmina Noubia Abdiche, Redwood City, CA (US); Weihsien Ho, Belmont, CA (US); Arvind Rajpal, San Francisco, CA (US); Sawsan Youssef, Menlo Park, CA (US)

(73) Assignee: Rinat Neuroscience Corp., South San Francisco, CA (US)

( * ) Notice: Subject to any disclaimer, the term of this patent is extended or adjusted under 35 U.S.C. 154(b) by 241 days.

(21) Appl. No.: 14/958,053

(22) Filed: Dec. 3, 2015

(65) Prior Publication Data

US 2016/0159905 A1 Jun. 9, 2016

Related U.S. Application Data

(60) Provisional application No. 62/251,973, filed on Nov. 6, 2015, provisional application No. 62/242,750, filed on Oct. 16, 2015, provisional application No. 62/089,658, filed on Dec. 9, 2014.

(51) Int. Cl.
| | |
|---|---|
| *C07K 16/28* | (2006.01) |
| *A61K 39/395* | (2006.01) |
| *A61K 39/39* | (2006.01) |
| *A61K 45/06* | (2006.01) |
| *A61K 39/00* | (2006.01) |

(52) U.S. Cl.
CPC .......... *A61K 39/39* (2013.01); *A61K 39/0011* (2013.01); *A61K 39/3955* (2013.01); *A61K 45/06* (2013.01); *C07K 16/2818* (2013.01); *C07K 16/2878* (2013.01); *A61K 2039/505* (2013.01); *A61K 2039/507* (2013.01); *A61K 2039/53* (2013.01); *A61K 2039/545* (2013.01); *C07K 2317/24* (2013.01); *C07K 2317/33* (2013.01); *C07K 2317/55* (2013.01); *C07K 2317/74* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,629,204 A | 5/1997 | Honjo et al. |
| 7,101,550 B2 | 9/2006 | Wood et al. |
| 7,488,802 B2 | 2/2009 | Collins et al. |
| 7,595,048 B2 | 9/2009 | Honjo et al. |
| 8,709,416 B2 | 4/2014 | Langermann et al. |
| 8,728,474 B2 | 5/2014 | Honjo et al. |
| 8,952,136 B2 | 2/2015 | Carven et al. |
| 2008/0025979 A1 | 1/2008 | Honjo |
| 2012/0114648 A1 | 5/2012 | Langermann |
| 2014/0044738 A1 | 2/2014 | Langermann |
| 2014/0234296 A1 | 8/2014 | Sharma |
| 2014/0294852 A1 | 10/2014 | Korman |
| 2015/0203579 A1 | 7/2015 | Papadopoulos |
| 2015/0232555 A1 | 8/2015 | Carven |
| 2017/0044259 A1* | 2/2017 | Tipton ............... C07K 16/3069 |

FOREIGN PATENT DOCUMENTS

| | | |
|---|---|---|
| WO | 2012145493 | 10/2012 |
| WO | 2014/159562 | 10/2014 |
| WO | 2014/179664 | 11/2014 |
| WO | 2015026684 | 2/2015 |
| WO | 2015054593 | 4/2015 |
| WO | 2015095423 | 6/2015 |
| WO | 2015112800 | 7/2015 |
| WO | 2015112900 | 7/2015 |

OTHER PUBLICATIONS

Freeman, G. et al., "Engagement of the PD-1 immunoinhibitory receptor by a novel B7 family member leads to negative regulation of lymphocyte activation," J Exp Med, 2000, 1027-34, vol. 192, No. 7.

Gubin, M. et al., "Checkpoint blockade cancer immunotherapy targets tumour-specific mutant antigens," Nature, 2014, 577-581, vol. 515, issue 7528.

Harshman, L. et al., "PD-1 blockade in renal cell carcinoma: to equilibrium and beyond," Cancer Immunol Res, 2014, 1132-1141, vol. 2, No. 12.

Kyi, C. and Postow, M., "Checkpoint blocking antibodies in cancer immunotherapy," FEBS Lett., 2014, 368-376, vol. 588, No. 2.

* cited by examiner

*Primary Examiner* — Ilia I Ouspenski
(74) *Attorney, Agent, or Firm* — David R. Marsh; Arnold & Porter Kaye Scholer LLP; Bryan Zielinski

(57) ABSTRACT

The present invention provides antagonizing antibodies that bind to programmed cell death protein 1 (PD-1) and methods of using same. The anti-PD-1 antibodies can be used therapeutically alone or in combination with other therapeutics to treat cancer and other diseases.

45 Claims, 7 Drawing Sheets

Specification includes a Sequence Listing.

SEQUENCE LISTING

```
<160> NUMBER OF SEQ ID NOS: 51

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140
```

```
Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
            165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285
```

<210> SEQ ID NO 2
<211> LENGTH: 113
<212> TYPE: PRT
<213> ORGANISM: Artificial Sequence
<220> FEATURE:
<223> OTHER INFORMATION: humanized antibody sequence

<400> SEQUENCE: 2

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Trp Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Tyr Trp Thr Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Leu Thr Phe Gly Gly Gly Thr Lys Val Glu Ile
            100                 105                 110

Lys
```

<210> SEQ ID NO 3
<211> LENGTH: 117
<212> TYPE: PRT
<213> ORGANISM: Artificial Sequence
<220> FEATURE:
<223> OTHER INFORMATION: humanized antibody sequence

<400> SEQUENCE: 3

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45
```

```
Gly Asn Ile Tyr Pro Gly Ser Ser Leu Thr Asn Tyr Asn Glu Lys Phe
        50                  55                  60

Lys Asn Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Leu Leu Thr Gly Thr Phe Ala Tyr Trp Gly Gln Gly Thr Leu
                100                 105                 110

Val Thr Val Ser Ser
            115

<210> SEQ ID NO 4
<211> LENGTH: 117
<212> TYPE: PRT
<213> ORGANISM: Artificial Sequence
<220> FEATURE:
<223> OTHER INFORMATION: humanized antibody sequence

<400> SEQUENCE: 4

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Trp Ile Asn Trp Val Arg Gln Ala Pro Gly Gln Gly Leu Glu Trp Met
             35                  40                  45

Gly Asn Ile Tyr Pro Gly Ser Ser Leu Thr Asn Tyr Asn Glu Lys Phe
        50                  55                  60

Lys Asn Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Leu Ser Thr Gly Thr Phe Ala Tyr Trp Gly Gln Gly Thr Leu
                100                 105                 110

Val Thr Val Ser Ser
            115

<210> SEQ ID NO 5
<211> LENGTH: 117
<212> TYPE: PRT
<213> ORGANISM: Artificial Sequence
<220> FEATURE:
<223> OTHER INFORMATION: humanized antibody sequence

<400> SEQUENCE: 5

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Trp Ile Asn Trp Val Arg Gln Ala Pro Gly Gln Gly Leu Glu Trp Met
             35                  40                  45

Gly Asn Ile Tyr Pro Gly Ser Ser Ile Thr Asn Tyr Asn Glu Lys Phe
        50                  55                  60

Lys Asn Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Leu Thr Thr Gly Thr Phe Ala Tyr Trp Gly Gln Gly Thr Leu
                100                 105                 110
```

```
Val Thr Val Ser Ser
        115

<210> SEQ ID NO 6
<211> LENGTH: 117
<212> TYPE: PRT
<213> ORGANISM: Artificial Sequence
<220> FEATURE:
<223> OTHER INFORMATION: humanized antibody sequence

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Trp Pro Gly Ser Ser Leu Thr Asn Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Leu Thr Gly Thr Phe Ala Tyr Trp Gly Gln Gly Thr Leu
            100                 105                 110

Val Thr Val Ser Ser
        115

<210> SEQ ID NO 7
<211> LENGTH: 113
<212> TYPE: PRT
<213> ORGANISM: Artificial Sequence
<220> FEATURE:
<223> OTHER INFORMATION: humanized antibody sequence

<400> SEQUENCE: 7

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Trp Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Tyr Trp Thr Ser Tyr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Leu Thr Phe Gly Gly Gly Thr Lys Val Glu Ile
            100                 105                 110

Lys

<210> SEQ ID NO 8
<211> LENGTH: 113
<212> TYPE: PRT
<213> ORGANISM: Artificial Sequence
<220> FEATURE:
<223> OTHER INFORMATION: humanized antibody sequence
```

-continued

```
<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Trp Asp Ser
            20                  25                  30

Gly Asn Gln Lys Asn Phe Leu Thr Trp Tyr Gln Lys Pro Gly Gln
        35                  40                  45

Pro Pro Lys Leu Leu Ile Tyr Trp Thr Ser Tyr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro His Thr Phe Gly Gly Gly Thr Lys Val Glu Ile
            100                 105                 110

Lys

<210> SEQ ID NO 9
<211> LENGTH: 113
<212> TYPE: PRT
<213> ORGANISM: Artificial Sequence
<220> FEATURE:
<223> OTHER INFORMATION: humanized antibody sequence

<400> SEQUENCE: 9

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Trp Asp Ser
            20                  25                  30

Thr Asn Gln Lys Asn Phe Leu Thr Trp Tyr Gln Lys Pro Gly Gln
        35                  40                  45

Pro Pro Lys Leu Leu Ile Tyr Trp Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Leu Thr Phe Gly Gly Gly Thr Lys Val Glu Ile
            100                 105                 110

Lys

<210> SEQ ID NO 10
<211> LENGTH: 17
<212> TYPE: PRT
<213> ORGANISM: Artificial Sequence
<220> FEATURE:
<223> OTHER INFORMATION: humanized antibody sequence

<400> SEQUENCE: 10

Lys Ser Ser Gln Ser Leu Trp Asp Ser Gly Asn Gln Lys Asn Phe Leu
1               5                   10                  15

Thr

<210> SEQ ID NO 11
<211> LENGTH: 7
<212> TYPE: PRT
<213> ORGANISM: Artificial Sequence
<220> FEATURE:
```

<223> OTHER INFORMATION: humanized antibody sequence

<400> SEQUENCE: 11

Trp Thr Ser Thr Arg Glu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: humanized antibody sequence

<400> SEQUENCE: 12

Gln Asn Asp Tyr Phe Tyr Pro Leu Thr
1               5

<210> SEQ ID NO 13
<211> LENGTH: 10
<212> TYPE: PRT
<213> ORGANISM: Artificial Sequence
<220> FEATURE:
<223> OTHER INFORMATION: humanized antibody sequence

<400> SEQUENCE: 13

Gly Tyr Thr Phe Thr Ser Tyr Trp Ile Asn
1               5                   10

<210> SEQ ID NO 14
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 14

Gly Tyr Thr Phe Thr Ser Tyr
1               5

<210> SEQ ID NO 15
<211> LENGTH: 5
<212> TYPE: PRT
<213> ORGANISM: Artificial Sequence
<220> FEATURE:
<223> OTHER INFORMATION: humanized antibody sequence

<400> SEQUENCE: 15

Ser Tyr Trp Ile Asn
1               5

<210> SEQ ID NO 16
<211> LENGTH: 6
<212> TYPE: PRT
<213> ORGANISM: Artificial Sequence
<220> FEATURE:
<223> OTHER INFORMATION: humanized antibody sequence

<400> SEQUENCE: 16

Tyr Pro Gly Ser Ser Leu
1               5

<210> SEQ ID NO 17
<211> LENGTH: 17
<212> TYPE: PRT
<213> ORGANISM: Artificial Sequence
<220> FEATURE:
<223> OTHER INFORMATION: humanized antibody sequence

<400> SEQUENCE: 17

Asn Ile Tyr Pro Gly Ser Ser Leu Thr Asn Tyr Asn Glu Lys Phe Lys
1               5                   10                  15

Asn

<210> SEQ ID NO 18
<211> LENGTH: 8
<212> TYPE: PRT
<213> ORGANISM: Artificial Sequence
<220> FEATURE:
<223> OTHER INFORMATION: humanized antibody sequence

<400> SEQUENCE: 18

Leu Leu Thr Gly Thr Phe Ala Tyr
1               5

<210> SEQ ID NO 19
<211> LENGTH: 15
<212> TYPE: PRT
<213> ORGANISM: Artificial Sequence
<220> FEATURE:
<223> OTHER INFORMATION: Synthetic linker

<400> SEQUENCE: 19

Gly Gly Gly Gly Ser Gly Gly Gly Gly Ser Gly Gly Gly Gly Ser
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 20

Trp Thr Ser Tyr Arg Glu Ser
1               5

<210> SEQ ID NO 21
<211> LENGTH: 9
<212> TYPE: PRT
<213> ORGANISM: Artificial Sequence
<220> FEATURE:
<223> OTHER INFORMATION: humanized antibody sequence

<400> SEQUENCE: 21

Gln Asn Asp Tyr Phe Tyr Pro His Thr
1               5

<210> SEQ ID NO 22
<211> LENGTH: 17
<212> TYPE: PRT
<213> ORGANISM: Artificial Sequence
<220> FEATURE:
<223> OTHER INFORMATION: humanized antibody sequence

<400> SEQUENCE: 22

Lys Ser Ser Gln Ser Leu Trp Asp Ser Thr Asn Gln Lys Asn Phe Leu
1               5                   10                  15

Thr

<210> SEQ ID NO 23
<211> LENGTH: 8
<212> TYPE: PRT

<213> ORGANISM: Artificial Sequence
<220> FEATURE:
<223> OTHER INFORMATION: humanized antibody sequence

<400> SEQUENCE: 23

Leu Ser Thr Gly Thr Phe Ala Tyr
1               5

<210> SEQ ID NO 24
<211> LENGTH: 6
<212> TYPE: PRT
<213> ORGANISM: Artificial Sequence
<220> FEATURE:
<223> OTHER INFORMATION: humanized antibody sequence

<400> SEQUENCE: 24

Tyr Pro Gly Ser Ser Ile
1               5

<210> SEQ ID NO 25
<211> LENGTH: 17
<212> TYPE: PRT
<213> ORGANISM: Artificial Sequence
<220> FEATURE:
<223> OTHER INFORMATION: humanized antibody sequence

<400> SEQUENCE: 25

Asn Ile Tyr Pro Gly Ser Ser Ile Thr Asn Tyr Asn Glu Lys Phe Lys
1               5                   10                  15

Asn

<210> SEQ ID NO 26
<211> LENGTH: 8
<212> TYPE: PRT
<213> ORGANISM: Artificial Sequence
<220> FEATURE:
<223> OTHER INFORMATION: humanized antibody sequence

<400> SEQUENCE: 26

Leu Thr Thr Gly Thr Phe Ala Tyr
1               5

<210> SEQ ID NO 27
<211> LENGTH: 6
<212> TYPE: PRT
<213> ORGANISM: Artificial Sequence
<220> FEATURE:
<223> OTHER INFORMATION: humanized antibody sequence

<400> SEQUENCE: 27

Trp Pro Gly Ser Ser Leu
1               5

<210> SEQ ID NO 28
<211> LENGTH: 17
<212> TYPE: PRT
<213> ORGANISM: Artificial Sequence
<220> FEATURE:
<223> OTHER INFORMATION: humanized antibody sequence

<400> SEQUENCE: 28

Asn Ile Trp Pro Gly Ser Ser Leu Thr Asn Tyr Asn Glu Lys Phe Lys
1               5                   10                  15

Asn

-continued

<210> SEQ ID NO 29
<211> LENGTH: 444
<212> TYPE: PRT
<213> ORGANISM: Artificial Sequence
<220> FEATURE:
<223> OTHER INFORMATION: humanized antibody sequence

<400> SEQUENCE: 29

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Leu Thr Asn Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Thr Gly Thr Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro

```
                    370                 375                 380
Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 30
<211> LENGTH: 17
<212> TYPE: PRT
<213> ORGANISM: Artificial Sequence
<220> FEATURE:
<223> OTHER INFORMATION: humanized antibody sequence

<400> SEQUENCE: 30

Lys Ser Ser Gln Ser Leu Leu Asp Ser Gly Asn Gln Lys Asn Phe Leu
1               5                   10                  15

Thr

<210> SEQ ID NO 31
<211> LENGTH: 9
<212> TYPE: PRT
<213> ORGANISM: Artificial Sequence
<220> FEATURE:
<223> OTHER INFORMATION: humanized antibody sequence

<400> SEQUENCE: 31

Gln Asn Asp Tyr Ser Tyr Pro Leu Thr
1               5

<210> SEQ ID NO 32
<211> LENGTH: 17
<212> TYPE: PRT
<213> ORGANISM: Artificial Sequence
<220> FEATURE:
<223> OTHER INFORMATION: humanized antibody sequence
<220> FEATURE:
<221> NAME/KEY: VARIANT
<222> LOCATION: (7)..(7)
<223> OTHER INFORMATION: Xaa is Trp or Leu
<220> FEATURE:
<221> NAME/KEY: VARIANT
<222> LOCATION: (10)..(10)
<223> OTHER INFORMATION: Xaa is Gly or Thr

<400> SEQUENCE: 32

Lys Ser Ser Gln Ser Leu Xaa Asp Ser Xaa Asn Gln Lys Asn Phe Leu
1               5                   10                  15

Thr

<210> SEQ ID NO 33
<211> LENGTH: 7
<212> TYPE: PRT
<213> ORGANISM: Artificial Sequence
<220> FEATURE:
<223> OTHER INFORMATION: humanized antibody sequence
<220> FEATURE:
<221> NAME/KEY: VARIANT
<222> LOCATION: (4)..(4)
<223> OTHER INFORMATION: Xaa is Thr or Tyr

<400> SEQUENCE: 33
```

```
Trp Thr Ser Xaa Arg Glu Ser
1               5
```

<210> SEQ ID NO 34
<211> LENGTH: 9
<212> TYPE: PRT
<213> ORGANISM: Artificial Sequence
<220> FEATURE:
<223> OTHER INFORMATION: humanized antibody sequence
<220> FEATURE:
<221> NAME/KEY: VARIANT
<222> LOCATION: (5)..(5)
<223> OTHER INFORMATION: Xaa is Phe or Ser
<220> FEATURE:
<221> NAME/KEY: VARIANT
<222> LOCATION: (8)..(8)
<223> OTHER INFORMATION: Xaa is Leu or His

<400> SEQUENCE: 34

```
Gln Asn Asp Tyr Xaa Tyr Pro Xaa Thr
1               5
```

<210> SEQ ID NO 35
<211> LENGTH: 17
<212> TYPE: PRT
<213> ORGANISM: Artificial Sequence
<220> FEATURE:
<223> OTHER INFORMATION: humanized antibody sequence

<400> SEQUENCE: 35

```
Asn Ile Tyr Pro Gly Ser Ser Ser Thr Asn Tyr Asn Glu Lys Phe Lys
1               5                   10                  15
Asn
```

<210> SEQ ID NO 36
<211> LENGTH: 17
<212> TYPE: PRT
<213> ORGANISM: Artificial Sequence
<220> FEATURE:
<223> OTHER INFORMATION: humanized antibody sequence
<220> FEATURE:
<221> NAME/KEY: VARIANT
<222> LOCATION: (3)..(3)
<223> OTHER INFORMATION: Xaa is Tyr or Trp
<220> FEATURE:
<221> NAME/KEY: VARIANT
<222> LOCATION: (8)..(8)
<223> OTHER INFORMATION: Xaa is Leu, Ile, or Ser

<400> SEQUENCE: 36

```
Asn Ile Xaa Pro Gly Ser Ser Xaa Thr Asn Tyr Asn Glu Lys Phe Lys
1               5                   10                  15
Asn
```

<210> SEQ ID NO 37
<211> LENGTH: 8
<212> TYPE: PRT
<213> ORGANISM: Artificial Sequence
<220> FEATURE:
<223> OTHER INFORMATION: humanized antibody sequence
<220> FEATURE:
<221> NAME/KEY: VARIANT
<222> LOCATION: (2)..(2)
<223> OTHER INFORMATION: Xaa is Leu or Ser

<400> SEQUENCE: 37

```
Leu Xaa Thr Gly Thr Phe Ala Tyr
1               5
```

<210> SEQ ID NO 38
<211> LENGTH: 443
<212> TYPE: PRT
<213> ORGANISM: Artificial Sequence
<220> FEATURE:
<223> OTHER INFORMATION: humanized antibody sequence

<400> SEQUENCE: 38

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Ser Ser Leu Thr Asn Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Thr Gly Thr Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365
```

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly
            435                 440

<210> SEQ ID NO 39
<211> LENGTH: 221
<212> TYPE: PRT
<213> ORGANISM: Artificial Sequence
<220> FEATURE:
<223> OTHER INFORMATION: humanized antibody sequence

<400> SEQUENCE: 39

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Trp Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Tyr Trp Thr Ser Tyr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro His Thr Phe Gly Gly Gly Thr Lys Val Glu Ile
            100                 105                 110

Lys Arg Gly Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val Thr Lys Ser Phe Asn Arg Gly Glu Cys
    210                 215                 220

<210> SEQ ID NO 40
<211> LENGTH: 351
<212> TYPE: DNA
<213> ORGANISM: Artificial sequence
<220> FEATURE:
<223> OTHER INFORMATION: mAb7 heavy chain variable region DNA sequence

<400> SEQUENCE: 40
caggtgcagc tggtgcagag cggcgccgaa gtgaagaaac caggagccag cgtgaaagtg       60

```
agttgtaagg catccggcta tacctttacc tcttactgga tcaattgggt gaggcaggca      120
cctggccagg gcctggaatg gatgggaaat atctatcccg gctctagctt gactaactac      180
aatgaaaagt ttaagaatcg cgtgaccatg acccgggaca ctagcacctc caccgtgtac      240
atggagctgt cctccctgcg gagcgaggac accgccgtct actattgtgc ccgcctgagt      300
accgggacct tgcctactg gggacagggt acactggtca ccgtctcctc a                351
```

<210> SEQ ID NO 41
<211> LENGTH: 339
<212> TYPE: DNA
<213> ORGANISM: Artificial sequence
<220> FEATURE:
<223> OTHER INFORMATION: mAb7 light chain variable region DNA sequence

<400> SEQUENCE: 41

```
gacatcgtga tgactcagtc tcccgatagc ctggcagtca gcctgggaga gcgggccacc      60
ataaactgca aaagctcgca gtcgctgtgg gacagtggta atcagaagaa tttcctgacc      120
tggtaccagc agaagcctgg ccagccaccc aagctgctga tctactggac ctcatatcgg      180
gagtccgggg tgcccgacag attctctgga agtggcagcg gtacggactt cacactgacc      240
atatccagtc tgcaagctga ggacgtggct gtttattact gccagaacga ctactttat       300 cctcacactt tcggaggcgg taccaaggtc gagatcaaa                             339
```

<210> SEQ ID NO 42
<211> LENGTH: 750
<212> TYPE: PRT
<213> ORGANISM: Homo sapiens

<400> SEQUENCE: 42

```
Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205
```

-continued

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
610                 615                 620

Tyr Ser Val Ser Phe Asp Ser Leu Phe Ser Ala Val Lys Asn Phe Thr

```
              625                 630                 635                 640
Glu Ile Ala Ser Lys Phe Ser Glu Arg Leu Gln Asp Phe Asp Lys Ser
                    645                 650                 655

Asn Pro Ile Val Leu Arg Met Met Asn Asp Gln Leu Met Phe Leu Glu
                660                 665                 670

Arg Ala Phe Ile Asp Pro Leu Gly Leu Pro Asp Arg Pro Phe Tyr Arg
                675                 680                 685

His Val Ile Tyr Ala Pro Ser Ser His Asn Lys Tyr Ala Gly Glu Ser
                690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                    725                 730                 735

Phe Thr Val Gln Ala Ala Ala Glu Thr Leu Ser Glu Val Ala
                740                 745                 750

<210> SEQ ID NO 43
<211> LENGTH: 2217
<212> TYPE: DNA
<213> ORGANISM: Artificial Sequence
<220> FEATURE:
<223> OTHER INFORMATION: Synthetic Construct

<400> SEQUENCE: 43
```

| | | | | | |
|---|---|---|---|---|---|
| atggctagcg | ccagacgccc | cagatggctg | tgtgctggcg | ctctggtgct | ggctggcggc | 60 |
| ttcttcctgc | tgggcttcct | gttcggctgg | ttcatcaagt | cctccaacga | ggccaccaac | 120 |
| atcaccccca | agcacaacat | gaaggccttt | ctggacgagc | tgaaggccga | aatatcaag | 180 |
| aagttcctgt | acaacttcac | ccagatcccc | acctggccg | caccgagca | aacttccag | 240 |
| ctggccaagc | agatccagtc | ccagtggaaa | gagttcggcc | tggactccgt | ggaactggcc | 300 |
| cactacgacg | tgctgctgtc | ctaccccaac | aagacccacc | ccaactacat | ctccatcatc | 360 |
| aacgaggacg | gcaacgaaat | cttcaacacc | tccctgttcg | agcccccacc | cccaggctac | 420 |
| gagaacgtgt | ccgacatcgt | gccccattc | tccgccttca | gtccacaagg | catgcccgag | 480 |
| ggcgacctgg | tgtacgtgaa | ctacgccagg | accgaggact | tcttcaagct | ggaacgcgac | 540 |
| atgaagatca | actgctccgg | caagatcgtg | atcgccagat | acggcaaggt | gttcagggc | 600 |
| aacaaagtga | agaacgccca | gctggctggg | gccaagggcg | tgatcctgta | ctccgacccc | 660 |
| gccgactact | ccgccccagg | cgtgaagtcc | taccccgacg | gatggaacct | gccaggcggc | 720 |
| ggagtgcaga | ggggcaacat | cctgaacctg | aacggcgctg | cgaccccct | gaccccagga | 780 |
| tacccagcca | acgagtacgc | ctacagaaga | ggaatcgccg | aggccgtggg | cctgccctct | 840 |
| atcccagtgc | accccatcgg | ctactacgac | gcccagaaac | tgctggaaaa | gatgggcggc | 900 |
| tccgcccac | ccgactcctc | ttggagaggc | tccctgaagg | tgccctacaa | cgtgggccca | 960 |
| ggcttcaccg | caacttctc | cacccagaaa | gtgaagatgc | acatccactc | caccaacgaa | 1020 |
| gtgaccagga | tctacaacgt | gatcggcacc | ctgagaggcg | ccgtggaacc | cgacagatac | 1080 |
| gtgatcctgg | cggccacag | ggacagctgg | gtgttcggcg | gcatcgaccc | acagtctggc | 1140 |
| gccgctgtg | tgcacgagat | cgtgcggtcc | ttcggaaccc | tgaagaaaga | gggatggcgc | 1200 |
| cccagaagga | ccatcctgtt | cgccagctgg | gacgccgagg | aattcggcct | gctgggatcc | 1260 |
| accgagtggg | ccgaggaaaa | ctccaggctg | ctgcaggaac | gcggcgtcgc | ctacatcaac | 1320 |
| gccgactcct | ccatcgaggg | caactacacc | ctgagggtgg | actgcacccc | cctgatgtac | 1380 |

```
tccctggtgc acaacctgac caaagagctg aagtcccccg acgagggctt cgagggcaag    1440
tccctgtacg agtcctggac caagaagtcc ccatccccg agttctccgg catgcccagg    1500
atctccaagc tgggctccgg caacgacttc gaggtgttct tccagaggct gggaatcgcc    1560
tccggcaggg ccagatacac caagaactgg agacaaaca agttctccgg atacccctg     1620 taccactccg tgtacgaaac ctacgagctg gtggaaaagt tctacgaccc catgttcaag    1680
taccacctga ccgtggccca gtccgcggga ggcatggtgt tcgagctggc caactccatc    1740
gtgctgccct tcgactgcag agactacgcc gtggtgctga ggaagtacgc cgacaaaatc    1800
tactccatct ccatgaagca ccccaggaa atgaagacct actccgtgtc cttcgactcc     1860
ctgttctccg ccgtgaagaa tttcaccgag atcgcctcca agttcagcga gaggctgcag    1920
gacttcgaca gtccaaccc aatcgtgctg aggatgatga cgaccagct gatgttcctg      1980 gaaagggcct tcatcgaccc cctgggcctg ccagacagac ccttctacag gcacgtgatc    2040
tacgccccat cctcccacaa caaatacgcc ggcgagtcct tccccggcat ctacgatgcc    2100
ctgttcgaca tcgagtccaa ggtggacccc tccaaggcct ggggcgaagt gaagaggcaa    2160
atctacgtgg ccgccttcac agtgcaagcc gctgccgaaa ccctgtccga ggtggcc      2217
```

<210> SEQ ID NO 44
<211> LENGTH: 33562
<212> TYPE: DNA
<213> ORGANISM: Artificial Sequence
<220> FEATURE:
<223> OTHER INFORMATION: Synthetic Construct

<400> SEQUENCE: 44

```
ccatcttcaa taatataccct caaactttt gtgcgcgtta atatgcaaat gaggcgtttg     60
aatttgggga ggaagggcgg tgattggtcg agggatgagc gaccgttagg ggcggggcga    120
gtgacgtttt gatgacgtgg ttgcgaggag gagccagttt gcaagttctc gtgggaaaag    180
tgacgtcaaa cgaggtgtgg tttgaacacg gaaatactca attttcccgc gctctctgac    240
aggaaatgag gtgtttctgg gcggatgcaa gtgaaacgg gccattttcg cgcgaaaact    300
gaatgaggaa gtgaaaatct gagtaatttc gcgtttatgg cagggaggag tatttgccga    360
gggccgagta gactttgacc gattacgtgg gggtttcgat taccgtgttt ttcacctaaa    420
tttccgcgta cggtgtcaaa gtccggtgtt tttactactg taatagtaat caattacggg    480
gtcattagtt catagcccat atatggagtt ccgcgttaca taacttacgg taaatggccc    540
gcctggctga ccgcccaacg acccccgccc attgacgtca ataatgacgt atgttcccat    600
agtaacgcca atagggactt tccattgacg tcaatgggtg gagtatttac ggtaaactgc    660
ccacttggca gtacatcaag tgtatcatat gccaagtacg cccctattg acgtcaatga    720 cggtaaatgg cccgcctggc attatgccca gtacatgacc ttatgggact ttcctacttg    780
gcagtacatc tacgtattag tcatcgctat taccatggtg atgcggtttt ggcagtacat    840
caatgggcgt ggatagcggt ttgactcacg gggatttcca agtctccacc ccattgacgt    900
caatgggagt ttgttttggc accaaaatca acgggacttt ccaaaatgtc gtaacaactc    960
cgccccattg acgcaaatgg gcggtaggcg tgtacggtgg gaggtctata taagcagagc   1020
tgtccctatc agtgatagag atctccctat cagtgataga gagtttagtg aaccgtcaga   1080
tccgctaggg taccgcgatc accatggcta gcgccagacg ccccagatgg ctgtgtgctg   1140
gcgctctggt gctggctggc ggcttcttcc tgctgggctt cctgttcggc tggttcatca    1200
agtcctccaa cgaggccacc aacatcaccc ccaagcacaa catgaaggcc tttctggacg   1260
```

```
agctgaaggc cgagaatatc aagaagttcc tgtacaactt cacccagatc ccccacctgg   1320
ccggcaccga gcagaacttc cagctggcca agcagatcca gtcccagtgg aaagagttcg   1380
gcctggactc cgtggaactg gcccactacg acgtgctgct gtcctacccc aacaagaccc   1440
accccaacta catctccatc atcaacgagg acggcaacga aatcttcaac acctccctgt   1500
tcgagccccc accccaggc tacgagaacg tgtccgacat cgtgccccca ttctccgcct   1560
tcagtccaca aggcatgccc gagggcgacc tggtgtacgt gaactacgcc aggaccgagg   1620
acttcttcaa gctggaacgc gacatgaaga tcaactgctc cggcaagatc gtgatcgcca   1680
gatacggcaa ggtgttcagg ggcaacaaag tgaagaacgc ccagctggct ggggccaagg   1740
gcgtgatcct gtactccgac cccgccgact acttcgcccc aggcgtgaag tcctaccccg   1800
acggatggaa cctgccaggc ggcggagtgc agagggcaa catcctgaac ctgaacggcg   1860
ctggcgaccc cctgaccccca ggatacccag ccaacgagta cgcctacaga agaggaatcg   1920
ccgaggccgt gggcctgccc tctatcccag tgcaccccat cggctactac gacgcccaga   1980
aactgctgga aaagatgggc ggctccgccc cacccgactc ctcttggaga ggctccctga   2040
aggtgcccta caacgtgggc ccaggcttca ccggcaactt ctccacccag aaagtgaaga   2100
tgcacatcca ctccaccaac gaagtgacca ggatctacaa cgtgatcggc accctgagag   2160
gcgccgtgga acccgacaga tacgtgatcc tgggcggcca cagggacagc tgggtgttcg   2220
gcggcatcga cccacagtct ggcgccgctg tggtgcacga gatcgtgcgg tccttcggaa   2280
ccctgaagaa agagggatgg cgccccagaa ggaccatcct gttcgccagc tgggacgccg   2340
aggaattcgg cctgctggga tccaccgagt gggccgagga aaactccagg ctgctgcagg   2400
aacgcggcgt cgcctacatc aacgccgact cctccatcga gggcaactac accctgaggg   2460
tggactgcac ccccctgatg tactccctgg tgcacaacct gaccaaagag ctgaagtccc   2520
ccgacgaggg cttcgagggc aagtcccctgt acgagtcctg gaccaagaag tccccatccc   2580
ccgagttctc cggcatgccc aggatctcca agctgggctc cggcaacgac ttcgaggtgt   2640
tcttccagag gctgggaatc gcctccggca gggccagata caccaagaac tgggagacaa   2700
acaagttctc cggatacccc ctgtaccact ccgtgtacga aacctacgag ctggtggaaa   2760
agttctacga ccccatgttc aagtaccacc tgaccgtggc ccaagtccgc ggaggcatgg   2820
tgttcgagct ggccaactcc atcgtgctgc ccttcgactg cagagactac gccgtggtgc   2880
tgaggaagta cgccgacaaa atctactcca tctccatgaa gcaccccag gaaatgaaga   2940 cctactccgt gtccttcgac tccctgttct ccgccgtgaa gaatttcacc gagatcgcct   3000
ccaagttcag cgagaggctg caggacttcg acaagtccaa cccaatcgtg ctgaggatga   3060
tgaacgacca gctgatgttc ctggaaaggg ccttcatcga cccctgggc ctgccagaca   3120 gaccettcta caggcacgtg atctacgccc catcctccca caacaaatac gccggcgagt   3180
ccttccccgg catctacgat gccctgttcg acatcgagtc caaggtggac ccctccaagg   3240
cctggggcga agtgaagagg caaatctacg tggccgcctt cacagtgcaa gccgctgccg   3300
aaaccctgtc cgaggtggcc tgaatcgcac ctcgagattt aaatctgatc ataatcagcc   3360
ataccacatt tgtagaggtt ttacttgctt taaaaaacct cccacacctc ccctgaacc   3420 tgaaacataa aatgaatgca attgttgttg ttaacttgtt tattgcagct tataatggtt   3480
acaaataaag caatagcatc acaaatttca caaataaagc atttttttca ctgcattcta   3540
gttgtggttt gtccaaactc atcaatgtat cttatatgct ggccaccgta catgtggctt   3600
```

```
cccatgctcg caagccctgg cccgagttcg agcacaatgt catgaccagg tgcaatatgc    3660
atctggggtc ccgccgaggc atgttcatgc cctaccagtg caacctgaat tatgtgaagg    3720
tgctgctgga gcccgatgcc atgtccagag tgagcctgac gggggtgttt gacatgaatg    3780
tggaggtgtg gaagattctg agatatgatg aatccaagac caggtgccga gcctgcgagt    3840
gcggagggaa gcatgccagg ttccagcccg tgtgtgtgga tgtgacggag gacctgcgac    3900
ccgatcattt ggtgttgccc tgcaccggga cggagttcgg ttccagcggg gaagaatctg    3960
actagagtga gtagtgttct ggggcggggg aggacctgca tgagggccag aataactgaa    4020
atctgtgctt ttctgtgtgt tgcagcagca tgagcggaag cggctccttt gagggagggg    4080
tattcagccc ttatctgacg gggcgtctcc cctcctgggc gggagtgcgt cagaatgtga    4140
tgggatccac ggtggacggc cggcccgtgc agcccgcgaa ctcttcaacc ctgacctatg    4200
caaccctgag ctcttcgtcg ttggacgcag ctgccgccgc agctgctgca tctgccgcca    4260
gcgccgtgcg cggaatggcc atgggcgccg gctactacgg cactctggtg gccaactcga    4320
gttccaccaa taatcccgcc agcctgaacg aggagaagct gttgctgctg atggcccagc    4380
tcgaggcctt gacccagcgc ctgggcgagc tgacccagca ggtggctcag ctgcaggagc    4440
agacgcgggc cgcggttgcc acggtgaaat ccaaataaaa aatgaatcaa taaataaacg    4500
gagacggttg ttgattttaa cacagagtct gaatctttat ttgatttttc gcgcgcggta    4560
ggccctggac caccggtctc gatcattgag cacccggtgg atcttttcca ggacccggta    4620
gaggtgggct tggatgttga ggtacatggg catgagcccg tcccgggggt ggaggtagct    4680
ccattgcagg gcctcgtgct cggggtggt gttgtaaatc acccagtcat agcaggggcg    4740
cagggcatgg tgttgcacaa tatctttgag gaggagactg atggccacgg gcagcccttt    4800
ggtgtaggtg tttacaaatc tgttgagctg gagggatgc atgcgggggg agatgaggtg    4860
catcttggcc tggatcttga gattggcgat gttaccgccc agatcccgcc tggggttcat    4920
gttgtgcagg accaccagca cggtgtatcc ggtgcacttg ggaatttat catgcaactt    4980 ggaagggaag gcgtgaaaga atttggcgac gcctttgtgc ccgcccaggt tttccatgca    5040
ctcatccatg atgatggcga tgggcccgtg gcggcggcc tggcaaaga cgtttcgggg    5100 gtcggacaca tcatagttgt ggtcctgggt gaggtcatca taggccattt taatgaattt    5160
ggggcggagg gtgccggact gggggacaaa ggtaccctcg atcccggggg cgtagttccc    5220
ctcacagatc tgcatctccc aggctttgag ctcgagggg gggatcatgt ccacctgcgg    5280
ggcgataaag aacacggttt ccggggcggg ggagatgagc tgggccgaaa gcaagttccg    5340
gagcagctgg gacttgccgc agccggtggg gccgtagatg accccgatga ccggctgcag    5400
gtggtagttg agggagagac agctgccgtc ctcccggagg agggggggcca cctcgttcat    5460 catctcgcgc acgtgcatgt tctcgcgcac cagttccgcc aggaggcgct ctcccccccag    5520 ggataggagc tcctggagcg aggcgaagtt tttcagcggc ttgagtccgt cggccatggg    5580
cattttggag agggtttgtt gcaagagttc caggcggtcc cagagctcgg tgatgtgctc    5640
tacggcatct cgatccagca gacctcctcg tttcgcgggt tgggacggct gcgggagtag    5700
ggcaccagac gatgggcgtc cagcgcagcc agggtccggt ccttccaggg tcgcagcgtc    5760
cgcgtcaggg tggtctccgt cacggtgaag gggtgcgcgc cgggctgggc gcttgcgagg    5820
gtgcgcttca ggctcatccg gctggtcgaa aaccgctccc gatcggcgcc ctgcgcgtcg    5880
gccaggtagc aattgaccat gagttcgtag ttgagcgcct cggccgcgtg gcctttggcg    5940
cggagcttac ctttggaagt ctgcccgcag gcgggacaga ggagggactt gagggcgtag    6000
```

```
agcttggggg cgaggaagac ggactcgggg gcgtaggcgt ccgcgccgca gtgggcgcag    6060
acggtctcgc actccacgag ccaggtgagg tcgggctggt cggggtcaaa aaccagtttc    6120
ccgccgttct ttttgatgcg tttcttacct ttggtctcca tgagctcgtg tccccgctgg    6180
gtgacaaaga ggctgtccgt gtccccgtag accgacttta tgggccggtc ctcgagcggt    6240
gtgccgcggt cctcctcgta gaggaacccc gcccactccg agacgaaagc ccgggtccag    6300
gccagcacga aggaggccac gtgggacggg tagcggtcgt tgtccaccag cgggtccacc    6360
ttttccaggg tatgcaaaca catgtccccc tcgtccacat ccaggaaggt gattggcttg    6420
taagtgtagg ccacgtgacc gggggtcccg gccgggggg tataaaaggg tgcgggtccc     6480
tgctcgtcct cactgtcttc cggatcgctg tccaggagcg ccagctgttg gggtaggtat    6540
tccctctcga aggcgggcat gacctcggca ctcaggttgt cagtttctag aaacgaggag    6600
gatttgatat tgacggtgcc ggcggagatg cctttcaaga gcccctcgtc catctggtca    6660
gaaaagacga tctttttgtt gtcgagcttg gtggcgaagg agccgtagag ggcgttggag    6720
aggagcttgg cgatggagcg catggtctgg ttttttttcct tgtcggcgcg ctccttggcg    6780
gcgatgttga gctgcacgta ctcgcgcgcc acgcacttcc attcggggaa gacggtggtc    6840
agctcgtcgg gcacgattct gacctgccag ccccgattat gcagggtgat gaggtccaca    6900
ctggtggcca cctcgccgcg caggggctca ttagtccagc agaggcgtcc gcccttgcgc    6960
gagcagaagg ggggcagggg gtccagcatg acctcgtcgg ggggtcggc atcgatggtg      7020 aagatgccgg gcaggaggtc ggggtcaaag tagctgatgg aagtggccag atcgtccagg    7080
gcagcttgcc attcgcgcac ggccagcgcg cgctcgtagg gactgagggg cgtgcccag     7140 ggcatgggat gggtaagcgc ggaggcgtac atgccgcaga tgtcgtagac gtagaggggc    7200
tcctcgagga tgccgatgta ggtggggtag cagcgccccc cgcggatgct ggcgcgcacg    7260
tagtcataca gctcgtgcga gggggcgagg agccccgggc ccaggttggt gcgactgggc    7320 tttcggcgc ggtagacgat ctggcggaaa atggcatgcg agttggagga gatggtgggc      7380
ctttggaaga tgttgaagtg ggcgtggggc agtccgaccg agtcgcggat gaagtgggcg    7440
taggagtctt gcagcttggc gacgagctcg gcggtgacta ggacgtccag agcgcagtag    7500
tcgagggtct cctggatgat gtcatacttg agctgtccct tttgtttcca cagctcgcgg    7560
ttgagaagga actcttcgcg gtccttccag tactcttcga gggggaaccc gtcctgatct    7620
gcacggtaag agcctagcat gtagaactgg ttgacggcct tgtaggcgca gcagcccttc    7680
tccacgggga gggcgtaggc ctgggcggcc ttgcgcaggg aggtgtgcgt gagggcgaaa    7740
gtgtccctga ccatgacctt gaggaactgg tgcttgaagt cgatatcgtc gcagcccccc    7800
tgctcccaga gctggaagtc cgtgcgcttc ttgtaggcgg ggttgggcaa agcgaaagta    7860
acatcgttga agaggatctt gcccgcgcgg ggcataaagt tgcgagtgat gcggaaaggt    7920
tggggcacct cggccggtt gttgatgacc tgggcggcga gcacgatctc gtcgaagccg      7980
ttgatgttgt ggcccacgat gtagagttcc acgaatcgcg gacggccctt gacgtgggc      8040 agtttcttga gctcctcgta ggtgagctcg tcggggtcgc tgagcccgtg ctgctcgagc    8100
gcccagtcgc cgagatgggg gttggcgcgg aggaaggaag tccagagatc cacggccagg    8160
gcggtttgca gacggtcccg gtactgacgg aactgctgcc cgacggccat ttttttcgggg    8220 gtgacgcagt agaaggtgcg ggggtccccg tgccagcgat cccatttgag ctggagggcg    8280
agatcgaggg cgagctcgac gagccggtcg tccccggaga gtttcatgac cagcatgaag    8340
```

```
gggacgagct gcttgccgaa ggaccccatc caggtgtagg tttccacatc gtaggtgagg    8400
aagagccttt cggtgcgagg atgcgagccg atggggaaga actggatctc ctgccaccaa    8460
ttggaggaat ggctgttgat gtgatggaag tagaaatgcc gacggcgcgc cgaacactcg    8520
tgcttgtgtt tatacaagcg gccacagtgc tcgcaacgct gcacgggatg cacgtgctgc    8580
acgagctgta cctgagttcc tttgacgagg aatttcagtg ggaagtggag tcgtggcgcc    8640
tgcatctcgt gctgtactac gtcgtggtgg tcggcctggc cctcttctgc ctcgatggtg    8700
gtcatgctga cgagcccgcg cgggaggcag gtccagacct cggcgcgagc gggtcggaga    8760
gcgaggacga gggcgcgcag gccggagctg tccagggtcc tgagacgctg cggagtcagg    8820
tcagtgggca gcggcggcgc gcggttgact tgcaggagtt tttccagggc gcgcgggagg    8880
tccagatggt acttgatctc caccgcgcca ttggtggcga cgtcgatggc ttgcagggtc    8940
ccgtgcccct ggggtgtgac caccgtcccc cgtttcttct tgggcggctg gggcgacggg    9000
ggcggtgcct cttccatggt tagaagcggc ggcgaggacg cgcgccgggc ggcaggggcg    9060
gctcggggcc cggaggcagg ggcggcaggg gcacgtcggc gccgcgcgcg ggtaggttct    9120
ggtactgcgc ccggagaaga ctggcgtgag cgacgacgcg acggttgacg tcctggatct    9180
gacgcctctg ggtgaaggcc acgggacccg tgagtttgaa cctgaaagag agttcgacag    9240
aatcaatctc ggtatcgttg acggcggcct gccgcaggat ctcttgcacg tcgcccgagt    9300
tgtcctggta ggcgatctcg gtcatgaact gctcgatctc ctcctcttga aggtctccgc    9360
ggccggcgcg ctccacggtg ccgcgaggt cgttggagat gcggcccatg agctgcgaga    9420
aggcgttcat gcccgcctcg ttccagacgc ggctgtagac cacgacgccc tcgggatcgc    9480
gggcgcgcat gaccacctgg gcgaggttga gctccacgtg gcgcgtgaag accgcgtagt    9540
tgcagaggcg ctggtagagg tagttgagcg tggtggcgat gtgctcggtg acgaagaaat    9600
acatgatcca gcggcggagc ggcatctcgc tgacgtcgcc cagcgcctcc aaacgttcca    9660
tggcctcgta aaagtccacg gcgaagttga aaaactggga gttgcgcgcc gagacggtca    9720
actcctcctc cagaagacgg atgagctcgg cgatggtggc gcgcacctcg cgctcgaagg    9780
cccccgggag ttcctccact tcctcttctt cctcctccac taacatctct tctacttcct    9840
cctcaggcgg cagtggtggc gggggagggg gcctgcgtcg ccggcggcgc acgggcagac    9900
ggtcgatgaa gcgctcgatg gtctcgccgc gccggcgtcg catggtctcg gtgacgcgc    9960 gcccgtcctc gcggggccgc agcgtgaaga cgccgccgcg catctccagg tggccggggg    10020
ggtccccgtt gggcagggag agggcgctga cgatgcatct tatcaattgc cccgtaggga    10080
ctccgcgcaa ggacctgagc gtctcgagat ccacgggatc tgaaaccgc tgaacgaagg    10140 cttcgagcca gtcgcagtcg caaggtaggc tgagcacggt ttcttctggc gggtcatgtt    10200
ggttgggagc ggggcgggcg atgctgctgg tgatgaagtt gaaataggcg gttctgagac    10260
ggcggatggt ggcgaggagc accaggtctt tgggcccggc ttgctggatg cgcagacggt    10320
cggccatgcc ccaggcgtgg tcctgacacc tggccaggtc cttgtagtag tcctgcatga    10380
gccgctccac gggcacctcc tcctcgcccg cgcggccgtg catgcgcgtg agcccgaagc    10440
cgcgctgggg ctgacgagc gccaggtcgg cgacgacgcg ctcggcgagg atggcttgct    10500
ggatctgggt gagggtggtc tggaagtcat caaagtcgac gaagcggtgg taggctccgg    10560
tgttgatggt gtaggagcag ttggccatga cggaccagtt gacggtctgg tggcccggac    10620
gcacgagctc gtggtacttg aggcgcgagt aggcgcgcgt gtcgaagatg tagtcgttgc    10680
aggtgcgcac caggtactgg tagccgatga ggaagtgcgg cggcggctgg cggtagagcg    10740
```

-continued

```
gccatcgctc ggtggcgggg gcgccgggcg cgaggtcctc gagcatggtg cggtggtagc      10800
cgtagatgta cctggacatc caggtgatgc cggcggcggt ggtggaggcg cgcgggaact      10860
cgcggacgcg gttccagatg ttgcgcagcg gcaggaagta gttcatggtg ggcacggtct      10920
ggcccgtgag gcgcgcgcag tcgtggatgc tctatacggg caaaaacgaa agcggtcagc      10980
ggctcgactc cgtggcctgg aggctaagcg aacgggttgg gctgcgcgtg taccccggtt      11040
cgaatctcga atcaggctgg agccgcagct aacgtggtat tggcactccc gtctcgaccc      11100
aagcctgcac caaccctcca ggatacggag gcgggtcgtt ttgcaacttt tttttggagg      11160
ccggatgaga ctagtaagcg cggaaagcgg ccgaccgcga tggctcgctg ccgtagtctg      11220
gagaagaatc gccagggttg cgttgcggtg tgccccggtt cgaggccggc cggattccgc      11280
ggctaacgag ggcgtggctg ccccgtcgtt tccaagaccc catagccagc cgacttctcc      11340
agttacggag cgagcccctc ttttgttttg tttgttttg ccagatgcat cccgtactgc      11400
ggcagatgcg ccccaccac cctccaccgc aacaacagcc cctccacag ccggcgcttc      11460
tgcccccgcc ccagcagcaa cttccagcca cgaccgccgc ggccgccgtg agcggggctg      11520
gacagagtta tgatcaccag ctggccttgg aagagggcga gggctggcg cgcctggggg      11580
cgtcgtcgcc ggagcggcac ccgcgcgtgc agatgaaaag ggacgctcgc gaggcctacg      11640
tgcccaagca gaacctgttc agagacagga gcggcgagga gcccgaggag atgcgcgcgg      11700
cccggttcca cgcggggcgg gagctgcggc gcggcctgga ccgaaagagg gtgctgaggg      11760
acgaggattt cgaggcggac gagctgacgg ggatcagccc cgcgcgcgcg cacgtggccg      11820
cggccaacct ggtcacggcg tacgagcaga ccgtgaagga ggagagcaac ttccaaaaat      11880
ccttcaacaa ccacgtgcgc accctgatcg cgcgcgagga ggtgaccctg gcctgatgc      11940
acctgtggga cctgctggag gccatcgtgc agaaccccac cagcaagccg ctgacggcgc      12000
agctgttcct ggtggtgcag catagtcggg acaacgaagc gttcagggag gcgctgctga      12060
atatcaccga gcccgaggc cgctggctcc tggacctggt gaacattctg cagagcatcg      12120
tggtgcagga gcgcgggctg ccgctgtccg agaagctggc ggccatcaac ttctcggtgc      12180
tgagtttggg caagtactac gctaggaaga tctacaagac cccgtacgtg cccatagaca      12240
aggaggtgaa gatcgacggg ttttacatgc gcatgaccct gaaagtgctg accctgagcg      12300
acgatctggg ggtgtaccgc aacgacagga tgcaccgtgc ggtgagcgcc agcaggcggc      12360
gcgagctgag cgaccaggag ctgatgcata gtctgcagcg ggccctgacc ggggccggga      12420
ccgagggga gagctacttt gacatgggcg cggacctgca ctggcagccc agccgccggg      12480
ccttggaggc ggcggcagga ccctacgtag aagaggtgga cgatgaggtg gacgaggagg      12540
gcgagtacct ggaagactga tggcgcgacc gtatttttgc tagatgcaac aacaacagcc      12600
acctcctgat cccgcgatgc gggcggcgct gcagagccag ccgtccggca ttaactcctc      12660
ggacgattgg acccaggcca tgcaacgcat catggcgctg acgacccgca accccgaagc      12720
ctttagacag cagccccagg ccaaccggct ctcggccatc ctggaggccg tggtgccctc      12780
gcgctccaac cccacgcacg agaaggtcct ggccatcgtg aacgcgctgg tggagaacaa      12840
ggccatccgc ggcgacgagg ccggcctggt gtacaacgcg ctgctggagc gcgtggcccg      12900
ctacaacagc accaacgtgc agaccaacct ggaccgcatg gtgaccgacg tgcgcgaggc      12960
cgtggcccag cgcgagcggt tccaccgcga gtccaacctg gatccatgg tggcgctgaa      13020
cgccttcctc agcacccagc ccgccaacgt gccccggggc caggaggact acaccaactt      13080
```

```
catcagcgcc ctgcgcctga tggtgaccga ggtgccccag agcgaggtgt accagtccgg   13140
gccggactac ttcttccaga ccagtcgcca gggcttgcag accgtgaacc tgagccaggc   13200
tttcaagaac ttgcagggcc tgtggggcgt gcaggcccg  gtcggggacc gcgcgacggt   13260
gtcgagcctg ctgacgccga actcgcgcct gctgctgctg ctggtggccc ccttcacgga   13320
cagcggcagc atcaaccgca actcgtacct gggctacctg attaacctgt accgcgaggc   13380
catcggccag gcgcacgtgg acgagcagac ctaccaggag atcacccacg tgagccgcgc   13440
cctgggccag gacgacccgg gcaacctgga agccaccctg aacttttgc  tgaccaaccg   13500
gtcgcagaag atcccgcccc agtacgcgct cagcaccgag gaggagcgca tcctgcgtta   13560
cgtgcagcag agcgtgggcc tgttcctgat gcaggagggg gccaccccca gcgccgcgct   13620
cgacatgacc gcgcgcaaca tggagcccag catgtacgcc agcaaccgcc cgttcatcaa   13680
taaactgatg gactacttgc atcgggcggc cgccatgaac tctgactatt tcaccaacgc   13740
catcctgaat ccccactggc tcccgccgcc ggggttctac acgggcgagt acgacatgcc   13800
cgaccccaat gacgggttcc tgtgggacga tgtggacagc agcgtgttct cccccccgacc  13860
gggtgctaac gagcgcccct gtgtggaagaa ggaaggcagc gaccgacgcc cgtcctcggc   13920
gctgtccggc cgcgagggtg ctgccgcggc ggtgcccgag gccgcagtc  ctttcccgag   13980
cttgcccttc tcgctgaaca gtatccgcag cagcgagctg gcaggatca  cgcgcccgcg   14040
cttgctgggc gaagaggagt acttgaatga ctcgctgttg agacccgagc gggagaagaa   14100
cttccccaat aacgggatag aaagcctggt ggacaagatg agccgctgga agacgtatgc   14160
gcaggagcac agggacgatc cccgggcgtc gcagggggcc acgagccggg gcagcgccgc   14220
ccgtaaacgc cggtggcacg acaggcagcg gggacagatg tgggacgatg aggactccgc   14280
cgacgacagc agcgtgttgg acttgggtgg gagtggtaac ccgttcgctc acctgcgccc   14340
ccgtatcggg cgcatgatgt aagagaaacc gaaaataaat gatactcacc aaggccatgg   14400
cgaccagcgt gcgttcgttt cttctctgtt gttgttgtat ctagtatgat gaggcgtgcg   14460
tacccggagg gtcctcctcc ctcgtacgag agcgtgatgc agcaggcgat ggcggcggcg   14520
gcgatgcagc ccccgctgga ggctccttac gtgcccccgc ggtacctggc gcctacggag   14580
gggcggaaca gcattcgtta ctcggagctg gcaccttgt  acgataccac ccggttgtac   14640
ctggtggaca acaagtcggc ggacatcgcc tcgctgaact accagaacga ccacagcaac   14700
ttcctgacca ccgtggtgca gaacaatgac ttcaccccca cggaggccag cacccagacc   14760
atcaactttg acgagcgctc gcggtggggc ggccagctga aaaccatcat gcacaccaac   14820
atgcccaacg tgaacgagtt catgtacagc aacaagttca aggcgcgggt gatggtctcc   14880
cgcaagaccc ccaatggggt gacagtgaca gaggattatg atggtagtca ggatgagctg   14940
aagtatgaat gggtggaatt tgagctgccc gaaggcaact tctcggtgac catgaccatc   15000
gacctgatga caacgccat  catcgacaat tacttggcgg tggggcggca gaacggggtg   15060
ctggagagcg acatcggcgt gaagttcgac actaggaact tcaggctggg ctgggacccc   15120
gtgaccgagc tggtcatgcc cggggtgtac accaacgagg cttccatcc  cgatattgtc   15180
ttgctgcccg gctgcgggt  ggacttcacc gagagccgcc tcagcaacct gctgggcatt   15240
cgcaagaggc agcccttcca ggaaggcttc cagatcatgt acgaggatct ggagggggc   15300
aacatcccg  cgctcctgga tgtcgacgcc tatgagaaaa gcaaggagga tgcagcagct   15360
gaagcaactg cagccgtagc taccgcctct accgaggtca ggggcgataa ttttgcaagc   15420
gccgcagcag tggcagcggc cgaggcggct gaaaccgaaa gtaagatagt cattcagccg   15480
```

```
gtggagaagg atagcaagaa caggagctac aacgtactac cggacaagat aaacaccgcc    15540
taccgcagct ggtacctagc ctacaactat ggcgaccccg agaagggcgt gcgctcctgg    15600
acgctgctca ccacctcgga cgtcacctgc ggcgtggagc aagtctactg gtcgctgccc    15660
gacatgatgc aagacccggt caccttccgc tccacgcgtc aagttagcaa ctacccggtg    15720
gtgggcgccg agctcctgcc cgtctactcc aagagcttct tcaacgagca ggccgtctac    15780
tcgcagcagc tgcgcgcctt cacctcgctt acgcacgtct tcaaccgctt ccccgagaac    15840
cagatcctcg tccgcccgcc cgcgcccacc attaccaccg tcagtgaaaa cgttcctgct    15900
ctcacagatc acgggaccct gccgctgcgc agcagtatcc ggggagtcca gcgcgtgacc    15960
gttactgacg ccagacgccg cacctgcccc tacgtctaca aggccctggg catagtcgcg    16020
ccgcgcgtcc tctcgagccg caccttctaa atgtccattc tcatctcgcc cagtaataac    16080
accggttggg gcctgcgcgc gcccagcaag atgtacggag gcgctcgcca acgctccacg    16140
caacaccccg tgcgcgtgcg cgggcacttc cgcgctccct ggggcgccct caagggccgc    16200
gtgcggtcgc gcaccaccgt cgacgacgtg atcgaccagg tggtggccga cgcgcgcaac    16260 tacaccccg ccgccgcgcc cgtctccacc gtggacgccg tcatcgacag cgtggtggcc    16320
gacgcgcgcc ggtacgcccg cgccaagagc cggcggcggc gcatcgcccg gcggcaccgg    16380 agcaccccg ccatgcgcgc ggcgcgagcc ttgctgcgca gggccaggcg cacgggacgc    16440
agggccatgc tcagggcggc cagacgcgcg gcttcaggcg ccagcgccgg caggacccgg    16500
agacgcgcgg ccacgcggc ggcagcggcc atcgccagca tgtcccgccc gcggcgaggg    16560
aacgtgtact gggtgcgcga cgccgccacc ggtgtgcgcg tgcccgtgcg cacccgcccc    16620
cctcgcactt gaagatgttc acttcgcgat gttgatgtgt cccagcggcg aggaggatgt    16680
ccaagcgcaa attcaaggaa gagatgctcc aggtcatcgc gcctgagatc tacggccctg    16740
cggtggtgaa ggaggaaaga aagccccgca aaatcaagcg ggtcaaaaag gacaaaaagg    16800
aagaagaaag tgatgtggac ggattggtgg agtttgtgcg cgagttcgcc ccccggcggc    16860
gcgtgcagtg gcgcgggcgg aaggtgcaac cggtgctgag acccggcacc accgtggtct    16920
tcacgcccgg cgagcgctcc ggcaccgctt ccaagcgctc ctacgacgag gtgtacgggg    16980
atgatgatat tctggagcag gcggccgagc gcctgggcga gtttgcttac ggcaagcgca    17040
gccgttccgc accgaaggaa gaggcggtgt ccatcccgct ggaccacggc aaccccacgc    17100
cgagcctcaa gcccgtgacc ttgcagcagg tgctgccgac cgcggcgccg cgccgggggt    17160
tcaagcgcga gggcgaggat ctgtacccca ccatgcagct gatggtgccc aagcgccaga    17220
agctggaaga cgtgctggag accatgaagg tggacccgga cgtgcagccc gaggtcaagg    17280
tgcggcccat caagcaggtg gccccgggcc tgggcgtgca gaccgtggac atcaagattc    17340
ccacggagcc catggaaacg cagaccgagc ccatgatcaa gcccagcacc agcaccatgg    17400
aggtgcagac ggatccctgg atgccatcgg ctcctagtcg aagacccggg cgcaagtacg    17460
gcgcggccag cctgctgatg cccaactacg cgctgcatcc ttccatcatc cccacgccgg    17520
gctaccgcgg cacgcgcttc taccgcggtc ataccagcag ccgccgccgc aagaccacca    17580
ctcgccgccg ccgtcgccgc accgccgctg caaccaccc tgccgccctg gtgcggagag    17640
tgtaccgccg cggccgcgca cctctgaccc tgccgcgcgc gcgctaccac ccgagcatcg    17700
ccatttaaac tttcgcctgc tttgcagatc aatggccctc acatgccgcc ttcgcgttcc    17760
cattacgggc taccgaggaa gaaaaccgcg ccgtagaagg ctggcgggga acgggatgcg    17820
```

```
tcgccaccac caccggcggc ggcgcgccat cagcaagcgg ttgggggag gcttcctgcc    17880 cgcgctgatc cccatcatcg ccgcggcgat cggggcgatc cccggcattg cttccgtggc    17940
ggtgcaggcc tctcagcgcc actgagacac acttggaaac atcttgtaat aaaccaatgg    18000
actctgacgc tcctggtcct gtgatgtgtt ttcgtagaca gatggaagac atcaattttt    18060
cgtccctggc tccgcgacac ggcacgcggc cgttcatggg cacctggagc gacatcggca    18120
ccagccaact gaacgggggc gccttcaatt ggagcagtct ctggagcggg cttaagaatt    18180
tcgggtccac gcttaaaacc tatggcagca aggcgtggaa cagcaccaca gggcaggcgc    18240
tgagggataa gctgaaagag cagaacttcc agcagaaggt ggtcgatggg ctcgcctcgg    18300
gcatcaacgg ggtggtggac ctggccaacc aggccgtgca gcggcagatc aacagccgcc    18360
tggacccggt gccgcccgcc ggctccgtgg agatgccgca ggtggaggag gagctgcctc    18420
ccctggacaa gcggggcgag aagcgacccc gccccgatgc ggaggagacg ctgctgacgc    18480
acacggacga gccgccccg tacgaggagg cggtgaaact gggtctgccc accacgcggc    18540
ccatcgcgcc cctggccacc ggggtgctga acccgaaaa gcccgcgacc ctggacttgc    18600
ctcctcccca gccttcccgc ccctctacag tggctaagcc cctgccgccg gtggccgtgg    18660
cccgcgcgcg accggggc accgcccgcc ctcatgcgaa ctggcagagc actctgaaca    18720
gcatcgtggg tctgggagtg cagagtgtga agcgccgccg ctgctattaa acctaccgta    18780
gcgcttaact tgcttgtctg tgtgtgtatg tattatgtcg ccgccgccgc tgtccaccag    18840
aaggaggagt gaagaggcgc gtcgccgagt tgcaagatgg ccaccccatc gatgctgccc    18900
cagtgggcgt acatgcacat cgccggacag gacgcttcgg agtacctgag tccgggtctg    18960
gtgcagtttg cccgcgccac agacacctac ttcagtctgg ggaacaagtt taggaaccc    19020 acggtggcgc ccacgcacga tgtgaccacc gaccgcagcc agcggctgac gctgcgcttc    19080
gtgcccgtgg accgcgagga caacacctac tcgtacaaag tgcgctacac gctggccgtg    19140
ggcgacaacc gcgtgctgga catggccagc acctactttg acatccgcgg cgtgctggat    19200
cggggcccta gcttcaaacc ctactccggc accgcctaca cagtctggc ccccaaggga    19260 gcacccaaca cttgtcagtg gacatataaa gccgatggtg aaactgccac agaaaaaacc    19320
tatacatatg gaaatgcacc cgtgcagggc attaacatca caaagatgg tattcaactt    19380 ggaactgaca ccgatgatca gccaatctac gcagataaaa cctatcagcc tgaacctcaa    19440
gtgggtgatg ctgaatggca tgacatcact ggtactgatg aaaagtatgg aggcagagct    19500
cttaagcctg ataccaaaat gaagccttgt tatggttctt ttgccaagcc tactaataaa    19560
gaaggaggtc aggcaaatgt gaaaacagga acaggcacta ctaaagaata tgacatagac    19620 atggcttct ttgacaacag aagtgcggct gctgctggcc tagctccaga aattgttttg    19680
tatactgaaa atgtggattt ggaaactcca gatacccata ttgtatacaa agcaggcaca    19740
gatgacagca gctcttctat taatttgggt cagcaagcca tgcccaacag acctaactac    19800
attggtttca gagacaactt tatcgggctc atgtactaca cagcactgg caatatgggg    19860 gtgctggccg tcaggcttc tcagctgaat gctgtggttg acttgcaaga cagaaacacc    19920
gagctgtcct accagctctt gcttgactct ctgggtgaca gaacccggta tttcagtatg    19980
tggaatcagg cggtggacag ctatgatcct gatgtgcgca ttattgaaaa tcatggtgtg    20040
gaggatgaac ttcccaacta ttgtttccct ctggatgctg ttggcagaac agatacttat    20100
cagggaatta aggctaatgg aactgatcaa accacatgga ccaaagatga cagtgtcaat    20160
gatgctaatg agataggcaa gggtaatcca ttcgccatgg aaatcaacat ccaagccaac    20220
```

```
ctgtggagga acttcctcta cgccaacgtg gccctgtacc tgcccgactc ttacaagtac   20280
acgccggcca atgttaccct gcccaccaac accaacacct acgattacat gaacggccgg   20340
gtggtggcgc cctcgctggt ggactcctac atcaacatcg gggcgcgctg gtcgctggat   20400
cccatggaca acgtgaaccc cttcaaccac caccgcaatg cggggctgcg ctaccgctcc   20460
atgctcctgg caacgggcg ctacgtgccc ttccacatcc aggtgcccca gaaattttc   20520 gccatcaaga gcctcctgct cctgcccggg tcctacacct acgagtggaa cttccgcaag   20580
gacgtcaaca tgatcctgca gagctccctc ggcaacgacc tgcgcacgga cggggcctcc   20640
atctccttca ccagcatcaa cctctacgcc accttcttcc ccatggcgca aacacggcc   20700 tccacgctcg aggccatgct gcgcaacgac accaacgacc agtccttcaa cgactacctc   20760
tcggcggcca acatgctcta ccccatcccg gccaacgcca ccaacgtgcc catctccatc   20820
ccctcgcgca actgggccgc cttccgcggc tggtccttca cgcgtctcaa gaccaaggag   20880
acgccctcgc tgggctccgg gttcgacccc tacttcgtct actcgggctc catcccctac   20940
ctcgacggca ccttctacct caaccacacc ttcaagaagg tctccatcac cttcgactcc   21000
tccgtcagct ggcccggcaa cgaccggctc ctgacgccca acgagttcga aatcaagcgc   21060
accgtcgacg gcgagggcta caacgtggcc cagtgcaaca tgaccaagga ctggttcctg   21120
gtccagatgc tggcccacta caacatcggc taccagggct tctacgtgcc cgagggctac   21180
aaggaccgca tgtactcctt cttccgcaac ttccagccca tgagccgcca ggtggtggac   21240
gaggtcaact acaaggacta ccaggccgtc accctggcct accagcacaa caactcgggc   21300
ttcgtcggct acctcgcgcc caccatgcgc cagggccagc cctaccccgc caactacccc   21360
tacccgctca tcggcaagag cgccgtcacc agcgtcaccc agaaaaagtt cctctgcgac   21420
agggtcatgt ggcgcatccc cttctccagc aacttcatgt ccatgggcgc gctcaccgac   21480
ctcggccaga acatgctcta tgccaactcc gcccacgcgc tagacatgaa tttcgaagtc   21540
gaccccatgg atgagtccac ccttctctat gttgtcttcg aagtcttcga cgtcgtccga   21600
gtgcaccagc cccaccgcgg cgtcatcgag gccgtctacc tgcgcacccc cttctcggcc   21660
ggtaacgcca ccacctaagc tcttgcttct tgcaagccat ggccgcgggc tccggcgagc   21720
aggagctcag ggccatcatc cgcgacctgg gctgcgggcc ctacttcctg gcgaccttcg   21780
ataagcgctt cccgggattc atggccccgc acaagctggc ctgcgccatc gtcaacacgg   21840
ccggccgcga accgggggc gagcactggc tggccttcgc ctggaacccg cgctcgaaca   21900
cctgctacct cttcgacccc ttcggttct cggacgagcg cctcaagcag atctaccagt   21960
tcgagtacga gggcctgctg cgccgcagcg ccctggccac cgaggaccgc tgcgtcaccc   22020
tggaaaagtc cacccagacc gtgcaggtgc cgcgctcggc cgcctgcggg ctcttctgct   22080
gcatgttcct gcacgccttc gtgcactggc ccgaccgccc catggacaag aaccccacca   22140
tgaacttgct gacgggggtg cccaacggca tgctccagtc gccccaggtg gaaccccacc   22200
tgcgccgcaa ccaggaggcg ctctaccgct tcctcaactc ccactccgcc tactttcgct   22260
cccaccgcgc gcgcatcgag aaggccaccg ccttcgaccg catgaatcaa gacatgtaaa   22320
ccgtgtgtgt atgttaaatg tctttaataa acagcacttt catgttacac atgcatctga   22380
gatgatttat ttagaaatcg aaagggttct gccgggtctc ggcatggccc gcgggcaggg   22440
acacgttgcg gaactggtac ttggccagcc acttgaactc ggggatcagc agtttgggca   22500
gcggggtgtc ggggaaggag tcggtccaca gcttccgcgt cagttgcagg gcgcccagca   22560
```

```
ggtcgggcgc ggagatcttg aaatcgcagt tgggacccgc gttctgcgcg cgggagttgc   22620
ggtacacggg gttgcagcac tggaacacca tcagggccgg gtgcttcacg ctcgccagca   22680
ccgtcgcgtc ggtgatgctc tccacgtcga ggtcctcggc gttggccatc ccgaaggggg   22740
tcatcttgca ggtctgcctt cccatggtgg gcacgcaccc gggcttgtgg ttgcaatcgc   22800
agtgcagggg gatcagcatc atctgggcct ggtcggcgtt catccccggg tacatggcct   22860
tcatgaaagc ctccaattgc ctgaacgcct gctgggcctt ggctccctcg gtgaagaaga   22920
ccccgcagga cttgctagag aactggttgg tggcgcaccc ggcgtcgtgc acgcagcagc   22980
gcgcgtcgtt gttggccagc tgcaccacgc tgcgccccca gcggttctgg gtgatcttgg   23040
cccggtcggg gttctccttc agcgcgcgct gcccgttctc gctcgccaca tccatctcga   23100
tcatgtgctc cttctggatc atggtggtcc cgtgcaggca ccgcagcttg ccctcggcct   23160
cggtgcaccc gtgcagccac agcgcgcacc cggtgcactc ccagttcttg tgggcgatct   23220
gggaatgcgc gtgcacgaag ccctgcagga agcggcccat catggtggtc agggtcttgt   23280
tgctagtgaa ggtcagcgga atgccgcggt gctcctcgtt gatgtacagg tggcagatgc   23340
ggcggtacac ctcgccctgc tcgggcatca gctggaagtt ggctttcagg tcggtctcca   23400
cgcggtagcg gtccatcagc atagtcatga tttccatacc cttctcccag gccgagacga   23460
tgggcaggct catagggttc ttcaccatca tcttagcgct agcagccgcg gccaggggt    23520
cgctctcgtc cagggtctca aagctccgct tgccgtcctt tcggtgatc cgcaccgggg    23580
ggtagctgaa gcccacggcc gccagctcct cctcggcctg tctttcgtcc tcgctgtcct   23640
ggctgacgtc ctgcaggacc acatgcttgg tcttgcgggg tttcttcttg gcggcagcg    23700
gcggcggaga tgttggagat ggcgaggggg agcgcgagtt ctcgctcacc actactatct   23760
cttcctcttc ttggtccgag gccacgcggc ggtaggtatg tctcttcggg ggcagaggcg   23820
gaggcgacgg gctctcgccg ccgcgacttg gcggatggct ggcagagccc cttccgcgtt   23880
cgggggtgcg ctcccggcgg cgctctgact gacttcctcc gcggccggcc attgtgttct   23940
cctagggagg aacaacaagc atggagactc agccatcgcc aacctcgcca tctgccccca   24000
ccgccgacga gaagcagcag cagcagaatg aaagcttaac cgccccgccg cccagccccg   24060
ccacctccga cgcggccgtc ccagacatgc aagagatgga ggaatccatc gagattgacc   24120
tgggctatgt gacgcccgcg gagcacgagg aggagctggc agtgcgcttt tcacaagaag   24180
agatacacca agaacagcca gagcaggaag cagagaatga gcagagtcag gctgggctcg   24240
agcatgacgg cgactacctc cacctgagcg ggggggagga cgcgctcatc aagcatctgg   24300
cccggcaggc caccatcgtc aaggatgcgc tgctcgaccg caccgaggtg cccctcagcg   24360
tggaggagct cagccgcgcc tacgagttga acctcttctc gccgcgcgtg ccccccaagc   24420
gccagcccaa tggcacctgc gagcccaacc cgcgcctcaa cttctacccg gtcttcgcgg   24480
tgcccgaggc cctggccacc taccacatct ttttcaagaa ccaaaagatc cccgtctcct   24540
gccgcgccaa ccgcacccgc cgcgacgccc ttttcaacct gggtcccggc gccgcctac    24600
ctgatatcgc ctccttggaa gaggttccca agatcttcga gggtctgggc agcgacgaga   24660
ctcgggccgc gaacgctctg caaggagaag gaggagagca tgagcaccac agcgccctgg   24720
tcgagttgga aggcgacaac gcgcggctgg cggtgctcaa acgcacggtc gagctgaccc   24780
atttcgccta cccggctctg aacctgcccc caaagtcat gagcgcggtc atggaccagg    24840
tgctcatcaa gcgcgcgtcg cccatctccg aggacgaggg catgcaagac tccgaggagg   24900
gcaagcccgt ggtcagcgac gagcagctgg cccggtggct gggtcctaat gctagtcccc   24960
```

```
agagtttgga agagcggcgc aaactcatga tggccgtggt cctggtgacc gtggagctgg   25020
agtgcctgcg ccgcttcttc gccgacgcgg agaccctgcg caaggtcgag gagaacctgc   25080
actacctctt caggcacggg ttcgtgcgcc aggcctgcaa gatctccaac gtggagctga   25140
ccaacctggt ctcctacatg ggcatcttgc acgagaaccg cctggggcag aacgtgctgc   25200
acaccaccct gcgcggggag gcccggcgcg actacatccg cgactgcgtc tacctctacc   25260
tctgccacac ctggcagacg ggcatgggcg tgtggcagca gtgtctggag gagcagaacc   25320
tgaaagagct ctgcaagctc ctgcagaaga acctcaaggg tctgtggacc gggttcgacg   25380
agcgcaccac cgcctcggac ctggccgacc tcatttttcc cgagcgcctc aggctgacgc   25440
tgcgcaacgg cctgcccgac tttatgagcc aaagcatgtt gcaaaacttt cgctctttca   25500
tcctcgaacg ctccggaatc ctgcccgcca cctgctccgc gctgccctcg gacttcgtgc   25560
cgctgacctt ccgcgagtgc ccccgccgc tgtggagcca ctgctacctg ctgcgcctgg   25620
ccaactacct ggcctaccac tcggacgtga tcgaggacgt cagcggcgag ggcctgctcg   25680
agtgccactg ccgctgcaac ctctgcacgc cgcaccgctc cctggcctgc aaccccagc   25740
tgctgagcga gacccagatc atcggcacct tcgagttgca agggcccagc gaaggcgagg   25800
gttcagccgc caagggggt ctgaaactca ccccgggct gtggacctcg gcctacttgc    25860
gcaagttcgt gcccgaggac taccatccct tcgagatcag gttctacgag gaccaatccc   25920
atccgcccaa ggccgagctg tcggcctgcg tcatcaccca gggggcgatc ctggcccaat   25980
tgcaagccat ccagaaatcc cgccaagaat tcttgctgaa aaagggccgc ggggtctacc   26040
tcgaccccca gaccggtgag gagctcaacc ccggcttccc ccaggatgcc ccgaggaaac   26100
aagaagctga agtggagct gccgcccgtg gaggatttgg aggaagactg ggagaacagc    26160
agtcaggcag aggaggagga gatggaggaa gactgggaca gcactcaggc agaggaggac   26220
agcctgcaag acagtctgga ggaagacgag gaggaggcag aggaggaggt ggaagaagca   26280
gccgccgcca gaccgtcgtc ctcggcgggg gagaaagcaa gcagcacgga taccatctcc   26340
gctccgggtc ggggtcccgc tcgaccacac agtagatggg acgagaccgg acgattcccg   26400
aaccccacca cccagaccgg taagaaggag cggcagggat acaagtcctg gcgggggcac   26460
aaaaacgcca tcgtctcctg cttgcaggcc tgcgggggca acatctcctt cacccggcgc   26520
tacctgctct tccaccgcgg ggtgaacttt ccccgcaaca tcttgcatta ctaccgtcac   26580
ctccacagcc cctactactt ccaagaagag gcagcagcag cagaaaaaga ccagcagaaa   26640
accagcagct agaaaatcca cagcggcggc agcaggtgga ctgaggatcg cggcgaacga   26700
gccggcgcaa acccgggagc tgaggaaccg gatctttccc accctctatg ccatcttcca   26760
gcagagtcgg gggcaggagc aggaactgaa agtcaagaac cgttctctgc gctcgctcac   26820
ccgcagttgt ctgtatcaca gagcgaaga ccaacttcag cgcactctcg aggacgccga    26880
ggctctcttc aacaagtact gcgcgctcac tcttaaagag tagcccgcgc cgcccagtc    26940
gcagaaaaag gcgggaatta cgtcacctgt gcccttcgcc ctagccgcct ccacccatca   27000
tcatgagcaa agagattccc acgccttaca tgtggagcta ccagcccag atgggcctgg    27060
ccgccggtgc cgcccaggac tactccaccc gcatgaattg gctcagcgcc gggccgcgca   27120
tgatctcacg ggtgaatgac atccgcgccc accgaaacca gatactccta gaacagtcag   27180
cgctcaccgc cacgccccgc aatcacctca atccgcgtaa ttggcccgcc gcctggtgt    27240
accaggaaat tccccagccc acgaccgtac tacttccgcg agacgcccag gccgaagtcc   27300
```

```
agctgactaa ctcaggtgtc cagctggcgg gcggcgccac cctgtgtcgt caccgccccg    27360
ctcagggtat aaagcggctg gtgatccggg gcagaggcac acagctcaac gacgaggtgg    27420
tgagctcttc gctgggtctg cgacctgacg gagtcttcca actcgccgga tcggggagat    27480
cttccttcac gcctcgtcag gccgtcctga ctttggagag ttcgtcctcg cagcccgct     27540
cgggtggcat cggcactctc cagttcgtgg aggagttcac tccctcggtc tacttcaacc    27600
ccttctccgg ctcccccggc cactaccgg acgagttcat cccgaacttc gacgccatca     27660
gcgagtcggt ggacggctac gattgaatgt cccatggtgg cgcagctgac ctagctcggc    27720
ttcgacacct ggaccactgc cgccgcttcc gctgcttcgc tcgggatctc gccgagtttg    27780
cctactttga gctgcccgag gagcaccctc agggcccggc ccacggagtg cggatcgtcg    27840
tcgaagggg cctcgactcc cacctgcttc ggatcttcag ccagcgtccg atcctggtcg     27900
agcgcgagca aggacagacc cttctgactc tgtactgcat ctgcaaccac cccggcctgc    27960
atgaaagtct tgttgtctg ctgtgtactg agtataataa aagctgagat cagcgactac     28020
tccggacttc cgtgtgttcc tgaatccatc aaccagtctt tgttcttcac cgggaacgag    28080
accgagctcc agctccagtg taagccccac aagaagtacc tcacctggct gttccagggc    28140
tccccgatcg ccgttgtcaa ccactgcgac aacgacggag tcctgctgag cggccctgcc    28200
aaccttactt tttccacccg cagaagcaag ctccagctct tccaacccttc cctcccggg    28260
acctatcagt gcgtctcggg accctgccat cacaccttcc acctgatccc gaataccaca    28320
gcgtcgctcc ccgctactaa caaccaaact aacctccacc aacgccaccg tcgctaggcc    28380
acaatacatg cccatattag actatgaggc cgagccacag cgacccatgc tccccgctat    28440
tagttacttc aatctaaccg gcggagatga ctgacccact ggccaacaac aacgtcaacg    28500
accttctcct ggacatggac ggccgcgcct cggagcagcg actcgcccaa cttcgcattc    28560
gccagcagca ggagagagcc gtcaaggagc tgcaggatgc ggtggccatc caccagtgca    28620
agagaggcat cttctgcctg gtgaaacagg ccaagatctc ctacgaggtc actccaaacg    28680
accatcgcct ctcctacgag ctcctgcagc agcgccagaa gttcacctgc ctggtcggag    28740
tcaaccccat cgtcatcacc cagcagtctg gcgataccaa ggggtgcatc cactgctcct    28800
gcgactcccc cgactgcgtc cacactctga tcaagaccct ctgcggcctc cgcgacctcc    28860
tccccatgaa ctaatcaccc ccttatccag tgaaataaag atcatattga tgatgatttt    28920
acagaaataa aaaataatca tttgatttga aataaagata caatcatatt gatgatttga    28980
gtttaacaaa aaaataaaga atcacttact tgaaatctga taccaggtct ctgtccatgt    29040
tttctgccaa caccacttca ctcccctctt cccagctctg gtactgcagg cccggcggg    29100
ctgcaaactt cctccacacg ctgaaggga tgtcaaattc ctcctgtccc tcaatcttca     29160
ttttatcttc tatcagatgt ccaaaaagcg cgtccgggtg gatgatgact cgacccgt      29220
ctaccctac gatgcagaca acgcaccgac cgtgcccttc atcaaccccc ccttcgtctc     29280
ttcagatgga ttccaagaga agcccctggg ggtgttgtcc ctgcgactgg ccgacccgt     29340
caccaccaag aacggggaaa tcaccctcaa gctgggagag ggggtggacc tcgattcctc    29400
gggaaaactc atctccaaca cggccaccaa ggccgccgcc cctctcagtt tttccaacaa    29460
caccattttcc cttaacatgg atcaccccttt ttacactaaa gatggaaaat tatccttaca   29520
agtttctcca ccattaaata tactgagaac aagcattcta aacacactag ctttaggttt    29580
tggatcaggt ttaggactcc gtggctctgc cttggcagta cagttagtct ctccacttac    29640
atttgatact gatggaaaca taaagcttac cttagacaga ggtttgcatg ttacaacagg    29700
```

```
agatgcaatt gaaagcaaca taagctgggc taaaggttta aaatttgaag atggagccat   29760
agcaaccaac attggaaatg ggttagagtt tggaagcagt agtacagaaa caggtgttga   29820
tgatgcttac ccaatccaag ttaaacttgg atctggcctt agctttgaca gtacaggagc   29880
cataatggct ggtaacaaag aagacgataa actcactttg tggacaacac ctgatccatc   29940
accaaactgt caaatactcg cagaaaatga tgcaaaacta acactttgct tgactaaatg   30000
tggtagtcaa atactggcca ctgtgtcagt cttagttgta ggaagtggaa acctaaaccc   30060
cattactggc accgtaagca gtgctcaggt gtttctacgt tttgatgcaa acggtgttct   30120
tttaacagaa cattctacac taaaaaaata ctgggggtat aggcagggag atagcataga   30180
tggcactcca tataccaatg ctgtaggatt catgcccaat ttaaaagctt atccaaagtc   30240
acaaagttct actactaaaa ataatatagt agggcaagta tacatgaatg agatgtttc    30300 aaaacctatg cttctcacta taaccctcaa tggtactgat gacagcaaca gtacatattc   30360
aatgtcattt tcatacacct ggactaatgg aagctatgtt ggagcaacat tgggggctaa   30420
ctcttatacc ttctcataca tcgcccaaga tgaacactg tatcccaccc tgcatgccaa    30480
cccttcccac cccactctgt ggaacaaact ctgaaacaca aaataaaata aagttcaagt   30540
gttttattga ttcaacagtt ttacaggatt cgagcagtta ttttcctcc accctcccag    30600 gacatggaat acaccaccct ctcccccgc acagccttga acatctgaat gccattggtg    30660
atggacatgc ttttggtctc cacgttccac acagtttcag agcgagccag tctcgggtcg   30720
gtcagggaga tgaaaccctc cgggcactcc cgcatctgca cctcacagct caacagctga   30780
ggattgtcct cggtggtcgg gatcacggtt atctggaaga agcagaagag cggcggtggg   30840
aatcatagtc cgcgaacggg atcggccggt ggtgtcgcat caggcccgc agcagtcgct    30900 gccgccgccg ctccgtcaag ctgctgctca gggggtccgg gtccagggac tccctcagca   30960
tgatgcccac ggccctcagc atcagtcgtc tggtgcggcg ggcgcagcag cgcatgcgga   31020
tctcgctcag gtcgctgcag tacgtgcaac acagaaccac caggttgttc aacagtccat   31080
agttcaacac gctccagccg aaactcatcg cgggaaggat gctacccacg tggccgtcgt   31140
accagatcct caggtaaatc aagtggtgcc ccctccagaa cacgctgccc acgtacatga   31200
tctccttggg catgtggcgg ttcaccacct cccggtacca catcaccctc tggttgaaca   31260
tgcagccccg gatgatcctg cggaaccaca gggccagcac cgccccgccc gccatgcagc   31320
gaagagaccc cgggtcccgg caatggcaat ggaggaccca ccgctcgtac ccgtggatca   31380
tctgggagct gaacaagtct atgttggcac agcacaggca tatgctcatg catctcttca   31440
gcactctcaa ctcctcgggg gtcaaaacca tatcccaggg cacggggaac tcttgcagga   31500
cagcgaaccc cgcagaacag ggcaatcctc gcacagaact tacattgtgc atggacaggg   31560
tatcgcaatc aggcagcacc gggtgatcct ccaccagaga agcgcgggtc tcggtctcct   31620
cacagcgtgg taaggggcc ggccgatacg ggtgatggcg ggacgcggct gatcgtgttc    31680
gcgaccgtgt catgatgcag ttgctttcgg acattttcgt acttgctgta gcagaacctg   31740
gtccgggcgc tgcacaccga tcgccggcgg cggtctcggc gcttggaacg ctcggtgttg   31800
aaattgtaaa acagccactc tctccagaccg tgcagcagat ctagggcctc aggagtgatg   31860
aagatcccat catgcctgat ggctctgatc acatcgacca ccgtggaatg ggccagaccc   31920
agccagatga tgcaattttg ttgggtttcg gtgacggcgg gggagggaag aacaggaaga   31980
accatgatta acttttaatc caaacggtct cggagtactt caaaatgaag atcgcggaga   32040
```

```
tggcacctct cgcccccgct gtgttggtgg aaaataacag ccaggtcaaa ggtgatacgg    32100
ttctcgagat gttccacggt ggcttccagc aaagcctcca cgcgcacatc cagaaacaag    32160
acaatagcga aagcgggagg gttctctaat tcctcaatca tcatgttaca ctcctgcacc    32220
atccccagat aatttccatt tttccagcct tgaatgattc gaactagttc ctgaggtaaa    32280
tccaagccag ccatgataaa gagctcgcgc agagcgccct ccaccggcat tcttaagcac    32340
accctcataa ttccaagata ttctgctcct ggttcacctg cagcagattg acaagcggaa    32400
tatcaaaatc tctgccgcga tccctgagct cctccctcag caataactgt aagtactctt    32460
tcatatcctc tccgaaattt ttagccatag gaccaccagg aataagatta gggcaagcca    32520
cagtacagat aaaccgaagt cctccccagt gagcattgcc aaatgcaaga ctgctataag    32580
catgctggct agaccggtg atatcttcca gataactgga cagaaaatcg cccaggcaat    32640
ttttaagaaa atcaacaaaa gaaaaatcct ccaggtggac gtttagagcc tcgggaacaa    32700
cgatgaagta aatgcaagcg gtgcgttcca gcatggttag ttagctgatc tgtagaaaaa    32760
acaaaaatga acattaaacc atgctagcct ggcgaacagg tgggtaaatc gttctctcca    32820
gcaccaggca ggccacgggg tctccggcgc gaccctcgta aaaattgtcg ctatgattga    32880
aaaccatcac agagagacgt tcccggtggc cggcgtgaat gattcgacaa gatgaataca    32940
cccccggaac attggcgtcc gcgagtgaaa aaagcgccc gaggaagcaa taggcacta    33000 caatgctcag tctcaagtcc agcaaagcga tgccatgcgg atgaagcaca aaattctcag    33060
gtgcgtacaa aatgtaatta ctcccctcct gcacaggcag caaagccccc gatccctcca    33120
ggtacacata caaagcctca gcgtccatag cttaccgagc agcagcacac aacaggcgca    33180
agagtcagag aaaggctgag ctctaacctg tccacccgct ctctgctcaa tatatagccc    33240
agatctacac tgacgtaaag gccaaagtct aaaaatacc gccaaataat cacacacgcc    33300
cagcacacgc ccagaaaccg gtgacacact caaaaaaata cgcgcacttc ctcaaacgcc    33360
caaaactgcc gtcatttccg ggttcccacg ctacgtcatc aaaacacgac tttcaaattc    33420
cgtcgaccgt taaaaacgtc acccgccccg cccctaacgg tcgcccgtct ctcagccaat    33480
cagcgccccg catccccaaa ttcaaacacc tcatttgcat attaacgcgc acaaaaagtt    33540
tgaggtatat tattgatgat gg                                             33562
```

<210> SEQ ID NO 45
<211> LENGTH: 34803
<212> TYPE: DNA
<213> ORGANISM: Artificial Sequence
<220> FEATURE:
<223> OTHER INFORMATION: Synthetic Construct

<400> SEQUENCE: 45

```
ccatcttcaa taatataacct caaacttttt gtgcgcgtta atatgcaaat gaggcgtttg      60
aatttgggga ggaagggcgg tgattggtcg agggatgagc gaccgttagg ggcggggcga     120
gtgacgtttt gatgacgtgg ttgcgaggag gagccagttt gcaagttctc gtgggaaaag     180
tgacgtcaaa cgaggtgtgg tttgaacacg gaaatactca attttcccgc gctctctgac     240
aggaaatgag gtgtttctgg gcggatgcaa gtgaaaacgg gccattttcg cgcgaaaact     300
gaatgaggaa gtgaaaatct gagtaatttc gcgtttatgg cagggaggag tatttgccga     360
gggccgagta gactttgacc gattacgtgg gggtttcgat taccgtgttt tcacctaaa      420 tttccgcgta cggtgtcaaa gtccggtgtt tttactactg taatagtaat caattacggg     480
gtcattagtt catagcccat atatggagtt ccgcgttaca taacttacgg taaatggccc     540
```

```
gcctggctga ccgcccaacg accccgccc attgacgtca ataatgacgt atgttcccat      600
agtaacgcca atagggactt tccattgacg tcaatgggtg gagtatttac ggtaaactgc      660
ccacttggca gtacatcaag tgtatcatat gccaagtacg cccctattg acgtcaatga      720 cggtaaatgg cccgcctggc attatgccca gtacatgacc ttatgggact ttcctacttg      780
gcagtacatc tacgtattag tcatcgctat taccatggtg atgcggtttt ggcagtacat      840
caatgggcgt ggatagcggt ttgactcacg gggatttcca gtctccacc ccattgacgt      900 caatgggagt ttgttttggc accaaaatca acgggacttt ccaaaatgtc gtaacaactc      960
cgccccattg acgcaaatgg gcggtaggcg tgtacggtgg gaggtctata taagcagagc     1020
tgtccctatc agtgatagag atctccctat cagtgataga gagtttagtg aaccgtcaga     1080
tccgctaggg taccaacatg gctagcatcg tcggagggtg ggagtgcgaa agcactcac      1140 agccatggca ggtcctggtc gcctcgcgcg gacgcgccgt gtgtggaggt gtgctggtcc     1200
acccgcagtg ggtgttgact gcggcccatt gcatcagaaa taagtccgtg atcctcttgg     1260
ggagacattc cctgtttcac cccgaagata ctggacaggt gttccaagtg agccactcct     1320
tcccgcatcc actgtacgac atgagcctgc tgaagaaccg ctttctgcgg ccaggggacg     1380
actcatcaca cgatttgatg ctgcttcggc tctcggaacc ggccgagctc accgacgcag     1440
tgaaggtcat ggacctccct acgcaagagc ctgctctcgg taccacttgt tacgcatcgg     1500 gatgggctc catcgagccg gaagaattcc tgaccccgaa aaagctgcag tgcgtggatc     1560
tgcacgtgat ttcgaatgac gtgtgcgcgc aagtgcatcc acaaaaggtc actaagttca     1620
tgctgtgcgc cggaaggtgg accggcggaa aatcgacctg ttccggcgac agcggaggcc     1680
cactcgtgtg caacggtgtg ctgcagggca tcactagctg gggatcagaa ccgtgcgcgc     1740
ttccggagcg gccctcgctc tacacgaagg tggtgcacta ccgcaaatgg attaaagata     1800
ccatcgtcgc aaaccctgga tccgaaggta gggttcatt attgacctgt ggagatgtcg     1860
aagaaaaccc aggacccgct agcaaagcag tgctgctggc gctcctgatg gctggactcg     1920
cgctgcagcc tggaaccgcc ctgctctgtt actcgtgcaa ggcccaagtc tcgaatgagg     1980
actgtttgca agtggaaaac tgcacccagc tcggagaaca atgctggact gcacggatcc     2040
gcgctgtcgg cctgctgacc gtgatctcca aagggtgctc attgaactgc gtggacgata     2100
gccaggacta ctacgtggga aagaagaata tcacttgttg cgacacggat ctttgcaacg     2160
cgtccggagc gcacgccctg cagccagcag ccgccattct ggccctgctt ccggccctgg     2220
ggttgctgct ctggggtccg ggccagctcg gatcccagac cctgaacttt gatctgctga     2280
aactggcagg cgatgtggaa agcaacccag gcccaatggc tagcgctcgc agaccgcggt     2340
ggctgtgtgc aggggcgctc gtcctggcgg gtggcttctt tttgctcggc tttcttttcg     2400
gatggttcat caaatcgtca aacgaagcta ccaatatcac cccgaagcac aacatgaagg     2460
cctttctgga tgagctgaag gctgagaaca ttaagaagtt cctctacaac ttcacccaga     2520
tcccacattt ggcgggcact gagcagaact ttcagttggc taagcagatc cagagccagt     2580
ggaaggaatt cggcctggac tccgtcgagc tggcgcatta cgatgtgctg ctgagctacc     2640
ctaataagac tcatccgaac tatatctcga ttatcaatga ggacgaaac gaaatctta      2700 acacgtccct cttcgagccg ccaccgcctg gatacgagaa cgtgtcagat atcgtgcctc     2760
cgttctcggc cttctcgccc cagggaatgc ccgaagggga cctggtgtac gtgaactacg     2820
caaggaccga ggacttcttc aagttggagc gggatatgaa gatcaattgc agcggaaaga     2880
```

```
tcgtcatcgc ccgctacggc aaagtgttcc gcggcaacaa ggtgaagaat gcacagttgg    2940
caggcgccaa gggcgtcatc ctctactcgg atcctgccga ctacttcgct cctggcgtga    3000
aatcctaccc tgatggttgg aatctgccag gaggaggggt gcagagggga aatatcctga    3060
acctgaacgg tgccggtgac ccacttactc cgggttaccc ggccaacgaa tacgcgtaca    3120
ggcggggtat cgcggaagcc gtcggactgc cgtccatccc ggtccatccg attggttact    3180
acgacgccca gaagctcctc gaaaagatgg gaggcagcgc ccctccggac tcgtcatgga    3240
gaggctcgct gaaggtgcca tacaacgtgg acccggatt cactggaaat tcagcactc    3300 aaaaagtgaa gatgcacatt cactccacta acgaagtcac caggatctac aacgtcatcg    3360
gaaccctccg gggagcggtg gaaccggacc gctacgtgat cctcggtgga caccgggata    3420
gctgggtgtt cggaggaatc gatcctcaat cgggcgcagc cgtcgtccat gaaatcgtca    3480
ggtcctttgg tactcttaag aaggagggct ggcgccctag acgcactatt ctgttcgcct    3540
cgtgggatgc cgaagaattt ggtctgctcg gcagcaccga atgggctgag gaaaactccc    3600
gcctgctcca agaacgcgga gtggcgtaca tcaatgccga ctcatccatc gaaggaaact    3660
acacgctgcg ggtggactgc actccactga tgtactcgct cgtgcacaac ctgaccaaag    3720
aactcaaatc cccagacgaa ggattcgagg gaaaatcgct gtacgagtcg tggaccaaga    3780
agagcccatc cccggagttc agcgggatgc cgcggatctc aaagctcgga tcaggaaatg    3840
atttcgaagt gttctttcag aggctgggaa ttgcgtcggg aagggctcgg tacacgaaaa    3900
actgggaaac taacaagttc tcgggatacc cgctgtacca ctcggtgtat gaaacttacg    3960
aactggtgga gaaattctac gatcctatgt ttaagtacca cctgactgtg gcccaagtga    4020
gaggcggaat ggtgttcgag ttggccaatt caattgtgct gccattcgat tgccgcgact    4080
acgccgtggt gctgagaaag tacgcagaca aatctactc aatcagcatg aagcacccac    4140
aagagatgaa aacctactca gtctccttcg actccctctt ctccgcggtg aagaacttca    4200
ccgagatcgc gagcaaattc tcggagcgcc ttcaagattt tgacaaatcc aatccgatcg    4260
tcctccgcat gatgaatgac cagctcatgt ttctcgaacg ggccttcatc gatccactgg    4320
gacttccgga ccgccgtttt taccgccacg tgatctacgc gccctcgtcg cataacaagt    4380
atgctggaga gagcttcccg ggtatctacg acgcattgtt cgacattgag tccaaggtgg    4440
atccgtccaa agcctggggt gaagtgaagc gccaaatcta cgtggcggcc tttaccgtcc    4500
aggcggcagc agaaaccttg agcgaggtgg cttgactcga gcctaagctt ctagataaga    4560
tatccgatcc accggatcta gataactgat cataatcagc cataccacat tgtagaggt    4620 tttacttgct ttaaaaaacc tcccacacct ccccctgaac ctgaaacata aaatgaatgc    4680
aattgttgtt gttaacttgt ttattgcagc ttataatggt tacaaataaa gcaatagcat    4740
cacaaatttc acaaataaag catttttttc actgcattct agttgtggtt tgtccaaact    4800
catcaatgta tcttatatgc tggccaccgt acatgtggct tcccatgctc gcaagccctg    4860
gcccgagttc gagcacaatg tcatgaccag gtgcaatatg catctggggt cccgccgagg    4920
catgttcatg ccctaccagt gcaacctgaa ttatgtgaag gtgctgctgg agcccgatgc    4980
catgtccaga gtgagcctga cggggtgtt tgacatgaat gtggaggtgt ggaagattct    5040
gagatatgat gaatccaaga ccaggtgccg agcctgcgag tgcggaggga agcatgccag    5100
gttccagccc gtgtgtgtgg atgtgacgga ggacctgcga cccgatcatt tggtgttgcc    5160
ctgcaccggg acgagttcg gttccagcgg ggaagaatct gactagagtg agtagtgttc    5220
tggggcgggg gaggacctgc atgagggcca gaataactga aatctgtgct tttctgtgtg    5280
```

```
ttgcagcagc atgagcggaa gcggctcctt tgagggaggg gtattcagcc cttatctgac     5340
ggggcgtctc ccctcctggg cgggagtgcg tcagaatgtg atgggatcca cggtggacgg     5400
ccggcccgtg cagcccgcga actcttcaac cctgacctat gcaaccctga gctcttcgtc     5460
gttggacgca gctgccgccg cagctgctgc atctgccgcc agcgccgtgc gcggaatggc     5520
catgggcgcc ggctactacg gcactctggt ggccaactcg agttccacca ataatcccgc     5580
cagcctgaac gaggagaagc tgttgctgct gatggcccag ctcgaggcct tgacccagcg     5640
cctgggcgag ctgacccagc aggtggctca gctgcaggag cagacgcggg ccgcggttgc     5700
cacggtgaaa tccaaataaa aaatgaatca ataaataaac ggagacggtt gttgatttta     5760
acacagagtc tgaatcttta tttgattttt cgcgcgcggt aggccctgga ccaccggtct     5820
cgatcattga gcacccggtg gatcttttcc aggacccggt agaggtgggc ttggatgttg     5880
aggtacatgg gcatgagccc gtcccggggg tggaggtagc tccattgcag ggcctcgtgc     5940
tcggggtggg tgttgtaaat cacccagtca tagcagggc gcaggcatg gtgttgcaca      6000 atatctttga ggaggagact gatggccacg gcagcccctt tggtgtaggt gtttacaaat     6060
ctgttgagct gggagggatg catgcggggg gagatgaggt gcatcttggc ctggatcttg     6120
agattggcga tgttaccgcc cagatcccgc ctggggttca tgttgtgcag gaccaccagc     6180
acggtgtatc cggtgcactt ggggaattta tcatgcaact tggaagggaa ggcgtgaaag     6240
aatttggcga cgcctttgtg cccgcccagg ttttccatgc actcatccat gatgatggcg     6300
atgggcccgt gggcggcggc ctgggcaaag acgtttcggg ggtcgacac atcatagttg      6360 tggtcctggg tgaggtcatc ataggccatt ttaatgaatt tggggcggag ggtgccggac     6420
tgggggacaa aggtaccctc gatcccgggg gcgtagttcc cctcacagat ctgcatctcc     6480
caggctttga gctcggaggg ggggatcatg tccacctgcg gggcgataaa gaacacggtt     6540
tccggggcgg gggagatgag ctgggccgaa agcaagttcc ggagcagctg ggacttgccg     6600
cagccggtgg ggccgtagat gaccccgatg accggctgca ggtggtagtt gagggagaga     6660
cagctgccgt cctcccggag gagggggggcc acctcgttca tcatctcgcg cacgtgcatg     6720
ttctcgcgca ccagttccgc caggaggcgc tctcccccca gggataggag ctcctggagc     6780
gaggcgaagt ttttcagcgg cttgagtccg tcggccatgg gcattttgga gagggtttgt     6840
tgcaagagtt ccaggcggtc ccagagctcg gtgatgtgct ctacggcatc tcgatccagc     6900
agacctcctc gtttcgcggg ttgggacggc tgcgggagta gggcaccaga cgatgggcgt     6960
ccagcgcagc cagggtccgg tccttccagg gtcgcagcgt ccgcgtcagg gtggtctccg     7020
tcacggtgaa ggggtgcgcg ccgggctggg cgcttgcgag ggtgcgcttc aggctcatcc     7080
ggctggtcga aaaccgctcc cgatcggcgc cctgcgcgtc ggccaggtag caattgacca     7140
tgagttcgta gttgagcgcc tcggccgcgt ggcctttggc gcggagctta cctttggaag     7200
tctgcccgca ggcgggacag aggagggact tgagggcgta gagcttgggg gcgaggaaga     7260
cggactcggg ggcgtaggcg tccgcgccgc agtgggcgca gacggtctcg cactccacga     7320
gccaggtgag gtcgggctgg tcgggtcaa aaaccagttt cccgccgttc ttttgatgc      7380 gtttcttacc tttggtctcc atgagctcgt gtccccgctg ggtgacaaag aggctgtccg     7440
tgtccccgta gaccgacttt atgggccggt cctcgagcgg tgtgccgcgg tcctcctcgt     7500
agaggaaccc cgcccactcc gagacgaaag cccgggtcca ggccagcacg aaggaggcca     7560
cgtgggacgg gtagcggtcg ttgtccacca gcgggtccac cttttccagg gtatgcaaac     7620
```

```
acatgtcccc ctcgtccaca tccaggaagg tgattggctt gtaagtgtag gccacgtgac   7680
cgggggtccc ggccgggggg gtataaaagg gtgcgggtcc ctgctcgtcc tcactgtctt   7740
ccggatcgct gtccaggagc gccagctgtt ggggtaggta ttccctctcg aaggcgggca   7800
tgacctcggc actcaggttg tcagtttcta gaaacgagga ggatttgata ttgacggtgc   7860
cggcggagat gcctttcaag agcccctcgt ccatctggtc agaaaagacg atcttttttgt  7920
tgtcgagctt ggtggcgaag gagccgtaga gggcgttgga gaggagcttg gcgatggagc   7980
gcatggtctg gtttttttcc ttgtcggcgc gctccttggc ggcgatgttg agctgcacgt   8040
actcgcgcgc cacgcacttc cattcgggga agacggtggt cagctcgtcg ggcacgattc   8100
tgacctgcca gccccgatta tgcagggtga tgaggtccac actggtggcc acctcgccgc   8160
gcagggctc attagtccag cagaggcgtc cgcccttgcg cgagcagaag gggggcaggg    8220
ggtccagcat gacctcgtcg ggggggtcgg catcgatggt gaagatgccg ggcaggaggt   8280
cggggtcaaa gtagctgatg gaagtggcca gatcgtccag ggcagcttgc cattcgcgca   8340
cggccagcgc gcgctcgtag ggactgaggg gcgtgcccca gggcatggga tgggtaagcg   8400
cggaggcgta catgccgcag atgtcgtaga cgtagagggg ctcctcgagg atgccgatgt   8460
aggtggggta gcagcgcccc ccgcggatgc tggcgcgcac gtagtcatac agctcgtgcg   8520
agggggcgag gagcccgggg cccaggttgg tgcgactggg cttttcggcg cggtagacga   8580
tctggcggaa aatggcatgc gagttggagg agatggtggg cctttggaag atgttgaagt   8640
gggcgtgggg cagtccgacc gagtcgcgga tgaagtgggc gtaggagtct gcagcttgg    8700
cgacgagctc ggcggtgact aggacgtcca gagcgcagta gtcgagggtc tcctggatga   8760
tgtcatactt gagctgtccc ttttgttttcc acagctcgcg gttgagaagg aactcttcgc  8820
ggtccttcca gtactcttcg aggggggaacc cgtcctgatc tgcacggtaa gagcctagca   8880
tgtagaactg gttgacggcc ttgtaggcgc agcagccctt ctccacgggg agggcgtagg   8940
cctgggcggc cttgcgcagg gaggtgtgcg tgagggcgaa agtgtccctg accatgacct   9000
tgaggaactg gtgcttgaag tcgatatcgt cgcagccccc ctgctcccag agctggaagt   9060
ccgtgcgctt cttgtaggcg gggttgggca aagcgaaagt aacatcgttg aagaggatct   9120
tgcccgcgcg gggcataaag ttgcgagtga tgcggaaagg ttggggcacc tcggcccggt   9180
tgttgatgac ctgggcggcg agcacgatct cgtcgaagcc gttgatgttg tggcccacga   9240
tgtagagttc cacgaatcgc ggacggccct tgacgtgggg cagtttcttg agctcctcgt   9300
aggtgagctc gtcggggtcg ctgagcccgt gctgctcgag cgccagtcg gcgagatggg    9360
ggttggcgcg gaggaaggaa gtccagagat ccacggccag ggcggtttgc agacggtccc   9420
ggtactgacg gaactgctgc ccgacggcca ttttttcggg ggtgacgcag tagaaggtgc    9480
gggggtcccc gtgccagcga tcccatttga gctggagggc gagatcgagg gcgagctcga   9540
cgagccggtc gtccccggag agtttcatga ccagcatgaa ggggacgagc tgcttgccga   9600
aggacccccat ccaggtgtag gttttccacat cgtaggtgag gaagagcctt tcggtgcgag  9660
gatgcgagcc gatggggaag aactggatct cctgccacca attggaggaa tggctgttga   9720
tgtgatggaa gtagaaatgc cgacggcgcg ccgaacactc gtgcttgtgt ttatacaagc   9780
ggccacagtg ctcgcaacgc tgcacgggat gcacgtgctg cacgagctgt acctgagttc   9840
ctttgacgag gaatttcagt gggaagtgga gtcgtggcgc ctgcatctcg tgctgtacta   9900
cgtcgtggtg gtcggcctgg ccctcttctg cctcgatggt ggtcatgctg acgagccgc    9960
gcgggaggca ggtccagacc tcggcgcgag cgggtcggag agcgaggacg agggcgcgca  10020
```

```
ggccggagct gtccagggtc ctgagacgct gcggagtcag gtcagtgggc agcggcggcg    10080
cgcggttgac ttgcaggagt ttttccaggg cgcgcgggag gtccagatgg tacttgatct    10140
ccaccgcgcc attggtggcg acgtcgatgg cttgcagggt cccgtgcccc tggggtgtga    10200
ccaccgtccc ccgtttcttc ttgggcggct ggggcgacgg gggcggtgcc tcttccatgg    10260
ttagaagcgg cggcgaggac gcgcgccggg cggcaggggc ggctcggggc ccggaggcag    10320
gggcggcagg ggcacgtcgg cgccgcgcgc gggtaggttc tggtactgcg cccggagaag    10380
actggcgtga gcgacgacgc gacggttgac gtcctggatc tgacgcctct gggtgaaggc    10440
cacgggaccc gtgagtttga acctgaaaga gagttcgaca gaatcaatct cggtatcgtt    10500
gacggcggcc tgccgcagga tctcttgcac gtcgcccgag ttgtcctggt aggcgatctc    10560
ggtcatgaac tgctcgatct cctcctcttg aaggtctccg cggccggcgc gctccacggt    10620
ggccgcgagg tcgttggaga tgcggcccat gagctgcgag aaggcgttca tgcccgcctc    10680
gttccagacg cggctgtaga ccacgacgcc ctcgggatcg cgggcgcgca tgaccacctg    10740
ggcgaggttg agctccacgt ggcgcgtgaa gaccgcgtag ttgcagaggc gctggtagag    10800
gtagttgagc gtggtggcga tgtgctcggt gacgaagaaa tacatgatcc agcggcggag    10860
cggcatctcg ctgacgtcgc ccagcgcctc caaacgttcc atggcctcgt aaaagtccac    10920
ggcgaagttg aaaaactggg agttgcgcgc cgagacggtc aactcctcct ccagaagacg    10980
gatgagctcg gcgatggtgg cgcgcacctc gcgctcgaag gccccgggga gttcctccac    11040
ttcctcttct tcctcctcca ctaacatctc ttctacttcc tcctcaggcg gcagtggtgg    11100
cggggagggg ggcctgcgtc gccggcggcg cacgggcaga cggtcgatga agcgctcgat    11160
ggtctcgccg cgccggcgtc gcatggtctc ggtgacggcg cgcccgtcct cgcggggccg    11220
cagcgtgaag acgccgccgc gcatctccag gtggccgggg gggtccccgt tgggcaggga    11280
gagggcgctg acgatgcatc ttatcaattg ccccgtaggg actccgcgca aggacctgag    11340
cgtctcgaga tccacgggat ctgaaaaccg ctgaacgaag gcttcgagcc agtcgcagtc    11400
gcaaggtagg ctgagcacgg tttcttctgg cgggtcatgt tggttgggag cggggcgggc    11460
gatgctgctg gtgatgaagt tgaaataggc ggttctgaga cggcggatgg tggcgaggag    11520
caccaggtct ttgggcccgg cttgctggat gcgcagacgg tcggccatgc cccaggcgtg    11580
gtcctgacac ctgccaggt ccttgtagta gtcctgcatg agccgctcca cgggcacctc    11640
ctcctcgccc gcgcggccgt gcatgcgcgt gagcccgaag ccgcgctggg gctggacgag    11700
cgccaggtcg gcgacgacgc gctcggcgag gatggcttgc tggatctggg tgagggtggt    11760
ctggaagtca tcaaagtcga cgaagcggtg gtaggctccg gtgttgatgg tgtaggagca    11820
gttggccatg acggaccagt tgacggtctg gtggcccgga cgcacgagct cgtggtactt    11880
gaggcgcgag taggcgcgcg tgtcgaagat gtagtcgttg caggtgcgca ccaggtactg    11940
gtagccgatg aggaagtgcg gcggcggctg cggtagagc ggccatcgct cggtggcggg    12000
ggcgccgggc gcgaggtcct cgagcatggt gcggtggtag ccgtagatgt acctggacat    12060
ccaggtgatg ccggcggcgg tggtggaggc gcgcgggaac tcgcggacgc ggttccagat    12120
gttgcgcagc ggcaggaagt agttcatggt gggcacggtc tggcccgtga ggcgcgcgca    12180
gtcgtggatg ctctatacgg gcaaaaacga aagcggtcag cggctcgact ccgtggcctg    12240
gaggctaagc gaacgggttg ggctgcgcgt gtaccccggt tcgaatctcg aatcaggctg    12300
gagccgcagc taacgtggta ttggcactcc cgtctcgacc caagcctgca ccaaccctcc    12360
```

```
aggatacgga ggcgggtcgt tttgcaactt ttttttggag gccggatgag actagtaagc   12420
gcggaaagcg gccgaccgcg atggctcgct gccgtagtct ggagaagaat cgccagggtt   12480
gcgttgcggt gtgccccggt tcgaggccgg ccggattccg cggctaacga gggcgtggct   12540
gccccgtcgt ttccaagacc ccatagccag ccgacttctc cagttacgga gcgagcccct   12600
cttttgtttt gtttgttttt gccagatgca tcccgtactg cggcagatgc gcccccacca   12660
ccctccaccg caacaacagc cccctccaca gccggcgctt ctgccccgc cccagcagca    12720 acttccagcc acgaccgccg cggccgccgt gagcggggct ggacagagtt atgatcacca   12780
gctggccttg gaagagggcg aggggctggc gcgcctgggg gcgtcgtcgc cggagcggca   12840
cccgcgcgtg cagatgaaaa gggacgctcg cgaggcctac gtgcccaagc agaacctgtt   12900
cagagacagg agcggcgagg agcccgagga gatgcgcgcg gcccggttcc acgcggggcg   12960
ggagctgcgg cgcggcctgg accgaaagag ggtgctgagg gacgaggatt cgaggcgga    13020 cgagctgacg gggatcagcc ccgcgcgcgc gcacgtggcc gcggccaacc tggtcacggc   13080
gtacgagcag accgtgaagg aggagagcaa cttccaaaaa tccttcaaca accacgtgcg   13140
caccctgatc gcgcgcgagg aggtgaccct gggcctgatg cacctgtggg acctgctgga   13200
ggccatcgtg cagaaccccca ccagcaagcc gctgacggcg cagctgttcc tggtggtgca   13260
gcatagtcgg gacaacgaag cgttcaggga ggcgctgctg aatatcaccg agcccgaggg   13320
ccgctggctc ctggacctgg tgaacattct gcagagcatc gtggtgcagg agcgcgggct   13380
gccgctgtcc gagaagctgg cggccatcaa cttctcggtg ctgagtttgg gcaagtacta   13440
cgctaggaag atctacaaga ccccgtacgt gcccatagac aaggaggtga agatcgacgg   13500
gttttacatg cgcatgaccc tgaaagtgct gaccctgagc gacgatctgg gggtgtaccg   13560
caacgacagg atgcaccgtg cggtgagcgc cagcaggcgg cgcgagctga gcgaccagga   13620
gctgatgcat agtctgcagc gggccctgac cggggccggg accgaggggg agagctactt   13680
tgacatgggc gcggacctgc actggcagcc cagccgccgg gccttggagg cggcggcagg   13740
accctacgta gaagaggtgg acgatgaggt ggacgaggag ggcgagtacc tggaagactg   13800
atggcgcgac cgtattttg ctagatgcaa caacaacagc cacctcctga tcccgcgatg    13860
cgggcggcgc tgcagagcca gccgtccggc attaactcct cggacgattg gacccaggcc   13920
atgcaacgca tcatggcgct gacgaccgcg aaccccgaag cctttagaca gcagcccag    13980 gccaaccggc tctcggccat cctggaggcc gtggtgccct cgcgctccaa ccccacgcac   14040
gagaaggtcc tggccatcgt gaacgcgctg gtggagaaca aggccatccg cggcgacgag   14100
gccggcctgg tgtacaacgc gctgctggag cgcgtggccc gctacaacag caccaacgtg   14160
cagaccaacc tggaccgcat ggtgaccgac gtgcgcgagg ccgtggccca gcgcgagcgg   14220
ttccaccgcg agtccaacct gggatccatg gtggcgctga cgccttcct cagcacccag    14280 cccgccaacg tgccccgggg ccaggaggac tacaccaact tcatcagcgc cctgcgcctg   14340
atggtgaccg aggtgcccca gagcgaggtg taccagtccg ggccggacta cttcttccag   14400
accagtcgcc agggcttgca gaccgtgaac ctgagccagg ctttcaagaa cttgcagggc   14460
ctgtggggcg tgcaggcccc ggtcggggac cgcgcgacgg tgtcgagcct gctgacgccg   14520
aactcgcgcc tgctgctgct gctggtggcc cccttcacgg acagcggcag catcaaccgc   14580
aactcgtacc tgggctacct gattaacctg taccgcgagg ccatcggcca ggcgcacgtg   14640
gacgagcaga cctaccagga gatcacccac gtgagccgcg ccctgggcca ggacgacccg   14700
ggcaacctgg aagccaccct gaacttttg ctgaccaacc ggtcgcagaa gatcccgccc    14760
```

```
cagtacgcgc tcagcaccga ggaggagcgc atcctgcgtt acgtgcagca gagcgtgggc   14820
ctgttcctga tgcaggaggg ggccaccccc agcgccgcgc tcgacatgac cgcgcgcaac   14880
atggagccca gcatgtacgc cagcaaccgc ccgttcatca ataaactgat ggactacttg   14940
catcgggcgc cgccatgaa ctctgactat ttcaccaacg ccatcctgaa tccccactgg   15000
ctcccgccgc cggggttcta cacgggcgag tacgacatgc ccgacccaa tgacgggttc   15060 ctgtgggaca tgtgtgacag cagcgtgttc tccccccgac cgggtgctaa cgagcgcccc   15120
ttgtggaaga aggaaggcag cgaccgacgc ccgtcctcgg cgctgtccgg ccgcgagggt   15180
gctgccgcgg cggtgcccga ggccgccagt ccttttcccga gcttgccctt ctcgctgaac   15240
agtatccgca gcagcgagct gggcaggatc acgcgcccgc gcttgctggg cgaagaggag   15300
tacttgaatg actcgctgtt gagacccgag cgggagaaga acttccccaa taacgggata   15360
gaaagcctgg tggacaagat gagccgctgg aagacgtatg cgcaggagca cagggacgat   15420
ccccgggcgt cgcaggggc cacgagccgg ggcagcgccg cccgtaaacg ccggtggcac   15480
gacaggcagc ggggacagat gtgggacgat gaggactccg ccgacgacag cagcgtgttg   15540
gacttgggtg ggagtggtaa cccgttcgct cacctgcgcc cccgtatcgg gcgcatgatg   15600
taagagaaac cgaaaataaa tgatactcac caaggccatg gcgaccagcg tgcgttcgtt   15660
tcttctctgt tgttgttgta tctagtatga tgaggcgtgc gtaccggag ggtcctcctc   15720 cctcgtacga gagcgtgatg cagcaggcga tggcggcggc ggcgatgcag cccccgctgg   15780
aggctcctta cgtgcccccg cggtacctgg cgcctacgga ggggcggaac agcattcgtt   15840
actcggagct ggcacccttg tacgatacca cccggttgta cctggtggac aacaagtcgg   15900
cggacatcgc ctcgctgaac taccagaacg accacagcaa cttcctgacc accgtggtgc   15960
agaacaatga cttcacccc acggaggcca gcacccagac catcaacttt gacgagcgct   16020
cgcggtgggg cggccagctg aaaaccatca tgcacaccaa catgcccaac gtgaacgagt   16080
tcatgtacag caacaagttc aaggcgcggg tgatggtctc ccgcaagacc cccaatgggg   16140
tgacagtgac agaggattat gatggtagtc aggatgagct gaagtatgaa tgggtggaat   16200
ttgagctgcc cgaaggcaac ttctcggtga ccatgaccat cgacctgatg aacaacgcca   16260
tcatcgacaa ttacttggcg gtggggcggc agaacggggt gctggagagc gacatcggcg   16320
tgaagttcga cactaggaac ttcaggctgg gctgggaccc cgtgaccgag ctggtcatgc   16380
ccggggtgta caccaacgag gctttccatc ccgatattgt cttgctgccc ggctgcgggg   16440
tggacttcac cgagagccgc ctcagcaacc tgctgggcat tcgcaagagg cagcccttcc   16500
aggaaggctt ccagatcatg tacgaggatc tggaggggg caacatcccc gcgctcctgg   16560
atgtcgacgc ctatgagaaa gcaaggagg atgcagcagc tgaagcaact gcagccgtag   16620
ctaccgcctc taccgaggtc aggggcgata attttgcaag cgccgcagca gtggcagcgg   16680
ccgaggcggc tgaaaccgaa agtaagatag tcattcagcc ggtggagaag gatagcaaga   16740
acaggagcta caacgtacta ccggacaaga taaacaccgc ctaccgcagc tggtacctag   16800
cctacaacta tggcgacccc gagaagggcg tgcgctcctg gacgctgctc accacctcgg   16860
acgtcacctg cggcgtggag caagtctact ggtcgctgcc cgacatgatg caagacccgg   16920
tcaccttccg ctccacgcgt caagttagca actaccggt ggtgggcgcc gagctcctgc   16980
ccgtctactc caagagcttc ttcaacgagc aggccgtcta ctcgcagcag ctgcgcgcct   17040
tcacctcgct tacgcacgtc ttcaaccgct tccccgagaa ccagatcctc gtccgcccgc   17100
```

```
ccgcgcccac cattaccacc gtcagtgaaa acgttcctgc tctcacagat cacgggaccc   17160
tgccgctgcg cagcagtatc cggggagtcc agcgcgtgac cgttactgac gccagacgcc   17220
gcacctgccc ctacgtctac aaggcccagg gcatagtcgc gccgcgcgtc ctctcgagcc   17280
gcaccttcta aatgtccatt ctcatctcgc ccagtaataa caccggttgg ggcctgcgcg   17340
cgcccagcaa gatgtacgga ggcgctcgcc aacgctccac gcaacacccc gtgcgcgtgc   17400
gcgggcactt ccgcgctccc tggggcgccc tcaagggccg cgtgcggtcg cgcaccaccg   17460
tcgacgacgt gatcgaccag gtggtggccg acgcgcgcaa ctacaccccc gccgccgcgc   17520
ccgtctccac cgtggacgcc gtcatcgaca cgtggtggc cgacgcgcgc cggtacgccc   17580
gcgccaagag ccggcggcgg cgcatcgccc ggcggcaccg gagcaccccc gccatgcgcg   17640
cggcgcgagc cttgctgcgc agggccaggc gcacgggacg cagggccatg ctcagggcgg   17700
ccagacgcgc ggcttcaggc gccagcgccg gcaggacccg gagacgcgcg gccacggcgg   17760
cggcagcggc catcgccagc atgtcccgcc cgcggcgagg gaacgtgtac tgggtgcgcg   17820
acgccgccac cggtgtgcgc gtgcccgtgc gcacccgccc ccctcgcact gaagatgtt   17880 cacttcgcga tgttgatgtg tcccagcggc gaggaggatg tccaagcgca aattcaagga   17940
agagatgctc caggtcatcg cgcctgagat ctacggccct gcggtggtga aggaggaaag   18000
aaagccccgc aaaatcaagc gggtcaaaaa ggacaaaaag gaagaagaaa gtgatgtgga   18060
cggattggtg gagtttgtgc gcgagttcgc ccccggcgg cgcgtgcagt ggcgcggggc   18120
gaaggtgcaa ccggtgctga cccggcac caccgtggtc ttcacgcccg gcgagcgctc   18180
cggcaccgct tccaagcgct cctacgacga ggtgtacggg gatgatgata ttctggagca   18240
ggcggccgag cgcctgggcg agtttgctta cggcaagcgc agccgttccg caccgaagga   18300
agaggcggtg tccatcccgc tggaccacgg caaccccacg ccgagcctca gcccgtgac   18360 cttgcagcag gtgctgccga ccgcggcgcc gcgccggggg ttcaagcgcg agggcgagga   18420
tctgtacccc accatgcagc tgatggtgcc caagcgccag aagctggaag acgtgctgga   18480
gaccatgaag gtggacccgg acgtgcagcc cgaggtcaag gtgcggccca tcaagcaggt   18540
ggccccgggc ctgggcgtgc agaccgtgga catcaagatt cccacggagc ccatggaaac   18600
gcagaccgag cccatgatca agcccagcac cagcaccatg gaggtgcaga cggatccctg   18660
gatgccatcg gctcctagtc gaagaccccg gcgcaagtac ggcgcggcca gcctgctgat   18720
gcccaactac gcgctgcatc cttccatcat ccccacgccg ggctaccgcg gcacgcgctt   18780
ctaccgcggt cataccagca gccgccgccg caagaccacc actcgccgcc gccgtcgccg   18840
caccgccgct gcaaccaccc ctgccgccct ggtgcggaga gtgtaccgcc gcggccgcgc   18900
acctctgacc ctgccgcgcg cgcgctacca cccgagcatc gccatttaaa ctttcgcctg   18960
ctttgcagat caatggccct cacatgccgc cttcgcgttc ccattacggg ctaccgagga   19020
agaaaaccgc gccgtagaag gctggcgggg aacgggatgc gtcgccacca ccaccggcgg   19080
cggcgcgcca tcagcaagcg gttggggga ggcttcctgc ccgcgctgat ccccatcatc   19140
gccgcggcga tcggggcgat ccccggcatt gcttccgtgg cggtgcaggc ctctcagcgc   19200
cactgagaca cacttggaaa catcttgtaa taaaccaatg gactctgacg ctcctggtcc   19260
tgtgatgtgt tttcgtagac agatggaaga catcaatttt tcgtccctgg ctccgcgaca   19320
cggcacgcgg ccgttcatgg gcacctggag cgacatcggc accagccaac tgaacggggg   19380
cgccttcaat tggagcagtc tctggagcgg gcttaagaat ttcgggtcca cgcttaaaac   19440
ctatggcagc aaggcgtgga acagcaccac agggcaggcg ctgagggata agctgaaaga   19500
```

```
gcagaacttc cagcagaagg tggtcgatgg gctcgcctcg ggcatcaacg gggtggtgga   19560
cctggccaac caggccgtgc agcggcagat caacagccgc ctggacccgg tgccgcccgc   19620
cggctccgtg gagatgccgc aggtggagga ggagctgcct cccctggaca gcggggcga    19680 gaagcgaccc cgccccgatg cggaggagac gctgctgacg cacacggacg agccgccccc   19740
gtacgaggag gcggtgaaac tgggtctgcc caccacgcgg cccatcgcgc cctggccac    19800 cggggtgctg aaacccgaaa agcccgcgac cctggacttg cctcctcccc agccttcccg   19860
cccctctaca gtggctaagc ccctgccgcc ggtggccgtg gcccgcgcgc gacccggggg   19920
caccgcccgc cctcatgcga actggcagag cactctgaac agcatcgtgg gtctgggagt   19980
gcagagtgtg aagcgccgcc gctgctatta aacctaccgt agcgcttaac ttgcttgtct   20040
gtgtgtgtat gtattatgtc gccgccgccg ctgtccacca aaggaggag tgaagaggcg    20100 cgtcgccgag ttgcaagatg gccaccccat cgatgctgcc ccagtgggcg tacatgcaca   20160
tcgccggaca ggacgcttcg gagtacctga gtccgggtct ggtgcagttt gcccgcgcca   20220
cagacaccta cttcagtctg ggaacaagt ttaggaaccc cacggtggcg cccacgcacg    20280
atgtgaccac cgaccgcagc cagcggctga cgctgcgctt cgtgcccgtg gaccgcgagg   20340
acaacaccta ctcgtacaaa gtgcgctaca cgctggccgt gggcgacaac cgcgtgctgg   20400
acatggccag cacctacttt gacatccgcg gcgtgctgga tcggggccct agcttcaaac   20460
cctactccgg caccgcctac aacagtctgg cccccaaggg agcacccaac acttgtcagt   20520
ggacatataa agccgatggt gaaactgcca cagaaaaaac ctatacatat ggaaatgcac   20580
ccgtgcaggg cattaacatc acaaaagatg gtattcaact tggaactgac accgatgatc   20640
agccaatcta cgcagataaa acctatcagc ctgaacctca agtgggtgat gctgaatggc   20700
atgacatcac tggtactgat gaaaagtatg gaggcagagc tcttaagcct gataccaaaa   20760
tgaagccttg ttatggttct tttgccaagc ctactaataa agaaggaggt caggcaaatg   20820
tgaaaacagg aacaggcact actaaagaat atgacataga catggctttc tttgacaaca   20880
gaagtgcggc tgctgctggc ctagctccag aaattgtttt gtatactgaa atgtggatt    20940 tggaaactcc agatacccat attgtataca aagcaggcac agatgacagc agctcttcta   21000
ttaatttggg tcagcaagcc atgcccaaca gacctaacta cattggtttc agagacaact   21060
ttatcgggct catgtactac aacagcactg gcaaatatgg ggtgctggcc ggtcaggctt   21120
ctcagctgaa tgctgtggtt gacttgcaag acagaaacac cgagctgtcc taccagctct   21180
tgcttgactc tctgggtgac agaacccggt atttcagtat gtggaatcag gcggtggaca   21240
gctatgatcc tgatgtgcgc attattgaaa atcatggtgt ggaggatgaa cttcccaact   21300
attgtttccc tctggatgct gttggcagaa cagatactta tcagggaatt aaggctaatg   21360
gaactgatca aaccacatgg accaaagatg acagtgtcaa tgatgctaat gagataggca   21420
agggtaatcc attcgccatg gaaatcaaca tccaagccaa cctgtggagg aacttcctct   21480
acgccaacgt ggccctgtac ctgcccgact cttacaagta cacgccggcc aatgttaccc   21540
tgcccaccaa caccaacacc tacgattaca tgaacggccg ggtggtggcg ccctcgctgg   21600
tggactccta catcaacatc ggggcgcgct ggtcgctgga tcccatggac aacgtgaacc   21660
ccttcaacca ccaccgcaat gcggggctgc gctaccgctc catgctcctg ggcaacgggc   21720
gctacgtgcc cttccacatc caggtgcccc agaaattttt cgccatcaag agcctcctgc   21780
tcctgcccgg gtcctacacc tacgagtgga acttccgcaa ggacgtcaac atgatcctgc   21840
```

```
agagctccct cggcaacgac ctgcgcacgg acggggcctc catctccttc accagcatca   21900
acctctacgc caccttcttc cccatggcgc acaacacggc ctccacgctc gaggccatgc   21960
tgcgcaacga caccaacgac cagtccttca acgactacct ctcggcggcc aacatgctct   22020
accccatccc ggccaacgcc accaacgtgc ccatctccat cccctcgcgc aactgggccg   22080
ccttccgcgg ctggtccttc acgcgtctca agaccaagga gacgccctcg ctgggctccg   22140
ggttcgaccc ctactcgtc tactcgggct ccatccccta cctcgacggc accttctacc    22200
tcaaccacac cttcaagaag gtctccatca ccttcgactc ctccgtcagc tggcccggca   22260
acgaccggct cctgacgccc aacgagttcg aaatcaagcg caccgtcgac ggcgagggct   22320
acaacgtggc ccagtgcaac atgaccaagg actggttcct ggtccagatg ctggcccact   22380
acaacatcgg ctaccagggc ttctacgtgc ccgagggcta caaggaccgc atgtactcct   22440
tcttccgcaa cttccagccc atgagccgcc aggtggtgga cgaggtcaac tacaaggact   22500
accaggccgt cacctggcc taccagcaca caactcggg cttcgtcggc tacctcgcgc     22560
ccaccatgcg ccagggccag ccctacccg ccaactaccc ctaccgctc atcggcaaga     22620 gcgccgtcac cagcgtcacc cagaaaaagt tcctctgcga cagggtcatg tggcgcatcc   22680
ccttctccag caacttcatg tccatgggcg cgctcaccga cctcggccag aacatgctct   22740
atgccaactc cgcccacgcg ctagacatga atttcgaagt cgaccccatg gatgagtcca   22800
cccttctcta tgttgtcttc gaagtcttcg acgtcgtccg agtgcaccag ccccaccgcg   22860
gcgtcatcga ggccgtctac ctgcgcaccc ccttctcggc cggtaacgcc accacctaag   22920
ctcttgcttc ttgcaagcca tggccgcggg ctccggcgag caggagctca gggccatcat   22980
ccgcgacctg ggctgcgggc cctacttcct gggcaccttc gataagcgct cccgggatt    23040 catggccccg cacaagctgg cctgcgccat cgtcaacacg gccggccgcg agaccggggg   23100
cgagcactgg ctggccttcg cctggaaccc gcgctcgaac acctgctacc tcttcgaccc   23160
cttcggggtc tcggacgagc gcctcaagca gatctaccag ttcgagtacg agggcctgct   23220
gcgccgcagc gccctggcca ccgaggaccg ctgcgtcacc ctggaaaagt ccacccagac   23280
cgtgcagggt ccgcgctcgg ccgcctgcgg gctcttctgc tgcatgttcc tgcacgcctt   23340
cgtgcactgg cccgaccgcc ccatggacaa gaaccccacc atgaacttgc tgacggggt    23400 gcccaacggg atgctccagt cgccccaggt ggaacccacc ctgcgccgca accaggaggc   23460
gctctaccgc ttcctcaact cccactccgc ctactttcgc tccaccgcg cgcgcatcga    23520 gaaggccacc gccttcgacc gcatgaatca agacatgtaa accgtgtgtg tatgttaaat   23580
gtctttaata aacagcactt tcatgttaca catgcatctg agatgattta tttagaaatc   23640
gaaagggttc tgccgggtct cggcatggcc cgcgggcagg acacgttgc ggaactggta    23700 cttggccagc cacttgaact cggggatcag cagtttgggc agcggggtgt cggggaagga   23760
gtcggtccac agcttccgcg tcagttgcag ggcgcccagc aggtcgggcg cggagatctt   23820
gaaatcgcag ttgggacccg cgttctgcgc gcggagttg cggtacacgg ggttgcagca    23880
ctggaacacc atcagggccg ggtgcttcac gctcgccagc accgtcgcgt cggtgatgct   23940
ctccacgtcg aggtcctcgg cgttggccat cccgaagggg gtcatcttgc aggtctgcct   24000
tcccatggtg ggcacgcacc cgggcttgtg gttgcaatcg cagtgcaggg ggatcagcat   24060
catctgggcc tggtcggcgt tcatcccccg gtacatggcc ttcatgaaag cctccaattg   24120
cctgaacgcg tgctgggcct tggctccctc ggtgaagaag accccgcagg acttgctaga   24180
gaactggttg gtggcgcacc cggcgtcgtg cacgcagcag cgcgcgtcgt tgttggccag   24240
```

```
ctgcaccacg ctgcgccccc agcggttctg ggtgatcttg gcccggtcgg ggttctcctt   24300
cagcgcgcgc tgcccgttct cgctcgccac atccatctcg atcatgtgct ccttctggat   24360
catggtggtc ccgtgcaggc accgcagctt gccctcggcc tcggtgcacc cgtgcagcca   24420
cagcgcgcac ccggtgcact cccagttctt gtgggcgatc tgggaatgcg cgtgcacgaa   24480
gccctgcagg aagcggccca tcatggtggt cagggtcttg ttgctagtga aggtcagcgg   24540
aatgccgcgg tgctcctcgt tgatgtacag gtggcagatg cggcggtaca cctcgccctg   24600
ctcgggcatc agctggaagt tggctttcag gtcggtctcc acgcggtagc ggtccatcag   24660
catagtcatg atttccatac ccttctccca ggccgagacg atgggcaggc tcatagggtt   24720
cttcaccatc atcttagcgc tagcagccgc ggccagggggg tcgctctcgt ccagggtctc   24780
aaagctccgc ttgccgtcct tctcggtgat ccgcaccggg gggtagctga agcccacggc   24840
cgccagctcc tcctcggcct gtctttcgtc ctcgctgtcc tggctgacgt cctgcaggac   24900
cacatgcttg gtcttgcggg gtttcttctt gggcggcagc ggcggcggag atgttggaga   24960
tggcgagggg gagcgcgagt tctcgctcac cactactatc tcttcctctt cttggtccga   25020
ggccacgcgg cggtaggtat gtctcttcgg gggcagaggc ggaggcgacg ggctctcgcc   25080
gccgcgactt ggcggatggc tggcagagcc ccttccgcgt tcggggtgc gctcccggcg   25140 gcgctctgac tgacttcctc cgcggccggc cattgtgttc tcctaggag gaacaacaag   25200 catggagact cagccatcgc caacctcgcc atctgccccc accgccgacg agaagcagca   25260
gcagcagaat gaaagcttaa ccgccccgcc gccagccccc gccacctccg acgcggcgt   25320 cccagacatg caagagatgg aggaatccat cgagattgac ctgggctatg tgacgcccgc   25380
ggagcacgag gaggagctgg cagtgcgctt ttcacaagaa gagatacacc aagaacagcc   25440
agagcaggaa gcagagaatg agcagagtca ggctgggctc gagcatgacg gcgactacct   25500
ccacctgagc ggggggggagg acgcgctcat caagcatctg gcccggcagg ccaccatcgt   25560
caaggatgcg ctgctcgacc gcaccgaggt gcccctcagc gtggaggagc tcagccgcgc   25620
ctacgagttg aacctcttct cgccgcgcgt gccccccaag cgccagccca atggcacctg   25680
cgagcccaac ccgcgcctca acttctaccc ggtcttcgcg gtgcccgagg ccctggccac   25740
ctaccacatc ttttttcaaga accaaaagat ccccgtctcc tgccgcgcca accgcacccg   25800
cgccgacgcc cttttcaacc tgggtccgg cgcccgccta cctgatatcg cctccttgga   25860
agaggttccc aagatcttcg agggtctggg cagcgacgag actcgggccg cgaacgctct   25920
gcaaggagaa ggaggagagc atgagcacca cagcgccctg gtcgagttgg aaggcgacaa   25980
cgcgcggctg gcggtgctca aacgcacggt cgagctgacc catttcgcct acccggctct   26040
gaacctgccc cccaaagtca tgagcgcggt catggaccag gtgctcatca agcgcgcgtc   26100
gcccatctcc gaggacgagg gcatgcaaga ctccgaggag ggcaagcccg tggtcagcga   26160
cgagcagctg gcccggtggc tgggtcctaa tgctagtccc cagagtttgg aagagcggcg   26220
caaactcatg atggccgtgg tcctggtgac cgtggagctg gagtgcctgc gccgcttctt   26280
cgccgacgcg gagaccctgc gcaaggtcga ggagaacctg cactacctct tcaggcacgg   26340
gttcgtgcgc caggcctgca gatctctcaa cgtggagctg accaacctgg tctcctacat   26400
gggcatcttg cacgagaacc gcctggggca gaacgtgctg cacaccaccc tgcgcgggga   26460
ggcccggcgc gactacatcc gcgactgcgt ctacctctac ctctgccaca cctgcgagac   26520
gggcatgggc gtgtggcagc agtgtctgga ggagcagaac ctgaaagagc tctgcaagct   26580
```

```
cctgcagaag aacctcaagg gtctgtggac cgggttcgac gagcgcacca ccgcctcgga  26640
cctggccgac ctcatttttcc ccgagcgcct caggctgacg ctgcgcaacg gcctgcccga  26700
ctttatgagc caaagcatgt tgcaaaactt tcgctctttc atcctcgaac gctccggaat  26760
cctgcccgcc acctgctccg cgctgccctc ggacttcgtg ccgctgacct tccgcgagtg  26820 cccccccgccg ctgtggagcc actgctacct gctgcgcctg gccaactacc tggcctacca  26880 ctcgacgtg atcgaggacg tcagcggcga gggcctgctc gagtgccact gccgctgcaa  26940
cctctgcacg ccgcaccgct ccctggcctg caaccccccag ctgctgagcg agacccagat  27000
catcggcacc ttcgagttgc aagggcccag cgaaggcgag ggttcagccg ccaaggggggg  27060 tctgaaactc accccggggc tgtggacctc ggcctacttg cgcaagttcg tgcccgagga  27120
ctaccatccc ttcgagatca ggttctacga ggaccaatcc catccgccca aggccgagct  27180
gtcggcctgc gtcatcaccc aggggggcgat cctggcccaa ttgcaagcca tccagaaatc  27240
ccgccaagaa ttcttgctga aaagggccg cggggtctac ctcgaccccc agaccggtga  27300
ggagctcaac cccggcttcc cccaggatgc cccgaggaaa caagaagctg aaagtggagc  27360
tgccgcccgt ggaggatttg gaggaagact gggagaacag cagtcaggca gaggaggagg  27420
agatggagga agactgggac agcactcagg cagaggagga cagcctgcaa gacagtctgg  27480
aggaagacga ggaggaggca gaggaggagg tggaagaagc agccgccgcc agaccgtcgt  27540
cctcggcggg ggagaaagca agcagcacgg ataccatctc cgctccgggt cggggtcccg  27600
ctcgaccaca cagtagatgg gacgagaccg acgattccc gaaccccacc acccagaccg  27660
gtaagaagga gcggcaggga tacaagtcct ggcgggggca caaaaacgcc atcgtctcct  27720
gcttgcaggc ctgcgggggc aacatctcct tcacccggcg ctacctgctc ttccaccgcg  27780
gggtgaactt tccccgcaac atcttgcatt actaccgtca cctccacagc cctactact  27840 tccaagaaga ggcagcagca gcagaaaaag accagcagaa aaccagcagc tagaaaatcc  27900
acagcggcgg cagcaggtgg actgaggatc gcggcgaacg agccggcgca aacccgggag  27960
ctgaggaacc ggatctttcc caccctctat gccatcttcc agcagagtcg ggggcaggag  28020
caggaactga aagtcaagaa ccgttctctg cgctcgctca cccgcagttg tctgtatcac  28080
aagagcgaag accaacttca gcgcactctc gaggacgccg aggctctctt caacaagtac  28140
tgcgcgctca ctcttaaaga gtagcccgcg cccgcccagt cgcagaaaaa ggcgggaatt  28200
acgtcacctg tgcccttcgc cctagccgcc tccacccatc atcatgagca aagagattcc  28260
cacgccttac atgtggagct accagcccca gatgggcctg gccgccggtg ccgcccagga  28320
ctactccacc cgcatgaatt ggctcagcgc cgggcccgcg atgatctcac gggtgaatga  28380
catccgcgcc caccgaaacc agatactcct agaacagtca gcgctcaccg ccacgccccg  28440
caatcacctc aatccgcgta attggcccgc cgccctggtg taccaggaaa ttccccagcc  28500
cacgaccgta ctacttccgc gagacgccca ggccgaagtc cagctgacta actcaggtgt  28560
ccagctggcg ggcggcgcca ccctgtgtcg tcaccgcccc gctcagggta taaagcggct  28620
ggtgatccgg ggcagaggca cacagctcaa cgacgaggtg gtgagctctt cgctgggtct  28680
gcgacctgac ggagtcttcc aactcgccgg atcggggaga tcttccttca cgcctcgtca  28740
ggccgtcctg actttggaga gttcgtcctc gcagccccgc tcgggtggca tcggcactct  28800
ccagttcgtg gaggagttca ctccctcggt ctacttcaac cccttctccg gctccccgg  28860 ccactacccg gacgagttca tcccgaactt cgacgccatc agcgagtcgg tggacggcta  28920
cgattgaatg tcccatggtg gcgcagctga cctagctcgg cttcgacacc tggaccactg  28980
```

```
ccgccgcttc cgctgcttcg ctcgggatct cgccgagttt gcctactttg agctgcccga    29040
ggagcaccct cagggcccgg cccacggagt gcggatcgtc gtcgaagggg gcctcgactc    29100
ccacctgctt cggatcttca gccagcgtcc gatcctggtc gagcgcgagc aaggacagac    29160
ccttctgact ctgtactgca tctgcaacca ccccggcctg catgaaagtc tttgttgtct    29220
gctgtgtact gagtataata aaagctgaga tcagcgacta ctccggactt ccgtgtgttc    29280
ctgaatccat caaccagtct tgttcttca ccgggaacga gaccgagctc cagctccagt    29340
gtaagcccca caagaagtac ctcacctggc tgttccaggg ctccccgatc gccgttgtca    29400
accactgcga caacgacgga gtcctgctga gcggccctgc caaccttact ttttccaccc    29460
gcagaagcaa gctccagctc ttccaaccct cctccccgg gacctatcag tgcgtctcgg    29520
gaccctgcca tcacaccttc cacctgatcc cgaataccac agcgtcgctc cccgctacta    29580
acaaccaaac taacctccac caacgccacc gtcgctaggc cacaatacat gcccatatta    29640
gactatgagg ccgagccaca gcgacccatg ctccccgcta ttagttactt caatctaacc    29700
ggcggagatg actgacccac tggccaacaa caacgtcaac gaccttctcc tggacatgga    29760
cggccgcgcc tcgagcagc gactcgccca acttcgcatt cgccagcagc aggagagagc    29820
cgtcaaggag ctgcaggatg cggtggccat ccaccagtgc aagagaggca tcttctgcct    29880
ggtgaaacag gccaagatct cctacgaggt cactccaaac gaccatcgcc tctcctacga    29940
gctcctgcag cagcgccaga agttcacctg cctggtcgga gtcaaccca tcgtcatcac    30000 ccagcagtct ggcgatacca aggggtgcat ccactgctcc tgcgactccc ccgactgcgt    30060
ccacactctg atcaagaccc tctgcggcct ccgcgacctc ctccccatga actaatcacc    30120
cccttatcca gtgaaataaa gatcatattg atgatgattt tacagaaata aaaaataatc    30180
atttgatttg aaataaagat acaatcatat tgatgatttg agtttaacaa aaaaataaag    30240
aatcacttac ttgaaatctg ataccaggtc tctgtccatg ttttctgcca acaccacttc    30300
actcccctct tcccagctct ggtactgcag gccccggcgg gctgcaaact tcctccacac    30360
gctgaagggg atgtcaaatt cctcctgtcc ctcaatcttc attttatctt ctatcagatg    30420
tccaaaaagc gcgtccgggt ggatgatgac ttcgaccccg tctacccta cgatgcagac    30480 aacgcaccga ccgtgcccct catcaacccc cccttcgtct cttcagatgg attccaagag    30540
aagcccctgg gggtgttgtc cctgcgactg gccgaccccg tcaccaccaa gaacggggaa    30600
atcaccctca gctggggaga gggggtggac ctcgattcct cgggaaaact catctccaac    30660
acggccacca aggccgccgc ccctctcagt ttttccaaca acaccatttc ccttaacatg    30720
gatcacccct tttacactaa agatggaaaa ttatccttac aagtttctcc accattaaat    30780
atactgagaa caagcattct aaacacacta gctttaggtt ttggatcagg tttaggactc    30840
cgtggctctg ccttggcagt acagttagtc tctccactta catttgatac tgatggaaac    30900
ataaagctta ccttagacag aggtttgcat gttacaacag gagatgcaat tgaaagcaac    30960
ataagctggg ctaaaggttt aaatttgaa gatggagcca tagcaaccaa cattggaaat    31020
gggttagagt ttggaagcag tagtacagaa acaggtgttg atgatgctta cccaatccaa    31080
gttaaacttg gatctggcct tagctttgac agtacaggag ccataatggc tggtaacaaa    31140
gaagacgata aactcacttt gtggacaaca cctgatccat caccaaactg tcaaatactc    31200
gcagaaaatg atgcaaaact aacactttgc ttgactaaat gtggtagtca atactggcc    31260 actgtgtcag tcttagttgt aggaagtgga aacctaaacc ccattactgg caccgtaagc    31320
```

-continued

```
agtgctcagg tgtttctacg tttttgatgca aacggtgttc ttttaacaga acattctaca    31380
ctaaaaaaat actgggggta taggcaggga gatagcatag atggcactcc atataccaat    31440
gctgtaggat tcatgcccaa tttaaaagct tatccaaagt cacaaagttc tactactaaa    31500
aataatatag tagggcaagt atacatgaat ggagatgttt caaaacctat gcttctcact    31560
ataaccctca atggtactga tgacagcaac agtacatatt caatgtcatt ttcatacacc    31620
tggactaatg gaagctatgt tggagcaaca tttggggcta actcttatac cttctcatac    31680
atcgcccaag aatgaacact gtatcccacc ctgcatgcca acccttccca ccccactctg    31740
tggaacaaac tctgaaacac aaaataaaat aaagttcaag tgttttattg attcaacagt    31800
tttacaggat tcgagcagtt attttttcctc caccctccca ggacatggaa tacaccaccc    31860
tctcccccccg cacagccttg aacatctgaa tgccattggt gatggacatg cttttggtct    31920
ccacgttcca cacagtttca gagcgagcca gtctcgggtc ggtcagggag atgaaaccct    31980
ccgggcactc ccgcatctgc acctcacagc tcaacagctg aggattgtcc tcggtggtcg    32040
ggatcacggt tatctggaag aagcagaaga gcggcggtgg gaatcatagt ccgcgaacgg    32100
gatcggccgg tggtgtcgca tcaggccccg cagcagtcgc tgccgccgcc gctccgtcaa    32160
gctgctgctc aggggtccg ggtccaggga ctccctcagc atgatgccca cggccctcag    32220
catcagtcgt ctggtgcggc gggcgcagca gcgcatgcgg atctcgctca ggtcgctgca    32280
gtacgtgcaa cacagaacca ccaggttgtt caacagtcca tagttcaaca cgctccagcc    32340
gaaactcatc gcgggaagga tgctacccac gtggccgtcg taccagatcc tcaggtaaat    32400
caagtggtgc cccctccaga acacgctgcc cacgtacatg atctccttgg gcatgtggcg    32460
gttcaccacc tcccggtacc acatcaccct ctggttgaac atgcagcccc ggatgatcct    32520
gcggaaccac agggccagca ccgccccgcc cgccatgcag cgaagagacc ccgggtcccg    32580
gcaatggcaa tggaggaccc accgctcgta cccgtggatc atctgggagc tgaacaagtc    32640
tatgttggca cagcacaggc atatgctcat gcatctcttc agcactctca actcctcggg    32700
ggtcaaaacc atatcccagg gcacggggaa ctcttgcagg acagcgaacc ccgcagaaca    32760
gggcaatcct cgcacagaac ttacattgtg catggacagg gtatcgcaat caggcagcac    32820
cgggtgatcc tccaccagag aagcgcgggt ctcggtctcc tcacagcgtg gtaaggggc    32880
cggccgatac gggtgatggc gggacgcggc tgatcgtgtt cgcgaccgtg tcatgatgca    32940
gttgctttcg gacattttcg tacttgctgt agcagaacct ggtccgggcg ctgcacaccg    33000
atcgccggcg gcggtctcgg cgcttggaac gctcggtgtt gaaattgtaa acagccact    33060
ctctcagacc gtgcagcaga tctagggcct caggagtgat gaagatccca tcatgcctga    33120
tggctctgat cacatcgacc accgtggaat gggccagacc cagccagatg atgcaatttt    33180
gttgggtttc ggtgacggcg ggggagggaa gaacaggaag aaccatgatt aactttaat    33240
ccaaacggtc tcggagtact tcaaaatgaa gatcgcggag atggcacctc tcgcccccgc    33300
tgtgttggtg gaaaataaca gccaggtcaa aggtgatacg gttctcgaga tgttccacgg    33360
tggcttccag caaagcctcc acgcgcacat ccagaaacaa gacaatagcg aaagcgggag    33420
ggttctctaa ttcctcaatc atcatgttac actcctgcac catccccaga taattttcat    33480
ttttccagcc ttgaatgatt cgaactagtt cctgaggtaa atccaagcca gccatgataa    33540
agagctcgcg cagagcgccc tccaccggca ttcttaagca caccctcata attccaagat    33600
attctgctcc tggttcacct gcagcagatt gacaagcgga atatcaaaat ctctgccgcg    33660
atccctgagc tcctcccctca gcaataactg taagtactct ttcatatcct ctccgaaatt    33720
```

```
tttagccata ggaccaccag gaataagatt agggcaagcc acagtacaga taaaccgaag     33780
tcctccccag tgagcattgc caaatgcaag actgctataa gcatgctggc tagacccggt     33840
gatatcttcc agataactgg acagaaaatc gcccaggcaa ttttaagaa atcaacaaa       33900 agaaaaatcc tccaggtgga cgtttagagc ctcgggaaca acgatgaagt aaatgcaagc    33960
ggtgcgttcc agcatggtta gttagctgat ctgtagaaaa aacaaaaatg aacattaaac    34020
catgctagcc tggcgaacag gtgggtaaat cgttctctcc agcaccaggc aggccacggg    34080
gtctccggcg cgaccctcgt aaaaattgtc gctatgattg aaaaccatca cagagagacg    34140
ttcccggtgg ccggcgtgaa tgattcgaca agatgaatac accccggaa cattggcgtc      34200 cgcgagtgaa aaaagcgcc cgaggaagca ataaggcact acaatgctca gtctcaagtc     34260
cagcaaagcg atgccatgcg gatgaagcac aaaattctca ggtgcgtaca aaatgtaatt    34320
actcccctcc tgcacaggca gcaaagcccc cgatccctcc aggtacacat acaaagcctc    34380
agcgtccata gcttaccgag cagcagcaca caacaggcgc aagagtcaga gaaaggctga    34440
gctctaacct gtccacccgc tctctgctca atatatagcc cagatctaca ctgacgtaaa    34500
ggccaaagtc taaaaatacc cgccaaataa tcacacacgc ccagcacacg cccagaaacc    34560
ggtgacacac tcaaaaaaat acgcgcactt cctcaaacgc ccaaaactgc cgtcatttcc    34620
gggttcccac gctacgtcat caaaacacga ctttcaaatt ccgtcgaccg ttaaaaacgt    34680
cacccgcccc gccctaacg gtcgcccgtc tctcagccaa tcagcgcccc gcatcccaa      34740 attcaaacac ctcatttgca tattaacgcg cacaaaaagt ttgaggtata ttattgatga    34800
tgg                                                                   34803

<210> SEQ ID NO 46
<211> LENGTH: 7182
<212> TYPE: DNA
<213> ORGANISM: Artificial Sequence
<220> FEATURE:
<223> OTHER INFORMATION: Synthetic Construct

<400> SEQUENCE: 46
ggcgtaatgc tctgccagtg ttacaaccaa ttaaccaatt ctgattagaa aaactcatcg      60
agcatcaaat gaaactgcaa tttattcata tcaggattat caataccata tttttgaaaa    120
agccgtttct gtaatgaagg agaaaactca ccgaggcagt tccataggat ggcaagatcc    180
tggtatcggt ctgcgattcc gactcgtcca acatcaatac aacctattaa tttcccctcg    240
tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcaaatgcaa ccggcgcagg    480
aacactgcca gcgcatcaac aatatttca cctgaatcag gatattcttc taatacctgg     540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
```

-continued

| | | | | | |
|---|---|---|---|---|---|
| acaatattgg | ctattggcca | ttgcatacgt | tgtatctata | tcataatatg | tacatttata | 960 |
| ttggctcatg | tccaatatga | ccgccatgtt | gacattgatt | attgactagt | tattaatagt | 1020 |
| aatcaattac | ggggtcatta | gttcatagcc | catatatgga | gttccgcgtt | acataactta | 1080 |
| cggtaaatgg | cccgcctggc | tgaccgccca | acgaccccg | cccattgacg | tcaataatga | 1140 |
| cgtatgttcc | catagtaacg | ccaatagggga | ctttccattg | acgtcaatgg | gtggagtatt | 1200 |
| tacggtaaac | tgcccacttg | gcagtacatc | aagtgtatca | tatgccaagt | ccgcccccta | 1260 |
| ttgacgtcaa | tgacggtaaa | tggcccgcct | ggcattatgc | ccagtacatg | accttacggg | 1320 |
| actttcctac | ttggcagtac | atctacgtat | tagtcatcgc | tattaccatg | gtgatgcggt | 1380 |
| tttggcagta | caccaatggg | cgtggatagc | ggtttgactc | acggggattt | ccaagtctcc | 1440 |
| accccattga | cgtcaatggg | agtttgtttt | ggcaccaaaa | tcaacgggac | tttccaaaat | 1500 |
| gtcgtaataa | ccccgccccg | ttgacgcaaa | tgggcggtag | gcgtgtacgg | tgggaggtct | 1560 |
| atataagcag | agctcgttta | gtgaaccgtc | agatcgcctg | gagacgccat | ccacgctgtt | 1620 |
| ttgacctcca | tagaagacac | cgggaccgat | ccagcctccg | cggccgggaa | cggtgcattg | 1680 |
| gaacgcggat | tccccgtgcc | aagagtgact | caccgtccgg | atctcagcaa | gcaggtatgt | 1740 |
| actctccagg | gtgggcctgg | cttccccagt | caagactcca | gggatttgag | gacgctgtg | 1800 |
| ggctcttctc | ttacatgtac | cttttgcttg | cctcaaccct | gactatcttc | caggtcagga | 1860 |
| tcccagagtc | aggggtctgt | attttcctgc | tggtggctcc | agttcaggaa | cagtaaaccc | 1920 |
| tgctccgaat | attgcctctc | acatctcgtc | aatctccgcg | aggactgggg | accctgtgac | 1980 |
| gaacatggct | agcattgtgg | gaggctggga | gtgcgagaag | cattcccaac | cctggcaggt | 2040 |
| gcttgtggcc | tctcgtggca | gggcagtctg | cggcggtgtt | ctggtgcacc | cccagtgggt | 2100 |
| cctcacagct | gcccactgca | tcaggaacaa | aagcgtgatc | ttgctgggtc | ggcacagctt | 2160 |
| gtttcatcct | gaagacacag | gccaggtatt | tcaggtcagc | cacagcttcc | cacacccgct | 2220 |
| ctacgatatg | agcctcctga | agaatcgatt | cctcaggcca | ggtgatgact | ccagccacga | 2280 |
| cctcatgctg | ctccgcctgt | cagagcctgc | cgagctcacg | gatgctgtga | aggtcatgga | 2340 |
| cctgcccacc | caggagccag | cactggggac | cacctgctac | gcctcaggct | ggggcagcat | 2400 |
| tgaaccagag | gagttcttga | ccccaaagaa | acttcagtgt | gtggacctcc | atgttatttc | 2460 |
| caatgacgtg | tgtgcgcaag | ttcaccctca | gaaggtgacc | aagttcatgc | tgtgtgctgg | 2520 |
| acgctggaca | gggggcaaaa | gcacctgctc | gggtgattct | gggggcccac | ttgtctgtaa | 2580 |
| tggtgtgctt | caaggtatca | cgtcatgggg | cagtgaacca | tgtgccctgc | cgaaaggcc | 2640 |
| ttccctgtac | accaaggtgg | tgcattaccg | gaagtggatc | aaggacacca | tcgtggccaa | 2700 |
| ccccggatcc | gaaggtaggg | gttcattatt | gacctgtgga | gatgtcgaag | aaaacccagg | 2760 |
| acccgctagc | aaggctgtgc | tgcttgccct | gttgatggca | ggcttggccc | tgcagccagg | 2820 |
| cactgccctg | ctgtgctact | cctgcaaagc | ccaggtgagc | aacgaggact | gcctgcaggt | 2880 |
| ggagaactgc | acccagctgg | gggagcagtg | ctggaccgcg | cgcatccgcg | cagttggcct | 2940 |
| cctgaccgtc | atcagcaaag | gctgcagctt | gaactgcgtg | gatgactcac | aggactacta | 3000 |
| cgtgggcaag | aagaacatca | cgtgctgtga | caccgacttg | tgcaacgcca | gcggggccca | 3060 |
| tgccctgcag | ccggctgccg | ccatccttgc | gctgctccct | gcactcggcc | tgctgctctg | 3120 |
| gggaccggc | cagctaggat | ccagacccct | gaactttgat | ctgctgaaac | tggcaggcga | 3180 |
| tgtgaaagc | aacccaggcc | caatggcaag | cgcgcgccgc | ccgcgctggc | tgtgcgctgg | 3240 |
| ggcgctggtg | ctggcgggtg | gcttcttttct | cctcggcttc | ctcttcgggt | ggtttataaa | 3300 |

```
atcctccaat gaagctacta acattactcc aaagcataat atgaaagcat ttttggatga    3360
attgaaagct gagaacatca agaagttctt atataatttt acacagatac cacatttagc    3420
aggaacagaa caaaactttc agcttgcaaa gcaaattcaa tcccagtgga agaatttgg     3480
cctggattct gttgagctgg cacattatga tgtcctgttg tcctacccaa ataagactca    3540
tcccaactac atctcaataa ttaatgaaga tggaaatgag attttcaaca catcattatt    3600
tgaaccacct cctccaggat atgaaaatgt ttcggatatt gtaccacctt tcagtgcttt    3660
ctctcctcaa ggaatgccag agggcgatct agtgtatgtt aactatgcac gaactgaaga    3720
cttctttaaa ttggaacggg acatgaaaat caattgctct gggaaaattg taattgccag    3780
atatgggaaa gttttcagag gaaataaggt taaaaatgcc cagctggcag ggccaaagg     3840
agtcattctc tactccgacc ctgctgacta ctttgctcct ggggtgaagt cctatccaga    3900
tggttggaat cttcctggag gtggtgtcca gcgtggaaat atcctaaatc tgaatggtgc    3960
aggagaccct ctcacaccag gttacccagc aaatgaatat gcttataggc gtggaattgc    4020
agaggctgtt ggtcttccaa gtattcctgt tcatccaatt ggatactatg atgcacagaa    4080
gctcctagaa aaaatgggtg gctcagcacc accagatagc agctggagag gaagtctcaa    4140
agtgccctac aatgttggac ctggctttac tggaaacttt tctacacaaa aagtcaagat    4200
gcacatccac tctaccaatg aagtgacaag aatttacaat gtgataggta ctctcagagg    4260
agcagtggaa ccagacagat atgtcattct gggaggtcac cgggactcat gggtgtttgg    4320
tggtattgac cctcagagtg gagcagctgt tgttcatgaa attgtgagga gctttggaac    4380
actgaaaaag gaagggtgga gacctagaag aacaattttg tttgcaagct gggatgcaga    4440
agaatttggt cttcttggtt ctactgagtg ggcagaggag aattcaagac tccttcaaga    4500
gcgtggcgtg gcttatatta atgctgactc atctatagaa ggaaactaca ctctgagagt    4560
tgattgtaca ccgctgatgt acagcttggt acacaaccta acaaaagagc tgaaaagccc    4620
tgatgaaggc tttgaaggca atctctttta tgaaagttgg actaaaaaaa gtccttcccc    4680
agagttcagt ggcatgccca ggataagcaa attgggatct ggaaatgatt ttgaggtgtt    4740
cttccaacga cttggaattg cttcaggcag agcacggtat actaaaaatt gggaaacaaa    4800
caaattcagc ggctatccac tgtatcacag tgtctatgaa acatatgagt ggtggtggaaa    4860
gttttatgat ccaatgttta aatatcacct cactgtggcc caggttcgag gagggatggt    4920
gtttgagctg gccaattcca tagtgctccc ttttgattgt cgagattatg ctgtagtttt    4980
aagaaagtat gctgacaaaa tctacagtat ttctatgaaa catccacagg aaatgaagac    5040
atacagtgta tcatttgatt cacttttttc tgcagtaaag aattttacag aaattgcttc    5100
caagttcagt gagagactcc aggactttga caaaagcaac ccaatagtat taagaatgat    5160
gaatgatcaa ctcatgtttc tggaaagagc atttattgat ccattagggt taccagacag    5220
gccttttttat aggcatgtca tctatgctcc aagcagccac aacaagtatg caggggagtc    5280
attcccagga atttatgatg ctctgtttga tattgaaagc aaagtggacc cttccaaggc    5340
ctggggagaa gtgaagagac agatttatgt tgcagccttc acagtgcagg cagctgcaga    5400
gactttgagt gaagtagcct aaagatctgg gccctaacaa acaaaaaga tggggttatt    5460
ccctaaactt catgggttac gtaattggaa gttggggggac attgccacaa gatcatattg    5520
tacaaaagat caaacactgt tttagaaaac ttcctgtaaa caggcctatt gattggaaag    5580
tatgtcaaag gattgtgggt cttttgggct ttgctgctcc atttacacaa tgtggatatc    5640
```

```
ctgccttaat gcctttgtat gcatgtatac aagctaaaca ggctttcact ttctcgccaa    5700
cttacaaggc ctttctaagt aaacagtaca tgaacccttta ccccgttgct cggcaacggc   5760
ctggtctgtg ccaagtgttt gctgacgcaa ccccactgg ctggggcttg ccataggcc      5820 atcagcgcat gcgtggaacc tttgtggctc ctctgccgat ccatactgcg gaactcctag   5880
ccgcttgttt tgctcgcagc cggtctggag caaagctcat aggaactgac aattctgtcg   5940
tcctctcgcg gaaatataca tcgtttcgat ctacgtatga tcttttttccc tctgccaaaa   6000 attatgggga catcatgaag ccccttgagc atctgacttc tggctaataa ggaaattta    6060 ttttcattgc aatagtgtgt tggaatttttt tgtgtctctc actcggaagg aattctgcat   6120
taatgaatcg gccaacgcgc ggggagaggc ggtttgcgta ttgggcgctc ttccgcttcc   6180
tcgctcactg actcgctgcg ctcggtcgtt cggctgcggc gagcggtatc agctcactca   6240
aaggcggtaa tacggttatc cacagaatca ggggataacg caggaaagaa catgtgagca   6300
aaaggccagc aaaaggccag gaaccgtaaa aaggccgcgt tgctggcgtt tttccatagg   6360
ctccgccccc ctgacgagca tcacaaaaat cgacgctcaa gtcagaggtg gcgaaacccg   6420
acaggactat aaagatacca ggcgtttccc cctggaagct ccctcgtgcg ctctcctgtt   6480
ccgaccctgc cgcttaccgg atacctgtcc gcctttctcc cttcgggaag cgtggcgctt   6540
tctcatagct cacgctgtag gtatctcagt tcggtgtagg tcgttcgctc caagctgggc   6600
tgtgtgcaca accccccgt tcagcccgac cgctgcgcct tatccggtaa ctatcgtctt    6660
gagtccaacc cggtaagaca cgacttatcg ccactggcag cagccactgg taacaggatt   6720
agcagagcga ggtatgtagg cggtgctaca gagttcttga agtggtggcc taactacggc   6780
tacactagaa gaacagtatt tggtatctgc gctctgctga agccagttac cttcggaaaa   6840
agagttggta gctcttgatc cggcaaacaa accaccgctg gtagcggtgg ttttttttgtt   6900 tgcaagcagc agattacgcg cagaaaaaaa ggatctcaag aagatccttt gatcttttct   6960
acggggtctg acgctcagtg gaacgaaaac tcacgttaag ggattttggt catgagatta   7020
tcaaaaagga tcttcaccta gatccttttta aattaaaaat gaagttttaa atcaatctaa   7080
agtatatatg agtaaacttg gtctgacagt taccaatgct taatcagtga ggcacctatc   7140
tcagcgatct gtctatttcg ttcatccata gttgcctgac tc                       7182
```

<210> SEQ ID NO 47
<211> LENGTH: 261
<212> TYPE: PRT
<213> ORGANISM: Homo sapiens

<400> SEQUENCE: 47

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
```

```
            100                 105                 110
Pro Gly Asp Asp Ser Ser His Asp Leu Met Leu Leu Arg Leu Ser Glu
            115                 120                 125

Pro Ala Glu Leu Thr Asp Ala Val Lys Val Met Asp Leu Pro Thr Gln
        130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 48
<211> LENGTH: 123
<212> TYPE: PRT
<213> ORGANISM: Homo sapiens

<400> SEQUENCE: 48

Met Lys Ala Val Leu Leu Ala Leu Leu Met Ala Gly Leu Ala Leu Gln
1               5                   10                  15

Pro Gly Thr Ala Leu Leu Cys Tyr Ser Cys Lys Ala Gln Val Ser Asn
            20                  25                  30

Glu Asp Cys Leu Gln Val Glu Asn Cys Thr Gln Leu Gly Glu Gln Cys
        35                  40                  45

Trp Thr Ala Arg Ile Arg Ala Val Gly Leu Leu Thr Val Ile Ser Lys
    50                  55                  60

Gly Cys Ser Leu Asn Cys Val Asp Asp Ser Gln Asp Tyr Tyr Val Gly
65                  70                  75                  80

Lys Lys Asn Ile Thr Cys Cys Asp Thr Asp Leu Cys Asn Ala Ser Gly
                85                  90                  95

Ala His Ala Leu Gln Pro Ala Ala Ala Ile Leu Ala Leu Leu Pro Ala
            100                 105                 110

Leu Gly Leu Leu Leu Trp Gly Pro Gly Gln Leu
        115                 120

<210> SEQ ID NO 49
<211> LENGTH: 24
<212> TYPE: DNA
<213> ORGANISM: Artificial Sequence
<220> FEATURE:
<223> OTHER INFORMATION: Synthetic Construct

<400> SEQUENCE: 49
tcgtcgtttt gtcgttttgt cgtt                                          24

<210> SEQ ID NO 50
<211> LENGTH: 21
```

```
<212> TYPE: DNA
<213> ORGANISM: Artificial Sequence
<220> FEATURE:
<223> OTHER INFORMATION: Synthetic Construct

<400> SEQUENCE: 50
tcgtcgtttt tcggtgcttt t                                              21

<210> SEQ ID NO 51
<211> LENGTH: 21
<212> TYPE: DNA
<213> ORGANISM: Artificial Sequence
<220> FEATURE:
<223> OTHER INFORMATION: Synthetic Construct

<400> SEQUENCE: 51
tcgtcgtttt tcggtcgttt t                                              21
```

ANTI-PD-1 ANTIBODIES AND METHODS OF USE THEREOF

CROSS-REFERENCE TO RELATED APPLICATIONS

This application claims priority, under 35 USC § 119(e), to the following US provisional applications: U.S. Patent Application No. 62/089,658, filed Dec. 9, 2014, U.S. Patent Application No. 62/242,750, filed Oct. 16, 2015, and U.S. Patent Application No. 62/251,973, filed Nov. 6, 2015, each of which is hereby incorporated by reference in its entirety.

REFERENCE TO SEQUENCE LISTING

This application is being filed electronically via EFS-Web and includes an electronically submitted sequence listing in .txt format. The .txt file contains a sequence listing entitled "PC72121A_SeqListing_ST25.txt" created on Nov. 10, 2015 and having a size of 139 KB. The sequence listing contained in this .txt file is part of the specification and is herein incorporated by reference in its entirety.

FIELD

The present invention relates to antibodies, e.g., full length antibodies that bind PD-1. The invention further relates to compositions comprising antibodies to PD-1, and methods of using anti-PD-1 antibodies as a medicament. Certain embodiments relate to methods of using anti-PD-1 antibodies for the treatment, prevention and/or diagnosis of various diseases, including hyperproliferative disease, such as cancer.

BACKGROUND

PD-1 is a 50-55 kDa type I transmembrane receptor that was originally identified in a T cell line undergoing activation-induced apoptosis. PD-1 is expressed on T cells, B cells, and macrophages. The ligands for PD-1 are the B7 family members PD-L1 (B7-H1) and PD-L2 (B7-DC).

PD-1 is a member of the immunoglobulin (Ig) superfamily that contains a single Ig V-like domain in its extracellular region. The PD-1 cytoplasmic domain contains two tyrosines, with the most membrane-proximal tyrosine (VAYEEL in mouse PD-1) located within an ITIM (immuno-receptor tyrosine-based inhibitory motif). The presence of an ITIM on PD-1 indicates that this molecule functions to attenuate antigen receptor signaling by recruitment of cytoplasmic phosphatases. Human and murine PD-1 proteins share about 60% amino acid identity with conservation of four potential N-glycosylation sites, and residues that define the Ig-V domain. The ITIM in the cytoplasmic region and the ITIM-like motif surrounding the carboxy-terminal tyrosine are also conserved between human and murine orthologues.

Cancer immunotherapy has traditionally involved complicated methods using cells and individualized and time-consuming preparations. Recently, monoclonal antibody-based cancer immunotherapy based on the interruption of suppressive signals that are delivered to the adaptive immune system has shown promise in the clinic within the setting of off-the-shelf systemic immunotherapy. However, there is a continuing need in the art to obtain safer and more effective treatments for cancer.

SUMMARY

Antibodies that selectively interact with PD-1 are provided. It is demonstrated that certain anti-PD-1 antibodies are effective in vivo to prevent and/or treat cancer. Advantageously, the anti-PD-1 antibodies provided herein bind human, cynomolgous monkey, and mouse PD-1. Also advantageously, the anti-PD-1 antibodies provided herein are effective in vivo to stimulate T cell proliferation.

Isolated antagonist antibodies that specifically bind to PD-1 and prevent or reduce the biological effect of PD-1 are provided herein. In some embodiments, the antagonist antibody can be, for example, a human, humanized, or chimeric antibody. The invention disclosed herein is directed to antibodies that bind to PD-1.

In one aspect, the invention provides an isolated antagonist antibody which specifically binds to PD-1, wherein the antibody comprises a heavy chain variable region (VH) comprising a VH complementarity determining region one (CDR1), VH CDR2, and VH CDR3 of the VH having an amino acid sequence selected group the group consisting of SEQ ID NO: 3, SEQ ID NO: 4; SEQ ID NO: 5; and SEQ ID NO: 6; and a light chain variable region (VL) comprising a VL CDR1, VL CDR2, and VL CDR3 of the VL having an amino acid sequence selected from the group consisting of SEQ ID NO: 2; SEQ ID NO:7; SEQ ID NO: 8; and SEQ ID NO: 9.

In some embodiments, the VH region comprises the amino acid sequence shown in SEQ ID NO: 3, 4, 5, or 6, or a variant with one or several conservative amino acid substitutions in residues that are not within a CDR and/or the VL region comprises the amino acid sequence shown in SEQ ID NO: 2, 7, 8, or 9, or a variant thereof with one or several amino acid substitutions in amino acids that are not within a CDR. In some embodiments, the antibody comprises a light chain comprising the sequence shown in SEQ ID NO: 39 and/or a heavy chain comprising the sequence shown in SEQ ID NO: 29 or 38. In some embodiments, the antibody comprises a VH region produced by the expression vector with ATCC Accession No. PTA-121183. In some embodiments, the antibody comprises a VL region produced by the expression vector with ATCC Accession No. PTA-121182.

In another aspect, the invention provides an isolated antibody which specifically binds to PD-1, wherein the antibody comprises a VH CDR1 comprising the amino acid sequence of SEQ ID NO: 13, 14, or 15, a VH CDR2 comprising the amino acid sequence of SEQ ID NO: 16, 17, 24, 25, 27, 28, 35, or 36, a VH CDR3 comprising the amino acid sequence shown in SEQ ID NO: 18, 23, 26, or 37, a VL CDR1 comprising the amino acid sequence shown in SEQ ID NO:10, 22, 30, or 32, a VL CDR2 comprising the amino acid sequence shown in SEQ ID NO: 11, 20, or 33 and a VL CDR3 comprising the amino acid sequence shown in SEQ ID NO: 12, 21, 31, or 34.

In some embodiments, the antibody can be a human antibody, a humanized antibody, or a chimeric antibody. In some embodiments, the antibody is a monoclonal antibody.

In some embodiments, the antibody comprises a constant region. In some embodiments, the antibody is of the human IgG$_1$, IgG$_2$, IgG$_{2\Delta a}$, IgG$_3$, IgG$_4$, IgG$_{4\Delta b}$, IgG$_{4\Delta c}$, IgG$_4$ S228P, IgG$_{4\Delta b}$ S228P, and IgG$_{4\Delta c}$ S228P subclass. In some embodiments, the antibody is of the IgG4 isotype and comprises a stabilized hinge, e.g., S228P.

In another aspect, the invention provides an isolated antibody which specifically binds to PD-1 and competes with and/or binds to the same PD-1 epitope as the antibodies as described herein.

In some embodiments, an anti-PD-1 antibody provided herein promotes IFNγ and/or TNF secretion from T cells.

In some embodiments, an anti-PD-1 antibody provided herein promotes proliferation of T cells.

In some embodiments, an anti-PD-1 antibody provided herein inhibits tumor growth.

In some embodiments, an anti-PD-1 antibody provided herein binds human PD-1 and mouse PD-1.

In another aspect, the invention provides a pharmaceutical composition comprising a therapeutically effective amount of a PD-1 antibody as described herein and a pharmaceutically acceptable carrier.

In another aspect, the invention provides an isolated polynucleotide comprising a nucleotide sequence encoding a PD-1 antibody as described herein. In another aspect, the invention provides a vector comprising the polynucleotide.

In another aspect, the invention provides an isolated host cell that recombinantly produces a PD-1 antibody as described herein.

In another aspect, the invention provides a method of producing an anti-PD-1 antagonist antibody, the method comprising: culturing a cell line that recombinantly produces the antibody as described herein under conditions wherein the antibody is produced; and recovering the antibody.

In another aspect, the invention provides a method of producing an anti-PD-1 antagonist antibody, the method comprising: culturing a cell line comprising nucleic acid encoding an antibody comprising a heavy chain comprising the amino acid sequence shown in SEQ ID NO: 29 or 38 and a light chain comprising the amino acid sequence shown in SEQ ID NO: 39 under conditions wherein the antibody is produced; and recovering the antibody.

In some embodiments, the heavy and light chains are encoded on separate vectors. In other embodiments, heavy and light chains are encoded on the same vector.

In another aspect, the invention provides a method for treating a condition in a subject comprising administering to the subject in need thereof an effective amount of the pharmaceutical composition as described herein. In some embodiments, the condition is a cancer. In some embodiments, the cancer is selected from the group consisting of gastric cancer, sarcoma, lymphoma, leukemia, head and neck cancer, thymic cancer, epithelial cancer, salivary cancer, liver cancer, stomach cancer, thyroid cancer, lung cancer, ovarian cancer, breast cancer, prostate cancer, esophageal cancer, pancreatic cancer, glioma, leukemia, multiple myeloma, renal cell carcinoma, bladder cancer, cervical cancer, choriocarcinoma, colon cancer, oral cancer, skin cancer, and melanoma. In some embodiments, the subject is a previously treated adult patient with locally advanced or metastatic melanoma, squamous cell head and neck cancer (SCHNC), ovarian carcinoma, sarcoma, or relapsed or refractory classic Hodgkin's Lymphoma (cHL). In some embodiments, the cancer can be a platinum resistant and/or platinum refractory cancer, such as, for example, platinum resistant and/or refractory ovarian cancer, platinum resistant and/or refractory breast cancer, or platinum resistant and/or refractory lung cancer. In some embodiments, an anti-PD-1 antibody is administered at a dosage of about 0.5 mg/kg, about 1.0 mg/kg, about 3.0 mg/kg, or about 10 mg/kg. In some embodiments, the anti-PD-1 antibody is administered once every 7, 14, 21, or 28 days. In some embodiments, the anti-PD-1 antibody is administered intravenously or subcutaneously.

In another aspect, the invention provides a method of inhibiting tumor growth or progression in a subject who has a tumor, comprising administering to the subject an effective amount of the pharmaceutical composition as described herein.

In another aspect, the invention provides a method of inhibiting or preventing metastasis of cancer cells in a subject, comprising administering to the subject in need thereof an effective amount of the pharmaceutical composition as described herein.

In another aspect, the invention provides a method of inducing tumor regression in a subject who has a PD-1 expressing tumor, comprising administering to the subject an effective amount of the pharmaceutical composition as described herein.

In some embodiments, the antibody herein can be administered parenterally in a subject. In some embodiments, the subject is a human.

In some embodiments, the method can further comprise administering an effective amount of a second therapeutic agent. In some embodiments, the second therapeutic agent is, for example, crizotinib, palbociclib, an anti-CTLA4 antibody, an anti-4-1BB antibody, or a second PD-1 antibody.

Also provided is the use of any of the anti-PD-1 antagonist antibodies provided herein in the manufacture of a medicament for the treatment of cancer or for inhibiting tumor growth or progression in a subject in need thereof. In some embodiments, the anti-PD-1 antagonist antibody reduces weight gain in the subject.

Also provided are anti-PD-1 antagonist antibodies for use in the treatment of a cancer or for inhibiting tumor growth or progression in a subject in need thereof. In some embodiments, the cancer is, for example without limitation, gastric cancer, sarcoma, lymphoma, Hodgkin's lymphoma, leukemia, head and neck cancer, thymic cancer, epithelial cancer, salivary cancer, liver cancer, stomach cancer, thyroid cancer, lung cancer (including, for example, non-small-cell lung carcinoma), ovarian cancer, breast cancer, prostate cancer, esophageal cancer, pancreatic cancer, glioma, leukemia, multiple myeloma, renal cell carcinoma, bladder cancer, cervical cancer, chonocarcinoma, colon cancer, oral cancer, skin cancer, and melanoma.

In another aspect, the present disclosure provides a method for enhancing the immunogenicity or therapeutic effect of a vaccine for the treatment of a cancer in a mammal, particularly a human, which method comprises administering to the mammal receiving the vaccine an effective amount of anti-PD-1 antagonist antibody provided by the present disclosure.

In another aspect, the present disclosure provides a method for treating a cancer in a mammal, particularly a human, which method comprises administering to the mammal (1) an effective amount of a vaccine capable of eliciting an immune response against cells of the cancer and (2) an effective amount of an anti-PD-1 antagonist antibody provided by the present disclosure.

BRIEF DESCRIPTION OF THE FIGURES/DRAWINGS

DETAILED DESCRIPTION

Figure 1A:
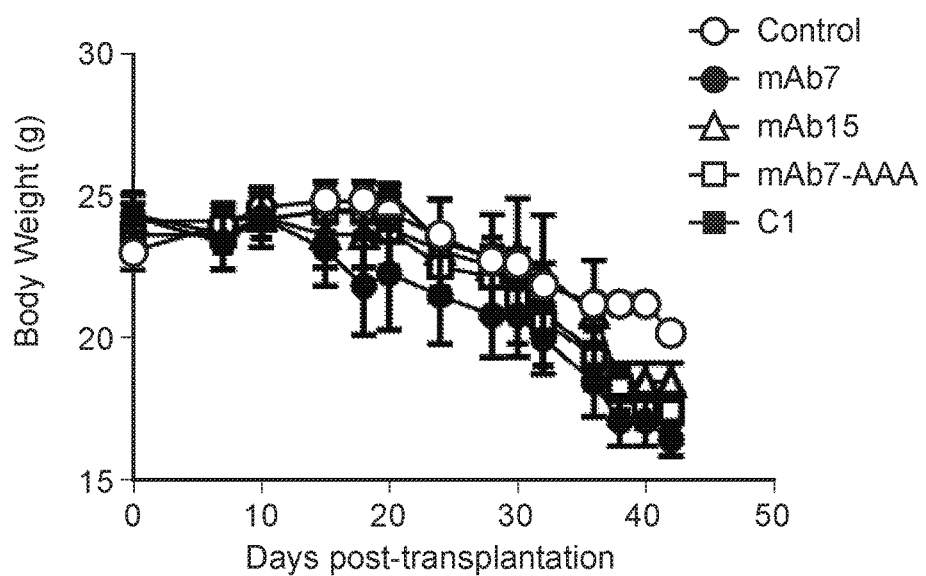
FIG. 1A depicts a graph summarizing body weight of mice treated with anti-PD-1 antagonist antibody.
Figure 1B:
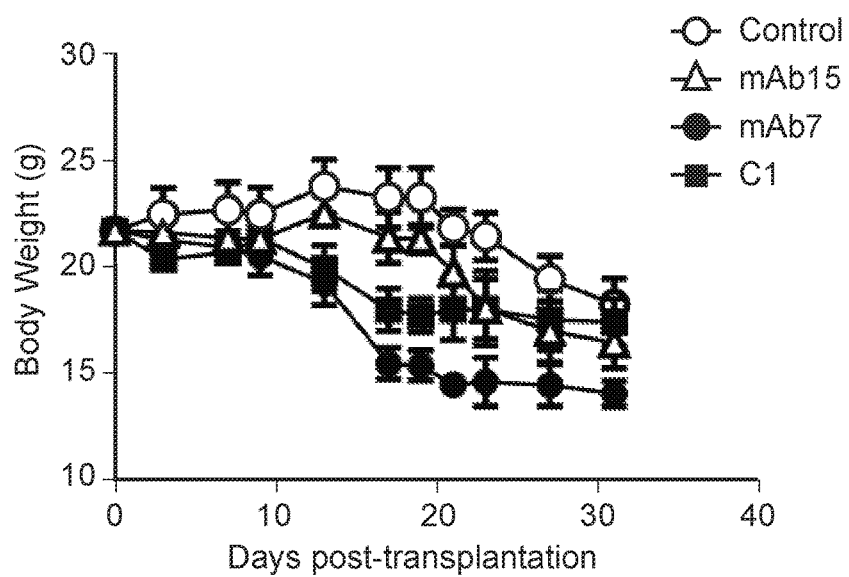
FIG. 1B depicts a graph summarizing body weight of mice treated with anti-PD-1 antagonist antibody.
Figure 1C:
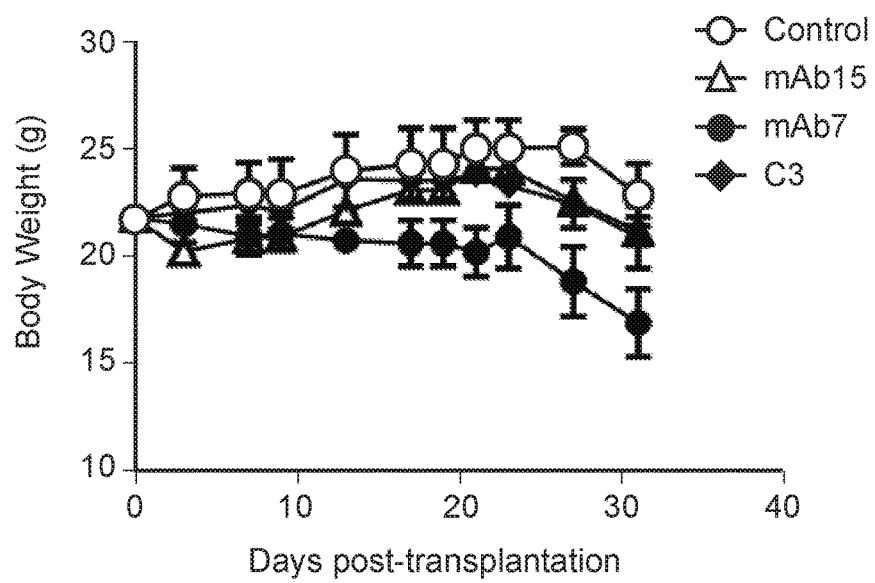
FIG. 1C depicts a graph summarizing body weight of mice treated with anti-PD-1 antagonist antibody.
Figure 1D:
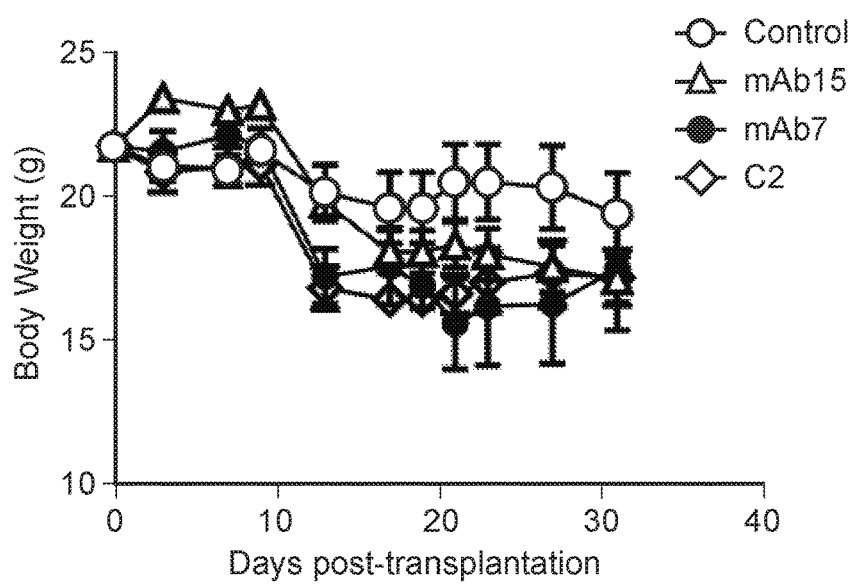
FIG. 1D depicts a graph summarizing body weight of mice treated with anti-PD-1 antagonist antibody.
Figure 1E:
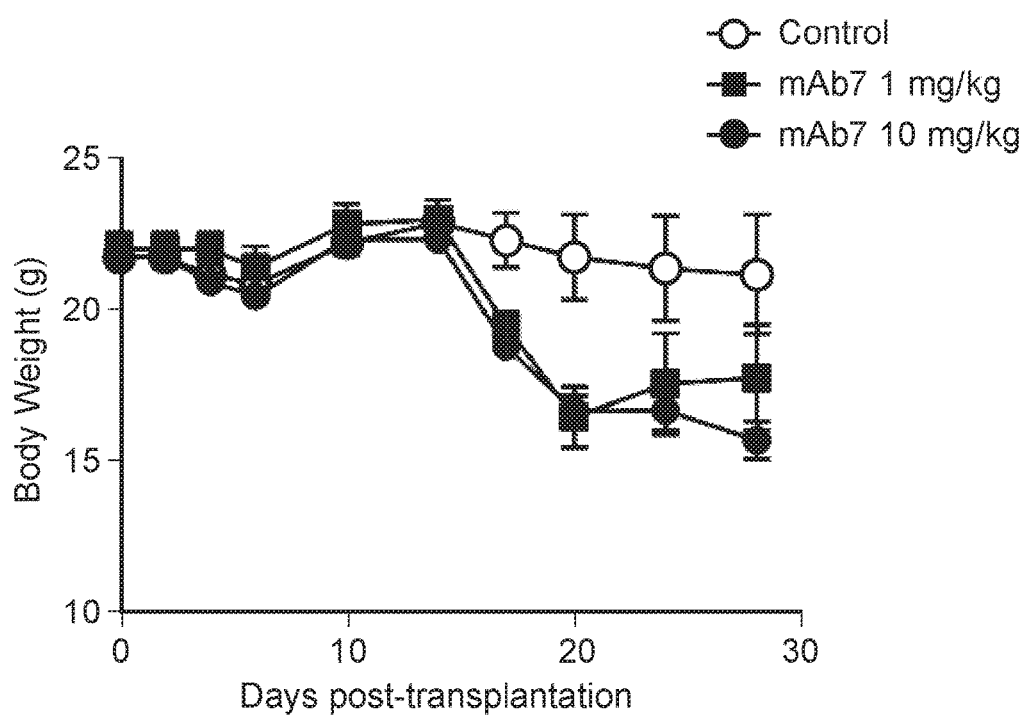
FIG. 1E depicts a graph summarizing body weight of mice treated with anti-PD-1 antagonist antibody.

Disclosed herein are antibodies that specifically bind to PD-1. Methods of making anti-PD-1 antibodies, compositions comprising these antibodies, and methods of using these antibodies as a medicament are provided. Anti-PD-1 antibodies can be used to inhibit tumor progression, and can be used in the prevention and/or treatment of cancer and/or other diseases.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

The following terms, unless otherwise indicated, shall be understood to have the following meanings: the term "isolated molecule" as referring to a molecule (where the molecule is, for example, a polypeptide, a polynucleotide, or an antibody) that by virtue of its origin or source of derivation (1) is not associated with naturally associated components that accompany it in its native state, (2) is substantially free of other molecules from the same source, e.g., species, cell from which it is expressed, library, etc., (3) is expressed by a cell from a different species, or (4) does not occur in nature. Thus, a molecule that is chemically synthesized, or expressed in a cellular system different from the system from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', F(ab')$_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$ and IgA$_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

A "variable region" of an antibody refers to the variable region of the antibody light chain or the variable region of the antibody heavy chain, either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonincal class as the subject variable region (Chothia and Lesk, J Mol Biol 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the AbM definition, the contact definition, and the conformational definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Nati Acad Sci (USA), 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As known in the art, a "constant region" of an antibody refers to the constant region of the antibody light chain or the constant region of the antibody heavy chain, either alone or in combination.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example. As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "epitope" refers to that portion of a molecule capable of being recognized by and bound by an antibody at one or more of the antibody's antigen-binding regions. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to PD-1, e.g., the antibodies compete for binding to the antigen.

As used herein, the term "PD-1" refers to any form of PD-1 and variants thereof that retain at least part of the activity of PD-1. Unless indicated differently, such as by specific reference to human PD-1, PD-1 includes all mammalian species of native sequence PD-1, e.g., human, canine, feline, equine, and bovine. One exemplary human PD-1 is found as Uniprot Accession Number Q15116 (SEQ ID NO: 1).

The term "agonist" refers to a substance which promotes (i.e., induces, causes, enhances, or increases) the biological activity or effect of another molecule. The term agonist encompasses substances which bind receptor, such as an antibody, and substances which promote receptor function without binding thereto (e.g., by activating an associated protein).

The term "antagonist" or "inhibitor" refers to a substance that prevents, blocks, inhibits, neutralizes, or reduces a biological activity or effect of another molecule, such as a receptor.

The term "antagonist antibody" refers to an antibody that binds to a target and prevents or reduces the biological effect of that target. In some embodiments, the term can denote an antibody that prevents the target, e.g., PD-1, to which it is bound from performing a biological function.

As used herein, an "anti-PD-1 antagonist antibody" refers to an antibody that is able to inhibit PD-1 biological activity and/or downstream events(s) mediated by PD-1. Anti-PD-1 antagonist antibodies encompass antibodies that block, antagonize, suppress or reduce (to any degree including significantly) PD-1 biological activity, including downstream events mediated by PD-1, such PD-L1 binding and downstream signaling, PD-L2 binding and downstream signaling, inhibition of T cell proliferation, inhibition of T cell activation, inhibition of IFN secretion, inhibition of IL-2 secretion, inhibition of TNF secretion, induction of IL-10, and inhibition of anti-tumor immune responses. For purposes of the present invention, it will be explicitly understood that the term "anti-PD-1 antagonist antibody" (interchangeably termed "antagonist PD-1 antibody", "antagonist anti-PD-1 antibody" or "PD-1 antagonist antibody") encompasses all the previously identified terms, titles, and functional states and characteristics whereby PD-1 itself, a PD-1 biological activity, or the consequences of the biological activity, are substantially nullified, decreased, or neutralized in any meaningful degree. In some embodiments, an anti-PD-1 antagonist antibody binds PD-1 and upregulates an anti-tumor immune response. Examples of anti-PD-1 antagonist antibodies are provided herein.

The terms "polypeptide", "oligopeptide", "peptide" and "protein" are used interchangeably herein to refer to chains of amino acids of any length. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, an antibody "interacts with" PD-1 when the equilibrium dissociation constant is equal to or less than 20 nM, preferably less than about 6 nM, more preferably less than about 1 nM, most preferably less than about 0.2 nM, as measured by the methods disclosed herein in Example 7.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a PD-1 epitope is an antibody that binds this epitope with greater affinity, avidity, more readily, and/or with greater duration than it binds to other PD-1 epitopes or non-PD-1 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3. As is known in the art, an Fc region can be present in dimer or monomeric form.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of a tumor, remission of cancer, decreasing symptoms resulting from cancer, increasing the quality of life of those suffering from cancer, decreasing the dose of other medications required to treat cancer, delaying the progression of cancer, curing a cancer, and/or prolong survival of patients having cancer.

"Ameliorating" means a lessening or improvement of one or more symptoms as compared to not administering an anti-PD-1 antagonist antibody. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. In more specific aspects, an effective amount prevents, alleviates or ameliorates symptoms of disease, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of a disease such as, for example, cancer including, for example without limitation, gastric cancer, sarcoma, lymphoma, Hodgkin's lymphoma, leukemia, head and neck cancer, squamous cell head and neck cancer, thymic cancer, epithelial cancer, salivary cancer, liver cancer, stomach cancer, thyroid cancer, lung cancer, ovarian cancer, breast cancer, prostate cancer, esophageal cancer, pancreatic cancer, glioma, leukemia, multiple myeloma, renal cell carcinoma, bladder cancer, cervical cancer, choriocarcinoma, colon cancer, oral cancer, skin cancer, and melanoma, decreasing the dose of other medications required to treat the disease, enhancing the effect of another medication, and/or delaying the progression of the cancer in patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals (e.g., cows, pigs, horses, chickens, etc.), sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$k_{on}$", as used herein, refers to the rate constant for association of an antibody to an antigen. Specifically, the rate constants ($k_{on}$ and $k_{off}$) and equilibrium dissociation constants are measured using full-length antibodies and/or Fab antibody fragments (i.e. univalent) and PD-1.

The term "$k_{off}$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range.

The term "immune-effector-cell enhancer" or "IEC enhancer" refers to a substance capable of increasing or enhancing the number, quality, or function of one or more types of immune effector cells of a mammal. Examples of immune effector cells include cytolytic CD8 T cells, CD4 T cells, NK cells, and B cells.

The term "immune modulator" refers to a substance capable of altering (e.g., inhibiting, decreasing, increasing, enhancing, or stimulating) the immune response (as defined herein) or the working of any component of the innate, humoral or cellular immune system of a host mammal. Thus, the term "immune modulator" encompasses the "immune-effector-cell enhancer" as defined herein and the "immune-suppressive-cell inhibitor" as defined herein, as well as substance that affects other components of the immune system of a mammal.

The term "immune response" refers to any detectable response to a particular substance (such as an antigen or immunogen) by the immune system of a host mammal, such as innate immune responses (e.g., activation of Toll receptor signaling cascade), cell-mediated immune responses (e.g., responses mediated by T cells, such as antigen-specific T cells, and non-specific cells of the immune system), and humoral immune responses (e.g., responses mediated by B cells, such as generation and secretion of antibodies into the plasma, lymph, and/or tissue fluids).

The term "immunogenic" refers to the ability of a substance to cause, elicit, stimulate, or induce an immune response, or to improve, enhance, increase or prolong a pre-existing immune response, against a particular antigen, whether alone or when linked to a carrier, in the presence or absence of an adjuvant.

The term "immune-suppressive-cell inhibitor" or "ISC inhibitor" refers to a substance capable of reducing or suppressing the number or function of immune suppressive cells of a mammal. Examples of immune suppressive cells include regulatory T cells ("T regs"), myeloid-derived suppressor cells, and tumor-associated macrophages.

The term "intradermal administration," or "administered intradermally," in the context of administering a substance to a mammal including a human, refers to the delivery of the substance into the dermis layer of the skin of the mammal. The skin of a mammal is composed of an epidermis layer, a dermis layer, and a subcutaneous layer. The epidermis is the outer layer of the skin. The dermis, which is the middle layer of the skin, contains nerve endings, sweat glands and oil (sebaceous) glands, hair follicles, and blood vessels. The subcutaneous layer is made up of fat and connective tissue that houses larger blood vessels and nerves. In contrast in intradermal administration, "subcutaneous administration" refers to the administration of a substance into the subcutaneous layer and "topical administration" refers to the administration of a substance onto the surface of the skin.

The term "neoplastic disorder" refers to a condition in which cells proliferate at an abnormally high and uncontrolled rate, the rate exceeding and uncoordinated with that of the surrounding normal tissues. It usually results in a solid lesion or lump known as "tumor." This term encompasses benign and malignant neoplastic disorders. The term "malignant neoplastic disorder", which is used interchangeably with the term "cancer" in the present disclosure, refers to a neoplastic disorder characterized by the ability of the tumor cells to spread to other locations in the body (known as "metastasis"). The term "benign neoplastic disorder" refers to a neoplastic disorder in which the tumor cells lack the ability to metastasize.

The term "preventing" or "prevent" refers to (a) keeping a disorder from occurring or (b) delaying the onset of a disorder or onset of symptoms of a disorder.

The term "tumor-associated antigen" or "TAA" refers to an antigen which is specifically expressed by tumor cells or expressed at a higher frequency or density by tumor cells than by non-tumor cells of the same tissue type. Tumor-associated antigens may be antigens not normally expressed by the host; they may be mutated, truncated, misfolded, or otherwise abnormal manifestations of molecules normally expressed by the host; they may be identical to molecules normally expressed but expressed at abnormally high levels; or they may be expressed in a context or milieu that is abnormal. Tumor-associated antigens may be, for example, proteins or protein fragments, complex carbohydrates, gangliosides, haptens, nucleic acids, or any combination of these or other biological molecules.

The term "vaccine" refers to an immunogenic composition for administration to a mammal for eliciting an immune response against a particular antigen in the mammal. A vaccine typically contains an agent (known as "antigen" or "immunogen") that resembles, or is derived from, the target of the immune response, such as a disease-causing microorganism or tumor cells. A vaccine intended for the treatment of a tumor, such as a cancer, typically contains an antigen that is derived from a TAA found on the target tumor and is able to elicit immunogenicity against the TAA on the target tumor.

The term "vaccine-based immunotherapy regimen" refers to a therapeutic regimen in which a vaccine is administered in combination with one or more immune modulators. The vaccine and the immune modulators may be administered together in a single formulation or administered separately It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

Exemplary methods and materials are described herein, although methods and materials similar or equivalent to those described herein can also be used in the practice or testing of the present invention. The materials, methods, and examples are illustrative only and not intended to be limiting.

Anti-PD-1 Antagonist Antibodies

Provided herein are anti-PD-1 antagonist antibodies that block, suppress or reduce (including significantly reduces) PD-1 biological activity, including downstream events mediated by PD-1. An anti-PD-1 antagonist antibody should exhibit any one or more of the following characteristics: (a) bind to PD-1 and block downstream signaling events; (b) block PD-L1 binding to PD-1; (c) upregulate a T cell-mediated immune response; (d) stimulate IFNγ secretion; (e) stimulate TNF secretion; (f) increase T cell proliferation; and (g) reduce inhibitory signal transduction through PD-1.

For purposes of this invention, the antibody preferably reacts with PD-1 in a manner that inhibits PD-1 signaling function. In some embodiments, the anti-PD-1 antagonist antibody specifically binds primate PD-1.

The antibodies useful in the present invention can encompass monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, the anti-PD-1 antagonist antibody is a monoclonal antibody. In some embodiments, the antibody is a human or humanized antibody.

The anti-PD-1 antagonist antibodies may be made by any method known in the art. General techniques for production of human and mouse antibodies are known in the art and/or are described herein.

Anti-PD-1 antagonist antibodies can be identified or characterized using methods known in the art, whereby reduction, amelioration, or neutralization of PD-1 biological activity is detected and/or measured. In some embodiments, an anti-PD-1 antagonist antibody is identified by incubating a candidate agent with PD-1 and monitoring binding and/or attendant reduction or neutralization of a biological activity of PD-1. The binding assay may be performed with, e.g., purified PD-1 polypeptide(s), or with cells naturally expressing (e.g., various strains), or transfected to express, PD-1 polypeptide(s). In one embodiment, the binding assay is a competitive binding assay, where the ability of a candidate antibody to compete with a known anti-PD-1 antagonist antibody for PD-1 binding is evaluated. The assay may be performed in various formats, including the ELISA format. In some embodiments, an anti-PD-1 antagonist antibody is identified by incubating a candidate antibody with PD-1 and monitoring binding.

Following initial identification, the activity of a candidate anti-PD-1 antagonist antibody can be further confirmed and refined by bioassays, known to test the targeted biological activities. In some embodiments, an in vitro cell assay is used to further characterize a candidate anti-PD-1 antagonist antibody. For example, a candidate antibody is incubated with primary human T cells, and PD-L1 is added, and IFNγ secretion is monitored. Alternatively, bioassays can be used to screen candidates directly.

The anti-PD-1 antagonist antibodies of the invention exhibit one or more of the following characteristics: (a) bind to PD-1 and block downstream signaling events; (b) block PD-L1 binding to PD-1; (c) upregulate a T cell-mediated immune response; (d) stimulate IFNγ secretion; (e) stimulate TNF secretion; (f) increase T cell proliferation; (g) reduce inhibitory signal transduction through PD-1; and (h) block PD-L2 binding to PD-1. Preferably, anti-PD-1 antibodies have two or more of these features. More preferably, the antibodies have three or more of the features. More preferably, the antibodies have four or more of the features. More preferably, the antibodies have five or more of the features. More preferably, the antibodies have six or more of the features. More preferably, the antibodies have seven or more of the features. Most preferably, the antibodies have all eight characteristics.

Anti-PD-1 antagonist antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an anti-PD-1 antagonist antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an anti-PD-1 antagonist antibody. In another example, the epitope to which the anti-PD-1 antagonist antibody binds can be determined in a systematic screening by using overlapping peptides derived from the PD-1 sequence and determining binding by the anti-PD-1 antagonist antibody. According to the gene fragment expression assays, the open reading frame encoding PD-1 is fragmented either randomly or by specific genetic constructions and the reactivity of the expressed fragments of PD-1 with the antibody to be tested is determined. The gene fragments may, for example, be produced by PCR and then transcribed and translated into protein in vitro, in the presence of radioactive amino acids. The binding of the antibody to the radioactively labeled PD-1 fragments is then determined by immunoprecipitation and gel electrophoresis. Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, alanine scanning mutagenesis experiments can be performed using a mutant PD-1 in which various residues of the PD-1 polypeptide have been replaced with alanine. By assessing binding of the antibody to the mutant PD-1, the importance of the particular PD-1 residues to antibody binding can be assessed.

Yet another method which can be used to characterize an anti-PD-1 antagonist antibody is to use competition assays with other antibodies known to bind to the same antigen, i.e., various fragments of PD-1, to determine if the anti-PD-1 antagonist antibody binds to the same epitope as other antibodies. Competition assays are well known to those of skill in the art, including in an ELISA format.

The binding affinity ($K_D$) of an anti-PD-1 antagonist antibody to PD-1 can be about 0.001 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, about 2 pM, or about 1 pM. In some embodiments, the binding affinity is less than any of about 250 nM, about 200 nM, about 100 nM, about 50 nM, about 10 nM, about 1 nM, about 500 pM, about 100 pM, about 50 pM, about 20 pM, about 10 pM, about 5 pM, or about 2 pM.

Accordingly, the invention provides any of the following, or compositions (including pharmaceutical compositions) comprising an antibody having a partial light chain sequence and a partial heavy chain sequence as found in Table 1, or variants thereof. In Table 1, the underlined sequences are CDR sequences. In Table 1, the $K_D$ indicates affinity for human PD-1 as measured using surface plasmon resonance at 25° C., unless indicated otherwise.

TABLE 1

Variable Regions Sequences of Anti-PD-1 antagonist Antibodies

| mAb | Light Chain | Heavy Chain | KD (nM) |
|---|---|---|---|
| mAb1 | DIVMTQSPDSLAVSLGERA TINCKSSQSLWDSGNQKNF LTWYQQKPGQPPKLLIYWT STRESGVPDRFSGSGSGT DFTLTISSLQAEDVAVYYCQ NDYFYPLTFGGGTKVEIK (SEQ ID NO: 2) | QVQLVQSGAEVKKPGASVKVS CKASGYTFTSYWINWVRQAP GQGLEWMGNIYPGSSLTNYN EKFKNRVTMTRDTSTSTVYME LSSLRSEDTAVYYCARLLTGTF AYWGQGTLVTSS (SEQ ID NO: 3) | 64.24 |

TABLE 1-continued

Variable Regions Sequences of Anti-PD-1 antagonist Antibodies

| mAb | Light Chain | Heavy Chain | KD (nM) |
| --- | --- | --- | --- |
| mAb2 | DIVMTQSPDSLAVSLGERA TINCKSSQSLWDSGNQKNF LTWYQQKPGQPPKLLIYWT SYRESGVPDRFSGSGSGT DFTLTISSLQAEDVAVYYCQ NDYFYPLTFGGGTKVEIK (SEQ ID NO: 7) | QVQLVQSGAEVKKPGASVKVS CKASGYTFTSYWINWVRQAP GQGLEWMGNIYPGSSLTNYN EKFKNRVTMTRDTSTSTVYME LSSLRSEDTAVYYCARLLTGTF AYWGQGTLVTVSS (SEQ ID NO: 3) | 2.22 |
| mAb3 | DIVMTQSPDSLAVSLGERA TINCKSSQSLWDSGNQKNF LTWYQQKPGQPPKLLIYWT SYRESGVPDRFSGSGSGT DFTLTISSLQAEDVAVYYCQ NDYFYPHTFGGGTKVEIK (SEQ ID NO: 8) | QVQLVQSGAEVKKPGASVKVS CKASGYTFTSYWINWVRQAP GQGLEWMGNIYPGSSLTNYN EKFKNRVTMTRDTSTSTVYME LSSLRSEDTAVYYCARLLTGTF AYWGQGTLVTVSS (SEQ ID NO: 3) | 1.43 |
| mAb4 | DIVMTQSPDSLAVSLGERA TINCKSSQSLWDSTNQKNF LTWYQQKPGQPPKLLIYWT STRESGVPDRFSGSGSGT DFTLTISSLQAEDVAVYYCQ NDYFYPLTFGGGTKVEIK (SEQ ID NO: 9) | QVQLVQSGAEVKKPGASVKVS CKASGYTFTSYWINWVRQAP GQGLEWMGNIYPGSSLTNYN EKFKNRVTMTRDTSTSTVYME LSSLRSEDTAVYYCARLLTGTF AYWGQGTLVTVSS (SEQ ID NO: 3) | 89 (at 37° C.) |
| mAb5 | DIVMTQSPDSLAVSLGERA TINCKSSQSLWDSGNQKNF LTWYQQKPGQPPKLLIYWT STRESGVPDRFSGSGSGT DFTLTISSLQAEDVAVYYCQ NDYFYPLTFGGGTKVEIK (SEQ ID NO: 2) | QVQLVQSGAEVKKPGASVKVS CKASGYTFTSYWINWVRQAP GQGLEWMGNIYPGSSLTNYN EKFKNRVTMTRDTSTSTVYME LSSLRSEDTAVYYCARLSTGTF AYWGQGTLVTVSS (SEQ ID NO: 4) | 12.82 |
| mAb6 | DIVMTQSPDSLAVSLGERA TINCKSSQSLWDSGNQKNF LTWYQQKPGQPPKLLIYWT SYRESGVPDRFSGSGSGT DFTLTISSLQAEDVAVYYCQ NDYFYPLTFGGGTKVEIK (SEQ ID NO: 7) | QVQLVQSGAEVKKPGASVKVS CKASGYTFTSYWINWVRQAP GQGLEWMGNIYPGSSLTNYN EKFKNRVTMTRDTSTSTVYME LSSLRSEDTAVYYCARLSTGTF AYWGQGTLVTVSS (SEQ ID NO: 4) | 1.16 |
| mAb7 | DIVMTQSPDSLAVSLGERA TINCKSSQSLWDSGNQKNF LTWYQQKPGQPPKLLIYWT SYRESGVPDRFSGSGSGT DFTLTISSLQAEDVAVYYCQ NDYFYPHTFGGGTKVEIK (SEQ ID NO: 8) | QVQLVQSGAEVKKPGASVKVS CKASGYTFTSYWINWVRQAP GQGLEWMGNIYPGSSLTNYN EKFKNRVTMTRDTSTSTVYME LSSLRSEDTAVYYCARLSTGTF AYWGQGTLVTVSS (SEQ ID NO: 4) | 0.73 |
| mAb8 | DIVMTQSPDSLAVSLGERA TINCKSSQSLWDSTNQKNF LTWYQQKPGQPPKLLIYWT STRESGVPDRFSGSGSGT DFTLTISSLQAEDVAVYYCQ NDYFYPLTFGGGTKVEIK (SEQ ID NO: 9) | QVQLVQSGAEVKKPGASVKVS CKASGYTFTSYWINWVRQAP GQGLEWMGNIYPGSSLTNYN EKFKNRVTMTRDTSTSTVYME LSSLRSEDTAVYYCARLSTGTF AYWGQGTLVTVSS (SEQ ID NO: 4) | 17.35 |
| mAb9 | DIVMTQSPDSLAVSLGERA TINCKSSQSLWDSGNQKNF LTWYQQKPGQPPKLLIYWT STRESGVPDRFSGSGSGT DFTLTISSLQAEDVAVYYCQ NDYFYPLTFGGGTKVEIK (SEQ ID NO: 2) | QVQLVQSGAEVKKPGASVKVS CKASGYTFTSYWINWVRQAP GQGLEWMGNIYPGSSITNYNE KFKNRVTMTRDTSTSTVYMEL SSLRSEDTAVYYCARLTTGTF AYWGQGTLVTVSS (SEQ ID NO: 5) | 13.54 |
| mAb10 | DIVMTQSPDSLAVSLGERA TINCKSSQSLWDSGNQKNF LTWYQQKPGQPPKLLIYWT SYRESGVPDRFSGSGSGT DFTLTISSLQAEDVAVYYCQ NDYFYPLTFGGGTKVEIK (SEQ ID NO: 7) | QVQLVQSGAEVKKPGASVKVS CKASGYTFTSYWINWVRQAP GQGLEWMGNIYPGSSITNYNE KFKNRVTMTRDTSTSTVYMEL SSLRSEDTAVYYCARLTTGTF AYWGQGTLVTVSS (SEQ ID NO: 5) | 0.98 |

TABLE 1-continued

Variable Regions Sequences of Anti-PD-1 antagonist Antibodies

| mAb | Light Chain | Heavy Chain | KD (nM) |
|---|---|---|---|
| mAb11 | DIVMTQSPDSLAVSLGERA TINC<u>KSSQSLWDSGNQKNF</u> LTWYQQKPGQPPKLLIY<u>WT SYRES</u>GVPDRFSGSGSGT DFTLTISSLQAEDVAVYYCQ <u>NDYFYPHT</u>FGGGTKVEIK (SEQ ID NO: 8) | QVQLVQSGAEVKKPGASVKVS CKASGYTFT<u>SYWIN</u>WVRQAP GQGLEWMG<u>NIYPGSSITNYNE KFKN</u>RVTMTRDTSTSTVYMEL SSLRSEDTAVYYCAR<u>LTTGTF AY</u>WGQGTLVTVSS (SEQ ID NO: 5) | 0.93 |
| mAb12 | DIVMTQSPDSLAVSLGERA TINC<u>KSSQSLWDSTNQKNF</u> LTWYQQKPGQPPKLLIY<u>WT STRES</u>GVPDRFSGSGSGT DFTLTISSLQAEDVAVYYCQ <u>NDYFYPLT</u>FGGGTKVEIK (SEQ ID NO: 9) | QVQLVQSGAEVKKPGASVKVS CKASGYTFT<u>SYWIN</u>WVRQAP GQGLEWMG<u>NIYPGSSITNYNE KFKN</u>RVTMTRDTSTSTVYMEL SSLRSEDTAVYYCAR<u>LTTGTF AY</u>WGQGTLVTVSS (SEQ ID NO: 5) | 17.27 |
| mAb13 | DIVMTQSPDSLAVSLGERA TINC<u>KSSQSLWDSGNQKNF</u> LTWYQQKPGQPPKLLIY<u>WT STRES</u>GVPDRFSGSGSGT DFTLTISSLQAEDVAVYYCQ <u>NDYFYPLT</u>FGGGTKVEIK (SEQ ID NO: 2) | QVQLVQSGAEVKKPGASVKVS CKASGYTFT<u>SYWIN</u>WVRQAP GQGLEWMG<u>NIWPGSSLTNYN EKFKN</u>RVTMTRDTSTSTVYME LSSLRSEDTAVYYCAR<u>LLTGTF AY</u>WGQGTLVTVSS (SEQ ID NO: 6) | 5.87 |
| mAb14 | DIVMTQSPDSLAVSLGERA TINC<u>KSSQSLWDSGNQKNF</u> LTWYQQKPGQPPKLLIY<u>WT SYRES</u>GVPDRFSGSGSGT DFTLTISSLQAEDVAVYYCQ <u>NDYFYPLT</u>FGGGTKVEIK (SEQ ID NO: 7) | QVQLVQSGAEVKKPGASVKVS CKASGYTFT<u>SYWIN</u>WVRQAP GQGLEWMG<u>NIWPGSSLTNYN EKFKN</u>RVTMTRDTSTSTVYME LSSLRSEDTAVYYCAR<u>LLTGTF AY</u>WGQGTLVTVSS (SEQ ID NO: 6) | 0.6 |
| mAb15 | DIVMTQSPDSLAVSLGERA TINC<u>KSSQSLWDSGNQKNF</u> LTWYQQKPGQPPKLLIY<u>WT SYRES</u>GVPDRFSGSGSGT DFTLTISSLQAEDVAVYYCQ <u>NDYFYPHT</u>FGGGTKVEIK (SEQ ID NO: 8) | QVQLVQSGAEVKKPGASVKVS CKASGYTFT<u>SYWIN</u>WVRQAP GQGLEWMG<u>NIWPGSSLTNYN EKFKN</u>RVTMTRDTSTSTVYME LSSLRSEDTAVYYCAR<u>LLTGTF AY</u>WGQGTLVTVSS (SEQ ID NO: 6) | 0.49 |
| mAb16 | DIVMTQSPDSLAVSLGERA TINC<u>KSSQSLWDSTNQKNF</u> LTWYQQKPGQPPKLLIY<u>WT STRES</u>GVPDRFSGSGSGT DFTLTISSLQAEDVAVYYCQ <u>NDYFYPLT</u>FGGGTKVEIK (SEQ ID NO: 9) | QVQLVQSGAEVKKPGASVKVS CKASGYTFT<u>SYWIN</u>WVRQAP GQGLEWMG<u>NIWPGSSLTNYN EKFKN</u>RVTMTRDTSTSTVYME LSSLRSEDTAVYYCAR<u>LLTGTF AY</u>WGQGTLVTVSS (SEQ ID NO: 6) | 7.51 |

The invention also provides CDR portions of antibodies to PD-1. Determination of CDR regions is well within the skill of the art. It is understood that in some embodiments, CDRs can be a combination of the Kabat and Chothia CDR (also termed "combined CDRs" or "extended CDRs"). In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. In general, "conformational CDRs" include the residue positions in the Kabat CDRs and Vernier zones which are constrained in order to maintain proper loop structure for the antibody to bind a specific antigen. Determination of conformational CDRs is well within the skill of the art. In some embodiments, the CDRs are the Kabat CDRs. In other embodiments, the CDRs are the Chothia CDRs. In other embodiments, the CDRs are the extended, AbM, conformational, or contact CDRs. In other words, in embodiments with more than one CDR, the CDRs may be any of Kabat, Chothia, extended, AbM, conformational, contact CDRs or combinations thereof.

In some embodiments, the antibody comprises three CDRs of any one of the heavy chain variable regions shown in Table 1. In some embodiments, the antibody comprises three CDRs of any one of the light chain variable regions shown in Table 1. In some embodiments, the antibody comprises three CDRs of any one of the heavy chain variable regions shown in Table 1, and three CDRs of any one of the light chain variable regions shown in Table 1.

Table 2 provides examples of CDR sequences of anti-PD-1 antagonist antibodies provided herein.

TABLE 2

Anti-PD-1 antagonist antibodies (mAbs) and their antigen-binding CDR sequences according to Kabat (underlined) and Chothia (bold)

| mAb | | CDR1 | CDR2 | CDR3 |
|---|---|---|---|---|
| mAb1 | L | KSSQSLWDSGNQKNFLT (SEQ ID NO: 10) | WTSTRES (SEQ ID NO: 11) | QNDYFYPLT (SEQ ID NO: 12) |
| | H | GYTFTSYWIN (SEQ ID NOs: 13 (whole), 14 and 15) | NIYPGSSLTNYNEKFKN (SEQ ID NOs: 16 and 17) | LLTGTFAY (SEQ ID NO: 18) |
| mAb2 | L | KSSQSLWDSGNQKNFLT (SEQ ID NO: 10) | WTSYRES (SEQ ID NO: 20) | QNDYFYPLT (SEQ ID NO: 12) |
| | H | GYTFTSYWIN (SEQ ID NOs: 13 (whole), 14 and 15) | NIYPGSSLTNYNEKFKN (SEQ ID NOs: 16 and 17) | LLTGTFAY (SEQ ID NO: 18) |
| mAb3 | L | KSSQSLWDSGNQKNFLT (SEQ ID NO: 10) | WTSYRES (SEQ ID NO: 20) | QNDYFYPHT (SEQ ID NO: 21) |
| | H | GYTFTSYWIN (SEQ ID NOs: 13 (whole), 14 and 15) | NIYPGSSLTNYNEKFKN (SEQ ID NOs: 16 and 17) | LLTGTFAY (SEQ ID NO: 18) |
| mAb4 | L | KSSQSLWDSTNQKNFLT (SEQ ID NO: 22) | WTSTRES (SEQ ID NO: 11) | QNDYFYPLT (SEQ ID NO: 12) |
| | H | GYTFTSYWIN (SEQ ID NOs: 13 (whole), 14 and 15) | NIYPGSSLTNYNEKFKN (SEQ ID NOs: 16 and 17) | LLTGTFAY (SEQ ID NO: 18) |
| mAb5 | L | KSSQSLWDSGNQKNFLT (SEQ ID NO: 10) | WTSTRES (SEQ ID NO: 11) | QNDYFYPLT (SEQ ID NO: 12) |
| | H | GYTFTSYWIN (SEQ ID NOs: 13 (whole), 14 and 15) | NIYPGSSLTNYNEKFKN (SEQ ID NOs: 16 and 17) | LSTGTFAY (SEQ ID NO: 23) |
| mAb6 | L | KSSQSLWDSGNQKNFLT (SEQ ID NO: 10) | WTSYRES (SEQ ID NO: 20) | QNDYFYPLT (SEQ ID NO: 12) |
| | H | GYTFTSYWIN (SEQ ID NOs: 13 (whole), 14 and 15) | NIYPGSSLTNYNEKFKN (SEQ ID NOs: 16 and 17) | LSTGTFAY (SEQ ID NO: 23) |
| mAb7 | L | KSSQSLWDSGNQKNFLT (SEQ ID NO: 10) | WTSYRES (SEQ ID NO: 20) | QNDYFYPHT (SEQ ID NO: 21) |
| | H | GYTFTSYWIN (SEQ ID NOs: 13 (whole), 14 and 15) | NIYPGSSLTNYNEKFKN (SEQ ID NOs: 16 and 17) | LSTGTFAY (SEQ ID NO: 23) |
| mAb8 | L | KSSQSLWDSTNQKNFLT (SEQ ID NO: 22) | WTSTRES (SEQ ID NO: 11) | QNDYFYPLT (SEQ ID NO: 12) |
| | H | GYTFTSYWIN (SEQ ID NOs: 13 (whole), 14 and 15) | NIYPGSSLTNYNEKFKN (SEQ ID NOs: 16 and 17) | LSTGTFAY (SEQ ID NO: 23) |
| mAb9 | L | KSSQSLWDSGNQKNFLT (SEQ ID NO: 10) | WTSTRES (SEQ ID NO: 11) | QNDYFYPLT (SEQ ID NO: 12) |
| | H | GYTFTSYWIN (SEQ ID NOs: 13 (whole), 14 and 15) | NIYPGSSITNYNEKFKN (SEQ ID NO: 24 and 25) | LTTGTFAY (SEQ ID NO: 26) |
| mAb10 | L | KSSQSLWDSGNQKNFLT (SEQ ID NO: 10) | WTSYRES (SEQ ID NO: 20) | QNDYFYPLT (SEQ ID NO: 12) |
| | H | GYTFTSYWIN (SEQ ID NOs: 13 (whole), 14 and 15) | NIYPGSSITNYNEKFKN (SEQ ID NO: 24 and 25) | LTTGTFAY (SEQ ID NO: 26) |
| mAb11 | L | KSSQSLWDSGNQKNFLT (SEQ ID NO: 10) | WTSYRES (SEQ ID NO: 20) | QNDYFYPHT (SEQ ID NO: 21) |
| | H | GYTFTSYWIN (SEQ ID NOs: 13 (whole), 14 and 15) | NIYPGSSITNYNEKFKN (SEQ ID NO: 24 and 25) | LTTGTFAY (SEQ ID NO: 26) |
| mAb12 | L | KSSQSLWDSTNQKNFLT (SEQ ID NO: 22) | WTSTRES (SEQ ID NO: 11) | QNDYFYPLT (SEQ ID NO: 12) |
| | H | GYTFTSYWIN (SEQ ID NOs: 13 (whole), 14 and 15) | NIYPGSSITNYNEKFKN (SEQ ID NO: 24 and 25) | LTTGTFAY (SEQ ID NO: 26) |

TABLE 2-continued

Anti-PD-1 antagonist antibodies (mAbs) and their antigen-binding CDR sequences according to Kabat (underlined) and Chothia (bold)

| mAb | CDR1 | CDR2 | CDR3 |
|---|---|---|---|
| mAb13 | L KSSQSLWDSGNQKN FLT (SEQ ID NO: 10) H GYTFTSYWIN (SEQ ID NOs: 13 (whole), 14 and 15) | WTSTRES (SEQ ID NO: 11) NIWPGSSLTNYNEKFK N (SEQ ID NO: 27 and 28) | QNDYFYPLT (SEQ ID NO: 12) LLTGTFAY (SEQ ID NO: 18) |
| mAb14 | L KSSQSLWDSGNQKN FLT (SEQ ID NO: 10) H GYTFTSYWIN (SEQ ID NOs: 13 (whole), 14 and 15) | WTSYRES (SEQ ID NO: 20) NIWPGSSLTNYNEKFK N (SEQ ID NO: 27 and 28) | QNDYFYPLT (SEQ ID NO: 12) LLTGTFAY (SEQ ID NO: 18) |
| mAb15 | L KSSQSLWDSGNQKN FLT (SEQ ID NO: 10) H GYTFTSYWIN (SEQ ID NOs: 13 (whole), 14 and 15) | WTSYRES (SEQ ID NO: 20) NIWPGSSLTNYNEKFK N (SEQ ID NO: 27 and 28) | QNDYFYPHT (SEQ ID NO: 21) LLTGTFAY (SEQ ID NO: 18) |
| mAb16 | L KSSQSLWDSTNQKNF LT (SEQ ID NO: 22) H GYTFTSYWIN (SEQ ID NOs: 13 (whole), 14 and 15) | WTSTRES (SEQ ID NO: 11) NIWPGSSLTNYNEKFK N (SEQ ID NO: 27 and 28) | QNDYFYPLT (SEQ ID NO: 12) LLTGTFAY (SEQ ID NO: 18) |

In some embodiments, the antibody comprises three light chain CDRs and three heavy chain CDRs from Table 2.

An alignment of light chain CDRs from anti-PD-1 antibodies is provided in Table 3. Variable residues are shown in bold. Consensus light chain CDR sequences are provided in the last row of Table 3.

TABLE 3

Alignment of anti-PD-1 light chain CDRs

| mAb | VL CDR1 | SEQ ID NO: | VL CDR2 | SEQ ID NO: | VL CDR3 | SEQ ID NO: |
|---|---|---|---|---|---|---|
| 1, 5, 9, 13 | KSSQSLWDSGNQKNFLT | 10 | WTSTRES | 11 | QNDYFYPLT | 12 |
| 2, 6, 10, 14 | KSSQSLWDSGNQKNFLT | 10 | WTSYRES | 20 | QNDYFYPLT | 12 |
| 3, 7, 11, 15 | KSSQSLWDSGNQKNFLT | 10 | WTSYRES | 20 | QNDYFYPHT | 21 |
| 4, 8, 12, 16 | KSSQSLWDSTNQKNFLT | 22 | WTSTRES | 11 | QNDYFYPLT | 12 |
| 17 | KSSQSLLDSGNQKNFLT | 30 | WTSTRES | 11 | QNDYSYPLT | 31 |
| | KSSQSL$X_1$DS$X_2$NQKNFLT, wherein $X_1$ is W or L, and $X_2$ is G or T | 32 | WTS$X_1$RES, wherein $X_1$ is T or Y | 33 | QNDY $X_1$YP$X_2$T, wherein $X_1$ is F or S, and $X_2$ is L or H | 34 |

An alignment of heavy chain CDRs from anti-PD-1 antibodies is provided in Table 4. Variable residues are shown in bold. Consensus heavy chain CDR sequences are provided in the last row of Table 4.

TABLE 4

Alignment of anti-PD-1 heavy chain CDRs

| mAb | VH CDR1 | SEQ ID NO: | VH CDR2 | SEQ ID NO: | VH CDR3 | SEQ ID NO: |
|---|---|---|---|---|---|---|
| 1-4 | GYTFTSYWIN | 13 | NIYPGSSLTNYNEKFKN | 17 | LLTGTFAY | 18 |
| 5-8 | GYTFTSYWIN | 13 | NIYPGSSLTNYNEKFKN | 17 | LSTGTFAY | 23 |
| 9-12 | GYTFTSYWIN | 13 | NIYPGSSITNYNEKFKN | 25 | LTTGTFAY | 26 |
| 13-16 | GYTFTSYWIN | 13 | NIWPGSSLTNYNEKFKN | 28 | LLTGTFAY | 18 |
| 17 | GYTFTSYWIN | 13 | NIYPGSSSTNYNEKFKN | 35 | LLTGTFAY | 18 |
|  | GYTFTSYWIN | 13 | NIX$_1$PGSSX$_2$TNYNEKFKN, wherein X$_1$ is Y or W, and X$_2$ is L, I, or S | 36 | LX$_1$TGTFAY, wherein X$_1$ is L or S | 37 |

In some embodiments, the antibody comprises three light chain CDRs from Table 3 and three heavy chain CDRs from Table 4.

In some embodiments, the antibody comprises the full-length heavy chain, with or without the C-terminal lysine, and/or the full-length light chain of anti-PD-1 antagonist antibody mAb7 or mAb15. The amino acid sequence of mAb7 full-length heavy chain (SEQ ID NO: 29) is shown below:

(SEQ ID NO: 29)
QVQLVQSGAEVKKPGASVKVSCKASGYTFTSYWINWVRQAPGQGLEWM

GNIYPGSSLTNYNEKFKNRVTMTRDTSTSTVYMELSSLRSEDTAVYYCAR

LSTGTFAYWGQGTLVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPK

DTLMISRTPEVTCVVVDVSQEDPEVQFNWYVDGVEVHNAKTKPREEQFN

STYRVVSVLTVLHQDWLNGKEYKCKVSNKGLPSSIEKTISKAKGQPREP

QVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLS

LGK

The amino acid sequence of mAb7 full-length heavy chain without the C-terminal lysine (SEQ ID NO: 38) is shown below:

(SEQ ID NO: 38)
QVQLVQSGAEVKKPGASVKVSCKASGYTFTSYWINWVRQAPGQGLEWM

GNIYPGSSLTNYNEKFKNRVTMTRDTSTSTVYMELSSLRSEDTAVYYCA

RLSTGTFAYWGQGTLVTVSSASTKGPSVFPLAPCSRSTSESTAALGCL

VKDYFPEPVTVSWNSGALTSGVHTFPAVLQSSGLYSLSSVVTVPSSSL

GTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAKG

QPREPQVYTLPPSQEEMTKNQVSLTCLVKGFYPSDIAVEWESNGQPE

NNYKTTPPVLDSDGSFFLYSRLTVDKSRWQEGNVFSCSVMHEALHNHY

TQKSLSLSLG

The amino acid sequence of mAb7 full-length light chain (SEQ ID NO: 39) is shown below:

(SEQ ID NO: 39)
DIVMTQSPDSLAVSLGERATINCKSSQSLWDSGNQKNFLTWYQQKPGQP

PKLLIYWTSYRESGVPDRFSGSGSGTDFTLTISSLQAEDVAVYYCQNDY

FYPHTFGGGTKVEIKRGTVAAPSVFIFPPSDEQLKSGTASVVCLLNNFY

PREAKVQWKVDNALQSGNSQESVTEQDSKDSTYSLSSTLTLSKADYE

KHKVYACEVTHQGLSSPVTKSFNRGEC

The invention also provides methods of generating, selecting, and making anti-PD-1 antagonist antibodies. The antibodies of this invention can be made by procedures known in the art. In some embodiments, antibodies may be made recombinantly and expressed using any method known in the art.

In some embodiments, antibodies may be prepared and selected by phage display technology. See, for example, U.S. Pat. Nos. 5,565,332; 5,580,717; 5,733,743; and 6,265,150; and Winter et al., Annu. Rev. Immunol. 12:433-455, 1994. Alternatively, the phage display technology (McCafferty et al., Nature 348:552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from human donors can be constructed and antibodies to a diverse array of antigens (including self-antigens) can be isolated essentially following the techniques described by Mark et al., J. Mol. Biol. 222:581-597, 1991, or Griffith et al., EMBO J. 12:725-734, 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783, 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

In some embodiments, antibodies may be made using hybridoma technology. It is contemplated that any mammalia subject including humans or antibody producing cells therefrom can be manipulated to serve as the basis for production of mammalian, including human, hybridoma cell lines. The route and schedule of immunization of the host animal are generally in keeping with established and conventional techniques for antibody stimulation and production, as further described herein. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., 1975, Nature 256:495-497 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the PD-1 monoclonal antibodies of the subject invention. The hybridomas or other immortalized B-cells are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for PD-1, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a PD-1 polypeptide, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

If desired, the anti-PD-1 antagonist antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329, 112; U.S. Pat. No. 7,314,622.

In some embodiments, the polynucleotide sequence may be used for genetic manipulation to "humanize" the antibody or to improve the affinity, or other characteristics of the antibody. Antibodies may also be customized for use, for example, in dogs, cats, primate, equines and bovines.

In some embodiments, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., domain, single chain, etc. are known in the art.

Immunoassays and flow cytometry sorting techniques such as fluorescence activated cell sorting (FACS) can also be employed to isolate antibodies that are specific for PD-1.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of a PD-1 monoclonal antibody herein.

Antibody fragments can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In some embodiments, a polynucleotide comprises a sequence encoding the heavy chain and/or the light chain variable regions of antibody mAb1, mAb2, mAb3, mAb4, mAb5, mAb6, mAb7, mAb8, mAb9, mAb10, mAb11, mAb12, mAb13, mAb14, mAb15, or mAb16. The sequence encoding the antibody of interest may be maintained in a vector in a host cell and the host cell can then be expanded and frozen for future use. Vectors (including expression vectors) and host cells are further described herein.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using, for example, Biacore™ surface plasmon resonance analysis, which detects differences in binding affinity of about 2-fold or greater, Kinexa® Biosensor, scintillation proximity assays, ELISA, ORI-GEN® immunoassay, fluorescence quenching, fluorescence transfer, and/or yeast display. Binding affinity may also be screened using a suitable bioassay. Biacore™ is particularly useful when the starting antibody already binds with a relatively high affinity, for example a $K_D$ of about 10 nM or lower.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., 1993, Gene 137(1):109-18.

The CDR may be heavy chain variable region (VH) CDR3 and/or light chain variable region (VL) CDR3. The CDR may be one or more of VH CDR1, VH CDR2, VH CDR3, VL CDR1, VL CDR2, and/or VL CDR3. The CDR may be a Kabat CDR, a Chothia CDR, an extended CDR, an AbM CDR, a contact CDR, or a conformational CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Kinexa™ biosensor analysis, and selection using any method known in the art for selection, including phage display, yeast display, and ribosome display.

To express the anti-PD-1 antibodies of the present invention, DNA fragments encoding VH and VL regions can first be obtained using any of the methods described above. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

The invention encompasses modifications to the variable regions shown in Table 1 and the CDRs shown in Tables 2, 3 or 4. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to PD-1. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 5 under the heading of "conservative substitutions." If such substitutions result in a change in biological activity, then more substantial changes, denominated "exemplary substitutions" in Table 5, or as further described below in reference to amino acid classes, may be introduced and the products screened.

TABLE 5

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala: Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar Norleucine, Met, Ala, Val, Leu, lie;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The antibodies may also be modified, e.g. in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ Of the antibody for PD-1, to increase or decrease $k_{off}$, or to alter the binding specificity of the antibody. Techniques in site-directed mutagenesis are well-known in the art. See, e.g., Sambrook et al. and Ausubel et al., supra.

A modification or mutation may also be made in a framework region or constant region to increase the half-life of an anti-PD-1 antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. In some embodiments, no more than one to five conservative amino acid substitutions are made within the framework region or constant region. In other embodiments, no more than one to three conservative amino acid substitutions are made within the framework region or constant region. According to the invention, a single antibody may have mutations in any one or more of the CDRs or framework regions of the variable domain or in the constant region.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracycline-regulated expression of β(1,4)-N-acetylglucosaminyl-transferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments, the Fc can be human $IgG_2$ or human $IgG_4$. In some embodiments, the antibody comprises a constant region of $IgG_4$ comprising the following mutations (Armour et al., 2003, Molecular Immunology 40 585-593): E233F234L235 to P233V234A235 ($IgG_{4Ac}$), in which the numbering is with reference to wild type $IgG_4$. In yet another embodiment, the Fc is human $IgG_4$ E233F234L235 to P233V234A235 with deletion G236 (IgG$_{4\Delta b}$). In some embodiments the Fc is any human IgG$_4$ Fc (IgG$_4$, IgG$_{4\Delta b}$ or IgG$_{4\Delta c}$) containing hinge stabilizing mutation S228 to P228 (Aalberse et al., 2002, Immunology 105, 9-19). In other embodiments, the Fc can be human IgG$_2$ containing the mutation A330P331 to S330S331 (IgG$_{2\Delta a}$), in which the amino acid residues are numbered with reference to the wild type IgG$_2$ sequence. Eur. J. Immunol., 1999, 29:2613-2624.

In some embodiments, the antibody comprises a modified constant region that has increased or decreased binding affinity to a human Fc gamma receptor, is immunologically inert or partially inert, e.g., does not trigger complement mediated lysis, does not stimulate antibody-dependent cell mediated cytotoxicity (ADCC), or does not activate microglia; or has reduced activities (compared to the unmodified antibody) in any one or more of the following: triggering complement mediated lysis, stimulating ADCC, or activating microglia. Different modifications of the constant region may be used to achieve optimal level and/or combination of effector functions. See, for example, Morgan et al., Immunology 86:319-324, 1995; Lund et al., J. Immunology 157: 4963-9 157:4963-4969, 1996; Idusogie et al., J. Immunology 164:4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 1999, 29:2613-2624; PCT Publication No. WO99/058572.

In some embodiments, an antibody constant region can be modified to avoid interaction with Fc gamma receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, e.g., U.S. Pat. Nos. 5,997,867 and 5,866,692.

In still other embodiments, the constant region is aglycosylated for N-linked glycosylation. In some embodiments, the constant region is aglycosylated for N-linked glycosylation by mutating the oligosaccharide attachment residue and/or flanking residues that are part of the N-glycosylation recognition sequence in the constant region. For example, N-glycosylation site N297 may be mutated to, e.g., A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

In some embodiments, the antibody comprises a modified constant region that has increased binding affinity for FcRn and/or an increased serum half-life as compared with the unmodified antibody.

In a process known as "germlining", certain amino acids in the VH and VL sequences can be mutated to match those found naturally in germline VH and VL sequences. In particular, the amino acid sequences of the framework regions in the VH and VL sequences can be mutated to match the germline sequences to reduce the risk of immunogenicity when the antibody is administered. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., 1992, J. Mol. Biol. 227:776-798; and Cox et al., 1994, Eur. J. Immunol. 24:827-836).

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of an anti-PD-1 antibody of the invention can be cleaved. In various embodiments of the invention, the heavy and light chains of the anti-PD-1 antibodies may optionally include a signal sequence.

Once DNA fragments encoding the VH and VL segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG$_1$, IgG$_2$, IgG$_3$, IgG$_4$, IgA, IgE, IgM or IgD constant region, but most preferably is an IgG$_1$ or IgG$_2$ constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the VH-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH- and VL-encoding DNA fragments are operatively linked to another fragment encoding a flexible linker such that the VH and VL sequences can be expressed as a contiguous single-chain protein, with the VL and VH regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. An example of a linking peptide is $(GGGGS)_3$ (SEQ ID NO: 19), which bridges approximately 3.5 nm between the carboxy terminus of one variable region and the amino terminus of the other variable region. Linkers of other sequences have been designed and used (Bird et al., 1988, supra). Linkers can in turn be modified for additional functions, such as attachment of drugs or attachment to solid supports. The single chain antibody may be monovalent, if only a single VH and VL are used, bivalent, if two VH and VL are used, or polyvalent, if more than two VH and VL are used. Bispecific or polyvalent antibodies may be generated that bind specifically to PD-1 and to another molecule. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

Other forms of single chain antibodies, such as diabodies, are also encompassed. Diabodies are bivalent, bispecific antibodies in which VH and VL are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad Sci. USA 90:6444-6448; Poljak, R. J., et al., 1994, Structure 2:1121-1123).

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

The invention also encompasses fusion proteins comprising one or more fragments or regions from the antibodies disclosed herein. In some embodiments, a fusion antibody may be made that comprises all or a portion of an anti-PD-1 antibody of the invention linked to another polypeptide. In another embodiment, only the variable domains of the anti-PD-1 antibody are linked to the polypeptide. In another embodiment, the VH domain of an anti-PD-1 antibody is linked to a first polypeptide, while the VL domain of an anti-PD-1 antibody is linked to a second polypeptide that associates with the first polypeptide in a manner such that the VH and VL domains can interact with one another to form an antigen binding site. In another preferred embodiment, the VH domain is separated from the VL domain by a linker such that the VH and VL domains can interact with one another. The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In some embodiments, a fusion polypeptide is provided that comprises at least 10 contiguous amino acids of the variable light chain region shown in SEQ ID NO: 2, 7, 8, or 9 and/or at least 10 amino acids of the variable heavy chain region shown in SEQ ID NO: 3, 4, 5, or 6. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises a light chain variable region and/or a heavy chain variable region, as shown in any of the sequence pairs selected from among SEQ ID NOs: 2 and 3, 7 and 3, 8 and 3, 8 9 and 3, 2 and 4, 7 and 4, 8 and 4, 9 and 4, 2 and 5, 7 and 5, 8 and 5, 9 and 5, 2 and 6, 7 and 6, 8 and 6, and 9 and 6. In another embodiment, the fusion polypeptide comprises one or more CDR(s). In still other embodiments, the fusion polypeptide comprises VH CDR3 and/or VL CDR3. For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

A fusion polypeptide can be created by methods known in the art, for example, synthetically or recombinantly. Typically, the fusion proteins of this invention are made by preparing and expressing a polynucleotide encoding them using recombinant methods described herein, although they may also be prepared by other means known in the art, including, for example, chemical synthesis.

In other embodiments, other modified antibodies may be prepared using anti-PD-1 antibody encoding nucleic acid molecules. For instance, "Kappa bodies" (Ill et al., 1997, Protein Eng. 10:949-57), "Minibodies" (Martin et al., 1994, EMBO J. 13:5303-9), "Diabodies" (Holliger et al., supra), or "Janusins" (Traunecker et al., 1991, EMBO J. 10:3655-3659 and Traunecker et al., 1992, Int. J. Cancer (Suppl.) 7:51-52) may be prepared using standard molecular biological techniques following the teachings of the specification.

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121:210). For example, bispecific antibodies or antigen-binding fragments can be produced by fusion of hybridomas or linking of Fab' fragments. See, e.g., Songsivilai & Lachmann, 1990, Clin. Exp. Immunol. 79:315-321, Kostelny et al., 1992, J. Immunol. 148:1547-1553. Traditionally, the recombinant production of bispecific antibodies was based on the coexpression of two immunoglobulin heavy chain-light chain pairs, with the two heavy chains having different specificities (Millstein and Cuello, 1983, Nature 305, 537-539). In addition, bispecific antibodies may be formed as "diabodies" or "Janusins." In some embodiments, the bispecific antibody binds to two different epitopes of PD-1. In some embodiments, the modified antibodies described above are prepared using one or more of the variable domains or CDR regions from an anti-PD-1 antibody provided herein.

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

This invention also provides compositions comprising antibodies conjugated (for example, linked) to an agent that facilitate coupling to a solid support (such as biotin or avidin). For simplicity, reference will be made generally to antibodies with the understanding that these methods apply to any of the PD-1 binding and/or antagonist embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the lung, heart, or heart valve.

An antibody or polypeptide of this invention may be linked to a labeling agent such as a fluorescent molecule, a radioactive molecule or any others labels known in the art. Labels are known in the art which generally provide (either directly or indirectly) a signal.

Polynucleotides, Vectors, and Host Cells

The invention also provides polynucleotides encoding any of the antibodies, including antibody fragments and modified antibodies described herein, such as, e.g., antibodies having impaired effector function. In another aspect, the invention provides a method of making any of the polynucleotides described herein. Polynucleotides can be made and expressed by procedures known in the art. Accordingly, the invention provides polynucleotides or compositions, including pharmaceutical compositions, comprising polynucleotides, encoding any of the following: the antibodies mAb1, mAb2, mAb3, mAb4, mAb5, mAb6, mAb7, mAb8, mAb9, mAb10, mAb11, mAb12, mAb13, mAb14, mAb15, mAb16, and mAb17 or any fragment or part thereof having the ability to antagonize PD-1.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a fragment thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a fragment thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors are further provided. Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as E. coli or B. subtillis) and yeast (such as S. cerevisae, S. pombe; or K. lactis). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to PD-1 or a PD-1 domain is effected by an immunoassay or FACS. A cell overexpressing the antibody or protein of interest can be identified.

An expression vector can be used to direct expression of an anti-PD-1 antagonist antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 1994, 14:2411, and in Woffendin, Proc. Natl. Acad. Sci., 1994, 91:1581.

Compositions

The invention also provides pharmaceutical compositions comprising an effective amount of an anti-PD-1 antibody described herein. Examples of such compositions, as well as how to formulate, are also described herein. In some embodiments, the composition comprises one or more PD-1 antibodies. In other embodiments, the anti-PD-1 antibody recognizes PD-1. In other embodiments, the anti-PD-1 antibody is a human antibody. In other embodiments, the anti-PD-1 antibody is a humanized antibody. In some embodiments, the anti-PD-1 antibody comprises a constant region that is capable of triggering a desired immune response, such as antibody-mediated lysis or ADCC. In other embodiments, the anti-PD-1 antibody comprises a constant region that does not trigger an unwanted or undesirable immune response, such as antibody-mediated lysis or ADCC. In other embodiments, the anti-PD-1 antibody comprises one or more CDR(s) of the antibody (such as one, two, three, four, five, or, in some embodiments, all six CDRs).

It is understood that the compositions can comprise more than one anti-PD-1 antibody (e.g., a mixture of PD-1 antibodies that recognize different epitopes of PD-1). Other exemplary compositions comprise more than one anti-PD-1 antibody that recognize the same epitope(s), or different species of anti-PD-1 antibodies that bind to different epitopes of PD-1. In some embodiments, the compositions comprise a mixture of anti-PD-1 antibodies that recognize different variants of PD-1.

The composition used in the present invention can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The anti-PD-1 antibody and compositions thereof can also be used in conjunction with, or administered separately, simultaneously, or sequentially with other agents that serve to enhance and/or complement the effectiveness of the agents.

The invention also provides compositions, including pharmaceutical compositions, comprising any of the polynucleotides of the invention. In some embodiments, the composition comprises an expression vector comprising a polynucleotide encoding the antibody as described herein. In other embodiment, the composition comprises an expression vector comprising a polynucleotide encoding any of the antibodies described herein.

Methods for Preventing or Treating Conditions Mediated by PD-1

The antibodies and the antibody conjugates of the present invention are useful in various applications including, but are not limited to, therapeutic treatment methods and diagnostic treatment methods.

In one aspect, the invention provides a method for treating a cancer. In some embodiments, the method of treating a cancer in a subject comprises administering to the subject in need thereof an effective amount of a composition (e.g., pharmaceutical composition) comprising any of the PD-1 antibodies as described herein. As used herein, cancers include, but are not limited to bladder cancer, breast cancer, cervical cancer, choriocarcinoma, colon cancer, esophageal cancer, gastric cancer, glioblastoma, glioma, brain tumor, head and neck cancer, kidney cancer, lung cancer, oral cancer, ovarian cancer, pancreatic cancer, prostate cancer, liver cancer, uterine cancer, bone cancer, leukemia, lymphoma, sacrcoma, blood cancer, thyroid cancer, thymic cancer, eye cancer, and skin cancer. In some embodiments, provided is a method of inhibiting tumor growth or progression in a subject, comprising administering to the subject in need thereof an effective amount of a composition comprising the PD-1 antibodies or the PD-1 antibody conjugates as described herein. In some embodiments, the tumor is a PD-L1 expressing tumor. In other embodiments, the tumor does not express PD-L1. In other embodiments, provided is a method of inhibiting metastasis of cancer cells in a subject, comprising administering to the subject in need thereof an effective amount of a composition comprising any of the PD-1 antibodies as described herein. In other embodiments, provided is a method of inducing regression of a tumor in a subject, comprising administering to the subject in need thereof an effective amount of a composition comprising any of the PD-1 antibodies as described herein.

In another aspect, provided is a method of detecting, diagnosing, and/or monitoring a cancer. For example, the PD-1 antibodies as described herein can be labeled with a detectable moiety such as an imaging agent and an enzyme-substrate label. The antibodies as described herein can also be used for in vivo diagnostic assays, such as in vivo imaging (e.g., PET or SPECT), or a staining reagent.

In some embodiments, the methods described herein further comprise a step of treating a subject with an additional form of therapy. In some embodiments, the additional form of therapy is an additional anti-cancer therapy including, but not limited to, chemotherapy, radiation, surgery, hormone therapy, and/or additional immunotherapy.

With respect to all methods described herein, reference to anti-PD-1 antagonist antibodies also includes compositions comprising one or more additional agents. These compositions may further comprise suitable excipients, such as pharmaceutically acceptable excipients including buffers, which are well known in the art. The present invention can be used alone or in combination with other methods of treatment.

The anti-PD-1 antagonist antibody can be administered to a subject via any suitable route. It should be apparent to a person skilled in the art that the examples described herein are not intended to be limiting but to be illustrative of the techniques available. Accordingly, in some embodiments, the anti-PD-1 antagonist antibody is administered to a subject in accord with known methods, such as intravenous administration, e.g., as a bolus or by continuous infusion over a period of time, by intramuscular, intraperitoneal, intracerebrospinal, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-PD-1 antagonist antibody can be aerosolized using a fluorocarbon formulation and a metered dose inhaler, or inhaled as a lyophilized and milled powder.

In some embodiments, an anti-PD-1 antagonist antibody is administered via site-specific or targeted local delivery techniques. Examples of site-specific or targeted local delivery techniques include various implantable depot sources of the anti-PD-1 antagonist antibody or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of an anti-PD-1 antagonist antibody may be used for administration. In some embodiments, the anti-PD-1 antagonist antibody may be administered neat. In some embodiments, anti-PD-1 antagonist antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000.

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

An anti-PD-1 antagonist antibody can be administered using any suitable method, including by injection (e.g., intraperitoneally, intravenously, subcutaneously, intramuscularly, etc.). Anti-PD-1 antibodies can also be administered topically or via inhalation, as described herein. Generally, for administration of anti-PD-1 antibodies, an initial candidate dosage can be about 2 mg/kg. For the purpose of the present invention, a typical daily dosage might range from about any of 3 µg/kg to 30 µg/kg to 300 µg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to reduce symptoms associated with cancer. The progress of this therapy is easily monitored by conventional techniques and assays. The dosing regimen (including the anti-PD-1 antagonist antibody used) can vary over time.

For the purpose of the present invention, the appropriate dosage of an anti-PD-1 antagonist antibody will depend on the anti-PD-1 antagonist antibody (or compositions thereof) employed, the type and severity of symptoms to be treated, whether the agent is administered for preventive or therapeutic purposes, previous therapy, the patients clinical history and response to the agent, the patient's clearance rate for the administered agent, and the discretion of the attending physician. Typically the clinician will administer an anti-PD-1 antagonist antibody until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms. Alternatively, sustained continuous release formulations of anti-PD-1 antagonist antibodies may be appropriate. Various formulations and devices for achieving sustained release are known in the art.

In one embodiment, dosages for an antagonist antibody may be determined empirically in individuals who have been given one or more administration(s) of an antagonist antibody. Individuals are given incremental dosages of an anti-PD-1 antagonist antibody. To assess efficacy, an indicator of the disease can be followed.

Administration of an anti-PD-1 antagonist antibody in accordance with the method in the present invention can be continuous or intermittent, depending, for example, upon the recipients physiological condition, whether the purpose of the administration is therapeutic or prophylactic, and other factors known to skilled practitioners. The administration of an anti-PD-1 antagonist antibody may be essentially continuous over a preselected period of time or may be in a series of spaced doses.

In some embodiments, more than one anti-PD-1 antagonist antibody may be present. At least one, at least two, at least three, at least four, at least five different, or more antagonist antibodies can be present. Generally, those anti-PD-1 antagonist antibodies may have complementary activities that do not adversely affect each other. An anti-PD-1 antagonist antibody can also be used in conjunction with other antibodies and/or other therapies. An anti-PD-1 antagonist antibody can also be used in conjunction with other agents that serve to enhance and/or complement the effectiveness of the agents.

In some embodiments, the anti-PD-1 antagonist antibody may be administered in combination with the administration of one or more additional therapeutic agents. These include, but are not limited to, the administration of a chemotherapeutic agent, a vaccine, a CAR-T cell-based therapy, radiotherapy, a cytokine therapy, a vaccine, an anti-PD-1 bispecific antibody, an inhibitor of other immunosuppressive pathways, an inhibitors of angiogenesis, a T cell activator, an inhibitor of a metabolic pathway, an mTOR inhibitor, an inhibitor of an adenosine pathway, a tyrosine kinase inhibitor including but not limited to inlyta, ALK inhibitors and sunitinib, a BRAF inhibitor, an epigenetic modifier, an inhibitors or depletor of Treg cells and/or of myeloid-derived suppressor cells, a JAK inhibitor, a STAT inhibitor, a cyclin-dependent kinase inhibitor, a biotherapeutic agent (including but not limited to antibodies to VEGF, VEGFR, EGFR, Her2/neu, other growth factor receptors, CD20, CD40, CD-40L, CTLA-4, OX-40, 4-1BB, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF). Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gammaII and calicheamicin phiII, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), pegylated liposomal doxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylomithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

In some embodiments, an anti-PD-1 antagonist antibody is used in conjunction with one or more other therapeutic agents targeting an immune checkpoint modulator, such as, for example without limitation, an agent targeting PD-1, PD-L1, CTLA-4, LAG-3, B7-H3, B7-H4, B7-DC (PD-L2), B7-H5, B7-H6, B7-H8, B7-H2, B7-1, B7-2, ICOS, ICOS-L, TIGIT, CD2, CD47, CD80, CD86, CD48, CD58, CD226, CD155, CD112, LAIR1, 2B4, BTLA, CD160, TIM1, TIM-3, TIM4, VISTA (PD-H1), OX40, OX40L, GITR, GITRL, CD70, CD27, 4-1BB, 4-BBL, DR3, TL1A, CD40, CD40L, CD30, CD30L, LIGHT, HVEM, SLAM (SLAMF1, CD150), SLAMF2 (CD48), SLAMF3 (CD229), SLAMF4 (2B4, CD244), SLAMF5 (CD84), SLAMF6 (NTB-A), SLAMCF7 (CS1), SLAMF8 (BLAME), SLAMF9 (CD2F), CD28, CEACAM1(CD66a), CEACAM3, CEACAM4, CEACAM5, CEACAM6, CEACAM7, CEACAM8, CEACAM1-3AS CEACAM3C2, CEACAM1-15, PSG1-11, CEACAM1-4C1, CEACAM1-4S, CEACAM1-4L, IDO, TDO, CCR2, CD39-CD73-adenosine pathway (A2AR), BTKs, TIKs, CXCR2, CCR4, CCR8, CCR5, VEGF pathway, CSF-1, or an innate immune response modulator. In some embodiments, an anti-PD-1 antagonist antibody is used in conjunction with, for example, an anti-PD-L1 antagonist antibody such, as for example, BMS-936559 (MDX-1105) and MPDL3280A; an anti-PD-1 antagonist antibody such as for example, nivolumab, pembrolizumab, and pidilizumab; an anti-CTLA-4 antagonist antibody such as for example ipilimumab; an anti-LAG-3 antagonist antibody such as BMS-986016 and IMP701; an anti-TIM-3 antagonist antibody; an anti-B7-H3 antagonist antibody such as for example MGA271; an-anti-VISTA antagonist antibody; an anti-TIGIT antagonist antibody; an anti-CD28 antagonist antibody; an anti-CD80 antibody; an anti-CD86 antibody; an-anti-B7-H4 antagonist antibody; an anti-ICOS agonist antibody; an anti-CD28 agonist antibody; an innate immune response modulator (e.g., TLRs, KIR, NKG2A), and an IDO inhibitor. In some embodiments, an anti-PD-1 antagonist antibody is used in conjunction with a 4-1BB (CD137) agonist such as, for example, PF-05082566 or BMS-663513. In some embodiments, an anti-PD-1 antagonist antibody is used in conjunction with an OX40 agonist such as, for example, an anti-OX-40 agonist antibody. In some embodiments, an anti-PD-1 antagonist antibody is used in conjunction with a GITR agonist such as, for example, an-anti-GITR agonist antibody such as, for example without limitation, TRX518. In some embodiments, an anti-PD-1 antagonist antibody is used in conjunction with an IDO inhibitor. In some embodiments, an anti-PD-1 antagonist antibody is used in conjunction with a cytokine therapy such as, for example without limitation, IL-15, CSF-1, MCSF-1, etc.

In some embodiments, an anti-PD-1 antagonist antibody is used in conjunction with one or more other therapeutic antibodies, such as, for example without limitation, an antibody targeting CD19, CD22, CD40, CD52, or CCR4.

In some embodiments, the anti-PD-1 antibody therapy may precede or follow the other agent treatment by intervals ranging from minutes to weeks. In embodiments where the other agents and/or a proteins or polynucleotides are administered separately, one would generally ensure that a significant period of time did not expire between each delivery, such that the agent and the composition of the present invention would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

In some embodiments, an anti-PD-1 antagonist antibody composition comprises a second agent selected from crizotinib, palbociclib, gemcitabine, cyclophosphamide, fluorouracil, FOLFOX, folinic acid, oxaliplatin, axitinib, sunitinib malate, tofacitinib, bevacizumab, rituximab, and trastuzumab.

In some embodiments, an anti-PD-1 antibody composition is combined with a treatment regimen further comprising a traditional therapy selected from the group consisting of: surgery, radiation therapy, chemotherapy, targeted therapy, immunotherapy, hormonal therapy, angiogenesis inhibition and palliative care.

Use of the PD-1 Antibodies in Vaccine-Based Immunotherapy Regimens for Cancer

In some particular embodiments, the present disclosure provides a method for enhancing the immunogenicity or therapeutic effect of a vaccine for the treatment of a cancer in a mammal, particularly a human, which method comprises administering to the mammal receiving the vaccine an effective amount of anti-PD-1 antagonist antibody provided by the present disclosure. In some other particular embodiments, the present disclosure provides a method for treating a cancer in a mammal, particularly a human, which method comprises administering to the mammal (1) an effective amount of a vaccine capable of eliciting an immune response against cells of the cancer and (2) an effective amount of an anti-PD-1 antagonist antibody provided by the present disclosure. The method of treating a neoplastic disorder in a mammal and the method of enhancing the immunogenicity or therapeutic effect of a vaccine for the treatment of a neoplastic disorder in a mammal described herein above are collectively referred to as "vaccine-based immunotherapy regimens for cancer" (or "VBIR for cancer").

In the VBIR for cancer, the vaccine may be in any form or formulations, such as (i) cell-based vaccines, (ii) subunit vaccines, (iii) protein-based vaccines, (iv) peptide-based vaccines, or (v) nucleic acid-based vaccines (such as DNA-based vaccines, RNA-based vaccines, plasmid-based vaccines, or viral vector-based vaccines).

The VBIR for cancer provided by the present disclosure may be applicable for any type of cancers. Examples of specific cancers include: small-cell lung cancer, non-small cell lung cancer, glioma, gastric cancer, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, bladder cancer, breast cancer, and head and neck cancer.

Vaccines intended for treating cancers typically contain an antigen (in the form of a peptide, protein, cell component, whole cell, or a nucleic acid molecule encoding a peptide-based antigen) that is capable of eliciting an immune response against a particular TAA expressed on or by cells of the target tumor. Many TAAs are known in the art. Examples of known TAAs include: PSA, PSCA, and PSMA for prostate cancer, CEA, MUC-1, Ep-CAM, 5T4, hCG-b, K-ras, and TERT for colorectal cancer, CEA, Muc-1, p53, mesothelin, Survivin, and NY-ESO-1 for ovarian cancer; Muc-1, 5T4, WT-1, TERT, CEA, EGF-R and MAGE-A3 for non-small cell lung cancer; 5T4 for renal cell carcinoma; and Muc-1, mesothelin, K-Ras, Annexin A2, TERT, and CEA for pancreatic cancer. In some particular embodiments, the vaccine used in the VBIR for cancer provided by the present disclosure is selected from the group consisting of:

(1) a vaccine capable of eliciting an immune response against a TAA selected from PSA, PSCA, PSMA, CEA, MUC-1, TERT, mesothelin, EGF-R, or MAGE-A3;

(2) a vaccine containing a peptide antigen derived from a TAA selected from PSA, PSCA, PSMA, CEA, MUC-1, TERT, mesothelin, EGF-R, or MAGE-A3; and (3) a vaccine containing a nucleic acid molecule that encodes a peptide antigen, wherein the peptide antigen is derived from a TAA selected from PSA, PSCA, PSMA, CEA, MUC-1, TERT, mesothelin, EGF-R, or MAGE-A3.

In still other particular embodiments, the vaccine contains a nucleic acid molecule that encodes one or more immunogenic polypeptides derived from PSA, one or more immunogenic polypeptides derived from PSCA, or one or more immunogenic polypeptides derived from PSMA.

In a specific embodiment, the nucleic acid molecule is selected from the group consisting of:

(1) a nucleic acid molecule encoding an immunogenic polypeptide derived from the human PSMA of SEQ ID NO:42;

(2) a nucleic acid molecule encoding an immunogenic polypeptide comprising amino acids 15-750 of SEQ ID NO:42;

(3) a nucleic acid molecule comprising the nucleotide sequence of SEQ ID NO: 43, or a degenerate variant thereof;

(4) a nucleic acid molecule comprising the nucleotide sequence of SEQ ID NO: 44, or a degenerate variant thereof;

(5) a nucleic acid molecule comprising the nucleotide sequence of SEQ ID NO: 45, or a degenerate variant thereof;

(6) a nucleic acid molecule comprising the nucleotide sequence of SEQ ID NO: 46, or a degenerate variant thereof;

(7) a nucleic acid molecule encoding an immunogenic polypeptide derived from the human PSA of SEQ ID NO:47;

(8) a nucleic acid molecule encoding an immunogenic polypeptide comprising amino acids 25-261 of SEQ ID NO:47;

(9) a nucleic acid molecule encoding an immunogenic polypeptide derived from the human PSCA of SEQ ID NO:48;

(10) a nucleic acid molecule encoding (i) an immunogenic polypeptide derived from the human PSMA of SEQ ID NO:42, (ii) an immunogenic polypeptide derived from the human PSA of SEQ ID NO:47, and (iii) an immunogenic polypeptide derived from the human PSCA of SEQ ID NO:48; and

(11) a nucleic acid molecule encoding (i) an immunogenic polypeptide comprising amino acids 15-750 of SEQ ID NO:42, (ii) an immunogenic polypeptide comprising amino acids 25-261 of SEQ ID NO:47, and (iii) an immunogenic polypeptide of SEQ ID NO:48.

The nucleic acid molecules that encode one or more immunogenic polypeptides derived from prostate-associated antigens may be in the form of plasmids or vectors. An example of such a plasmid is the nucleic acid construct of SEQ ID NO:46 (also referred to as Plasmid 458). The nucleotide sequence of a vector that expresses an immunogenic polypeptide derived from human PSMA is set forth in SEQ ID NO:44 (also referred to as vector AdC68W). The nucleotide sequence of a vector that expresses an immunogenic polypeptide derived from human PSMA, an immunogenic polypeptide derived from human PSA, and an immunogenic polypeptide derived from human PSCA is set forth in SEQ ID NO:45 and a vector human PSMA (vector AdC68W-734). Various immunogenic polypeptides derived from human PSMA, PSA, and PSCA, nucleic acid constructs (including plasmids and vectors) encoding such immunogenic polypeptides, and methods for preparing the immunogenic polypeptides and nucleic acid constructs, including Plasmid 458, and vector AdC68W and AdC68W-734, are disclosed in Internationals Application Publications WO2013/164754 and WO 2015/063647, each of which is incorporated herein by reference in its entirety.

In one aspect, the invention provides an isolated antagonist antibody which specifically binds to PD-1, wherein the antibody comprises a heavy chain variable region (VH) comprising a VH complementarity determining region one (CDR1), VH CDR2, and VH CDR3 of the VH having an amino acid sequence selected group the group consisting of SEQ ID NO: 3, SEQ ID NO: 4; SEQ ID NO: 5; and SEQ ID NO: 6; and a light chain variable region (VL) comprising a VL CDR1, VL CDR2, and VL CDR3 of the VL having an amino acid sequence selected from the group consisting of SEQ ID NO: 2; SEQ ID NO:7; SEQ ID NO: 8; and SEQ ID NO: 9.

Any anti-PD-1 antagonist antibodies disclosed in the present disclosure may be used in the VBIR for cancer. In some embodiments, the anti-PD-1 antagonist antibody comprises a VH region and/or a VL region, wherein the VH region comprises the amino acid sequence shown in SEQ ID NO: 3, 4, 5, or 6, or a variant with one or several conservative amino acid substitutions in residues that are not within a CDR, and wherein the VL region comprises the amino acid sequence shown in SEQ ID NO: 2, 7, 8, or 9, or a variant thereof with one or several amino acid substitutions in amino acids that are not within a CDR. In some embodiments, the antibody comprises a light chain comprising the sequence shown in SEQ ID NO: 39 and/or a heavy chain comprising the sequence shown in SEQ ID NO: 29 or 38. In some particular embodiments, the antibody comprises a VH region produced by the expression vector with ATCC Accession No. PTA-121183. In some embodiments, the antibody comprises a VL region produced by the expression vector with ATCC Accession No. PTA-121182.

The VBIR for cancer provided by the present disclosure may further comprise one or more other immune modulators (in addition to the PD-1 antagonist antibody provided by the present disclosure). The other immune modulators may be an immune-effector-cell enhancer ("IEC enhancer") or an immune-suppressive-cell inhibitor ("ISC inhibitor"). The additional IEC enhancer or additional ISC inhibitor may be used alone in combination with the VBIR for cancer. The additional IEC enhancer and additional ISC inhibitor may also be used together in combination with the VBIR for cancer.

Examples of classes of ISC inhibitors include protein kinase inhibitors, cyclooxygenase-2 (COX-2) inhibitors, phosphodiesterase type 5 (PDE5) inhibitors, and DNA crosslinkers. Examples of COX-2 inhibitors include celecoxib and rofecoxib. Examples of PDE5 inhibitors include avanafil, lodenafil, mirodenafil, sildenafil, tadalafil, vardenafil, udenafil, and zaprinast. An example of DNA crosslinkers is cyclophosphamide. The term "protein kinase inhibitor" refers to any substance that acts as a selective or non-selective inhibitor of a protein kinase. Examples of specific protein kinase inhibitors suitable for use in the VBIR for cancer include Lapatinib, AZD 2171, ET18OCH 3, Indirubin-3'-oxime, NSC-154020, PD 169316, Quercetin, Roscovitine, Triciribine, ZD 1839, 5-Iodotubercidin, Adaphostin, Aloisine, Alsterpaullone, Aminogenistein, API-2, Apigenin, Arctigenin, ARRY-334543, Axitinib (AG-013736), AY-22989, AZD 2171, Bisindolylmaleimide IX, CCI-779, Chelerythrine, DMPQ, DRB, Edelfosine, ENMD-981693, Erbstatin analog, Erlotinib, Fasudil, Gefitinib (ZD1839), H-7, H-8, H-89, HA-100, HA-1004, HA-1077, HA-1100, Hydroxyfasudil, Kenpaullone, KN-62, KY12420, LFM-A13, Luteolin, LY294002, LY-294002, Mallotoxin, ML-9, MLN608, NSC-226080, NSC-231634, NSC-664704, NSC-680410, NU6102, Olomoucine, Oxindole I, PD 153035, PD 98059, Phloridzin, Piceatannol, Picropodophyllin, PKI, PP1, PP2, PTK787/ZK222584, PTK787/ZK-222584, Purvalanol A, Rapamune, Rapamycin, Ro 31-8220, Rottlerin, SB202190, SB203580, Sirolimus, SL327, SP600125, Staurosporine, STI-571, SU1498, SU4312, SU5416, SU5416 (Semaxanib), SU6656, SU6668, syk inhibitor, TBB, TCN, Tyrphostin AG 1024, Tyrphostin AG 490, Tyrphostin AG 825, Tyrphostin AG 957, U0126, W-7, Wortmannin, Y-27632, Zactima (ZD6474), ZM 252868. gefitinib (Iressa®), sunitinib malate (SUTENT; SU11248), erlotinib (TARCEVA: OSI-1774), lapatinib (GW572016; GW2016), canertinib (CI 1033), semaxinib (SU5416), vatalanib (PTK787/ZK222584), sorafenib (BAY 43-9006), imatinib (Gleevec®; ST1571), dasatinib (BMS-354825), leflunomide (SU101), vandetanib (ZACTIMA; ZD6474), and nilotinib.

In some particular embodiments, the tyrosine kinase inhibitor is sunitinib malate Sorafenib tosylate, or Axitinib. Sunitinib malate, which is marketed by Pfizer Inc. under the trade name SUTENT, is described chemically as butanedioic acid, hydroxy-, (2S)-, compound with N-[2-(diethylamino)ethyl]-5-[(Z)-(5-fluoro-1,2-dihydro-2-oxo-3H-indol-3-ylidine)methyl]-2,4-dimethyl-H-pyrrole-3-carboxamide (1:1). The compound, its synthesis, and particular polymorphs are described in U.S. Pat. No. 6,573,293. Sunitinib malate has been approved in the U.S. for the treatment of gastrointestinal stromal tumor, advanced renal cell carcinoma, and progressive, well-differentiated pancreatic neuroendocrine tumors in patients with unresectable locally advanced or metastatic disease. The recommended dose of sunitinib malate for gastrointestinal stromal tumor (GIST) and advanced renal cell carcinoma (RCC) for humans is 50 mg taken orally once daily, on a schedule of 4 weeks on treatment followed by 2 weeks off (Schedule 4/2). The recommended dose of sunitinib malate for pancreatic neuroendocrine tumors is 37.5 mg taken orally once daily. In the VBIR for cancer, sunitinib malate may be administered orally in a single dose or multiple doses. Typically, sunitinib malate is delivered for two, three, four or more consecutive weekly doses followed by an "off" period of about 1 or 2 weeks, or more where no sunitinib malate is delivered. In one embodiment, the doses are delivered for about 4 weeks, with 2 weeks off. The effective amount of sunitinib malate administered orally to a human is typically below 40 mg per person per day, such as 37.5, 31.25, 25, 18.75, 12.5, or 6.25 mg per person per day. In some embodiments, sunitinib malate is administered orally in the range of 1-25 mg per person per day. In some other embodiments, sunitinib malate is administered orally in the range of 6.25, 12.5, or 18.75 mg per person per dose. Other dosage regimens and variations are foreseeable, and will be determined through physician guidance.

Sorafenib tosylate, which is marketed under the trade name NEXAVAR, has the chemical name is 4-(4-{3-[4-Chloro-3-(trifluoromethyl)phenyl]ureido}phenoxy)-N-methylpyrid-ine-2-carboxamide. It is approved in the U.S. for the treatment of primary kidney cancer (advanced renal cell carcinoma) and advanced primary liver cancer (hepatocellular carcinoma). The recommended daily dose is 400 mg taken orally twice daily. In the VBIR for cancer provided by the present disclosure, the effective amount of sorafenib tosylate administered orally is typically below 400 mg per person per day. In some embodiments, the effective amount of sorafenib tosylate administered orally is in the range of 10-300 mg per person per day. In some other embodiments, the effective amount of sorafenib tosylate administered orally is between 10-200 mg per person per day, such as 10, 20, 60, 80, 100, 120, 140, 160, 180, or 200 mg per person per day.

Axitinib, which is marketed under the trade name INLYTA, has the chemical name is (N-Methyl-2-[3-((E)-2-pyridin-2-yl-vinyl)-H-indazol-6-ylsulfanyl]-benzamide. It is approved for the treatment of advanced renal cell carcinoma after failure of one prior systemic therapy. The starting dose is 5 mg orally twice daily. Dose adjustments can be made based on individual safety and tolerability. In the VBIR for cancer provided by the present disclosure, the effective amount of axitinib administered orally is typically below 5 mg twice daily. In some other embodiments, the effective amount of axitinib administered orally is between 1-5 mg twice daily. In some other embodiments, the effective amount of axitinib administered orally is between 1, 2, 3, 4, or 5 mg twice daily.

Examples of IEC enhancers that may be used in the VBIR for cancer provided by the present disclosure include TNFR agonists, CTLA-4 antagonists, TLR agonists, other PD-1 antagonists (such as BMS-936558 and anti-PD-1 antibody CT-011), programmed cell death protein 1 ligand 1 (PD-L1) antagonists (such as BMS-936559), lymphocyte-activation gene 3 (LAG3) antagonists, and T cell Immunoglobulin- and mucin-domain-containing molecule-3 (TIM-3) antagonists. Examples of TNFR agonists include agonists of OX40, 4-1BB (such as BMS-663513), GITR (such as TRX518), and CD40. Examples of specific CD40 agonists are described in details herein below.

In certain other embodiments, the additional immune modulator is an anti-CD40 agonist antibody. The antibody can be a human, humanized or part-human chimeric anti-CD40 antibody. Examples of specific anti-CD40 monoclonal antibodies include the G28-5, mAb89, EA-5 or S2C6 monoclonal antibody, and CP870893. In a particular embodiment, the anti-CD40 agonist antibody is CP870893 or dacetuzumab (SGN-40).

CP-870,893 is a fully human agonistic CD40 monoclonal antibody that has been investigated clinically as an anti-tumor therapy. The structure and preparation of CP870,893 is disclosed in WO2003040170, in which antibody CP870,893 is identified as antibody "21.4.1". The amino acid sequences of the heavy chain and light chain of CP-870,893 are set forth in SEQ ID NO: 46 and SEQ ID NO: 48, respectively, as well as in Table 7, in WO2003040170. In clinical trials, CP870,893 was administered by intravenous infusion at doses generally in the ranges of 0.05-0.25 mg/kg per infusion. In the VBIR for cancer provided by the present disclosure, CP-870,893 may be administered intradermally, subcutaneously, or topically. The effective amount of CP870893 to be administered in the regimen is generally below 0.2 mg/kg, typically in the range of 0.01 mg-0.15 mg/kg, or 0.05-0.1 mg/kg.

Dacetuzumab (also known as SGN-40 or huS2C6; CAS number 88-486-59-9) is another anti-CD40 agonist antibody that has been investigated in clinical trials for indolent lymphomas, diffuse large B cell lymphomas and Multiple Myeloma. In the VBIR for cancer provided by the present disclosure, dacetuzumab may be administered intradermally, subcutaneously, or topically. The effective amount of dacetuzumab to be administered is generally below 16 mg/kg, typically in the range of 0.2 mg-14 mg/kg, or 0.5-8 mg/kg, or 1-5 mg/kg.

In still other embodiments, the additional immune modulator is an anti CTLA-4 antagonist. Examples of suitable anti-CTLA-4 antagonist include anti-CTLA-4 antibodies (such as human anti-CTLA-4 antibodies, mouse anti-CTLA-4 antibodies, mammalian anti-CTLA-4 antibodies, humanized anti-CTLA-4 antibodies, monoclonal anti-CTLA-4 antibodies, polyclonal anti-CTLA-4 antibodies, chimeric anti-CTLA-4 antibodies, anti-CTLA-4 domain antibodies), and inhibitors of CTLA-4 that agonize the co-stimulatory pathway. In some embodiments, the CTLA-4 inhibitor is Ipilimumab or Tremelimumab.

Ipilimumab (marketed as YERVOY; also known as MEX-010, MDX-101, or by its CAS Registry No. 477202-00-9) is disclosed as antibody 10DI in PCT Publication No. WO 01/14424, incorporated herein by reference in its entirety and for all purposes. Examples of pharmaceutical composition comprising Ipilimumab are provided in PCT Publication No. WO 2007/67959. Ipilimumab is approved in the U.S. for the treatment of unresectable or metastatic melanoma. In the methods provided by the present invention, Ipilimumab may be administered intradermally or subcutaneously. The effective amount of Ipilimumab administered locally is typically in the range of 5-200 mg/dose per person. In some embodiments, the effective amount of Ipilimumab is in the range of 10-150 mg/dose per person per dose. In some particular embodiments, the effective amount of Ipilimumab is about 10, 25, 50, 75, 100, 125, 150, 175, or 200 mg/dose per person.

Tremelimumab (also known as CP-675,206) is a fully human IgG2 monoclonal antibody and has the CAS number 745013-59-6. Tremelimumab is disclosed as antibody 11.2.1 in U.S. Pat. No. 6,682,736, incorporated herein by reference in its entirety and for all purposes. In the VBIR for cancer provided by the present invention, Tremelimumab may be administered intravenously, intradermally, or subcutaneously. The effective amount of Tremelimumab administered intradermally or subcutaneously is typically in the range of 5-200 mg/dose per person. In some embodiments, the effective amount of Tremelimumab is in the range of 10-150 mg/dose per person per dose. In some particular embodiments, the effective amount of Tremelimumab is about 10, 25, 50, 75, 100, 125, 150, 175, or 200 mg/dose per person.

In still other embodiments, the additional immune modulator is a Toll-like Receptor (TLR) agonist. The term "toll-like receptor agonist" or "TLR agonist" refers to a compound that acts as an agonist of a toll-like receptor (TLR).

This includes agonists of TLR1, TLR2, TLR3, TLR4, TLR5, TLR6, TLR7, TLR8, TLR9, TLR10, and TLR11 or a combination thereof.

TLR agonists useful in the method of the present invention include both small organic molecules and large biological molecules. Examples of small molecule TLR agonists include 4-amino-alpha, alpha, 2-trimethyl-IH-imidazo[4,5-c]qumolin-I-ethanol, N-(2-{2-[4-amino-2-(2-methoxyethyl)-IH-imidazo[4,5-c]quinolin-I-yl]ethoxy-}ethyl)-N-methylmorpholine-4-carboxamide, I~(2~amino-2-methylpropyl)-2-(ethoxymethyl-)-IH-imidazo[4,5-c]quinolin-4-amine, N-[4-(4-amino-2-ethyl-IH-imidazo[4,5-c]quinolin-1-yl)butyl]methanesulfonamide, N-[4-(4-amino-2-propyl-IH-imidazo[4,5-c]quinolin-I-yl)butyl] methanesulfonamide, and imiquimod. Some TLR agonists particularly useful in the methods or regimen provided by the present disclosure are discussed in review article: Folkert Steinhagen, et al.: TLR-based immune adjuvants. Vaccine 29 (2011): 3341-3355. In some embodiments, the TLR agonists are TLR9 agonists, particularly CpG oligonucleotides (or CpG.ODN). A CpG oligonucleotide is a short nucleic acid molecule containing a cytosine followed by a guanine linked by a phosphate bond in which the pyrimidine ring of the cytosine is unmethylated. Examples of particular CpG oligonucleotides useful in the methods provided by the present disclosure include:

```
                           (CpG 7909; SEQ ID NO: 49)
5' TCGTCGTTTTGTCGTTTTGTCGTT3';

(CpG 24555; SEQ ID NO: 50)
5' TCGTCGTTTTTCGGTGCTTTT3';
and
                           (CpG 10103; SEQ ID NO: 51)
5' TCGTCGTTTTTCGGTCGTTTT3'.
```

CpG7909, a synthetic 24mer single stranded, has been extensively investigated for the treatment of cancer as a monotherapy and in combination with chemotherapeutic agents, as well as an adjuvant for vaccines against cancer and infectious diseases. In the methods provided by the present disclosure, CpG7909 may be administered by injection into the muscle or any other suitable methods. For use with a nucleic acid-based vaccine, such as a DNA vaccine, a CpG may be co-formulated with the vaccine in a single formulation and administered by intramuscular injection coupled with electroporation. The effective amount of CpG7909 by intramuscular, intradermal, or subcutaneous administration is typically in the range of 10 μg/dose-10 mg/dose. In some embodiments, the effective amount of CpG7909 is in the range of 0.05 mg-14 mg/dose. In some particular embodiments, the effective amount of CpG7909 is about 0.05, 0.1, 0.2, 0.3, 0.4, 0.5, 05 1 mg/dose. Other CpG oligonucleotides, including CpG 24555 and CpG 10103, may be administered in similar manner and dose levels.

In the VBIR for cancer, the anti-PD-1 antagonist, the vaccine, and the additional immune modulators may be administered either simultaneously or sequentially. In some embodiments, a vaccine is administered sequentially with respect to the anti-PD-1 antagonist antibody, but simultaneously (e.g., in a mixture) with respect to one or more additional immune modulators. In cases where a nucleic acid vaccine is administered in combination with a CpG, the vaccine and CpG may be contained in a single formulation and administered together by any suitable method. In some embodiments, the nucleic acid vaccine and CpG in a co-formulation (mixture) is administered by intramuscular injection in combination with electroporation.

Formulations

Therapeutic formulations of the anti-PD-1 antagonist antibody used in accordance with the present invention are prepared for storage by mixing an antibody having the desired degree of purity with optional pharmaceutically acceptable carriers, excipients or stabilizers (Remington, The Science and Practice of Pharmacy 20th Ed. Mack Publishing, 2000), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cydohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the anti-PD-1 antagonist antibody are prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The formulations to be used for in vivo administration must be sterile. This is readily accomplished by, for example, filtration through sterile filtration membranes. Therapeutic anti-PD-1 antagonist antibody compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from about 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing an anti-PD-1 antagonist antibody with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Kits

The invention also provides kits comprising any or all of the antibodies described herein. Kits of the invention include one or more containers comprising an anti-PD-1 antagonist antibody described herein and instructions for use in accordance with any of the methods of the invention described herein. Generally, these instructions comprise a description of administration of the anti-PD-1 antagonist antibody for the above described therapeutic treatments. In some embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In some embodiments, the antibody is a human antibody. In some embodiments, the antibody is a humanized antibody. In some embodiments, the antibody is a monoclonal antibody. The instructions relating to the use of an anti-PD-1 antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-PD-1 antibody. The container may further comprise a second pharmaceutically active agent.

Kits may optionally provide additional components such as buffers and interpretive information. Normally, the kit comprises a container and a label or package insert(s) on or associated with the container.

Biological Deposit

Representative materials of the present invention were deposited in the American Type Culture Collection, 10801 University Boulevard, Manassas, Va. 20110-2209, USA, on Apr. 29, 2014. Vector msb7-LC having ATCC Accession No. PTA-121182 is a polynucleotide encoding the mAb7 light chain variable region, and vector mab7-HC having ATCC Accession No. PTA-121183 is a polynucleotide encoding the mAb7 heavy chain variable region. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. § 122 and the Commissioner's rules pursuant thereto (including 37 C.F.R. § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1: Effect of Anti-PD-1 Antibody on IFN-γ and TNF Secretion

This example illustrates the effect of anti-PD-1 antibody on IFN-γ and TNF secretion in a mixed lymphocyte reaction (MLR) assay.

Primary human T cell isolated from whole blood (Stanford University blood bank) were activated by allogeneic dendritic cells (DC) expressing high levels of PD-L1 and PD-L2, that were previously differentiated using IL-4 and GM-CSF from CD14+ myeloid cells. In this study, the following antibodies were used: isotype control (IgG4 kappa hinge stabilized), anti-PD-1 antogonist antibody C1, anti-PD-1 antagonist antibody C2, anti-PD-1 antagonist antibody C3, EH12.1 (BD Biosciences mouse anti human anti-PD-1 antibody, mouse isotype IgG1 Kappa), mAb7-G4, mAb15-G4, mAb-AAA, mAb15-AAA (G4=IgG4 hinge stabilized; AAA=mutant IgG1 which does not bind FcγR). Antibodies were tested at the following concentrations: 0, 0.1, 1, or 10 μg/ml).

For the MLR assay, cultures were incubated with test or control antibody in 96 well plates in triplicates at ratios of 1:10 DC:T cells and incubated in humidified incubator at 37° C. with 5% $CO_2$. Supernatants were harvested at day 5 and cytokines were measured using Cytometric Bead Array (CBA) using Human Soluble Protein Flex Set System kit (BD Biosciences, cat #558265) according to the manufacturer's protocol with the following human analytes: IFNγ (BD Biosciences, cat #558269), TNF (BD Biosciences, cat #558273). Briefly, 96 well filter plates (Millipore, cat #MSBVN1250) were washed with Wash Buffer (BD Biosciences proprietary formula) and aspirated by vacuum manifold. Standards provided by the kit and samples were diluted in Assay Diluent (BD Biosciences proprietary formula) and added to the plates with Capture Beads (capture bead are beads coated with antibodies for a specific soluble protein coated with a distinct fluorescence). Plates were mixed for 5 minutes at 500 rpm using a plate shaker, and incubated for 1 hour at room temperature. Detection Reagent (phycoerythrin (PE)-conjugated antibodies, provided by the k) was added to the plates and plates were mixed for 5 minutes. Plates were incubated for 2 hours at room temperature. Then were with wash Buffer for 5 minutes, and samples were acquired on the BD Fortessa platforms. Data were analyzed using FCAP Array v3 (BD). The results of the MLR assay are shown in Tables 6A and B below. Table 6A shows IFNγ levels (in pg/ml), and Table shows 6B TNF levels (in pg/ml). Data are presented as an average±S.E.M of biological triplicates. Samples are a representative of one MLR experiment.

TABLE 6A

IFNγ secretion

| | IFNγ Levels (pg/ml) Antibody Concentration (μg//ml) | | | | | | | |
|---|---|---|---|---|---|---|---|---|
| | 0 | | 0.1 | | 1 | | 10 | |
| Anti-body | Ave | SE | Ave | SE | Ave | SE | Ave | SE |
| Isotype Control | 1190.598 | 173.4735 | 3760 | 367.4262 | 3693.972 | 1033.879 | 3525.655 | 744.676 |
| EH12.1 | 1190.598 | 173.4735 | 3443.495 | 749.905 | 6196.637 | 576.9022 | 7111.465 | 2619.065 |
| mAb15-G4 | 1190.598 | 173.4735 | 4728.295 | 2.035 | 8893.595 | 365.125 | 7790.95 | 1700.012 |
| mAb7-G4 | 1190.598 | 173.4735 | 8567.203 | 2085.826 | 11876.86 | 1259.788 | 11794.82 | 1827.243 |
| mAb7-AAA | 1190.598 | 173.4735 | 10978.78 | 1006.925 | 10177.68 | 1907.027 | 9048.097 | 2022.583 |
| mAb15-AAA | 1190.598 | 173.4735 | 9068.905 | 1332.045 | 7083.987 | 2109.455 | 8644.313 | 1797.077 |
| C1 | 1190.598 | 173.4735 | 5891.74 | 583.57 | 6992.53 | 338.89 | 7523.7 | 1907.073 |
| C2 | 1190.598 | 173.4735 | 3433.687 | 52.36606 | 8121.305 | 195.315 | 4295.95 | 3124.257 |
| C3 | 1190.598 | 173.4735 | 9698.06 | 529.47 | 11650.97 | 143.025 | 8282.573 | 2332.477 |

TABLE 6B

TNF secretion

| | TNF Levels (pg/ml) Antibody Concentration (µg//ml) | | | | | | | |
|---|---|---|---|---|---|---|---|---|
| | 0 | | 0.1 | | 1 | | 10 | |
| Anti-body | Ave | SE | Ave | SE | Ave | SE | Ave | SE |
| Isotype Control | 371.3233 | 17.01197 | 407.4133 | 49.58195 | 486.7167 | 14.42418 | 501.17 | 5.033334 |
| EH12.1 | 371.3233 | 17.01197 | 571.1233 | 60.43963 | 667.0033 | 35.72991 | 799.3033 | 7.836955 |
| mAb15-G4 | 371.3233 | 17.01197 | 743.1167 | 56.75547 | 686.32 | 45.63348 | 798.8533 | 9.143657 |
| mAb7-G4 | 371.3233 | 17.01197 | 730.47 | 33.35488 | 793.05 | 21.19019 | 930.6233 | 16.04937 |
| mAb7-AAA | 371.3233 | 17.01197 | 795.1133 | 58.01784 | 773.32 | 32.32587 | 798.68 | 17.37746 |
| mAb15-AAA | 371.3233 | 17.01197 | 803.87 | 34.20712 | 869.4867 | 43.04225 | 731.33 | 37.8211 |
| C1 | 371.3233 | 17.01197 | 641.5533 | 58.65366 | 809.1767 | 55.78437 | 656.6467 | 36.03128 |
| C2 | 371.3233 | 17.01197 | 724.9133 | 35.53936 | 769.6367 | 22.06726 | 772.5367 | 49.44021 |
| C3 | 371.3233 | 17.01197 | 692.1067 | 39.12236 | 642.25 | 21.44117 | 744.0067 | 49.58307 |

Treatment of activated T cells with anti-PD-1 antagonist antibodies resulted in increased IFNγ levels compared to isotype control (Table 6A). For example, treatment with 0.1 µg/ml mAb15-G4 and mAb7-G4 resulted in an IFNγ level of 4728.295±2.035 pg/ml and 8567.203±2085.826 pg/ml, respectively. Treatment with 1 µg/ml mAb15-G4 and mAb7-G4 resulted in an IFNγ level of 8893.595±365.125 pg/ml and 11876.86±1259.788 pg/ml, respectively. Treatment with 10 µg/ml mAb15-G4 and mAb7-G4 resulted in an IFNγ level of 7790.95±1700.012 pg/ml and 11794.82±1827.243 pg/ml, respectively. In contrast, treatment with 0.1, 1, or 10 µg/ml isotype control resulted in IFNγ levels of 3760±367.4262 pg/ml, 3693.972±1033.879 pg/ml, and 3525.655±744.676 pg/ml, respectively.

Treatment of activated T cells with anti-PD-1 antagonist antibodies resulted in increased TNF levels compared to isotype control (Table 6B). For example, treatment with 0.1 µg/ml mAb15-G4 or mAb7-G4 resulted in a TNF level of 743.1167±56.75547 pg/ml and 730.47±33.35488 pg/ml, respectively. Treatment with 1 µg/ml mAb15-G4 and mAb7-G4 resulted in a TNF level of 686.32±45.63348 pg/ml and 793.05±21.19019 pg/ml, respectively. Treatment with 10 µg/ml mAb15-G4 or mAb7-G4 resulted in a TNF level of 798.853±9.14366 pg/ml and 930.623±16.0494 pg/ml, respectively. In contrast, treatment with 0.1, 1, or 10 µg/ml isotype control resulted in TNF levels of 407.4133±49.58195 pg/ml, 486.7167±4.4241 pg/ml, and 501.17±5.033334 pg/ml, respectively.

These results demonstrate that anti-PD-1 antibodies mAb7 and mAb15 stimulate IFNγ and TNF secretion from T cells at least as well as or better than anti-PD-1 antibodies C1, C2, and C3.

A second MLR study was conducted to test the effect of lower antibody concentrations on T cell activation. Primary human T cell isolated from whole blood were activated as described above. The following antibodies were tested in the second study: mAb7 (G4), mAb15 (G4), C1 (G4), EH12.1, and G4 isotype control. Antibodies were tested at the following concentrations: 0.0001, 0.001, 0.01, 0.1, 1, and 10 pig/ml. The MLR assay was conducted as described above. Results are summarized in Tables 7A and 7B below.

TABLE 7A

IFNγ secretion

| | IFNγ Levels (pg/ml) Antibody Concentration (µg/ml) | | | | | |
|---|---|---|---|---|---|---|
| Anti-body | 0.0001 | 0.001 | 0.01 | 0.1 | 1 | 10 |
| Isotype Control | 558.9629 ± 489.4828 | 753.3767 ± 291.6092 | 1074.37 ± 324.2031 | 1667.96 ± 144.7286 | 1867.96 ± 282.7461 | 2501.293 ± 220.1829 |
| EH12.1 | 1703.907 ± 417.5669 | 2284.153 ± 408.1215 | 4384.477 ± 396.1451 | 4726.87 ± 1201.688 | 9914.05 ± 1188.064 | 15110.19 ± 1864.176 |
| C1 | 1774.38 ± 290.6059 | 2804.017 ± 598.5177 | 4148.123 ± 194.2466 | 6883.113 ± 1480.168 | 9598.413 ± 617.4762 | 10283.24 ± 1008.533 |
| mAb7 (G4) | 2082.07 ± 720.9931 | 3062.09 ± 370.2791 | 5067.823 ± 111.4903 | 7082.667 ± 1336.082 | 11928.81 ± 1457.723 | 11862.13 ± 800.586 |
| mAb15 (G4) | 1678.27 ± 233.82 | 1410.758 ± 439.9474 | 4734.49 ± 322.2087 | 5416 ± 1054.075 | 9140.337 ± 1320.499 | 10992.13 ± 1008.533 |

TABLE 7B

TNF secretion

| | TNF Levels (pg/ml) Antibody Concentration (µg/ml) | | | | | |
|---|---|---|---|---|---|---|
| Anti-body | 0.0001 | 0.001 | 0.01 | 0.1 | 1 | 10 |
| Isotype Control | 452.7133 ± 62.85 | 282.9287 ± 56.77266 | 310.9144 ± 21.7811 | 358.948 ± 81.09122 | 338.1107 ± 46.88385 | 331.008 ± 31.35559 |

TABLE 7B-continued

TNF secretion

| | TNF Levels (pg/ml) Antibody Concentration (μg/ml) | | | | | |
|---|---|---|---|---|---|---|
| Anti-body | 0.0001 | 0.001 | 0.01 | 0.1 | 1 | 10 |
| EH12.1 | 752.87 ± 32.81303 | 687.3733 ± 29.09567 | 859.0367 ± 89.3586 | 744.98 ± 131.3658 | 978.7567 ± 227.9979 | 1950.73 ± 155.2098 |
| C1 | 446.98 ± 26.89211 | 444.7867 ± 59.03216 | 465.0933 ± 65.75044 | 1045.45 ± 146.9018 | 997.6067 ± 79.17846 | 895.7267 ± 60.92022 |
| mAb7 (G4) | 227.6 ± 50.63436 | 394.4233 ± 30.47005 | 452.65 ± 30.64335 | 1089.377 ± 174.7824 | 1583.52 ± 267.2131 | 1419.88 ± 108.711 |
| mAb15 (G4) | 494.7967 ± 48.18105 | 489.2333 ± 30.63302 | 593.34 ± 65.87622 | 811.16 ± 89.50238 | 1143.54 ± 136.3954 | 1109.063 ± 57.70232 |

Treatment of activated T cells with anti-PD-1 antagonist antibodies resulted in increased IFNγ levels compared to isotype control (Table 7A). In cultures without antibody, the IFNγ level was 901.453±216.472 pg/ml. In cultures given 0.0001, 0.001, 0.01, 0.1, 1, or 10 μg/ml isotype control antibody, the IFNγ levels were 558.9629±489.4828 pg/ml, 753.3767±291.6092 pg/ml, 1074.37±324.2031 pg/ml, 1667.96±144.7286 pg/ml, 1867.96±282.7461 pg/ml, 2501.293±220.1829 pg/ml, respectively. In contrast, in cultures treated with 0.0001, 0.001, 0.01, 0.1, 1, or 10 μg/ml mAb7 (G4), the IFNγ levels were 2082.07±720.9931 pg/ml, 3062.09±370.2791 pg/ml, 5067.823±111.4903 pg/ml, 7082.667±1336.082 pg/ml, 11928.81±1457.723 pg/ml, 11862.13±800.586 pg/ml, respectively. In cultures treated with 0.0001, 0.001, 0.01, 0.1, 1, or 10 μg/ml mAb15 (G4), the IFNγ levels were 1678.27±233.82 pg/ml, 1410.758±439.9474 pg/ml, 4734.49±322.2087 pg/ml, 5416±1054.075 pg/ml, 9140.337±1320.499 pg/ml, and 10992.13±1008.533 pg/ml, respectively.

Treatment of activated T cells with anti-PD-1 antagonist antibodies resulted in increased TNF levels compared to isotype control (Table 7B). In cultures without antibody, the TNF level was 365.523±84.6607 pg/ml. In cultures treated with 0.0001, 0.001, 0.01, 0.1, 1, or 10 μg/ml isotype control antibody, the TNF levels were 452.7133±62.85 pg/ml, 282.9287±56.77266 pg/ml, 310.9144±21.7811 pg/ml, 358.948±81.09122 pg/ml, 338.1107±46.88385 pg/ml, and 331.008±31.35559 pg/ml, respectively. In contrast, in cultures treated with 0.0001, 0.001, 0.01, 0.1, 1, or 10 μg/ml mAb7 (G4), the TNF levels were 227.6±50.63436 pg/ml, 394.4233±30.47005, 452.65±30.64335 pg/ml, 1089.377±174.7824 pg/ml, 1583.52±267.2131 pg/ml, and 1419.88±108.711 pg/ml, respectively. In cultures given 0.0001, 0.001, 0.01, 0.1, 1, or 10 μg/ml mAb15 (G4), the TNF levels were 494.7967±48.1810 pg/ml, 489.2333±30.63302 pg/ml, 593.34±65.87622 pg/ml, 811.16±89.50238 pg/ml, 1143.54±136.3954 pg/ml, and 1109.063±57.70232 pg/ml, respectively.

These results demonstrate that that anti-PD-1 antibodies mAb7 and mAb15 block PD-1 signaling and promote IFNγ and TNF secretion from primary human T cells.

Example 2: Effect of Anti-PD-1 Antibodies on T Cell Proliferation

This example illustrates the effect of anti-PD-1 antibodies on T cell proliferation.

In this study, T cell proliferation was measured in an MLR assay in which T cells were cultured in the presence of anti-PD-1 antagonist or isotype control antibodies.

For the MLR, primary human T cell isolate from whole blood (obtained from Stanford University blood bank) were activated by allogeneic dendritic cells (DC) expressing high levels of PD-L1 and PD-L2, that were previously differentiated using IL-4 and GM-CSF from CD14+ myeloid cells. Two experiments were conducted.

In the first experiment, mAb7 (IgG4 kappa hinge stabilized), mAb15 (IgG4 kappa hinge stabilized), C1, EH12.1 and isotype control were compared. In the second experiment, clones mAb7, mAb15, C2, EH12.1 and isotype control were compared. In both experiments antibodies were added at the following concentrations: 0, 0.0001; 0.001; 0.01; 0.1; 1 and 10 μg/ml.

For both experiments, cultures were incubated with antibody in 96 well plates in triplicates at ratios of 1:10 DC:T cells and incubated in humidified incubator at 37° C. with 5% $CO_2$. On day 5, cultures were pulsed for 18 h with 1 μCi per well of [$^3$H]-thymidine before harvesting. Plates then harvested on DNA specific filter papers (Perkin Elmer) using Harvester96 (Tomtec Life Sciences). The radiolabeled filters were covered with beta scintillation liquid (Perkin Elmer) and read in Microbeta® counter plates (Perkin Elmer). Thymidine incorporation were analyzed as counts per minute (CPM). Results are shown as mean of triplicates±SEM.

TABLE 8A

| Antibody concentration (μg/ml) | Thymidine Incorporation (CPM) | | | | |
|---|---|---|---|---|---|
| | isotype control | EH12.1 | mAb7 | mAb15 | C1 |
| 0 | 183419.3 ± 4049.932 | 183419.3 ± 4049.932 | 183419.3 ± 4049.932 | 183419.3 ± 4049.932 | 183419.3 ± 4049.932 |
| 0.0001 | 205190 ± 7769.199 | 227412.3 ± 7769.199 | 226145 ± 9610.045 | 217278.7 ± 24472.76 | 211881.3 ± 10119.4 |
| 0.001 | 197943 ± 13904.69 | 218722 ± 13904.69 | 235367.3 ± 15199.75 | 193192 ± 11885.7 | 212198.3 ± 36451.79 |
| 0.01 | 175973.3 ± 10177.52 | 253913.3 ± 10177.52 | 265654.3 ± 12087.89 | 219167.3 ± 8928.691 | 232600 ± 26403.78 |

TABLE 8A-continued

| Antibody | Thymidine Incorporation (CPM) | | | | |
|---|---|---|---|---|---|
| concentration (μg/ml) | isotype control | EH12.1 | mAb7 | mAb15 | C1 |
| 0.1 | 192495.3 ± 16825.35 | 248270.7 ± 16825.35 | 264057.7 ± 10339.94 | 257924 ± 3376.669 | 278997.3 ± 18441.4 |
| 1 | 210104.7 ± 11484.23 | 210104.7 ± 11484.23 | 298696.7 ± 6164.177 | 276531 ± 3855.779 | 276141.3 ± 18516.97 |
| 10 | 206281.7 ± 16001.33 | 294602.7 ± 16001.33 | 301293 ± 6313.417 | 286260.7 ± 11483.22 | 264223.7 ± 9809.792 |

TABLE 8B

| Antibody | Thymidine Incorporatin (CPM) | | | | |
|---|---|---|---|---|---|
| concentration (μg/ml) | isotype control | EH12.1 | mAb7 | mAb15 | C2 |
| 0 | 229959 ± 5794.112 | 229959 ± 27771.7 | 229959 ± 27771.7 | 229959 ± 5794.112 | 229959 ± 27771.7 |
| 0.0001 | 299107 ± 3193 | 258428.3 ± 36794.25 | 280415.3 ± 14101.94 | 241112.7 ± 40486.56 | 258069.7 ± 23962.19 |
| 0.001 | 277197 ± 17518 | 272289 ± 29320.04 | 260183 ± 24634.25 | 233184 ± 28899.06 | 267117.7 ± 16388.83 |
| 0.01 | 278072.3 ± 32671.62 | 324891.3 ± 3396.229 | 365625.3 ± 30171.07 | 317377 ± 31915.29 | 381936.3 ± 31901.57 |
| 0.1 | 268939.7 ± 12332.06 | 342131.3 ± 19839.88 | 380054.3 ± 9774.328 | 360226.3 ± 1802.69 | 381110.7 ± 16996.97 |
| 1 | 241164 ± 13776.81 | 388757.7 ± 15684.37 | 392256.7 ± 15341.19 | 421229 ± 27865.13 | 401219 ± 1816.754 |
| 10 | 231897.7 ± 25865.95 | 408098 ± 20237.34 | 372889.7 ± 14826.49 | 323441.3 ± 64476.55 | 391925.3 ± 46054.82 |

Treatment of activated T cells with anti-PD-1 antagonist antibodies at a concentration of 0.01 μg/ml or greater resulted in significantly increased T cell proliferation compared to isotype control (Tables 8A and 8B).

For example, treatment with 0.01, 0.1, 1, or 10 μg/ml mAb7 resulted in thymidine incorporation rates of 365625.3±30171.07 CPM, 380054.3±9774.328 CPM, 392256.7±15341.19 CPM, and 372889.7±14826.49 CPM, respectively (Table 8B). Treatment with 0.01, 0.1, 1, or 10 μg/ml mAb15-G4 and mAb7 resulted in thymidine incorporation rates of 317377±31915.29 CPM, 360226.3±1802.69 CPM, 421229±27865.13 CPM, and 323441.3±64476.55 CPM, respectively (Table 8B). In contrast, treatment with 0.01, 0.1, 1, or 10 μg/ml isotype control resulted in thymidine incorporation rates of 278072.3±32671.62 CPM, 268939.7±12332.06 CPM, 241164±13776.81 CPM, and 231897.7±25865.95 CPM, respectively (Table 8B).

These results demonstrate that that anti-PD-1 antibodies mAb7 and mAb15 block PD-1 signaling and promote proliferation of primary human T cells.

Example 3: Effect of Anti-PD-1 Antibodies in a Mouse Model of GvHD

This example illustrates the effect of anti-PD-1 antibodies on T cell proliferation and body weight loss in a mouse model of graft versus host disease (GvHD).

NOD-scid-IL-2 receptor gamma chain null (NSG) mice were used in this study to test the effects of anti-PD-1 antagonist antibodies on T cell proliferation in vivo. Because NSG mice lack T cells and B cells and have impaired NK cells, high engraftment of human cells is readily achieved. When human PBMCs are engrafted in these mice, human T cell proliferation occurs and induces GvHD. The GvHD involves the myeloid compartment of the host as well as the human cells. Massive proliferation of human lymphocytes can be seen in the blood at early stages followed by high infiltration of these cells into the mouse organs, such as the liver, spleen, kidney, gut etc., resulting in body weight loss of the mice as well as skin lesions, hunched back, and death. The severity of the models depends on the donor PBMCs, and may differ between donors.

In this study, the following anti-PD-1 antagonist antibodies were used: mAb7 (human IgG4 hinge stabilized or AAA), mAb15 (human IgG4 hinge stabilized), C1, C2, and C3. For the negative control, an isotype control human IgG4 hinge stabilized antibody was used. Primary human PBMCs were isolated from whole blood (Stanford University blood bank), using Ficoll gradient. $10^7$ human PBMCs were injected into NSG mice (females 8 weeks old, Jackson Laboratories). At day 0 mice were randomized based on body weight and PBMCs were injected intravenously. For experiments 1-4, on day 2 and day 8 antibodies were administered intraperitoneally at 10 mg/kg. For experiment 5, on day 2 and day 8, antibodies were administered intraperitoneally at 1 mg/kg or 10 mg/kg. Table 9 summarizes the antibodies used in each experiment.

TABLE 9

Antibodies Used in Experiments 1-5

| Experiment 1 | Experiment 2 | Experiment 3 | Experiment 4 | Experiment 5 |
|---|---|---|---|---|
| isotype control | isotype control | isotype control | isotype control | isotype control |
| mAb7 | mAb15 | mAb15 | mAb15 | mAb7 |

TABLE 9-continued

Antibodies Used in Experiments 1-5

| Experiment 1 | Experiment 2 | Experiment 3 | Experiment 4 | Experiment 5 |
|---|---|---|---|---|
| mAb15 | mAb7 | mAb7 | mAb7 | |
| mAb7-AAA | C1 | C3 | C2 | |
| C1 | | | | |

Bodyweight was measured periodically. Results are summarized in FIGS. 1A-1E. Mice were bled periodically to assess T cell proliferation. Treatment with anti-PD-1 antibody accelerated disease course as measured by rate of body weight loss. Compared to control mice, mice treated with anti-PD-1 antagonist antibody had more rapid body weight loss (FIGS. 1A-1E).

Proliferation of human T cells was measured by flow cytometry using CD45 as a marker (clone H130; BD Biosciences). Flow cytometry results are summarized below in Table 10. T cell proliferation was higher in mice treated with anti-PD-1 antagonist antibody than in mice treated with isotype control. Higher percentage CD45 indicates higher level of proliferation of the CD45 cells and therefore more severe GvHD.

In Experiment 1, the percentage of CD45 positive blood cells was 63.86% in control mice (Table 10). In contrast, the percentage of CD45 positive blood cells in mice treated with anti-PD-1 antibody mAb7, mAb15, C1, or mAb7-AA was 80.34%, 77.62%, 77.26% and 76.9%, respectively (Table 10).

TABLE 10

T cell proliferation as measured by presence of CD45, animals treated

Experiment 1: % CD45 positive cells in blood at day 17

Antibodies (10 mg/ml)

| | control | mAb7 | mAb15 | C1 | mAb7-AAA |
|---|---|---|---|---|---|
| | 51.5 | 72.4 | 70 | 87.6 | 66.6 |
| | 52 | 76.8 | 69 | 82 | 81 |
| | 74.7 | 82.5 | 85.8 | 64.7 | 71 |
| | 65.3 | 84 | 93.3 | 80 | 85.883 |
| | 75.8 | 86 | 70 | 72 | 80 |
| Average | 63.86 | 80.34 | 77.62 | 77.26 | 76.8966 |
| SEM | 5.892643719 | 2.80258809 | 5.608074536 | 4.48826247 | 3.937116896 |

Experiment 2: % CD45 positive cells in blood at day 12

Antibodies

| | control | mAb7 | C1 | mAb15 |
|---|---|---|---|---|
| | 59 | 81 | 80 | 78.1 |
| | 51 | 80.078 | 75 | 79.3 |
| | 66 | 82.5 | 78 | 69.9 |
| | 75 | 84 | 80 | 81.8 |
| | 66 | 86 | 86 | 83.9 |
| Average | 63.4 | 82.7156 | 79.8 | 78.6 |
| SEM | 4.480513 | 1.182785 | 2.012461 | 2.678152 |

Experiment 3: % CD45 positive cells in blood at day 12

Antibodies (10 mg/ml)

| | control | mAb7 | C3 | mAb15 |
|---|---|---|---|---|
| | 51.5 | 72.4 | 70 | 72 |
| | 66 | 80 | 69 | 74.8 |
| | 74.7 | 82.5 | 85.8 | 86.9 |
| | 65.3 | 84 | 93.3 | 90.2 |
| | 75.8 | 86 | 70 | 79.4 |
| Average | 66.66 | 80.98 | 77.62 | 80.66 |
| SEM | 4.875269 | 2.63638 | 5.608075 | 3.880013 |

Experiment 4: % CD45 positive cells in blood at day 12

Antibodies (10 mg/ml)

| | control | mAb7 | C2 | mAb15 |
|---|---|---|---|---|
| | 67 | 92.23 | 83.1 | 88.1 |
| | 77.98 | 88.71 | 82.3 | 74.8 |
| | 78 | 82.5 | 85.8 | 86.9 |
| | 90 | 93 | 93.3 | 90.2 |
| | 86.8 | 80.1 | 90 | 79.4 |
| Average | 79.956 | 87.308 | 86.9 | 83.88 |
| SEM | 4.495211 | 2.890314 | 2.336932 | 3.253729 |

TABLE 10-continued

T cell proliferation as measured by presence of CD45, animals treated

Experiment 5: % CD45 positive cells in blood at day 10

| | | Antibodies | |
|---|---|---|---|
| | Control | mAb7 (1 mg/kg) | mAb7 (10 mg/kg) |
| | 70 | 72.4 | 77 |
| | 66 | 79 | 77 |
| | 74.7 | 82.5 | 85.8 |
| | 65.3 | 84 | 93.3 |
| | 70 | 86 | 90 |
| Average | 69.2 | 80.78 | 84.62 |
| SEM | 1.887127 | 2.668895 | 3.723305 |

In summary, mice treated with anti-PD-1 antibody had more rapid body weight loss and increased T cell proliferation compared to mice treated with isotype control. These results demonstrate that treatment with anti-PD-1 antibody stimulates proliferation of human T cells in vivo.

Example 4: Binding of Anti-PD-1 Antibodies

This example illustrates anti-PD-1 antibody binding on activated human T cells and cynomolgus monkey (cyno) T cells.

Primary human T cells were isolated from PBMCs (Stanford University blood bank) using a human PAN T cell isolation kit according to the manufacturer protocol (Miltenyi Biotec; 130-096-353). Cyno PBMCs were purchased from (BioreclamationIVT), and PAN T cells were isolated using non-human primate PAN T cell isolation kit according to the manufacturer protocol (Miltenyi Biotec; 130-091-993). Human T cells were activated for 3 days with DYNABEADS™ human T-Activator CD3/CD28 for cell expansion and activation (Life Technologies; 11131D). Ratio of beads to cell used was 1:1 bead:T cell, respectively. Cyno T cells were activated for 3 days using T Cell Activation/Expansion Kit, non-human primate according to the manufacturer protocol (Miltenyi Biotec; 130-092-919). Ratio of beads to cells used was 1:1 bead:T cell; respectively. After 3 days cultures were harvested beads were separated form activated T cell using magnetic force. Cells were washed and incubated with FACS buffer (including 2% FBS) and human Fc Receptor binding inhibito (Affymetrix eBioscience cat. no. 16-9161-73). For cyno cells were used Fc Block reagent (BD Biosciences cat. no. 564765). Cells were incubated for 10 minutes at room temperature and then were then stained with live dead color to exclude dead cells (LIVE/DEAD® Fixable Blue Dead Cell Stain Kit, for UV excitation; catalog #A10346) for another 5 minutes. Anti PD-1 antibodies were added (concentrations of anti-PD-1 clones were incubated on cell in 1:3 serial dilution ratios starting 10 µg/ml-0 µg/ml) 1×10 cells were used in each reaction in total of 100 µl and cells were incubated on ice for 30 minutes. Cells then washed with FACS buffer to remove access of primary antibodies and incubated with anti human (AffiniPure F(ab')$_2$ Fragment Donkey Anti-Human IgG (H+L) secondary conjugated with Allophycocyanin (APC); cat. no. 709-136-149). Cells were stained for 30 minutes on ice. Cells were washed and kept on ice until read using BD LSRFortessa Cell Analyzer, (BD Biosciences, cat. no. 647465). Data were analyzed using FlowJo™ software. Results are summarized in FIGS. 2A and 2B.

Figure 2A:
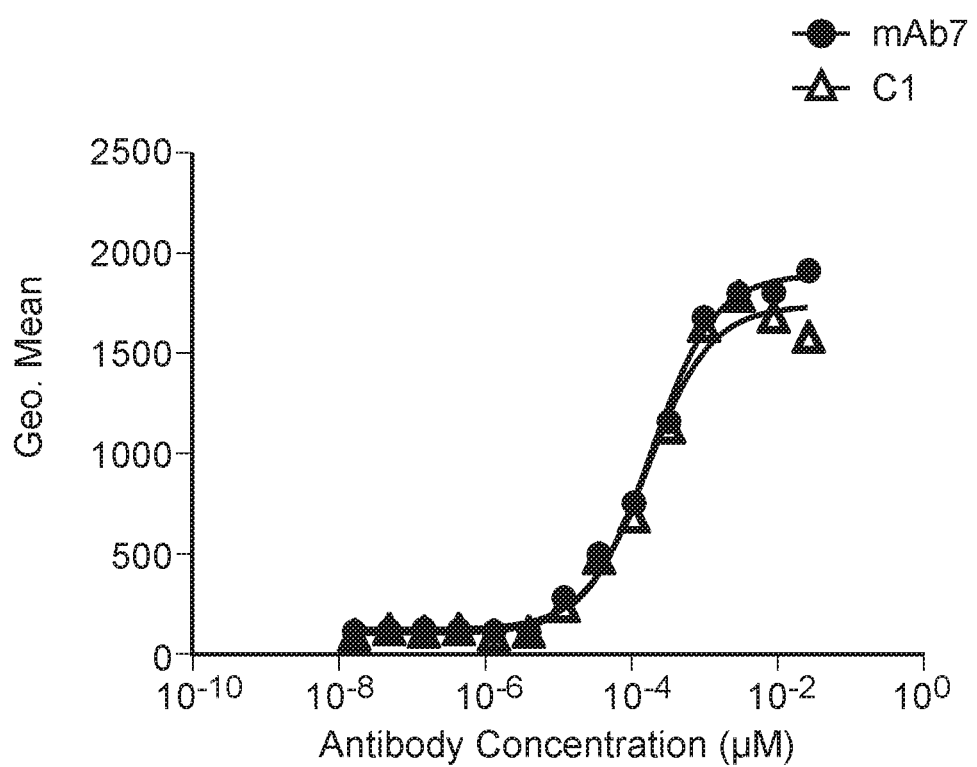
FIG. 2A depicts a graph summarizing EC50 for anti-PD-1 antibody binding to primary human activated T cells.
Figure 2B:
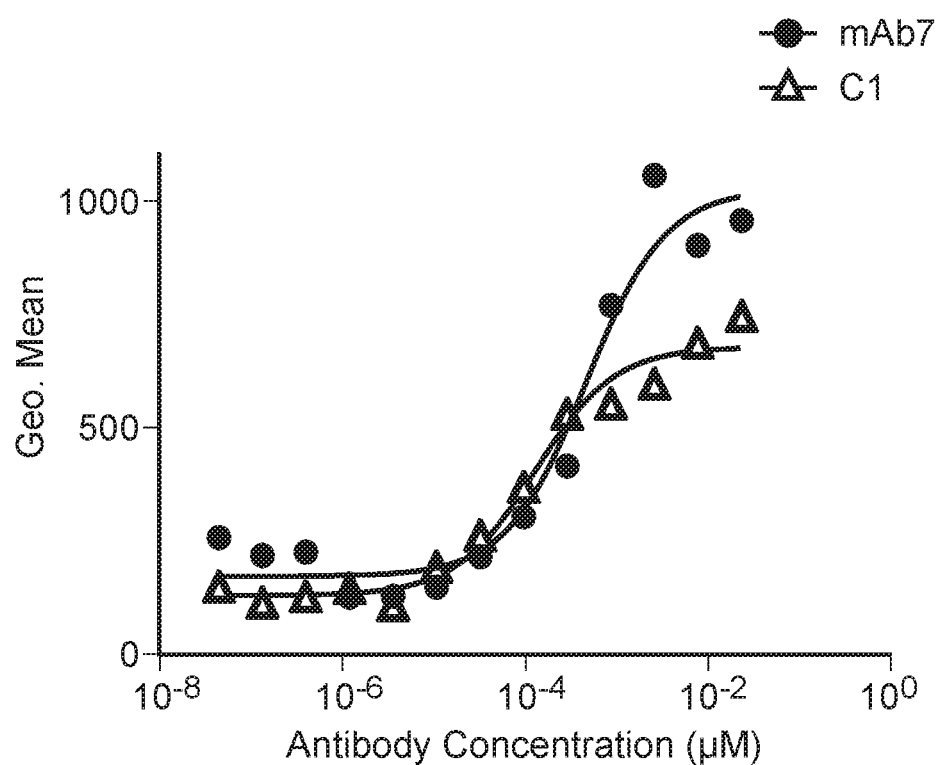
FIG. 2B depicts a graph summarizing EC50 for anti-PD-1 antibody binding to primary cyno activated T cells.

FIG. 2A shows EC50 measured for anti-PD-1 antibody binding to human activated cells, and FIG. 2B shows EC50 measured for anti-PD-1 antibody binding to cyno activated cells. Anti-PD-1 antibodies mAb7 and C1 bind activated T cells with similar EC50 (FIGS. 2A and 2C).

Example 5: Inhibition of PD-L1 Binding by Anti-PD-1 Antibody

This example illustrates inhibition of PD-1 ligand (PD-L1) binding by anti-PD-1 antibody.

Primary human T cells were isolated from PBMCs (Stanford University blood bank) using human PAN T cell isolation kit according to the manufacturer protocol (Miltenyi Biotec; 130-096-353). Cynomolgus Monkey PBMCs were purchased from (BioreclamationIVT), and PAN T cells were isolated using non-human primate PAN T cell isolation kit according to the manufacturer protocol (Miltenyi Biotec; 130-091-993). Human T cells were activated for 3 days with DYNABEADS™ human T-Activator CD3/CD28 (for cell expansion and activation, Life Technologies; 11131D). Ratio of beads to cell used was 1:1; respectively. Cyno T cells were activated for 3 days using T Cell Activation/Expansion Kit, non-human primate according to the manufacturer protocol (Miltenyi Biotec; 130-092-919). Ratio of beads to cells used was 1:1; respectively. After 3 days cultures were harvested beads were separated form activated T cell using magnetic force. Cells were washed and incubated with FACS buffer (including 2% FBS) and human Fc Receptor binding inhibitor (Affymetrix eBioscience; cat. no. 16-9161-73). For cyno cells were used Fc Block reagent (BD Biosciences; cat. no. 564765). Cells were incubated for 10 minutes at room temperature and then were stained with live dead color to exclude dead cells (LIVE/DEAD® Fixable Blue Dead Cell Stain Kit, for UV excitation; cat. no. A10346) for another 5 minutes. Human Recombinant PD-L1 Fc (R&D Systems, cat. no. 156-B7) or buffer alone was incubated with cells at 10 ng/ml. Each ligand was incubated separately and incubated on ice for 30 minutes. Cells then were washed and incubated with anti PD-1 antibodies (concentrations of anti-PD-1 clones were incubated on cell in 1:3 serial dilution ratios starting at 1 µg/ml-0 µg/ml) 1×10$^6$ cells were used in each reaction in total of 100 µl and cells were incubated on ice for 30 minutes. Cells then washed with FACS buffer to remove access of primary antibodies and incubated with anti-human kappa conjugated with Allophycocyanin (APC) (Life Technologies; cat no. MH10515). Cells were stained for 30 minutes on ice, then washed and kept on ice until read using BD LSRFortessa Cell Analyzer, (BD Biosciences, cat. no. 647465). Data were analyzed using FlowJo™ software and Mean fluoresce intensity (MFI) and geometrical means (Geo.M) of APC staining on live cells were calculated in the FlowJo™ software. After Geo mean calculation IC50 were calculated using in GraphPD Prism software. Results are summarized in Tables 11 and 12 below.

TABLE 11

Anti-PD-1 blockade of PD-L1 binding to PD-1 on human T cells

| Antibody concentration | Geo Mean | |
|---|---|---|
| (µg/ml) | mAb7 | C1 |
| 0.0083375 | 107 | 143 |
| 0.00416875 | 129 | 190 |
| 0.002084375 | 162 | 245 |
| 0.001042188 | 205 | 327 |
| 0.000521094 | 482 | 415 |
| 0.000260547 | 358 | 469 |
| 0.000130273 | 445 | 484 |
| 0.000065137 | 503 | 458 |
| 0.000032568 | 450 | 420 |
| IC50 (µM) | 0.001117 | 0.00224 |

TABLE 12

Anti-PD-1 blockade of PD-L1 binding to PD-1 on cyno T cells

| Antibody concentration | Geo Mean | |
|---|---|---|
| (µg/ml) | mAb7 | C1 |
| 0.0083375 | 114 | 108 |
| 0.00416875 | 135 | 144 |
| 0.002084375 | 174 | 183 |
| 0.001042188 | 240 | 264 |
| 0.000521094 | 322 | 325 |
| 0.000260547 | 440 | 404 |
| 0.000130273 | 494 | 469 |
| 0.000065137 | 491 | 472 |
| 0.000032568 | 410 | 406 |
| IC50 (µM) | 0.00092 | 0.00108 |

These results demonstrate that anti-PD-1 antibodies mAb7 and C1 inhibit PD-L1 binding to human and cyno T cells with similar IC50.

Example 6: Effect of Anti-PD-1 Antibody on T Cell Proliferation

Figure 3:
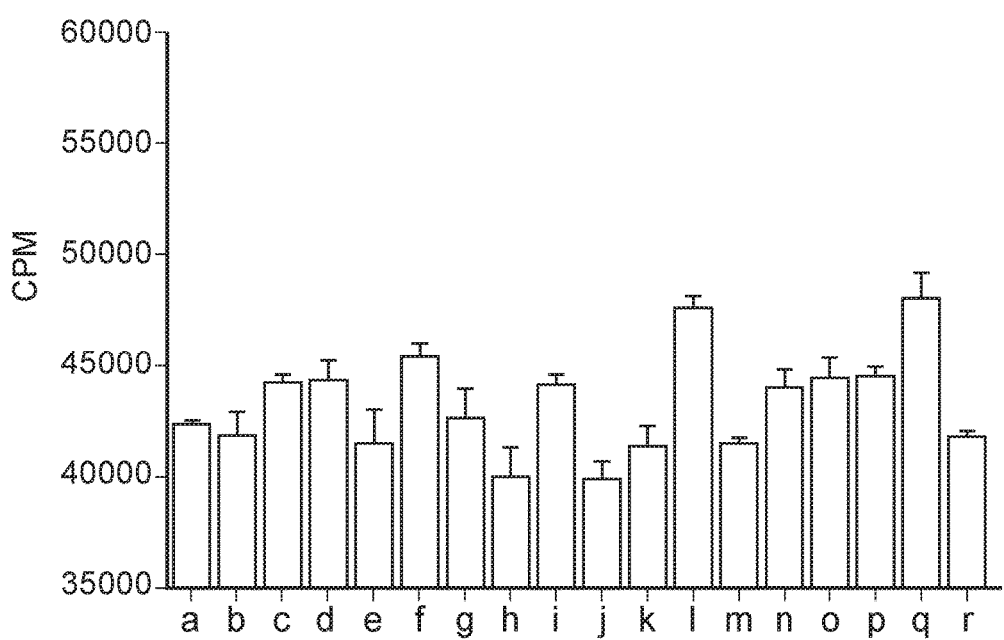
FIG. 3 depicts a bar graph summarizing proliferation of cultured activated CD4 T cells treated as follows (a) no antibody; (b) isotype control; (c) EH12.1; (d) C1; (e) C2; (f) C3; (g) mAb1; (h) mAbX; (i) mAb4; (j) mAb5; (k) mAb6; (l) mAb7; (m) mAb9; (n) mAb10; (o) mAb11; (p) mAb14; (q) mAb15; (r) mAb16.
Figure 4:
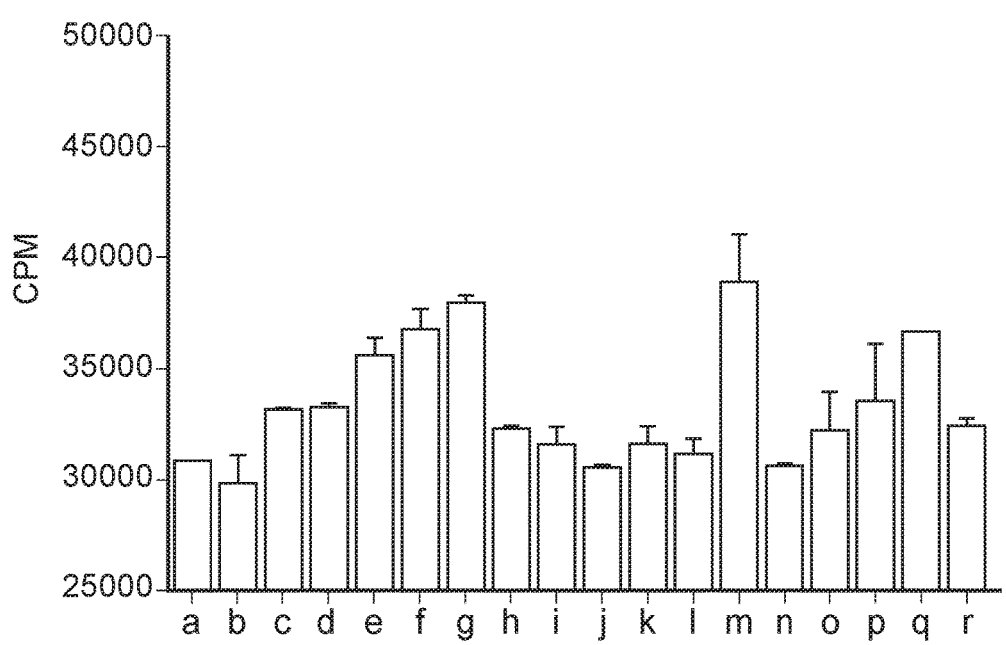
FIG. 4 depicts a bar graph summarizing proliferation of cultured activated CD8 T cells treated as follows (a) no antibody; (b) isotype control; (c) EH12.1; (d) C1; (e) C2; (f) C3; (g) mAb1; (h) mAbX; (i) mAb4; (j) mAb5; (k) mAb6; (l) mAb7; (m) mAb9; (n) mAb10; (o) mAb11; (p) mAb14; (q) mAb15; (r) mAb16.

This example illustrates the effect of anti-PD-1 antibody on T cell proliferation. CD4 and CD8 (AllCells, LLC) were activated for 2 days with DYNABEADS™ human T-Activator CD3/CD28 (or cell expansion and activation (Life Technologies; 11131D). Ratio of beads to cell used was 1:1; respectively to induce PD-1. At day 2, cultures were harvested and beads were separated from activated T cell using magnetic force. Cells then activated on PD-L1 expressing dendritic cells and cells were incubated with different anti-PD-1 clones at 1 µg/ml in 96 well plates in triplicates at ratios of 1:10 DC:T cells and incubated in humidified incubator at 37° C. with 5% $CO_2$. On day 3, cultures were pulsed for 18 h with 1 µCi per well of [$^3$H]-thymidine before harvesting. Plates then harvested on DNA specific filter papers (PerkinElmer) using Harvester96 (Tomtec Life Sciences). The radiolabeled filters were covered with beta scintillation liquid (Perkin Elmer) and read in Microbeta® counter plates (Perkin Elmer). Thymidine Incorporation were analyzed as counts per minute (CPM). Results are shown as mean of triplicates±SEM in FIGS. 3 and 4.

Example 7: Kinetic and Affinity Determination of Human, Cynomolgus Monkey and Mouse PD-1 Interacting with Humanized Anti-PD-1 Antibodies This example illustrates binding of anti-PD-1 antibodies to human, cyno, or mouse PD-1.

All interaction analysis was performed on label-free biosensors at 25° C. unless stated otherwise. Surface plasmon resonance biosensors (ProteOn-XPR™ from BioRad™, and Biacore 2000™ and Biacore T200™ from GE Life Sciences) were used to study human and cynomolgus monkey PD-1 and a biolayer interferometry biosensor (Octet-Red384, Fortebio/Pall Life Sciences) was used to study mouse PD-1. ProteOn experiments were performed in PBS pH 7.4+0.01% Tween-20 (PBST) running buffer. Biacore experiments were performed in 10 mM Hepes pH 7.4, 150 mM NaCl, 0.05% Tween-20 (HBST+) and Octet experiments were performed in HBST+ with 1 g/l BSA. The ProteOn data were processed in the ProteOn Manager software, the Biacore data were processed in Biaevaluation, and the Octet data were simply aligned to zero in the control software. The SPR data were double-referenced (Myszka, 1999, *J Mol Recognit* 12(5):279-284) and fit globally to a simple Langmuir model to determine the equilibrium dissociation constant, $K_D$, from the ratio of the kinetic rate constants ($K_D=k_d/k_a$).

Calibration-Free Concentration Analysis (CFCA)

The active concentration of human PD-1 (hPD-1) monomer (Sino Biologicals, cat. no. 10377-H08H) for use as analyte in the kinetic experiments with immobilized IgGs was determined empirically using a CFCA assay on a Biacore T200™ equipped with CM5 sensor chip. To prepare the surfaces for these experiments, a high capacity (approximately 12,000 RU) of mAb15 hIgG4 (or in some experiments, competitor antibody C2-hIgG1) was amine-coupled onto flow cell 2, leaving flow cell 1 blank (just "activated and blocked", without any IgG) to provide a reference surface. The hPD-1 samples were injected at nominal concentrations of 0.1, 1, and 10 µg/ml for 36 sec at both low (5 µl/min) and high (100 µl/min) flow rates. Surfaces were regenerated with a cocktail of 2:1 v/v Pierce IgG elution buffer (pH 2.8):4 M NaCl. Data were analyzed in the CFCA tool in the T200 software to derive an apparent activity value for the hPD-1 analyte, which was used to correct its "nominal" protein concentration, as determined by absorbance at 280 nm with appropriate extinction coefficient, into an "active" protein concentration. Some lots were found to be 32% active, while others were 100% active.

Kinetic Analysis of Human PD-1 (hPD-1) Binding to Amine-Coupled mAb7, mAb15, C1, C2, C3, and C4, mAbs A ProteOn-XPR36 equipped with GLC sensor chips (Bio-Rad™, Hercules, Calif.), was used to determine the kinetics and affinity of hPD-1 monomer binding to a panel of amine-coupled anti-hPD-1 mAbs (mAb7, mAb15, C1, C2, C3, and C4) in PBST running buffer. The surfaces for these experiments were prepared in three steps; (1) the ligand channels were minimally activated for two min using a freshly prepared mixture of the activation reagents at final 0.8 mM EDC and 0.2 mM sulfo-NHS in water, (2) the IgGs were coupled for three min at 15 µg/ml in 10 mM sodium acetate pH 4.5, and (3) excess reactive esters were blocked for three min with 1 M ethanolamine HCl pH 8.5. Final levels of coupled IgG ranged from 400 RU to 1157 RU. The hPD-1 monomer was injected in a one-shot kinetic mode (Bravman et al., 2006, *Anal Biochem* 358(2):281-288) along the "analyte" channels as a threefold dilution series with top "active" concentrations of 30, 44 or 36 nM, depending on the experiment. Association and dissociation times were 3 min and 20 min, respectively and all analytes were injected in duplicate binding cycles. Surfaces were regenerated with a cocktail of 2:1 v/v Pierce IgG elution buffer (pH 2.8):4 M NaCl.

TABLE 13

Kinetic analysis of hPD-1 monomer binding to amine-coupled IgGs

| IgG | $k_a$ (1/Ms) × $10^5$ | $k_d$ (1/s) × $10^{-4}$ | $K_D$ (pM) at 25° C. |
|---|---|---|---|
| mAb7 IgG1 AAA | 4.97 | <0.43* | <86 |
| mAb7 IgG4 | 4.53, 4.45 | <0.43* | <94, <96 (N = 2) |
| mAb15 IgG1 AAA | 8.13 | <0.43* | <53 |
| mAb15 IgG4 | 7.32 | <0.43* | <58 |
| C4 hIgG1 | 5.57, 4.84 | 5.25, 5.89 | 943, 1217 (N = 2) |
| C3 hIgG2 | 4.56 | 5.21 | 1143 |
| C3 hIgG4 | 5.59 | 4.03 | 721 |
| C2 hIgG2 | 4.88 | 6.07 | 1244 |
| C2 hIgG4 | 5.84 | 4.33 | 741 |
| C1 hIgG2 | 14.8 | 7.55 | 510 |
| C1 | 11.1, 8.34 | 5.57, 5.73 | 502, 687 (N = 2) |

The interactions of hPD-1 monomer with mAb7 and mAb15 showed no visible decay in binding response within the allowed dissociation phase, so an upper limit was placed on their $k_d$ and $K_D$ values, according to the "5% rule" (Katsamba et al, 2008, *Anal Biochem* 352(2):208-221) was applied to place an upper limit on their $k_d$ and $K_D$ values. N=2 refers to two independent experiments on different chips.

Cross-Reaction of mAb7 and mAb15 to Cynomolgus Monkey PD-1

The binding kinetics of recombinant purified Fab fragments (mAb7 and mAb15) to both hPD-1-hFc1 (R&D systems cat. no. 1086PD) and cynoPD-1-hFc1 (prepared in-house) was determined using a Biacore 2000™ equipped with a CM4 sensor chip and HBST+ running buffer. An anti-hFc polyclonal antibody was amine-coupled to the chip and used to capture approximately 90 RU hPD-1-hFc1 and 125 RU cynoPD-1-hFc1 on flow cells 2 and 3, leaving flow cell 1 blank (naked anti-hFc capture surface) to provide a reference channel. Recombinant purified Fabs were injected for two min as analyte at 0, 10, and 100 nM over freshly captured PD-1-hFc1 fusion proteins, allowing a 15-min dissociation time. Capture surfaces were regenerated using 75 mM phosphoric acid and the mAb7 Fab samples were injected in duplicate binding cycles. All Fab/PD-1 complexes were very stable, such that none of the interactions showed any visible decay in their binding responses within the allowed dissociation time, so the "5% rule" (Katsamba et al, 2008) was applied to place an upper limit on their $k_d$ and $K_D$ values.

TABLE 14

Affinity determination of mAb7 and mAb15 Fabs towards hPD-1-hFc1 and cynoPD-1-hFc1 fusion proteins

| Analyte | on chip | $k_a$ (1/Ms) × $10^5$ | *$k_d$ (1/s) × $10^{-5}$ | $K_D$ (pM) at 25° C. |
|---|---|---|---|---|
| mAb7 Fab | hPD-1-hFc1 | 5.67 | <5.7 | <101 |
| mAb7 Fab | cynoPD-1-hFc1 | 5.26 | <5.7 | <108 |

TABLE 14-continued

Affinity determination of mAb7 and mAb15 Fabs towards hPD-1-hFc1 and cynoPD-1-hFc1 fusion proteins

| Analyte | on chip | $k_a$ (1/Ms) × $10^5$ | *$k_d$ (1/s) × $10^{-5}$ | $K_D$ (pM) at 25° C. |
|---|---|---|---|---|
| mAb15 Fab | hPD-1-hFc1 | 9.16 | <5.7 | <62 |
| mAb15 Fab | cynoPD-1-hFc1 | 8.24 | <5.7 | <69 |

Temperature Dependence of the hPD-1 Binding Affinity Towards mAb15, mAb7, and C3

A Biacore T200™ equipped with CM4 sensor chip was used to determine the kinetics and affinities of hPD-1 monomer binding to a panel of hIgG4 molecules (mAb15, mAb7, and C3) that were captured at low levels via amine-coupled anti-hFc polyclonal antibody. The hIgG4 mAbs were captured at 10 µg/ml on individual flow cells, leaving flow cell 1 blank to serve as a reference surface (naked capture surface). The hPD-1 was injected at active concentrations of 0, 10, and 100 nM for three minutes allowing an 18-min dissociation phase. The capture surfaces were regenerated with 75 mM phosphoric acid after each binding cycle

TABLE 15

Kinetic analysis of hPD-1 monomer binding as analyte to anti-hFc-captured hIgG4 molecules

| hIgG4 on chip | Temp (25° C.) | ka (1/Ms) | kd (1/s) | $K_D$ (nM) |
|---|---|---|---|---|
| mAb15 | 25 | 3.49 × $10^5$ | 1.71 × $10^{-4}$ | 0.49 |
| mAb15 | 37 | 6.94 × $10^5$ | 3.73 × $10^{-4}$ | 0.54 |
| mAb7 | 25 | 2.37 × $10^5$ | 1.73 × $10^{-4}$ | 0.73 |
| mAb7 | 37 | 4.28 × $10^5$ | 3.63 × $10^{-4}$ | 0.85 |
| C3 | 25 | 2.14 × $10^5$ | 2.25 × $10^{-3}$ | 10.5 |
| C3 | 37 | 9.70 × $10^5$ | 1.56 × $10^{-2}$ | 16.1 |

Cross-Reaction of mAb7 to Mouse-PD-1

An Octet-Red384 equipped with streptavidin sensor tips was used to determine whether mouse PD-1 binds to mAb7. An avidity-prone assay format was chosen to increase the detection sensitivity of the assay. Sensors were coated with biotinylated anti-human kappa polyclonal and used to capture a panel of hIgG4 anti-hPD-1 mAbs (mAb7, C1, C2, and C3) at 10 µg/ml; each mAb was captured on eight sensors. As a positive control, eight streptavidin sensors were coated with biotinylated J43 (eBioSciences), an anti-mouse PD-1 antibody. Each mAb-coated sensor was exposed to the following analytes; buffer, 1 µM binding sites mouse PD-1-hFc, 1 µM binding sites hPD-1-hFc (positive control) or 1 µM binding sites hGHR-hFc (negative control). All recombinant Fc-fusion proteins were from R&D systems. Each analyte/mAb interaction was therefore tested on duplicate sensors.

Anti-PD-1 antibodies C1, C2, and C3 did not bind mouse-PD-1-hFc1 (data not shown). Anti-PD-1 antibody mAb7 bound mouse-PD-1-hFc1 weakly (data not shown). All anti-PD-1 antibodies tested bound to hPD-1-hFc. These results demonstrate that mAb7 is weakly cross-reactive with mouse PD-1 whereas C1, C2, and C3 are not cross-reactive with mouse PD-1.

Example 8: Treatment of Cancer with Anti-PD-1 Antibodies

This is a prophetic example illustrating use of the anti-PD-1 antibodies of the present invention for treating cancer. Patients with histologically confirmed, previously untreated, measurable metastatic colorectal cancer are selected for treatment with an anti-PD-1 antibody. Patients are assigned to one of two treatment groups: chemotherapy plus placebo or chemotherapy plus mAb7. A dynamic randomization algorithm is utilized to achieve balance overall and within each of the following categories: study center, baseline ECOG performance status (0 vs. ≥1), site of primary disease (colon vs. rectum), and number of metastatic sites (1 vs. >1). The chemotherapy treatment is administered weekly for the first 6 weeks of each 8-week cycle. Chemotherapy is continued until study completion (96 weeks) or disease progression. mAb7 5 mg/kg or placebo is administered every 2 weeks. Patients in the mAb7 arm who have a confirmed complete response or experienced unacceptable toxicity as a result of chemotherapy treatment are allowed to discontinue chemotherapy and continue receiving mAb7 alone as first-line treatment. Only patients who are randomized to the mAb7 group may receive mAb7 as a component of second-line treatment. After completing the study, patients are followed for any subsequent treatment and survival every 4 months until death, loss to follow-up, or termination of the study.

Patients will undergo an assessment of tumor status at baseline and at completion of every 8-week cycle using appropriate radiographic techniques, typically spiral CT scanning. Tumor response, or progression, will be determined by both the investigator and an independent radiology facility (IRF) utilizing the Response Evaluation Criteria in Solid Tumors. Therasse et al. (2000). The IRF assessment will be performed without knowledge of the treatment assignment or investigator assessment. In addition, patients will complete the Functional Assessment of Cancer Therapy-Colorectal (FACT-C), Version 4, a validated instrument for assessing quality of life (QOL) in colorectal cancer patients, at baseline and prior to each treatment cycle until disease progression. Ward et al. (1999) *Qual. Life Res.* 8: 181-195.

Safety is assessed from reports of adverse events, laboratory test results, and vital sign measurements. Adverse events and abnormal laboratory results are categorized using the National Cancer Institute Common Toxicity Criteria (NCI-CTC), Version 2. Prespecified safety measures include four adverse events of special interest (hypertension, proteinuria, thrombosis, and bleeding).

The primary outcome measure is duration of overall survival. Secondary outcome measures include: progression-free survival, objective response rate (complete and partial), response duration, and change in the FACT-C QOL score. Survival duration is defined as the time from randomization to death. For patients alive at the time of analysis, duration of survival will be censored at the date of last contact. Progression-free survival is defined as the time from randomization to the earlier of disease progression or death on study, defined as death from any cause within 30 days of the last dose of study drug or chemotherapy. For patients alive without disease progression at the time of analysis, progression-free survival will be censored at their last tumor assessment, or day 1 (the first day of study treatment) if no postbaseline assessment was performed. In the analysis of objective response, patients without tumor assessments are categorized as nonresponders. Disease progression and response analyses are based on the IRF assessments. Change in quality of life is analyzed as time to deterioration in QOL (TDQ), defined as the length of time from randomization to the earliest of a ≥3-point decrease from baseline in colon-cancer specific FACT-C subscale score (CCS), disease progression, or death on study. TDQ will also be determined for the TOI-C (sum of CCS, physical and functional well-being) and total FACT-C for changes from baseline.

Example 9: Treatment of Cancer with Anti-PD-1 Antibodies

This example illustrates use of the anti-PD-1 antibodies of the present invention for treating cancer.

The study in this example is a Phase 1, open-label, multi center, multiple-dose, dose escalation, safety, PK, and PD study of anti-PD-1 monoclonal antibody mAb7 administered intravenously in previously treated adult patients with locally advanced or metastatic melanoma, squamous cell head and neck cancer (SCHNC), ovarian carcinoma, sarcoma, or relapsed or refractory classic Hodgkin's Lymphoma (cHL). The study protocol is summarized below in Table 16.

TABLE 16

| Arms | Assigned Interventions |
| --- | --- |
| Arm 1: mAb7 0.5 mg/kg every 21 days | Drug mAb7 IV every 21 days |
| Arm 1: mAb7 1.0 mg/kg every 21 days | Drug mAb7 IV every 21 days |
| Arm 1: mAb7 3.0 mg/kg every 21 days | Drug mAb7 IV every 21 days |
| Arm 1: mAb7 10 mg/kg every 21 days | Drug mAb7 IV every 21 days |

Inclusion Criteria: —Histological or cytological diagnosis of locally advanced or metastatic melanoma, SCCHN, ovarian cancer, sarcoma, or relapsed or refractory cHL: —Patient should have received at least 1 and no more than 5 prior lines of therapy for recurrent or metastatic disease, including both standards of care and investigational therapies. —At least one measurable lesion as defined by RECIST version 1.1, or (for cHL) at least 1 fluordeoxyglucose positron emission tomography (FDG PET) avid (Deauville 4/5) measurable lesion >1.5 cm as defined by Response Criteria for Malignant Lymphoma that has not previously been irradiated. —For Part 1B expansion and all Part 2 cohorts: patient has consented to undergo a pre treatment and on treatment biopsy. —Adequate Renal, Liver, bone marrow function Exclusion Criteria—Active brain or leptomeningeal metastases. —Ocular melanoma—Active, known or suspected autoimmune disease. Patients with vitiligo, type I diabetes mellitus, residual hypothyroidism due to autoimmune condition only requiring hormone replacement, psoriasis not requiring systemic treatment, or conditions not expected to recur in the absence of an external trigger are permitted to enroll. Diagnosis of prior immunodeficiency or organ transplant requiring immunosuppressive therapy, —For Part 2: prior treatment with a PD 1 or PD L1 antibody. —History of Grade ≥3 immune mediated AE (including AST/ALT elevations that where considered drug related and cytokine release syndrome) that was considered related to prior immune modulatory therapy (eg, immune checkpoint inhibitors, co stimulatory agents, etc.) and required immunosuppressive therapy.

The number of patients with ORR (Objective Response Rate) will be measured at baseline and every six weeks until disease progression or unacceptable toxicity up to 24 months.

Example 9: Antagonistic Activity of Anti-PD-1 Antibodies in Human and Cynomolgus Monkey Primary T Cells This example illustrates the activity of anti-PD-1 antibodies in human and cynomolgus monkey primary T cells.

In this study, the antagonistic activities of anti-PD-1 monoclonal antibody mAb7 were examined in vitro using a mixed lymphocyte reaction (MLR). Primary T cells were isolated from human and cynomolgus monkey-peripheral blood mononuclear cells (PBMCs). Following mAb7 exposure, cell proliferation and cytokine secretion were evaluated in vitro under different activation conditions using a MLR for human and cynomolgus monkey and cytokine release assay using cynomolgus monkey-blood activated with *Staphylococcal enterotoxin* B (SEB) super antigen.

Methods

Human T Lymphocytes

Human buffy coat was purchased from Stanford Blood Center (Stanford, Calif.), diluted with phosphate buffered saline (PBS) and layered over Ficoll for the isolation of PBMCs. The hu-PBMCs were washed 4 times with PBS and T lymphocytes were isolated using a human-specific Pan T-cell isolation kit with negative selection as described in the manufacturer's protocol (Miltenyi Biotec, San Diego, Calif.).

Cynomolgus Monkey T Lymphocytes

Fresh cynomolgus monkey-PBMCs were purchased from Bioreclamation IVT (New York, N.Y.) and washed twice with PBS. T lymphocytes were isolated using a non-human primate specific for pan T-cell isolation kit with negative selection as described in the manufacturer's protocol (Miltenyi Biotec, San Diego, Calif.).

Generating Human Dendritic Cells Expressing High Levels of PD-L1

Human buffy coat was purchased from Stanford Blood Center (Stanford, Calif.), diluted with PBS and layered over Ficoll for the isolation of hu-PBMCs. The hu-PBMCs were washed 4 times with PBS and cluster of differentiation 14 ($CD14^+$) monocytes were isolated using a human specific CD14 cell isolation kit with positive selection, as described in the manufacturer's protocol (Miltenyi Biotec, San Diego, Calif.). Cells were then seeded at $5\times10^5$ cells/mL in complete Roswell Park Memorial Institute (RPMI) 1640 media supplemented with 10% fetal bovine serum (FBS) for 7 days. Cultures were supplemented with recombinant human (rh-) IL-4 (1000 U/mL) (R&D Systems, Minneapolis, Minn.) and with rh-granulocyte-macrophage colony-stimulating factor (GM-CSF) (rh-GMCSF) (500 U/mL) (R&D Systems, Minneapolis, Minn.) at Days 0, 2 and 5. Immature DCs were harvested, washed, and counted on Day 7. A sample of each preparation was tested for PD-L1 expression using r-phycoerythrin (RPE) labeled anti-hu-PD-L1 (eBioscience/Affymatrix, San Diego, Calif.) by flow cytometry using a LSRFortessa™ analyzer (BD Biosciences, San Jose, Calif.).

Generation of Cynomolgus Monkey Dendritic Cells Expressing High Levels of PD-L1

Fresh cynomolgus monkey-PBMCs were purchased from Bioreclamation IVT (New York, N.Y.) and washed twice with PBS. CD14+ monocytes were isolated using a non-human primate specific CD14 cell isolation kit with positive selection as described in the manufacturer's protocol (Miltenyi Biotech, San Diego, Calif.). Cells were then seeded as $5\times10^5$ cells/mL in complete RPMI 1640 media supplemented with 10% FBS for 7 days. Cultures were supplemented with rhIL-4 (1000 U/mL) (R&D Systems, Minneapolis) and rh-GMCSF (500 U/mL) (R&D Systems, Minneapolis, Minn.) at Days 0, 2, and 5. Immature DCs were harvested, washed, and counted on Day 7. A sample of each preparation was tested for PD-L1 expression using RPE-labeled anti-hu-PD-L1 (eBioscience/Affymatnx, San Diego, Calif.) by flow cytometry using a LSRFortessa™ analyzer (BD Biosciences, San Jose, Calif.).

Generation of JeKo-1-Luc-Green Fluorescent Protein Cell Clones Expressing High Levels of Human PD-L1

The JeKo-1 cell line (a Mantle Cell Lymphoma) was purchased from American Type Culture Collection (ATCC, Manassas, Va.). The JeKo-1-luc-2A-GFP cell line was produced at Pfizer (South San Francisco, Calif.) by a transduction process that used lentiviral particles expressing individually firefly luciferase (luc2A) and green fluorescent protein (GFP) through a bicistronic system with a blasticidin marker (AMSBIO, LVP323, $1\times10E^7$ particles per 200 µL) according to the manufacturer's protocol. JeKo-1 cells were pelleted and diluted to $1\times10^6$ cells/mL in RPMI with 20% FBS medium. Lentiviral particles were added to the diluted cells at a ratio of 50 µL virus per 0.5 mL cells. To generate a JeKo-1 cell line expressing hu-PD-L1, hu-PD-L1 cDNA was custom synthesized and cloned into generic expression vector (pcDNA3.1) by Life Technologies (San Diego, Calif.). A JeKo-1-Luc-GFP cell line stably expressing hu-PDL-1 was produced at Pfizer (South San Francisco, Calif.) by electroporation using the Amaxa® Nucleofector system (Lonza, Walkersville, Md.) and Kit V used according to the manufacturer's protocol (Lonza, Walkersville, Md.). Cells were then grown in the presence of 250 µg/mL hygromycin for 2 weeks and then selected by cell sorting using BD FACSAria™ II cell sorter (BD Biosciences, San Jose, Calif.). The sorting of cells was conducted with the anti-hu-PD-L1 antibody clone MIH-1 (Affymetrix/eBioscience, San Diego, Calif.) labeled directly with allophycocyanin (APC) label. Positive clones were expanded and tested for high PD-L1 expression using flow cytometry (LSRFortessa™ analyzer, BD Biosciences, San Jose, Calif.). Clones that were generated from single sorted cells and contained high levels of PD-L1 expression were selected.

Generation of Antibodies mAb7 was generated in CHO cells (Pharmaceutical Sciences, Pfizer Inc, Saint Louis, Mo.) using Good Laboratory Practices (GLP) material (Lot No STL0005717) and provided in 20 mM histidine, 85 mg/mL sucrose, 0.2 mg/mL polysorbate-80, 0.05 mg/mL disodium EDTA, pH 5.5 buffer. Endotoxin was measured as ≤0.01 EU/mg.

The control antibody used in all in vitro assays was an anti-bovine herpes virus cloned into an IgG4-HG framework (the same framework as MAB7). The control antibody was generated at Pfizer (South San Francisco, Calif.), Lot No 4945, with ≤0.3 EU/mg endotoxin.

Two anti-hu-PD-1 antibodies were generated from sequences published in previous patents and expressed in the IgG4-HG framework resembling the one used for MAB7. The antibodies were generated at Pfizer (South San Francisco, Calif.) and were designated as positive control 1 and positive control 2 (Lot No 5053 and 4255, respectively). Endotoxin measured was ≤0.13 EU/mg and ≤0.056 EU/mg, respectively.

Human Assay Using Dendritic Cells Expressing High Levels of PD-L1

The protocol was adapted from Kruisbeek et al, 2004, with some modifications. Differentiated primary hu-DCs were harvested on Day 7 and verified by flow cytometry for high levels of PD-L1 expression and co-stimulatory signals necessary for T-cell activation; markers included CD80 and CD86 (antibodies purchased from BD Bioscience, San Jose, Calif.). Cells were counted and irradiated at 3000 radiation units (rads) using a RS2000 x-ray machine (Radsource, Brentwood, Tenn.) to prevent DCs from secreting cytokines but functioning only as Ag presentation support to the T cells. Thus, the outcome of the assay was only induced by T cells. At Day 7, freshly isolated hu-T cells from allogenic donors were harvested. T cells were plated with irradiated DCs at a ratio of 10:1 (optimal assay conditions were determined as $2 \times 10^5$ T cells incubated with $2 \times 10^4$ DCs in 200 µL cultures) in the presence of different concentrations of mAb7, negative and positive control antibodies, or media alone (to evaluate the baseline reaction). All conditions were plated in 96-well flat bottom tissue culture treated plates (Fisher Scientific Pittsburgh, Pa.). Cells were cultured using serum free X-vivo15 media (Lonza, Walkersville, Md.) to prevent human serum variability between experiments. Cultures were incubated at 37° C. with 5% CO2 for 5 days. On Day 5, supernatants were collected and cytokine concentrations were measured using cytometric beads array (CBA) (BD Biosciences, San Jose, Calif.) according to the manufacturer's protocol. Data were acquired using flow cytometry (LSRFortessa™ analyzer, BD Bisceinces, San Jose, Calif.) and data analysis was performed using BD FCAP Array Software Version 3.0 (BD Bisceinces, San Jose, Calif.). Proliferation was measured in parallel cultures by adding 1 µCi of 3H methyl-titrated thymidine (Perkin Elmer, Waltham, Mass.) to each well and further incubated for 16 to 18 hours. Cultures were then harvested on deoxyribonucleic acid (DNA) incorporation filters (Perkin Elmer, Waltham, Mass.), and tritiated thymidine incorporation provided an index of cell proliferation measured as counts per minutes (cpm) using the MicroBeta2 Machine (Perkin Elmer, Waltham, Mass.).

Human Assay Using JeKo1-PD-L1 Expressing Cell Line

This assay was performed using a 5:1 ratio of T cells to JeKo-1-PD-L1 cell line was used since this ratio provided a more ideal approach to capture cytokine secretion on Day 5. Thus, each well was incubated with $2 \times 10^5$ T cells with $4 \times 10^4$ JeKo-1-PD-L1. On Day 5, supernatants were collected and cytokine concentrations were measured using CBA (BD Biosciences, San Jose, Calif.) according to the manufacturer's protocol. This cell line expresses a very modest amount of co-stimulatory molecules (CD80 and CD86), and thus, enhanced proliferation is very mild following antibody treatment. In contrast, cytokine secretion, including IL-2, is robust, thereby allowing the measurement of cytokine secretion following mAb7 treatment and not T-cell proliferation.

Cynomolgus Monkey Assay Using Dendritic Cells Expressing High Levels of PD-L

Differentiated DCs were harvested on Day 7 and verified by flow cytometry (using LSRFortessa™ analyzer, BD Bisceinces, San Jose, Calif.) for high PD-L1 expression and co-stimulatory signals necessary for T-cell activation; markers included CD80 and CD86 (antibodies from BD Bioscience, San Jose, Calif.). Cells were counted and irradiated at 3000 rads using RS2000 X-ray machine (Radsource, Brentwood, Tenn.). Freshly-isolated cynomolgus monkey T cells from allogenic donors were harvested. T cells were plated with irradiated DCs using a ratio of 10:1 T-cells to DCs (optimal assay when $2 \times 10^5$ T cells were incubated with $2 \times 10^4$ DCs in 200 µL culture) in the presence of different concentrations of mAb7, negative and positive control antibodies, or media alone to evaluate the baseline reaction. All conditions were plated in 96-well flat-bottom-tissue culture-treated plates (Fisher Scientific, Pittsburgh, Pa.). Cells were cultured using serum free X-vivo15 media (Lonza, Walkersville, Md.) to prevent serum variability between experiments. Cultures were incubated at 37° C. with 5% CO2 for 5 days. On Day 5, supernatants were collected and cytokine concentrations were measured using CBA (BD Biosciences, San Jose, Calif.) according to the manufacturer's protocol. Data were acquired using flow cytometry (LSRFortessa™ analyzer, BD Bisceinces San Jose, Calif.), and data analysis was performed using BD FCAP Array Software Version 3.0 (BD Biosciences, San Jose, Calif.). At the same time and in similar cultures, 1 µCi of 3H methyl-titrated thymidine (Perkin Elmer, Waltham, Mass.) was added to each well; cells were further cultured for 16 to 18 hours to measure proliferation. Cultures were harvested on DNA incorporation filters Glass Printed filtermate A (Perkin Elmer, Waltham, Mass.) and tritiated thymidine incorporation, providing an index of cell proliferation, was measured as cpm using MicroBeta2 Machine (Perkin Elmer, Waltham, Mass.).

Cytokine Release from Cynomolgus Monkey Blood Induced by Superantigen Stimulation (*Staphylococcal Enterotoxin* B)

Whole blood from cynomolgus monkey was collected; 225 µL of blood were aliquoted into tissue-culture treated 96 well plates (Fisher Scientific, Pittsburgh, Pa.). Samples were incubated in duplicate at 37° C. in 5% CO2 in the presence of mAb7 or an isotype-matched negative control antibody at concentrations ranging from 0.1 to 100 µg/mL. One hour after the antibody addition, samples were stimulated with 0.1 µg/mL SEB (Toxic Technologies, Sarasota, Fla.) and cultures were incubated for 3 days. On Day 3, plasma was harvested, pooled, and frozen at −80° C. Concentrations of IFN-γ, IL-2, and TNF-α in thawed serum samples were measured in duplicate according to the manufacturer's protocol using MSD immunoassay plates (Meso Scale Diagnostics, Rockville, Md.) and an MSD Reader (Model 1200) with MSD Discovery Workbench software (Version 4.0.12). The means of the duplicates were reported.

Results

Antagonistic Activity of mAb7 on Human Primary T Cells

When primary human T cells were activated in MLR with allogenic hu-DCs expressing PD L1, mAb7 increased T-cell proliferation (measured by tritiated thymidine incorporation) and T-cell activation (measured by pro-inflammatory cytokine secretion) in a dose-dependent manner. Treatment of T-cells with mAb7 (10 µg/mL) resulted in an increase in T-cell proliferation of up to 2.5-fold over treatment with a negative control antibody (10 µg/mL). IFN-γ and TNF-α levels were increased up to 8- and 5-fold, respectively, when compared to negative control antibody. IFN-γ increase was superior to the TNF-α increase. IL-2 expression was not detected in these cultures. When primary human T cells were activated in MLR, using the tumor cell line JeKo 1 PD-L1 as allogenic antigen presenting cells, mAb7 induced a dose-dependent increase of IFN-γ (up to 2.5-fold), TNF-α (up to 2-fold), and IL-2 (up to 5-fold) secretion as compared to negative control antibody. The effect of mAb7 in this assay resembled the data obtained with both positive control antibodies. Increased T-cell proliferation was not observed under these conditions. Cell proliferation was minimal with a weak signal provided by CD80 and CD86 in comparison to MLR mediated by primary DCs. IL-10, IL-4, IL-17A and IL-6 were minimal to non-detected in all assays described above.

Antagonistic Activity of mAb7 on Cynomolugs Monkey Primary T Cells

The binding affinity of mAb7, when in solution, to hu-PD-1 and cynomolgus monkey PD-1 were very similar in the kinetic exclusion assay (KinExA) (KD=23 and 28 pM for human and cynomolgus monkey PD-1, respectively). The EC50 of mAb7 on cells expressing human PD-1 and cynomolgus monkey PD-1 was also similar. In a MLR functional assay that used T cells and DCs isolated from different cynomolgus monkeys, mAb7 induced T cell proliferation and activation in a dose dependent manner (measured by tritiated thymidine incorporation). This effect was also observed with positive control (antibody 1 and antibody 2) but not with the negative control antibody. mAb7 also enhanced cytokine secretion (ie, IFN-γ and TNF-α, up to 5-fold and 3-fold, compared to treatment with negative control antibody. IL-2 expression was not detected in these cultures. In a different cytokine-release assay using cynomolgus monkey whole blood stimulated with 0.1 μg/mL of SEB superantigen for 3 days, mAb7 (0.1-100 μg/mL) induced greater IFN-γ, IL-2, and TNF-α secretion when compared with the negative control antibody.

MLR studies were used to create an in vitro setting resembling tumor microenvironment where T cells are activated and expressing high levels of PD-1 in the presence of allogeneic DCs or tumor cells expressing PD-L1. PD-1/PD-L1 interaction inhibits further T-cell proliferation and cytokine release Addition of anti-PD-1 antibodies in these MLRs restored T-cell activation and increased proliferation and cytokine secretion, especially IFN-γ, due to block of the PD-1/PD-L1 axis.

mAb7 accelerated the proliferation and secretion of IFN-γ, TNF-α, and IL-2 by human T cells when cultured with allogenic cells expressing high levels of PD-L1 (DCs or JeKo 1 PD-L1 cell line). In contrast, the negative control antibody, which proved similar to media alone, did not enhance these effects. Similarly, mAb7 enhanced T cell proliferation, IFN-γ and TNF-α secretion in the cynomolgus monkey-MLR system, as well as enhanced cytokine release from cynomolgus monkey whole blood using super antigen SEB.

These results demonstrate that anti-PD-1 antibody mAb7 enhanced T-cell proliferation and pro-inflammatory cytokine secretion including interferon-gamma (IFN-γ), tumor necrosis factor alpha (TNF-α), and interleukin (IL)-2. These activities were observed both in primary human and cynomolgus monkey T cells.

Example 10: Effect of Anti-PD-1 Antibodies in Graft Versus Host Disease

This example illustrates the effect of anti-PD-1 antibodies on T-cell activation and expansion in vivo using a xeno-aGvHD model in NSG mice transferred with hu-PBMCs.

In this study, the effect of anti-PD-1 antibody mAb7 on T-cell activation and expansion in vivo was studied in a xeno acute graft versus host disease (aGvHD) model in non-obese diabetic (NOD), severe-combined immunodeficiency (SCID), interleukin 2 receptor gamma null (IL2rγ$^{null}$) (NSG) mice using hu-peripheral blood mononuclear cells (PBMCs).

Immunocompromised NSG female mice (5 per group) aged 8 to 10 weeks (formal name, NOD, Cg-Prkdc$^{scid}$Il2rg$^{tm1Wjl}$/SzJ) were purchased from the Jackson Laboratory (Bar Harbor, Me.). All animals were housed in a pathogen free facility at Pfizer (South San Francisco, Calif.) in accordance with the Institutional Animal Care and Use Committee (IACUC).

Human buffy coat was purchased from Stanford Blood Center (Standord, Calif.), diluted with phosphate buffered saline (PBS) and layered over Ficoll for the isolation of PBMCs. The PBMCs were washed 2 times with PBS. Red blood cells (RBCs) were lysed using ammonium-chloride-potassium (ACK) lysing buffer as indicated in the manufacturer's protocol (Life Technologies; San Diego, Calif.). After the RBC lysis, cells were washed once more and diluted in PBS at $5 \times 10^7$ cells per mL.

For induction of xeno-aGvHD, NSG mice were injected intravenously via tail vein with hu-PBMCs. Each mouse received $1 \times 10^7$ cells in 200 μL of PBS. In all experiments, mice were weighed 3 times weekly and monitored for the appearance of xeno-aGvHD-like symptoms including weight loss, hunched posture, ruffled fur, reduced mobility, and in some cases, diarrhea. Mice were euthanized after loss of 20% body weight or the loss of 1 g/day over 2 days; this time point was recorded as the survival time. mAb7, negative control antibody, and positive control antibodies were generated as described above in Example 9.

NSG mice were treated with negative control antibodies, positive control antibodies, or mAb7, at doses range between 0.1-10 milligrams per kilograms (mg/kg). Antibodies were administered to mice using the appropriate vehicle on Day 2 and Day 8 post hu-PBMC transfer. The route of antibody administration was intraperitoneal (ip).

Peripheral blood, spleens, and livers were harvested from mice transplanted with hu-PBMCs. Single-cell suspensions from each organ were prepared as follows: Peripheral blood was collected and RBCs were lysed using ACK-lysing buffer and washed with PBS. Spleens and livers were mechanically homogenized using the back of a syringe plunger to macerate the cells through a 70 μM filter and washed once with PBS. RBCs were lysed and cells were washed 2 more times and macerated again through the 70 μM filter. At this stage, spleen cells were ready. For isolating leukocytes from liver, single cell suspensions were layered using Percoll gradient at 30% to 80% (Percoll® Plus, GE Healthcare Bio-Sciences, Pittsburgh, Pa.) and subjected to high-speed centrifugation. Leucocytes were harvested from the intermediate layer and washed twice with PBS. All single cell suspensions were counted and $1 \times 10^6$ cells from each sample were used for fluorescence-activated cell sorting (FACS). For human cytokine secretion assays, mouse CD45$^+$ cells were depleted using a mouse specific CD45 cell isolation kit by positive selection, as described in the manufacturer's protocol (Miltenyi Biotec, San Diego, Calif.), to ensure that cytokine-secretion was from human immune cells alone. Cells were counted, and $1 \times 10^6$ cells from each sample were used in the assay.

Single cell suspensions from peripheral blood, spleens, and livers were obtained from xeno-aGvHD mice. A total of $1 \times 10^6$ cells per sample were incubated for 30 minutes at 4° C. under protection from light with a mixture of appropriate fluorescently-labeled monoclonal antibodies in FACS buffer including 1×PBS containing 2% fetal bovine serum (FBS), then cells were washed with FACS buffer. For intracellular staining of Kiel 67 protein (Ki67, to measure proliferating cells), the cells were fixed after surface staining using Intracellular Fixation & Permeabilization Buffer Set (Affymetrix/eBioscience, San Diego, Calif.) according to the manufacturer's protocol. Intracellular staining was performed for 30 minutes at 4° C. in the dark. At the end of staining, samples were washed and subjected to multicolor flow cytometry using BD LSR Fortessa™ cell analyzer (BD Biosciences, San Jose, Calif.). Data analyses were done using FlowJo software (FLOWJO LLC, Ashland, Oreg.). Antibodies used in different combinations for recognition of the cell surface molecules were: anti-hu-CD45 Pacific Blue (PB) or Amcyan, anti-mouse CD45-Brilliant Violet (BV)-711, anti-hu-CD3-PerCPCy5.5, anti-hu-CD8 phycoerythrin-Cy7 (PE-Cy7) or BV-786, anti-hu-CD4-fluorescein isothiocyanate (FITC) or BV-650, anti-hu-PD-1 (done EH12.1) BV-786 or PE, anti-hu-PD-1 (clone MIH-4) PE or FITC, anti-hu-Ki67 allophycocyanin (APC) (all antibodies from BD Biosciences, San Jose, Calif.), anti-hu-PD-L1 (PE- Affymatrix-eBioscience, San Diego, Calif.) and blue fluorescent reactive dye for Live/Dead staining (Life Technologies, Grand Island, N.Y.).

Single cell suspensions of human CD45 enriched population from spleens and livers were obtained from xeno-aGvHD mice (after mouse CD45 depletion). A total of $1 \times 10^6$ cells per sample was incubated in flat bottom tissue culture treated 96-well plates (Fisher Scientific; Pittsburgh, Pa.) in 200 μL X-vivo 15 media. Cells were then left unstimulated or stimulated with phorbol myristate acetate (PMA) 10 ng/mL and ionomycin (iono) 125 ng/mL, as the low stimulation condition or PMA 50 ng/mL and ionomycin 1 μg/mL as the high stimulation condition (both obtained from Sigma-Aldrich, Saint Louis, Mo.). Cultures were incubated for 8 hours at 37° C. in 5% $CO_2$ to ensure maximal cytokine secretion. Supernatants were collected and human cytokine concentrations were measured using cytometric beads array (CBA) specific for human cytokines (BD Biosciences, San Jose, Calif.) according to the manufacturer's protocol. Data were acquired using flow cytometry (LSRFortessa™ analyzer, BD Biosciences, San Jose, Calif.), and data analysis was performed using FCAP Array™ Software Version 3.0 (BD Biosciences, San Jose, Calif.). Hu-IFN-γ, hu-TNF-α, and hu-IL-2 bead array kits were purchased from BD Biosciences (San Jose, Calif.), and it was confirmed that they did not cross-react with mouse cytokines.

All analyses involved a comparison of means using the independent-sample t-test or 2-way ANOVA using Graphpad Prism (Graphpad Software, San Diego, Calif.). Values of p≤0.05 were considered statistically significant. Engraftment data are depicted in figures as mean concentrations including the standard error of the mean (sem).

Treatment of NSG immunocompromised mice with anti-PD-1 antibody mAb7 accelerated body weight loss (Table 17) and induced other disease signs that are commonly seen in this model, such as hunched posture, ruffled fur, decreased mobility, and in some cases, diarrhea. In this model, body weight loss is expected to accelerate between Day 20 and Day 30 post transfer (see, e.g., Schroeder and DiPersio, 2011). Because treatment with mAb7 and positive controls 1 and 2 accelerated xeno-aGvHD symptoms, mice had to be euthanized at earlier time points and a survival curve could not be obtained; therefore, body weight loss was the primary outcome measurement. In the first experiment, mice were treated with 0.1, 1, and 10 mg/kg of mAb7 or negative control antibody at 10 mg/kg. In Table 17, body weight loss was calculated by normalizing the body weight differences between the treated groups at Day 23 relative to Day 0. Values indicate an average of 5 mice per group±sem.

Mice were treated with the indicated antibodies on Day 2 and Day 8 post-hu-PBMC transfer. While body weight loss became apparent in the control group on Day 23, body weight loss and disease progression were detected in individual mice from all anti-PD-1 antibody mAb7 treated groups starting Day 10-11 post hu-PBMCs transfer. In both the 1 mg/kg and 10 mg/kg treated groups body weight loss reached significance between Days 14 to 23, when compared to the negative control treated group (p≤0.0001). On Day 23, a 15% weight loss was detected in the 1 mg/kg and 10 mg/kg treated groups and a 7.9% weight loss was detected in the 0.1 mg/kg treated group (Table 17).

FACS analyses of peripheral blood, liver, and spleen demonstrated an increase in the percentage of hu-CD45 positive cells and hu-CD3 positive T cells in the mAb7 treated group versus the control group. Representative data from spleens also showed increase in hu-CD8 positive T-cell counts, and hu-CD4 positive T-cell counts (but to a lesser extent) in mAb7 versus the negative control antibody treatment group. Similar increase was also noted in hu-T cell counts in the liver and blood. To assess whether the increase in T cells was due to blockade of PD-1 through binding of mAb7 to human T cells, the T cells were stained with a commercial antibody for PD-1 (clone EH12.1) that competes with binding of mAb7. mAb7-treated lymphocytes from all organs (analyzed by FACS) showed no binding to EH12.1. To confirm that T cells treated with mAb7 still express PD-1, T cells were stained with a different anti-hu-PD-1 clone (done MIH4) that partially competes with mAb7 for binding to T cells. Results showed that T cells treated with mAb7 partially bound MIH4; thus, indicating that PD-1 was expressed on treated T cells and that PD-1 blockade by mAb7 was evident (data not shown, maintained in Pfizer internal records). No detectable changes were observed for hu-PD-L1 expression in the spleen, on T cells (hu-CD3 positive), or on non-hu-T cells (hu-CD3 negative). Ki67, a marker for lymphocyte proliferation, was elevated in hu-CD3 positive cells from the PF-0681591-treated group versus the negative control treated group in the spleen middle panel). Similar results were seen in the blood and liver.

To examine the effects of mAb7 on cytokine release during xeno-aGvHD, hu-CD45 positive cells (from livers and spleens) were further isolated from mouse CD45 positive cells. These lymphocytes were then treated with a mixture of PMA and ionomycin (in 2 concentrations: low versus high) or left untreated for 8 hours at 37° C. Cytokine secretion was measured in the supernatants by CBA (Table 18). No detectable cytokines were obtained without stimulation (Table 18). Following mAb7 treatment, hu-IFN-γ, hu-IL-2, and hu-TNF-α were elevated in human lymphocytes isolated from both mouse spleen and liver compartments compared to the control groups. Under weak ex vivo stimulation conditions, mAb7 treated T cells increased hu-IFN-γ secretion to levels that were significantly higher than those of T cells isolated from the negative control group (p≤0.05). Under strong ex vivo stimulation conditions, all cytokines were induced in all groups but further increased in mAb7 treated T cells compared to T cells isolated from negative controls. Table 18 shows data collected from 5 different mice in each group. In Table 18, *p<0.05, **p<0.01 in unpaired t-test comparing mAb7 versus negative control group; aGvHD=Acute graft versus host disease; Hu=Human; IFN-γ=Interferon gamma; IL-2=Interleukin-2; Ino=Ionomycin; N=Number, ns=Not significant: P=P value; PMA=Phorbol myristate acetate; TNFα=Tumor necrosis factor alpha; Xeno=Xenogeneic.

TABLE 17

| Treatment Groups | Body weight Day 0 | Body weight Day 14 | Body weight Day 23 | # per group | Body weight loss |
|---|---|---|---|---|---|
| Negative control mAb: 10 mg/kg | 20.68 ± 0.36 | 22.00 ± 0.36 | 20.88 ± 1.11 | 5 | 0% |
| mAb7: 10 m/kg | 20.78 ± 0.36 | 17.76 ± 0.57 | 17.74 ± 0.86 | 5 | 15% |
| mAb7: 1 mg/kg | 21.52 ± 0.36 | 19.26 ± 0.35 | 17.7 ± 0.58 | 5 | 15% |
| mAb7: 0.1 mg/kg | 20.5 ± 0.78 | 19.78 ± 1.38 | 19.22 ± 1.95 | 5 | 7.95% |

TABLE 18

| Organ-Hu Lymphocyte Isolated | Ex Vivo Stimulation Conditions (PMA/Iono) (ng/mL) | Hu-Cytokine pg/mL | Treatment In Vivo | | N | Statistics Unpaired t-test |
|---|---|---|---|---|---|---|
| | | | mAb7 10 mg/kg | negative control mAb 10 mg/kg | | |
| Liver | Weak | IFN-γ | 414.1 ± 59.4 | 163.9 ± 43.41 | 5 | **P < 0.05 |
| Spleen | (10/125 | | 2599.96 ± 863.45 | 503.9 ± 111.9 | 5 | *P < 0.01 |
| Liver | ng/mL) | IL-2 | 783.1 ± 776.26 | 19.41 ± 5.29 | 5 | ns |
| Spleen | | | 1813.98 ± 840.26 | 14.26 ± 1.40 | 5 | ns |
| Liver | | TNF-α | 80.75 ± 60.45 | 9.92 ± 2.55 | 5 | ns |
| Spleen | | | 368.81 ± 209.73 | 14.1 ± 2.51 | 5 | ns |
| Liver | Strong | IFN-γ | 3838.65 ± 178.84 | 2931.26 ± 556.98 | 5 | ns |
| Spleen | (50/1000 | | 3084.1 ± 204.1 | 2523.9 ± 141.2 | 5 | ns |
| Liver | ng/mL) | IL-2 | 7759.44 ± 809.24 | 4565.26 ± 1240.8 | 5 | ns |
| Spleen | | | 16735.57 ± 1417 | 13204.5 ± 1834.3 | 5 | ns |
| Liver | | TNF-α | 1611.9 ± 150.82 | 758.1 ± 188.2 | 5 | **P < 0.01 |
| Spleen | | | 2842.6 ± 224.2 | 2311.7 ± 281.36 | 5 | ns |
| Liver | None | IFN-γ | 3.1 ± 1.25 | 4.6 ± 0.96 | 5 | ns |
| Spleen | (0/0 | | 3.94 ± 0.97 | 4.86 ± 1.16 | 5 | ns |
| Liver | ng/mL) | IL-2 | 3.9 ± 0.14 | 4.66 ± 0.41 | 5 | ns |
| Spleen | | | 3.23 ± 0.77 | 4.39 ± 0.55 | 5 | ns |
| Liver | | TNF-α | 0.1 ± 0.09 | 0.3 ± 0.2 | 5 | ns |
| Spleen | | | 0.4 ± 0.15 | 0.27 ± 0.3 | 5 | ns |

These results demonstrate that treatment of xeno-aGvHD with anti-PD-1 antibody mAb7 accelerated xeno-aGvHD development in NSG mice, as measured by body weight loss, T-cell proliferation, and increased cytokine secretion including interferon-gamma (IFN-γ) and interleukin-2 (IL-2).

Example 11: Characterization of Anti-PD-1 Antibodies

This example illustrates binding affinity, specificity, and ligand blocking activity of anti-PD-1 antibody mAb7 on cells expressing surface receptor PD-1.

mAb7, negative control antibody, and positive control antibodies were generated as described above in Example 9. Anti-hu-PD-1 antibody clone EH12.1, primary labeled with phycoerythrin (PE) or Brilliant Violet (BV)-786 and isotype control antibodies labeled with the same dyes were purchased from BD Biosciences (San Jose, Calif.). PE-labeled anti-mouse PD-1 clone J43 and anti-hamster IgG isotype control antibody were purchased from Affymetrix/eBioscience (San Diego, Calif.). Biotinylated hu-PD-L1 and biotinylated hu-PD-L2 (CD273), were obtained from ACRO Biosystems (Newark, Del.). Cynomolgus monkey PD-L1 and PD-L2 were purchased from Creative BioMart® Recombinant Proteins (Shirley, N.Y.), and both were labeled in-house with Alexa Fluor® 647 dye using an Alexa Fluor® 647 protein labeling kit (LifeTechnologies, San Diego, Calif.) as instructed by the manufacturer's protocol. Cynomolgus monkey PD-L1 and PD-L2 were tested for binding to the cynomolgus monkey PD-1 expressing cell line. Rat- and mouse-PD-L1-Fc-Tags (Fc region of human IgG1 at the C-terminus) were purchased from Creative BioMart® Recombinant Proteins (Shirley, N.Y.). Detection of biotinylated PD-L1 and PD-L2 was achieved using streptavidin PE or allophycocyanin (APC) (Affymetrix/eBiosciense, San Diego, Calif.). Detection of rat or mouse-PD-L1 was achieved using APC labeled Fc gamma (Fcγ) Fragment Specific donkey-anti-human affiniPure F(ab')$_2$ IgG (Jackson ImmunoResearch Laboratories Inc, West Grove, Pa.).

Vectors for Transient Transfection

Hu-PD-1 expression plasmid (in pCMV6-Entry vector) was purchased from OriGene Technologies, Inc (Rockville, Md.), Catalog No RC210364/Accession No NM_005018.

Mouse-PD-1 expression plasmid (in pCMV6-Entry vector) was purchased from OriGene Technologies, Inc (Rockville, Md.), Catalog No MR227347/Accession No NM_008798. Cynomolgus monkey-PD-1 was codon optimized and synthesized by Life Technologies (San Diego, Calif.), Lot No 1482149/Accession No EF443145. It was cloned into a proprietary Pfizer (San Francisco, Calif.) cytomegalovirus (CMV)-based expression plasmid, in frame with a mouse kappa secretory signal sequence which added a C-terminal FLAG tag to the C-terminus.

Rat-PD-1 deoxyribonucleic acid (DNA) was custom synthesized according to the sequence from Accession No NM_001106927 and cloned into BamHI-NotI sites of expression vector pEF1V5-His from LifeTechnologies (San Diego, Calif.), Lot No1598305.

PD-1 Expression Vectors for Stable Transfection

Hu-PD-1 DNA was custom synthesized according to the sequence from Accession No NM_005018 and cloned into BamHI-NotI sites of InVitroGen expression vector pEF1V5-His B; Lot No 513478.

Cynomolgus monkey-PD-1 DNA was custom synthesized according to the Accession No EF443145 and cloned into BamHI-NotI sites of InVitroGen expression vector pEF1V5-His B, Lot No 1482149.

Mouse-PD-1 DNA was custom synthesized according to the Accession No NM_008798 and cloned into BamHI-NotI sites of InVitroGen expression vector pEF1V5-His B, Lot No 1513476.

All vectors were synthesized and cloned into InVitroGen expression vector pEF1V5-His B by Life Technologies (San Diego, Calif.). All vectors contain the complete PD-1 sequence including extracellular domain, membrane domain, and cytosolic domain. All vectors encoded a V5-6His epitope tag at the C-terminus of PD-1. The neomycin resistance gene was included in each vector for selection using G418 sulfate antibiotics.

Transient Transfection Using HEK-293T Cell Line

HEK-293T cells were purchased from American Type Culture Collection (ATCC®, Manassas, Va.), and cells were maintained in Dulbecco's Modified Eagle's medium (DMEM) (Corning CellGro, Manassas, Va.) supplemented with 10% fetal bovine serum (FBS) and 1× Penicillin/Streptomycin (Pen/Strep) and grown in 6% carbon dioxide ($CO_2$) at 37° C. One day prior to transfection, cells were trypsinized and plated at $4 \times 10^6$ cells per T75 flask (Fisher Scientific, Pittsburgh, Pa.). On the day of transfection, pre-warmed, antibiotic-free growth media replaced the old media and cells were further incubated for 2 hours at 37° C. in 6% CO2. Expression vector or empty vector (10 µg) was added to 1.5 mL OptiMEM media (Life Technologies, San Diego, Calif.). Lipofectamine 2000 Reagent (20 µl) (Life Technologies, San Diego, Calif.) was then added to another 1.5 ml OptiMEM. The plasmid OptiMEM and Lipofectamine OptiMEM tubes were then mixed together and incubated at room temperature for 25 minutes. The OptiMEM mixture was then added drop-wise to the appropriate culture flask, and the flask was left overnight at 37° C. in 6% CO2. The following day, the media was removed from the flask and replaced with complete growth media. Forty-eight (48) hours following transfection, cells were harvested using the StemPro-Accutase (Life Technologies, San Diego, Calif.), thereby, allowing cells to be gently removed from the culture surface without affecting PD-1 surface expression. Cells were then subjected to antibody binding and fluorescence-activated cell sorting (FACS) analyses.

Stable Transfection Using Jurkat Cell Line

The Jurkat cell line, (clone E6-1-TIB-152™, ATCC®, Manassas, Va.), was used to stably express hu- and cynomolgus monkey-PD-1. Cell lines were generated using electroporation via Amaxa necluotransfector system (Lonza, Walkersville, Md.). Transfections were performed at Pfizer (San Francisco, Calif.) using a Kit V as instructed by the manufacturer's protocol (Lonza, Walkersville, Md.). Cells were maintained in growth media Roswell Park Memorial Institute (RPMI)-1640 supplemented with 10% FBS and 1×L-glutamine (LifeTechnologies, San Diego, Calif.) at 37° C. in 5% CO2 at a density between 0.3 to $1.0 \times 10^6$ cells/ml. For each of the vectors, 2 µg/mL was used to transfect $2 \times 10^6$ cells. After the transfection, cells were grown in the presence of G418 Sulfate (600 µg/mL) for 2 weeks for selection and maintenance of the stably-transfected cells. To prevent long term contamination, 1× Pen/Strep was added to the media. Single cell clones were selected by culturing the cells in a dilution of 1:200 (1 cell in 200 µL complete media supplemented with G418 sulfate antibiotics). To select for clones expressing high hu- or cynomolgus monkey-PD-1, PE-labeled-anti-hu-PD-1 clone EH12.1 was used in flow cytometry assays. Samples were collected using BD LSR-Fortessa™ cell analyzer (BD Biosciences, San Jose, Calif.). Data analyses and mean fluorescence intensity (MFI) were calculated using Flowjo software (FLOWJO LLC, Ashland, Oreg.). Cell lines with high MFI were chosen for assay development.

HEK-293T cells transfected with hu-, cynomologus monkey-, mouse- or rat-PD-1 vectors, or empty vector were harvested at 48 hours post transfection. Prior to binding with mAb7, cells from each specific transfection were tested with commercial antibodies or ligands to ensure that the appropriate PD-1 receptor was highly expressed on the cell surface. For human and cynomolgus monkey, cross reactive commercial anti-PD-1 antibody (clone EH12.1) was used. For mouse, a commercial anti-mouse-PD-1 antibody (clone J43) was used. For rat, a rat-PD-L1 ligand was used (since there was no commercial rat cross-reactive anti-PD-1 antibody available). After appropriate PD-1 expression was confirmed, cells were counted, and $2 \times 10^5$ cells were incubated with hu-Fc Receptor Binding Inhibitor Functional Grade mixture (Fc-γ receptor block at 1 µg/$1 \times 10^8$ cells, Affymetrix/eBiosciense, San Diego, Calif.) for 20 minutes and blue fluorescent reactive dye, used for Live/Dead staining, was added to the mixture (Life Technologies, San Diego, Calif.). Serial dilutions of mAb7 or negative control (1-0.00001 µg/mL) antibody were added to the cell mixtures and then allowed to incubate on ice for 1 hour. Cells were then washed and APC-labeled-donkey-anti-human-affiniPure F(ab')$_2$ Fragment IgG, Fcγ Specific (1:100 dilution) (Jackson ImmunoResearch Laboratories Inc, West Grove, Pa.) was added to the mixture, and cells were, thereafter, incubated on ice for another 30 minutes. Data were acquired on the BD LSRFortessa™ cell analyzer (BD Biosciences, San Jose, Calif.), and analyzed using Flowjo software (FLOWJO LLC, Ashland, Oreg.).

Stable Jurkat cell clones that were transfected with either the hu-, cynomolgus monkey-, or mouse-PD-1 receptor were generated. PD-1 Cell clones chosen for these assays from each species expressed similar amounts of PD-1 receptors (~400,000 receptors/cell; receptors were quantified previously during the generation of these cell lines). After appropriate PD-1 expression was confirmed, cells were counted, and $2 \times 10^5$ cells were incubated with hu-Fc Receptor Binding Inhibitor Functional Grade (Fc-γ receptor Block at 1 µg/$1 \times 10^6$ cells, Affymetrix/eBiosciense, San Diego, Calif.) for 20 minutes and blue fluorescent reactive dye, used for Live/Dead staining, was added to the mixture (Life Technologies, San Diego, Calif.). Serial dilutions (1:3) of mAb7, positive control 1, positive control 2, or negative control antibodies (using an IgG4 framework) were added to the cell mixture and then allowed to incubate on ice for 1 hour. Cells were then washed and APC-labeled-donkey-anti-human-affiniPure F(ab')$_2$ Fragment IgG, Fcγ Specific (1:100 dilution) (Jackson ImmunoResearch Laboratories Inc, West Grove, Pa.) was added to the mixture and cells were then allowed to incubate on ice for another 30 minutes. Data were acquired on the BD LSRFortessa™ cell analyzer (BD Biosciences, San Jose, Calif.). Analyses were done using Flowjo software (FLOWJO LLC, Ashland, Oreg.) and geometrical means were calculated. $EC_{50}$ values were calculated using Graph Pad Prism (Log agonistic versus response [binding]).

Activated T cells expressing high levels of PD-1 receptors were generated. Appropriate PD-1 expression was confirmed for the T cells, obtained from each species, using commercial reagents (anti-hu-PD-1 clone EH12.1 for human and cynomolgus monkey, anti-mouse-PD-1 done J43 for mouse-PD-1, and rat-PD-L1 for rat-PD-1). Cells were counted and $1 \times 10^6$ cells were incubated with hu-Fc Receptor Binding Inhibitor Functional Grade (Fc-γ receptor Block at 1 µg/$1 \times 10^6$ cells, Affymetrix/eBiosciense, San Diego, Calif.) for 20 minutes and blue fluorescent reactive dye, used for Live/Dead staining, was added to the mixture (Life Technologies, San Diego, Calif.). Serial dilutions of mAb7 (dilution 1:3) were added to the cell mixture and then allowed to incubate on ice for 1 hour. Cells were then washed before APC-labeled-donkey-anti-human-affiniPure F(ab')$_2$ Fragment IgG, Fcγ specific secondary antibody (1:100 dilution) (Jackson ImmunoResearch Laboratories Inc, West Grove, Pa.) was added, and cells were allowed to incubate on ice for 30 minutes. Data were acquired on the BD LSRFortessa™ cell analyzer (BD Biosciences, San Jose, Calif.). Data analyses were done using Flowjo software (FLOWJO LLC, Ashland, Oreg.). Geometrical means were counted and EC$_{50}$ values were calculated using Pad Graph Prism (Log agonistic versus response [binding]).

Stable Jurkat cell clones expressing high levels of hu-PD-1 were chosen for the assay. Twenty (20) μg/mL of either biotinylated-hu-PD-L1 or biotinylated-hu-PD-L2 saturated all PD-1 receptors on this cell line (after previse binding titration assays). Therefore, this concentration was chosen as the optimal concentration in our studies. Hu-PD-1 expressing Jurkat cells (2×10$^5$) were incubated with hu-Fc Receptor Binding Inhibitor Functional Grade (Fc-γ receptor block at 1 μg/1×10$^6$ cells, Affymetrix/eBiosciense, San Diego, Calif.) for 20 minutes, and blue fluorescent reactive dye, used for Live/Dead staining, was added to the mixture as well (Life Technologies, San Diego, Calif.). Biotinylated-hu-PD-L1 or biotinylated-hu-PD-L2 were added to the cells at 20 μg/mL, immediately followed by addition of serial dilutions of mAb7, positive control 1, positive control 2, or negative control antibodies (all in IgG4 backbone and in 1:3 serial dilutions). Cells were allowed to incubate on ice for 1 hour. Cells were then washed and PE Streptavidin (1:100 dilution) (Affymetrix/eBiosciense, San Diego, Calif.) was added and the cells allowed to incubate on ice for 30 minutes. Data were then acquired on the BD LSRFortessa™ cell analyzer (BD Biosciences, San Jose, Calif.) and analyzed using Flowjo software (FLOWJO LLC, Ashland, Oreg.) and geometrical means were calculated. The IC50 values were calculated using Graph Pad Prism (Log inhibitor versus response [binding]).

Jurkat cells were stably transfected with high levels of hu- or cynomolgus monkey-PD-1 receptors. Cells expressing cynomolgus monkey-PD-1 receptors (~400,000 receptors/cell) were chosen for this assay. Cynomolgus monkey-PD-L1 and PD-L2 binding was tested using these cells and results showed that 20 μg/mL of either cynomolgus monkey-PD-L1 or PD-L2 was enough to saturate all PD-1 receptors based on the geometrical mean tested for different concentrations (50 ng/mL-50 μg/mL) of these ligands when bound to this cell line. Cynomolgus monkey-PD-1 expressing Jurkat cells (2×10$^5$) were incubated with hu-Fc Receptor Binding Inhibitor Functional Grade (Fc-γ receptor Block at 1 μg/1×10$^6$ cells, Affymetrix/eBiosciense, San Diego, Calif.) for 20 minutes and blue fluorescent reactive dye, used for Live/Dead staining, was added to the mixture (Life Technologies, San Diego, Calif.). Alexa-Fluor®-647-cynomolgus monkey PD-L1 or Alexa-Fluor®-647-cynomolgus monkey PD-L2 were added to the cells at t 20 μg/mL immediately followed by different concentrations of mAb7, positive control 1, positive control 2, or negative control antibodies (using the IgG4 backbone, in 1:3 serial dilution). Cells were then allowed to incubate on ice for 1 hour. After washing, cells were acquired on the BD LSRFortessa™ cell analyzer (BD Biosciences, San Jose, Calif.). Data analyses were done using Flowjo software (FLOWJO LLC, Ashland, Oreg.), and geometrical means were calculated. IC50 values were calculated with Graph Pad Prism (Log inhibitor versus response [binding]).

Human buffy coat, purchased from Stanford Blood Center (Stanford, Calif.), was diluted with PBS and layered over Ficoll for the isolation of PBMCs. The PBMCs were washed 4 times with PBS. RBCs were lysed using ACK lysing buffer as indicated in the manufacturers protocol (Life Technologies, San Diego, Calif.). After the RBC lysis, cells were washed once more and diluted in PBS at 5×10$^7$ cells per mL. Half of the PBMCs were counted and frozen down in freezing media (90% FBS with 10% dimethyl sulfoxide [DMSO]) and the remaining cells were subjected to T-cell purification. From the remaining PBMCs, T lymphocytes were isolated using a hu-specific Pan T-cell isolation kit with negative selection as described in the manufacturer's protocol (Miltenyi Biotec, San Diego, Calif.).

For the ADCC assay, freshly-isolated T cells (target cells) were counted, and 1×10$^6$ T cells per mL were cultured in serum free X-vivo 15 media (Lonza, Walkersville, Md.) and stimulated using beads coated with anti-CD3 and anti-CD28 (Dynabeads® Human T-Activator CD3/CD28 for T-Cell Expansion and Activation (Life Technologies, San Diego, Calif.) and 100 U/mL of recombinant-human (rh)-IL-2 (R&D Systems, Minneapolis, Minn.). Cultures were incubated at 37° C. in 5% CO2 for 72 hours. When T-cell activation reached the 48 hour time point, PBMCs (effector cells derived from the same donor) were thawed, counted, and then stimulated with rh-IL-2 (50 U/mL to 5×10$^6$ cells/mL culture) for a total of 18 to 24 hours in complete RPMI-1640 media with 10% FBS. On the day of the assay, both cell types were counted and tested by flow cytometry to ensure appropriate activation. For T cells, expression of high PD-1 was examined and for PBMCs expression level of receptors CD16, CD32, and CD64 (Fc-gamma receptor-[FcγR] III [a and b], FcγRIIa, FcγRI, respectively) that mediate ADCC was examined. Cells were plated in 5:1 effector to target ratio (as this was an optimal ratio) in flat-bottom 96-well tissue culture-treated plates (Fisher Scientific, Pittsburgh, Pa.) following the addition of antibodies: mAb7(IgG4 and IgG1 frameworks), and positive control antibodies. All antibodies were tested at concentrations of 0.01 to 100 μg/mL (in 1:10 serial dilutions). Assay controls were added, including target cells alone, to evaluate maximal lysis, effector cells alone, and effector to target at a 5:1 ratio with no addition of antibody. Assay plates were incubated at 37° C. in 5% CO2 for 4 hours. Data were analyzed using CytoTox 96® Non-Radioactive Cytotoxicity Assay (Promega US, Madison, Wis.) as instructed by the manufacturer's protocol. The assay quantitatively measured lactate dehydrogenase (LDH), a stable cytosolic enzyme that is released upon cell lysis. Percent (%) of cytotoxicity was measured as =100×(Experimental LDH Release [OD490]/Maximum LDH Release [OD490]). Maximum LDH release was calculated when target cell alone (T cells) cells were lysed chemically to obtain maximum killing.

The ability of mAb7 to bind to hu-, cynomolgus monkey-, mouse-, and rat-PD-1 was evaluated using flow cytometry (FACS) cell-based binding assays that included transiently transfected HEK-293T cell line, primary activated T cells, and Jurkat cells stably transfected with either hu-PD-1 or cynomolgus monkey- and mouse-PD-1. mAb7 bound to both hu-PD-1 and cynomolgus monkey-PD-1 with high affinity and showed similar EC$_{50}$ values for the 2 species (the amino acid sequence for these isoforms are the most similar of the species analyzed). The data are summarized in Tables 19, 20, and 21. Binding to mouse-PD-1 was only achieved at a high concentration of mAb7 that is biologically irrelevant and could be due to the affinity maturation process. No binding of mAb7 was detected for rat-PD-1 when using transfected cells or activated primary T cells (Table 19).

TABLE 19 mAb7 Binding on Primary Naïve and Activated T Cells by FACS

| | mAb7 (% Binding) | | Negative Control (% Binding) | |
|---|---|---|---|---|
| Species | Naïve | Activated | Naïve | Activated |
| Human T cells | 9.68 ± 4.82 | 87.95 ± 1.65 | 3.49 ± 0.59 | 4.75 ± 0.59 |
| Cynomolgus Monkey T cells | 9.21 ± 0.89 | 84.35 ± 0.75 | 5.385 ± 0.38 | 4.67 ± 0.47 |
| Mouse T cells | 4.63 ± 0.62 | 4.14 ± 1.87 | 0.93 ± 0.07 | 0.68 ± 0.10 |
| Rat T cells | 3.82 ± 1.72 | 0.74 ± 0.05 | 0.82 ± 0.16 | 4.36 ± 0.34 |

TABLE 20 mAb7 Binding to Activated Primary T Cells Obtained Expressing
PD-1 From Individual Human and Cynomolgus Monkey (EC50)

| Individual | Human T Cells (pM) | Cynomolgus Monkey T Cells (pM) |
|---|---|---|
| Individual 1 | 45.9 | 73.61 |
| Individual 2 | 56.11 | 97.07 |
| Average ± sem | 51.04 ± 5.07 | 85.34 ± 11.73 |

In Table 20, each number represents $EC_{50}$ values for mAb7 binding to a different donor. The bottom row represents the average±sem. sem=Standard error mean.

TABLE 21 mAb7 Binding to Stably-Transfected Jurkat Cell Lines with Human
PD-1 or Cynomolgus Monkey PD-1 (EC50)

| mAb (IgG4) | Repeat Number | Jurkat/Human-PD-1 (pM) | Jurkat/Cynomolgus Monkey-PD-1 (pM) |
|---|---|---|---|
| mAb7 | 1 | 62.84 | 181.3 |
|  | 2 | 66.61 | 263.8 |
|  | *Average ± sem | 64.725 ± 1.89 | 222.55 ± 41.3 |
| Positive control mAb1 | 1 | 54.52 | 265.2 |
|  | 2 | 57.60 | 267.2 |
|  | *Average ± sem | 56.01 ± 1.55 | 266.2 ± 1.0 |
| Positive control mAb2 | 1 | 181.6 | 380.4 |
|  | 2 | 179.6 | 375.9 |
|  | *Average ± sem | 180.6 ± 1.0 | 378.15 ± 2.5 |

In Table 21, each number represents $EC_{50}$ values for mAb7 binding in a single experiment. *indicates the average±sem. mAb (IgG4)=Monoclonal antibody with IgG4 framework; PD-1=Programmed death-1; sem=Standard error mean.

mAb7 binding to both hu- and cynomolgus monkey-PD-1 was examined using different cell based assay systems. In all systems the binding was found to be with high affinity and specificity in both species. Using HEK-293T transiently-transfected cell lines that expressed either hu- or cynomolgus monkey-PD-1, mAb7 showed similar binding patterns as indicated by MFI. Minimal to no binding was observed in the parental cell line transfected with empty vector (vehicle).

$EC_{50}$ values of mAb7 binding to activated hu- and cynomolgus monkey-primary T cells were determined at 72 hours post activation, when PD-1 expression on cell surface and cell viability were optimal (Table 19). $EC_{50}$ values were calculated for 2 different donors of each species (Table 20). In both hu- and cynomolgus monkey-activated T cells, low $EC_{50}$ values were obtained and $EC_{50}$ values were found to be dose between the 2 species, 51.04±5.07 pM and 85.34±11.73 pM, respectively (mean±standard error mean [sem]). No binding was observed with the negative control antibody above the baseline values.

The Jurkat T cell line, which minimally expresses hu-PD-1 receptors, was used to generate stably-transfected hu-PD-1, cynomolgus monkey-PD-1, and mouse-PD-1 cell lines. Cell lines were sub-cloned and clones expressing high levels of hu-PD-1 and cynomolgus monkey-PD-1 receptors were selected (~400,000 PD-1 receptors per cell was the highest expression obtained). In this system, mAb7 showed high affinity for hu-PD-1 and cynomolgus monkey-PD-1 receptors. $EC_{50}$ values for the two species were similar to the primary activated T-cell data (Table 21); $EC_{50}$=64.725±1.89 for hu-PD-1 and 222.55±41.3 for cynomolgus monkey-PD-1. $EC_{50}$ values for cynomolgus monkey-PD-1 expressing cells were more variable than human $EC_{50}$ values between the 2 experimental runs. Data for the two species were similar to data obtained with the positive control antibodies used in any given repeat (Table 21). Negative control antibody did not exhibit binding above the baseline values in any of the experimental repeats. The ability of mAb7 to block PD-L1 and PD-L2 ligands from interacting with the PD-1 receptor was examined in a PD-1-transfected Jurkat Cell line (expressing either hu-PD-1 or cynomolgus monkey-PD-1). In this assay, cells were incubated with labeled ligands at saturating concentrations following incubation with unlabeled mAb7 at different concentrations. As shown in Table 22, mAb7 inhibited PD-L1 and PD-L2 ligands from binding to the PD-1 receptor in a dose-dependent manner. Positive control antibodies for PD-1 showed comparable inhibition. The IC50 of mAb7 was comparable between hu- and cynomolgus monkey-PD-1 (880.15±289.85 and 1058±355.4 for hu-PD-L1 and hu-PD-L2, respectively; and 942.9±110.1 and 839±89.5 for cynomolgus monkey-PD-L1 and cynomolgus monkey-PD-L2, respectively). A summary of IC50 values is provided in Table 22. In Table 22, each number represents $IC_{50}$ values for mAb7 in a single experiment; *indicates the average±sem; ‡ indicates the repeat number in parentheses; mAb IgG4=monoclonal antibody with IgG4 framework; PD-1=Programmed death-1; PD-L1=Programmed death-ligand 1; PD-L2=Programmed death-ligand 2; sem=Standard error mean.

TABLE 22

Inhibitory Concentrations ($IC_{50}$; pM) for Blockade of Human PD-1 or Cynomolgus
Monkey-PD-1 Binding to PD-L1 and PD-L2 Using Stably-Transfected Jurkat
Cell Line System

| | Human-PD-1/Jurkat | | Cynomolgus Monkey-PD-1/Jurkat | |
|---|---|---|---|---|
| mAb (IgG4) | PD-1/PD-L1 Blockade | PD-1/PD-L2 Blockade | PD-1/PD-L1 Blockade | PD-1/PD-L2 Blockade |
| mAb7 | | | | |
| (1)‡ | 590.3 | 703.2 | 832.8 | 749.5 |
| (2)‡ | 1170 | 1414 | 1053 | 928.5 |
| *Average ± sem | 880.15 ± 289.85 | 1058 ± 355.4 | 942.9 ± 110.1 | 839 ± 89.5 |
| C1 | | | | |
| (1)‡ | 1022 | 1226 | 1286 | 1316 |
| (2)‡ | 629 | 811.1 | 861.8 | 1289 |
| *Average ± sem | 825.5 ± 196.5 | 1081.55 ± 207.45 | 1073.9 ± 212.1 | 1302.5 ± 13.5 |

TABLE 22-continued

Inhibitory Concentrations (IC$_{50}$; pM) for Blockade of Human PD-1 or Cynomolgus Monkey-PD-1 Binding to PD-L1 and PD-L2 Using Stably-Transfected Jurkat Cell Line System

| | Human-PD-1/Jurkat | | Cynomolgus Monkey-PD-1/Jurkat | |
|---|---|---|---|---|
| mAb (IgG4) | PD-1/PD-L1 Blockade | PD-1/PD-L2 Blockade | PD-1/PD-L1 Blockade | PD-1/PD-L2 Blockade |
| C2 | | | | |
| (1)‡ | 1715 | 1972 | 1809 | 1961 |
| (2)‡ | 1597 | 1560 | 1881 | 2111 |
| *Average ± sem | 1656 ± 59 | 1766 ± 206 | 1845 ± 36 | 2036 ± 75 | mAb7 showed weak binding for the complement component 1, q subcomponent (C1q) and CD64. C1q and CD64 (for IgG4 framework) are considered to be potential surrogates for complement dependent cytotoxicity (CDC) and ADCC, respectively. To further investigate the lack of ability of mAb7 to induce the killing of T cells in vitro, an ADCC assay was performed with activated T cells (target cells) expressing high levels of PD-1 receptors and PBMCs (effector cells) that expressed high levels of Fcγ receptors. Cells were selected from 2 healthy donors. mAb7 (in its original IgG4 framework) showed minimal ADCC activity in both donors. The lack of ADCC activity was in accordance with the activity exhibited by anti PD-1 positive control antibody in the IgG4 framework and both were similar to the negative control IgG4 antibody. When the anti-PD-1 (mAb7 or positive control anti-PD-1 antibodies) were assessed in the human IgG1 framework, which is known to induce a stronger ADCC, anti-PD-1 induced ADCC up to 4-fold higher than when the antibody is in the IgG4 framework. Maximum LDH release was calculated when target cells alone (T cells) were chemically lysed to obtain maximum killing (killing was estimated as 100% lysis for each donor according the assay calculation). T cell lysis using the IgG1 framework corresponds to the level of PD-1 on activated T cells (donor 1 PD-1 expression as well as lysis is higher than that of donor 2), confirming the accuracy of the assay.

These results demonstrate that anti-PD-1 antibody mAb7 binds with high affinity to hu- and cynomolgus monkey-PD-1 receptors expressed on cells with EC$_{50}$ values ranging between 46 to 270 pM, depending on the test system. mAb7 did not bind to cells expressing mouse-PD-1 or to rat-PD-1 in physiological concentrations. mAb7 blocked PD-L1 and PD-L2 ligands from interacting with cell surface PD-1 receptors; IC50 values ranged from 500 to 1000 pM indicating its high antagonistic function in blocking PD-1 function induced via ligand binding. mAb7, in its IgG4 framework, triggered minimal to no antibody-induced cytotoxicity which is consistent with IgG4 antibody properties.

Example 12: Characterization of Anti-PD-1 Antibody mAb7 Binding to PD-1, FcRn FcγRs, and C1Q Using Label-Free Biosensors and ELISA This example illustrates the in vitro binding affinities of mAb7 towards recombinant purified PD-1 from various species relevant to toxicology studies using SPR biosensors. The ability of the Fc region of mAb7 to engage FCGRs and the FcRn was also tested by SPR to confirm that it exhibited properties consistent with those of an isotype-matched control. By ELISA, mAb7 and an isotype-matched control were assayed for binding to human C1q. The ability of mAb7 to block the binding interaction of PD-1 with its ligands, PD-L1 and PD-L2, was also tested by label-free biosensors to support its mechanism of action.

All kinetic and affinity experiments were conducted at 25° C. in phosphate buffered saline (PBS)+0.01% Tween 20 running buffer, unless stated otherwise. Kinetic studies were performed on a SPR ProteOn XPR36 biosensor equipped with NLC (neutravidin-coated) chips (BioRad, Hercules, Calif.). The ProteOn was also used to determine the active concentrations of hu-PD-1 and cynomologus monkey-PD-1 analytes via titration against mAb7 as the reference standard. Concentrations of the protein analytes used here refer to "active" or "nominal" values. The active concentration of human Fc gamma receptor (hu-FCGR) I, human neonatal Fc receptor (hu-FcRn) (Lot No R3091), and cynomolgus monkey-neonatal Fc receptor (cynomolgus monkey-FcRn) (Lot No JCR) were determined using calibration-free concentration analysis (CFCA) experiments on a Biacore T200 equipped with CM5 sensor chips (GE Life Sciences, Marlborough, Mass.). All other analytes were used at their nominal concentrations as determined by light absorbance at A280 nm with an appropriate extinction coefficient. Solution affinities were determined at room temperature (approximately 23° C.) using a KinExA instrument 3000 or 3200 equipped with autosampler (Sapidyne). Secondary detection antibodies were labeled with DyLight 650 (Pierce Biotechnology, Grand Island, N.Y.) according to the manufacturer's instructions. Immunoglobulin G (IgG) biotinylations were performed at an equimolar ratio of linker:IgG using EZ-Link™ Sulfo-NHS-LC-LC-Biotin (Pierce Biotechnology Grand Island, N.Y.) according to the manufacturer's instructions. Unless stated otherwise, immobilized IgGs were regenerated with a "Pierce/salt" cocktail comprising a 2:1 v/v mixture of Pierce IgG elution buffer (pH 2.8)/4 M sodium chloride (NaCl).

The binding interactions of hu-PD-1 and cynomolgus monkey-PD-1 (both His-tagged monomers) towards mAb7 were determined in solution using the KinExA method in a running buffer of PBS+0.01% Tween 20 and a sample buffer of PBS+0.01% Tween 20+1 μg/l bovine serum albumin (BSA). Two different assay formats were employed. In the first assay format, mAb7 was titrated into a constant concentration of hu-PD-1 (nominal 200, 400, or 4000 pM) and samples were allowed to reach equilibrium. Free hu-PD-1 was captured on polymethylmethacrylate (PMMA) beads that had been coated (by adsorption) with anti-hu-PD-1 monoclonal antibody mAb7 (prepared in-house under non-Good Laboratory Practices (GLP) conditions [Lot No R5432]). Bead-captured hu-PD-1 was then detected with 0.5 μg/mL Dylight-labeled anti-His mAb (R&D Systems, Minneapolis, Minn.). In the second assay format, hu-PD-1 or cynomolgus monkey-PD-1 were titrated into a constant concentration of mAb7 (20, 50, 100, or 500 pM) and these mixtures were allowed to equilibrate. Free mAb7 was captured on PMMA beads that had been adsorbed with a blocker anti-idiotypic mouse anti-mAb7 mAb 1699.1H6 that binds specifically to free mAb7 but not PD-1-saturated mAb7.

Bead-captured mAb7 was then detected with Dylight-labeled goat anti-hu-IgG (H+L) (Jackson ImmunoResearch Inc, West Grove, Pa.). All titrations were prepared as a 12-membered 2-fold dilution series varying the top nominal binding site concentration to fall within the range 1 nM to 10 nM, depending on the experiment. Samples were allowed to equilibrate for up to 48 hours and injection volumes were adjusted per experiment to give a total signal that fell within the range 0.7 V to 1.9 V. All samples were injected in duplicate cycles. The data from up to 4 independent experiments per interaction were analyzed globally using the N-curve tool in the analysis software and fit to a simple bimolecular model where mAb7's concentration was used as the reference concentration. The global analysis reports the best fit values (and 95% confidence interval) for the $K_D$ and the apparent active binding site concentration of PD-1.

The binding affinities of hu-PD-1 and cynomolgus monkey-PD-1 towards mAb7 in solution were indistinguishable from one another when studied using a KinExA assay; the apparent equilibrium dissociation constant ($K_D$) values at 23° C. were determined to be 17 pM or 23 pM for hu-PD-1 (when studied in opposing assay orientations) and 28 pM for cynomolgus monkey-PD-1; these three values were statistically-indistinguishable from one another. These values were recapitulated by surface plasmon resonance (SPR) biosensor measurements, which yielded $K_D$ values of 42 pM for hu-PD-1 and 69 pM for cynomolgus monkey-PD-1 at 25° C., and 109 pM for hu-PD-1 and 115 pM for cynomolgus monkey-PD-1 at 37° C. mAb7 bound mouse-PD-1 with a $K_D$ value of 0.9 µM and no binding was detected towards rat-PD-1 when tested at 0.5 µM with SPR kinetic analysis. Label-free biosensors were used to demonstrate that mAb7 blocks hu-PD-1 from binding to its natural ligands, human programmed death-ligand 1 (hu-PD-L1) and human programmed death-ligand 2 (hu-PD-L2). SPR was further used to confirm that mAb7 bound a range of fragment crystallizable (Fc) gamma receptors (FCGR) and the neonatal Fc receptor (FcRn) from both human and cynomolgus monkey species with the same kinetics and specificity as an isotype-matched control. By ELISA, mAb7 showed negligible binding to complement component 1, q subcomponent (C1q), consistent with the behavior of an isotype-matched control. Overall, mAb7 binds both hu-PD-1 and cynomolgus monkey-PD-1 with high binding affinity and specificity but has low affinity towards mouse-PD-1 and negligible binding towards rat-PD-1.

Table 23 summarizes the kinetic and affinity data obtained for the interaction analysis of mAb7 with PD-1 from various species. mAb7 bound hu-PD-1 and cynomolgus monkey-PD-1 with statistically indistinguishable apparent affinities when these interactions were measured in solution at 23° C. using the KinExA method; apparent $K_D$ values were 17 pM and 23 pM for hu-PD-1 (when studied in two opposing assay orientations) and 28 pM for cynomolgus monkey-PD-1. The KinExA values were corroborated by kinetic measurements performed by SPR, which gave apparent $K_D$ values at 25° C. of 42±11 pM (n=10) for hu-PD-1 and 69±24 pM (n=10) for cynomolgus monkey-PD-1. SPR measurements at 37° C. showed 2-fold weaker affinities than those at 25° C.; $K_D$ values at 37° C. were determined to be 109±8 pM (n=15) for hu-PD-1 and 115±15 pM (n=8) for cynomolgus monkey-PD-1. mAb7 bound mouse PD-1 with an apparent $K_D$ of 0.9±0.1 pM (n=5) when measured at 25° C. by SPR, corresponding to a 20,000-fold weaker affinity than that for hu-PD-1. No binding was detected for rat-PD-1 when tested at 0.5 µM at 25° C. by SPR, although the rat-PD-1 proteins were confirmed active via their clear binding to positive controls, mouse-PD-L1 and mouse-PD-L2. The $K_D$ values for the KinExA measurements represent the best fit and 95% confidence interval of a global analysis of N independent experiments, while those for the SPR measurements represent the mean±standard deviation of n independent experiments on a ProteOn NLC sensor chip. In Table 23, h or hu=Human; $k_a$=Association rate constant; $k_d$=Dissociation rate constant; $K_D$=Equilibrium dissociation constant; KinExA=Kinetic exclusion assay; mAb=Monoclonal antibody; Ms=Molar per second; n=Number; ND=Not determined; PD-1=Programmed death-1; s=Second; SPR=Surface plasmon resonance; Temp=Temperature; *mAb7's interaction with hu-PD-1 was studied in two opposing assay orientations as described in Bee et al, 2012.

TABLE 23

Summary of Kinetic and Affinity Constants Obtained for the Interactions of PF 06801591 with Human PD-1, Cynomologus Monkey PD-1, and Mouse PD-1

| Temp (° C.) | Method | PD-1 | $k_a$ (1/Ms) | $k_d$ (1/s) | $K_D$ (pM) | n |
|---|---|---|---|---|---|---|
| 23 | KinExA | Human (Titrate mAb)* | ND | ND | 23 (28-18) | 3 |
| 23 | KinExA | Human (Titrate PD-1)* | ND | ND | 17 (24-12) | 3 |
| 25 | SPR | Human | $(4.2 \pm 0.6) \times 10^5$ | $(1.8 \pm 0.4) \times 10^{-5}$ | 42 ± 11 | 10 |
| 37 | SPR | Human | $(8.4 \pm 2.0) \times 10^5$ | $(8.5 \pm 1.2) \times 10^{-5}$ | 109 ± 28 | 15 |
| 23 | KinExA | Cynomologus Monkey (Titrate PD-1) | ND | ND | 28 (34-23) | 4 |
| 25 | SPR | Cynomologus Monkey | $(4.3 \pm 1.4) \times 10^5$ | $(2.9 \pm 0.4) \times 10^{-5}$ | 69 ± 24 | 10 |
| 37 | SPR | Cynomologus Monkey | $(9.8 \pm 1.1) \times 10^5$ | $(1.12 \pm 0.07) \times 10^{-4}$ | 115 ± 15 | 8 |
| 25 | SPR | Mouse | $(6.0 \pm 0.5) \times 10^3$ | $(5.2 \pm 0.4) \times 10^{-3}$ | $(9.0 \pm 1.0) \times 10^5$ | 5 |

Table 24 shows that binding kinetics and specificity for mAb7 over a range of Fc receptors, including FCGRs and FcRn from both human and cynomolgus monkey recapitulated those values expected for an isotype-matched control, hu-IgG4. For example, mAb7 bound hu-FCGRI with an apparent $K_D$ value (mean±standard deviation) at 25° C. of 146±42 pM (n=14) compared with 177±71 pM (n=4) for the isotype control. All other interactions were characterized by weak affinities ($K_D$ values~1 µM or higher). Kinetic analysis was performed on a ProteOn NLC chip at pH 7.4 for FCGR and pH 5.9 for FcRn. In Table 24, CD=Cluster of differentiation; cy=Cynomologus monkey; FCGR=Fc gamma receptor; FcRn=Neonatal Fc receptor; hu=Human; $k_a$=Association rate constant; $k_d$=Dissociation rate constant; $K_D$=Equilibrium dissociation constant; Ms=Molar per second; n=Number; s=Second.

TABLE 24

| Analyte | mAb7 | Isotype-matched Control |
| --- | --- | --- |
| hu-FCGRI (hu-CD64) | $k_a = (9.1 \pm 1.7) \times 10^6$ (1/Ms) $k_d = (1.3 \pm 0.3) \times 10^{-3}$ (1/s) $K_D = 146 \pm 42$ pM (n = 14) | $k_a = (1.0 \pm 0.3) \times 10^6$ (1/Ms) $k_d = (1.8 \pm 0.4) \times 10^{-3}$ (1/s) $K_D = 177 \pm 71$ pM (n = 4) |
| hu-FCGRIIa (hu-CD32a) 131H | 3.6 µM | 3.9 µM |
| hu-FCGRIIa (hu-CD32a) 131R | 0.8 µM | 0.4 µM |
| hu-FCGRIIb (hu-CD32b) | 1.1 µM | 0.7 µM |
| hu-FCGRIIIa (hu-CD16a) 158F | Barely binds at 5 µM | Barely binds at 5 µM |
| hu-FCGRIIIa (hu-CD16a) 158V | Barely binds at 1 µM | Barely binds at 1 µM |
| hu-FcRn | 0.93 µM | 0.82 ± 0.06 µM (n = 3) |
| Cynomolgus Monkey-FCGRIIa | 2.4 µM | 2.6 ± 0.5 µM (n = 3) |
| Cynomolgus Monkey-FCGRIIIa 42R | 2.7 µM | 3.2 ± 0.1 µM (n = 3) |
| Cynomolgus Monkey-FCGRIIIa 42S | 1.6 µM | 1.9 ± 0.2 µM (n = 3) |
| Cynomolgus Monkey-FcRn | 0.61 µM | 0.57 ± 0.04 µM (n = 3) |

In addition, mAb7 barely bound C1q by ELISA, consistent with the behavior of the isotype-matched control, hu-IgG4 (data not shown). Its binding was even lower than the low binding of human immunoglobulin G2 (hu-IgG2). In contrast, the positive controls, hu-IgG1 and human immunoglobulin G3 (hu-IgG3), gave high binding signals. Using both SPR and Octet biosensors and different assay formats (both premix and classical sandwich assay formats), it was demonstrated that mAb7 blocked hu-PD-1 binding to its natural ligands, hu-PD-L1 and hu-PD-L2.

These data demonstrate that that mAb7 binds with high affinity and high specificity towards hu-PD-1. When measured in solution at 23° C. using the KinExA method, mAb7 bound hu-PD-1 and cynomolgus monkey-PD-1 with statistically-indistinguishable apparent $K_D$ values of 17 pM and 23 pM for hu-PD-1 (when studied in alternate assay orientations) and 28 pM for cynomolgus monkey-PD-1. mAb7 showed a 20,000-fold weaker affinity to mouse-PD-1 (apparent $K_D$ of 0.9 µM at 25° C. by SPR) and no detectable binding to rat-PD-1 when tested at 0.5 µM. mAb7 and an isotype-matched control hu-IgG4 bound with similar kinetics and specificity when tested against a panel of hu- and cynomolgus monkey-Fc receptors, when measured at 25° C. by SPR. mAb7 bound hu-C1q with negligible signal when tested by ELISA, consistent with hu-IgG4 isotype controls, and its binding was even lower than that of hu-IgG2. It was demonstrated that mAb7 blocks hu-PD-1 from binding to its natural ligands, hu-PD-L1 and hu-PD-L2.

Example 13: Combination Treatment with Anti-PD-1 Antibody and Anti-OX40 Antibody This example illustrates the effects of treatment with anti-PD-1 antibody in combination with anti-OX40 antibody in a mouse model for colon cancer.

For this study, C57B6/J female mice (6-8 weeks old) were inoculated subcutaneously with the MC-38 murine colon tumour (a grade III adenocarcinomat) at $5 \times 10^5$ cells/mouse. At Day 10, mice were randomized and treatment began at 10 mg/kg anti-mouse-PD-1 and 1 mg/kg anti-mouse-OX-40. Treatments were administered i.p. at 15 days 10, 12, and 14 for anti-OX40 antibody (1 mg/kg); and at days 10, 12, 14, 17, 23, and 25 for anti-PD-1 antibody (10 mg/kg). Tumor volume was measured twice a week. The study was terminated at day 34. Statistical analyses were performed using 2-way Anova to compare the averages between each two groups at a single time point. The results are summarized in Table 25. Vin table 25, values indicate tumor volume at the indicated day average of 8 mice per group±(standard error mean) sem; N=number per group, $mm^2$=cubic millimeter. The isotype control included the appropriate isotype of each antibody at 1 mg/kg for anti-OX40 and 10 mg/kg for anti-PD-1.

TABLE 25

Tumor volume in MC38 bearing mice after treatment with anti-PD-1 antibody and anti-OX40 antibody

| Treatment Groups | Tumor volume ($mm^2$) | | | | N | % of Tumor free mice |
| --- | --- | --- | --- | --- | --- | --- |
| | Day 10 | Day 24 | Day 27 | Day 34 | | |
| Isotype control | 67. ± 7.9 | 832. ± 139.0 | 1408 ± 252.4 | 1866 ± 279.0 | 8 | 0% |
| Anti-PD-1 | 67 ± 8.0 | 312 ± 63.2 | 540 ± 125.0 | 939 ± 169.0 | 8 | 0% |
| Anti-OX40 | 67 ± 7.5 | 302 ± 64.1 | 370 ± 77.2 | 720 ± 145.0 | 8 | 0% |
| Anti-PD-1 + Anti-OX40 | 67 ± 7.4 | 190 ± 38.0 | 255 ± 51.2 | 423.0 ± 90.0 | 8 | 12.5% |

Beginning at Day 24, all anti-PD-1 antibody and/or anti-OX-40 antibody treated groups showed significantly smaller tumor volumes when compared to the control group (Table 25). At Day 24, the combination (anti-PD-1 antibody plus anti-OX40 antibody) treated group showed significance of $p \leq 0.0001$ when compared to the isotype control group, while each single antibody treatment showed significance of $p \leq 0.01$ when compared to the control group. At Day 34, all treated groups showed significance of $p \leq 0.0001$ when compared to the control group. At Day 34 the combination treated grouped showed differences when compared to either anti-PD-1 antibody alone treated group or anti OX-40 antibody alone treated group. These results demonstrate that treatment with both anti-PD-1 antibody and anti-OX40 antibody slowed tumor growth when compared to treatment with either antibody alone.

Example 14: Effect of Vaccine on Expression of PD-1 on Activated T Cells

This example illustrates the effect of a DNA-based vaccine expressing a human Prostate Specific Membrane Antigen (PSMA) on the expression of PD-1 on CD3$^+$CD4 (Table 26) and CD3$^+$CD8 T cells (Table 27) in the presence of anti-CTLA4 monoclonal antibody tremelimumab (a checkpoint inhibitor).

In Vivo Study Procedures.

Three groups of Chinese cynomolgus macaques (n=8/group) were used in the study. Animals in Groups 1 and 2 were intramuscularly injected with a vaccine that contains an AdC68 adenovirus vector (SEQ ID NO:44) encoding amino acids 15-750 of the human PSMA (at a total dose of 2e11 VP) while animals in Group 3 received no vaccination. The complete sequence of the AdC68 adenovirus vector is provided in SEQ ID NO:44. In addition, immediately following vaccination animals in Group 2 were treated with 50 mg anti-CTLA4 monoclonal antibody tremelimumab by subcutaneous injections. Whole blood samples from each animal before (Pre) and after vaccination were collected at Days 9, 15 and 29 and analyzed for the frequency of PD-1 expressing CD3+CD4 and CD3'CD8 T cells by flow cytometry.

CD3+ CD4 and CD8 T Cell Phenotyping.

Leukocyte populations were phenotyped by performing multi-color flow cytometry analysis on freshly collected whole blood. Briefly, whole blood was stained for 20 min at room temperature with an antibody cocktail containing CD3-V500 (done SP34-2), CD4-BV605 (done L200), CD8-APC.H7 (Clone SK1), PD1-AF488 (clone EH12.2H7, Biolegend), PDL1-BV421 (done MIH1), Lag3-PE.Cy7 (done 11E3, Novus), CD69-PE.Texas Red (clone TP1.553, Beckman Coulter), TIM3-APC (clone 344823, R&D Systems), CD20-PE.Cy5.5 (clone 2H7, eBioscience), CD14-AF700 (done M5E2), CD16-PE.Cy5 (done 3G8), CD56-PerCP.Cy5.5 (done B159), and CD11c-PE (done SHCL3). All antibodies were purchased from BD unless otherwise indicated. The samples were treated with RBC lysis buffer (BD), washed, mixed with 50 ml of liquid counting beads (BD) and acquired on LSR Fortessa (BD). The data were analyzed using FlowJo (Tree Star Inc, USA). Results of PD-1 expression on CD3$^+$CD4 T cells are presented in Table 26 and results of PD-1 expression on CD3$^+$CD8 T cells are presented in Table 27. The induction of PD-1 was observed 9 days after vaccination and resolved to levels seen in naive animals (Group 3) by day 29 post vaccination. These results indicate that the vaccine vector given together with anti-CTLA4 antibody can elicit PD-1 expression on CD3$^+$ CD4 and CD8 T cells in nonhuman primates.

TABLE 26

PD-1 Expression Kinetics on CD3$^+$CD4 T Cells in Cynomolgus Macaques

| Time point | Group | Individual % PD-1$^+$ CD3$^+$CD4 T cells in total CD3$^+$CD4 T cells | | | | | | | |
|---|---|---|---|---|---|---|---|---|---|
| | | 1 | 2 | 3 | 4 | 5 | 6 | 7 | 8 |
| Pre | 1 | 16.0 | 7.473 | 8.275 | 12.441 | 12.935 | 12.481 | 10.93 | 12.649 |
| | 2 | 9.757 | 11.383 | 7.795 | 5.943 | 13.279 | 24.959 | 12.112 | 10.375 |
| | 3 | 11.577 | 7.577 | 9.943 | | | | | |
| Day 9 | 1 | 18.124 | 11.72 | 11.977 | 18.861 | 20.657 | 10.623 | 11.766 | 12.792 |
| | 2 | 32.07 | 29.001 | 38.593 | 27.516 | 25.962 | 34.568 | 27.435 | 28.378 |
| | 3 | 18.608 | 10.101 | 13.205 | | | | | |
| Day 15 | 1 | 14.87 | 10.302 | 8.27 | 15.742 | 13.609 | 8.763 | 10.407 | 9.82 |
| | 2 | 16.421 | 14.578 | 18.138 | 15.667 | 20.927 | 27.778 | 16.612 | 17.583 |
| | 3 | 16.878 | 10.607 | 10.878 | | | | | |
| Day 29 | 1 | 14.819 | 9.39 | 8.412 | 14.051 | 14.436 | 9.576 | 10.524 | 11.116 |
| | 2 | 11.594 | 10.209 | 12.971 | 8.293 | 20.989 | 26.388 | 14.126 | 13.868 |
| | 3 | 14.182 | 9.098 | 14.138 | | | | | |

TABLE 27

PD-1 Expression Kinetics on CD3$^+$CD8 T Cells in Cynomolgus Macaques

| Time point | Group | Individual % PD-1$^+$ CD3$^+$CD8 T cells in total CD3$^+$CD8 T cells | | | | | | | |
|---|---|---|---|---|---|---|---|---|---|
| | | 1 | 2 | 3 | 4 | 5 | 6 | 7 | 8 |
| Pre | 1 | 10.8 | 4.9 | 10.1 | 5.7 | 11.9 | 13.5 | 7.1 | 9.6 |
| | 2 | 5.3 | 19.4 | 5.0 | 20.2 | 16.9 | 29.8 | 7.7 | 8.7 |
| | 3 | 8.8 | 6.9 | 4.3 | | | | | |
| Day 9 | 1 | 5.3 | 7.0 | 12.3 | 8.1 | 16.1 | 13.2 | 5.8 | 11.3 |
| | 2 | 15.6 | 22.5 | 7.4 | 29.5 | 20.7 | 26.2 | 11.41 | 10.2 |
| | 3 | 11.5 | 5.8 | 5.7 | | | | | |
| Day 15 | 1 | 7.4 | 6.9 | 11.7 | 8.2 | 16.2 | 15.4 | 6.8 | 14.0 |
| | 2 | 7.6 | 21.6 | 10.8 | 21.8 | 27.1 | 25.7 | 14.2 | 10.5 |
| | 3 | 12.3 | 7.4 | 6.4 | | | | | |
| Day 29 | 1 | 9.4 | 7.5 | 15.3 | 9.8 | 14.7 | 16.7 | 5.9 | 14.7 |
| | 2 | 8.5 | 20.3 | 8.0 | 22.5 | 26.0 | 22.4 | 9.1 | 9.9 |
| | 3 | 11.6 | 8.6 | 8.5 | | | | | |

Example 15. Effect of Anti-PD-1 Antibody on Antigen-Specific T-Cell Response Induced by a Vaccine Expressing Human PSMA This example illustrates the effect of anti-PD1 antibodies on the IFNγ CD4 and CD8 T-cell responses induced by a vaccine containing an AdC68 adenovirus vector that expresses human PSMA in cynomolgus macaques.

Intracellular Cytokine Staining (ICS) Assay.

Briefly, PBMCs from individual animals were co-incubated with pools of peptides from a 15mer peptide library overlapping by 11 amino acids spanning the entire sequence of the respective antigen, each peptide at 2 µg/ml. The plates were incubated ~16 hours at 37° C., 5% $CO_2$. The cells were then stained to detect intracellular IFNγ expression from $CD8^+$ T cells and fixed. Cells were acquired on a flow cytometer. The frequency of response was normalized to the number of IFNγ $CD8^+$ T cells per million $CD8^+$ T cells, with the responses in dimethyl sulfoxide control wells, which contained no peptide, subtracted. The antigen specific responses in the tables represent the sum of the responses to the corresponding antigen specific peptide pools.

In Vivo Study Procedures.

Briefly, Five groups of Chinese cynomolgus macaques (n=8/group) were intramuscularly injected with a vaccine containing an AdC68 adenovirus (SEQ ID NO:44) that encodes amino acid 15-750 of human PSMA (hPSMA) at total dose of 2e11 VP. The vaccination in Groups 2, 4 and 5 was immediately followed by subcutaneous injections of 50 mg anti-CTLA4 monoclonal antibody tremelimumab and/or anti-PD-1 monoclonal antibody mAb7 given subcutaneously (groups 3 and 4) or intravenously (group 5) at 10 mg/kg. PBMCs were isolated from each animal and subjected to an ICCS assay to measure human PSMA specific IFN☐ CD4 (Day 9 or day 29) or CD8 T-cell responses (Day 29). The amino acid sequence of the full length human PSAM is provided in SEQ ID NO:42. The sequence of the AdC68 adenovirus vector expressing amino acids 15-750 of the human PSMA is provided in SEQ ID NO:44.

Results.

Results are presented in Tables 29, 30, and 31. The data demonstrated that both anti-CTLA4 and anti-PD-1 individually can increase the frequency of IFNγ CD4 and CD8 T-cell responses induced by the vaccine.

TABLE 28

Peptide sequence information for peptide pools used in the ELISpot and ICCS assays to induce antigen-specific IFNγ T-cell responses.

| Antigen | Peptide library pools |
|---|---|
| Human PSMA | 185 sequential 15mer peptides, overlapping by 11 amino acids, covering the entire full length hPSMA protein sequence (amino acid sequence: 1-750) assayed as three separate pools. |

TABLE 29

IFNγ CD8 T-cell Responses Induced by the vaccine on Day 9

| | | | Individual hPSMA specific IFNγ CD8 T-cell titer ($IFN\gamma^+CD8$ cells/1e6 CD8 T cells, background adjusted) | | | | | | | | Geo |
|---|---|---|---|---|---|---|---|---|---|---|---|
| Group | Checkpoint inhibitor(s) | MAB7 route | 1 | 2 | 3 | 4 | 5 | 8 | 7 | 8 | mean |
| 1 | None | n/a | 1072 | 1 | 1453 | 6722 | 1 | 1 | 1055 | 503 | 92.91 |
| 2 | tremelimumab | n/a | 7278 | 356 | 423 | 6009 | 954 | 15862 | 935 | 2511 | 1977 |
| 3 | mAb7 | SC | 2077 | 6537 | 3138 | 449 | 1302 | 4063 | 769 | 487 | 1575 |
| 4 | tremelimumab mAb7 | SC | 222 | 667 | 1199 | 6879 | 933 | 1959 | 40349 | 6901 | 2235 |
| 5 | tremelimumab mAb7 | IV | 1037 | 1735 | 2371 | 489 | 7435 | 1 | 20947 | 4613 | 1052 |

TABLE 30

IFNγ CD4 T-cell Responses Induced by the Vaccine on Day 9

| | | | Individual hPSMA specific IFNγ CD4 T-cell titer ($IFN\gamma^+CD4$ cells/1e6 CD4 T cells, background adjusted) | | | | | | | | Geo |
|---|---|---|---|---|---|---|---|---|---|---|---|
| Group | Checkpoint inhibitor(s) | mAb7 route | 1 | 2 | 3 | 4 | 5 | 6 | 7 | 8 | mean |
| 1 | None | n/a | 1 | 1 | 1 | 1 | 1 | 1 | 1 | 1 | 1 |
| 2 | tremelimumab | n/a | 665 | 259 | 1 | 11914 | 271 | 326 | 1 | 1747 | 154 |
| 3 | mAb7 | SC | 174 | 669 | 457 | 193 | 194 | 1 | 192 | 159 | 125 |
| 4 | tremelimumab + mAb7 | SC | 1955 | 1 | 435 | 1764 | 736 | 1307 | 1852 | 471 | 401 |
| 5 | tremelimumab + mAb7 | IV | 858 | 1567 | 1398 | 1102 | 163 | 705 | 4938 | 1029 | 1024 |

TABLE 31

IFNγ CD4 T-cell Responses Induced by the Vaccine on Day 29

| Group | Checkpoint inhibitor(s) | mAb7 route | Individual hPSMA specific IFNγ CD4 T-cell titer (IFNγ+CD4 cells/1e6 CD4 T cells, background adjusted) | | | | | | | | Geo mean |
|---|---|---|---|---|---|---|---|---|---|---|---|
| | | | 1 | 2 | 3 | 4 | 5 | 6 | 7 | 8 | |
| 1 | None | n/a | 1 | 506 | 246 | 143 | 504 | 1 | 1 | 1 | 24 |
| 2 | tremelimumab | n/a | 175 | 63 | 1021 | 2845 | 867 | 662 | 265 | 372 | 230 |
| 3 | mAb7 | SC | 129 | 1 | 145 | 1 | 230 | 1 | 97 | 1 | 12 |
| 4 | tremelimumab + mAb7 | SC | 816 | 107 | 527 | 315 | 168 | 1084 | 1131 | 135 | 377 |
| 5 | tremelimumab + mAb7 | IV | 332 | 1496 | 559 | 360 | 221 | 361 | 1164 | 248 | 468 |

Example 16. Effect of Anti-PD-1 Antibodies on IFNγ T-Cell Responses Induced by a Vaccine Co-Expressing a Human Prostate Specific Membrane Antigen (PSMA), Prostate Stem Cell Antigen (PSCA), and Prostate Specific Antigen (PSA)

In Vivo Study Procedures.

Briefly, three groups of Chinese cynomolgus macaques (n=4/group) were used in the study. Animals in Group 1 were intramuscularly injected with vehicle. Animals in Group 2 were administered the anti-PD-1 monoclonal antibody mAb7 subcutaneously at 20 mg/kg. Animals in Group 3 were treated with a vaccine containing an AdC68 adenovirus vector co-expressing three human prostate associated antigens (PSMA, PSCA and PSA) (Vector AdC68W-734), at a total dose of 6e11 VP, immediately followed by subcutaneous injections of 150 mg anti-CTLA4 antibody tremelimumab and anti-PD-1 monoclonal antibody mAb7 at 20 mg/kg. Twenty eight days after the injections, animals were boosted with vehicle (group 1), anti-PD-1 monoclonal antibody mAb7 subcutaneously at 20 mg/kg (group 2) or a DNA plasmid (Plasmid 458) expressing three human prostate cancer antigens (PSMA, PSCA and PSA) delivered by electroporation immediately followed by subcutaneous injections of 150 mg anti-CTLA4 and anti-PD-1 monoclonal antibody at 20 mg/kg (group 3). Forty three days after the prime first injections, PBMCs were isolated from each animal and subjected to an ELISPOT assays, to measure PSMA, PSCA, and PSA specific, IFNγ T-cell responses.

The complete sequence of Vector AdC68W-734 used in the study is provided in SEQ ID NO:45 of the present disclosure and in SEQ ID NO:63 of International Application Publication WO2015/063647. The construction of Vector AdC68W-734 is also described in WO2015/063647, the disclosure of which is incorporated herein by reference. The AdC68W-734 vector and Plasmid 458 each comprises (1) a nucleotide sequence encoding amino acids 15-750 of human PSMA having the sequence of SEQ ID NO:42, (2) a nucleotide sequence encoding amino acids 25-261 of human PSA having the sequence of SEQ ID NO:47, and (3) a nucleotide sequence encoding the full length human PSCA of SEQ ID NO:48.

IFNγ ELISPOT Assay.

Briefly, peripheral blood mononuclear cells (PBMCs) from individual animals were co-incubated in duplicate with pools of peptides from a 15mer peptide library overlapping by 11 amino acids spanning the entire sequence of the respective antigen, each peptide at 2 µg/ml. The plates were incubated for ~16 hours at 37° C., 5% $CO_2$, then washed and developed, as per manufacturer's instruction. The number of IFNγ spot forming cells (SFC) was counted with a CTL reader. The average of the duplicates was calculated and the response of the negative control wells, which contained no peptides, subtracted. The SFC counts were then normalized to describe the response per 1e6 PBMCs. The antigen specific responses in the tables represent the sum of the responses to the corresponding antigen specific peptide pools.

Results.

The ELISpot results, which are presented in Table 33, demonstrate that the animals that received the vaccine with subcutaneous anti-PD-1 antibody and anti-CTLA4 antibody exhibited a robust increase in IFNγ T-cell response to at least one prostate cancer antigen, while there were no IFNγ T-cell responses to these antigens in the vehicle group (Group 1) or the group administered anti-PD-1 antibody alone (Group 2).

TABLE 32

Peptide sequence information for peptide pools used in the ELISpot and ICCS assays to induce antigen-specific IFNγ T-cell responses

| Antigen | Peptide library pools |
|---|---|
| PSMA | 185 sequential 15mer peptides, overlapping by 11 amino acids, covering the entire full length PSMA protein sequence (amino acid sequence: 1-750) assayed as three separate pools. |
| PSCA | 28 sequential 15mer peptides, overlapping by 11 amino acids, covering the entire full length PSCA protein sequence (amino acid sequence: 1-123) assayed as a single separate pool. |
| PSA | 62 sequential 15mer peptides, overlapping by 11 amino acids, covering the entire full length PSA protein sequence (amino acid sequence: 1-246) assayed as one single separate pool. |

TABLE 33

Effect of Anti-PD-1 antibody on antigen-specific IFNγ ELISpot T-cell responses induced by vaccine in cynomolgus macaques.

| Group | Vaccine | Checkpoint inhibitor(s) | Stimulating antigen | Individual IFNγ ELISpot T-cell titer (SFC/1e6 PBMCs, background subtracted) | | | |
|---|---|---|---|---|---|---|---|
| 1 | n/a | n/a | PSMA | 2 | 2 | 2 | 4 |
| 2 | n/a | mAb7 | | 10 | 1 | 7 | 3 |
| 3 | + | tremelimumab + mAb7 | | 1360 | 1263 | 2441 | 3224 |

TABLE 33-continued

Effect of Anti-PD-1 antibody on antigen-specific IFNγ ELISpot T-cell responses induced by vaccine in cynomolgus macaques.

| Group | Vaccine | Checkpoint inhibitor(s) | Stimulating antigen | Individual IFNγ ELISpot T-cell titer (SFC/1e6 PBMCs, background subtracted) | | | |
|---|---|---|---|---|---|---|---|
| 1 | n/a | n/a | PSCA | 0 | 0 | 1 | 1 |
| 2 | n/a | mAb7 | | 0 | 0 | 4 | 4 |
| 3 | + | tremelimumab + mAb7 | | 91 | 18 | 488 | 416 |
| 1 | n/a | n/a | PSA | 0 | 0 | 5 | 2 |
| 2 | n/a | mAb7 | | 0 | 0 | 3 | 0 |
| 3 | + | tremelimumab + mAb7 | | 404 | [1267] | 527 | 512 |

Values in bracket represent the responses where at least one assay replicate was above the upper limit of quantification for the assay (1333 SFC/1e6 PBMC). Values of 0 SFC/1e6 PBMC were converted to 1 for calculation of Geometric mean.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

It is claimed:

1. An isolated antagonist antibody that specifically binds to PD-1 and comprises:
   a heavy chain variable region (VH) comprising a VH complementarity determining region one (CDR1), VH CDR2, and VH CDR3 of the VH having an amino acid sequence selected from the group consisting of SEQ ID NO: 3, SEQ ID NO: 4, SEQ ID NO: 5, and SEQ ID NO: 6, and
   a light chain variable region (VL) comprising a VL CDR1, VL CDR2, and VL CDR3 of the VL having an amino acid sequence selected from the group consisting of SEQ ID NO: 2, SEQ ID NO:7, SEQ ID NO: 8, and SEQ ID NO: 9.

2. The isolated antagonist antibody of claim 1, wherein the antibody comprises a VH CDR1 comprising the amino acid sequence of SEQ ID NO: 13, 14, or 15, a VH CDR2 comprising the amino acid sequence of SEQ ID NO: 16, 17, 24, 25, 27, 28, 35, or 36, a VH CDR3 comprising the amino acid sequence shown in SEQ ID NO: 18, 23, 26, or 37, a VL CDR1 comprising the amino acid sequence shown in SEQ ID NO: 10, 22, 30, or 32, a VL CDR2 comprising the amino acid sequence shown in SEQ ID NO: 11, 20, or 33, and a VL CDR3 comprising the amino acid sequence shown in SEQ ID NO: 12, 21, 31, or 34.

3. The isolated antagonist antibody of claim 1, wherein the antibody comprises a VH comprising the amino acid sequence shown in SEQ ID NO: 3, 4, 5, or 6, or a variant thereof with one or several conservative amino acid substitutions in residues that are not within a CDR.

4. The isolated antagonist antibody of claim 3, wherein the antibody comprises a VL comprising the amino acid sequence shown in SEQ ID NO: 2, 7, 8, or 9, or a variant thereof with one or several amino acid substitutions in amino acids that are not within a CDR.

5. The isolated antagonist antibody of claim 1, wherein the antibody comprises a VH comprising the amino acid sequence shown in SEQ ID NO: 3, 4, 5, or 6, and a VL comprising the amino acid sequence shown in SEQ ID NO: 2, 7, 8, or 9.

6. The isolated antagonist antibody of claim 1, wherein the antibody comprises a heavy chain comprising the amino acid sequence shown in SEQ ID NO: 29 or 38 and a light chain comprising the amino acid sequence shown in SEQ ID NO: 39.

7. The isolated antagonist antibody of claim 1, wherein the antibody comprises a constant region.

8. The isolated antagonist antibody of claim 7, wherein the antibody has an isotype that is selected from the group consisting of $IgG_2$, $IgG_{2\Delta a}$, $IgG_4$, $IgG_{4\Delta b}$, $IgG_{4\Delta c}$, $IgG_4$ S228P, $IgG_{4\Delta b}$ S228P, and $IgG_{4\Delta c}$ S228P.

9. The isolated antagonist antibody of claim 7, wherein the constant region is $IgG_4$ S228P.

10. The isolated antagonist antibody of claim 1, wherein each CDR of the antibody is defined in accordance with the Kabat definition, the Chothia definition, the combination of the Kabat definition and the Chothia definition, the AbM definition, or the contact definition of CDR.

11. An isolated anti-PD-1 antibody, wherein the antibody comprises a VH CDR1 comprising the amino acid sequence of SEQ ID NO: 13, a VH CDR2 comprising the amino acid sequence of SEQ ID NO: 17, a VH CDR3 comprising the amino acid sequence shown in SEQ ID NO: 23, a VL CDR1 comprising the amino acid sequence shown in SEQ ID NO: 10, a VL CDR2 comprising the amino acid sequence shown in SEQ ID NO: 20, and a VL CDR3 comprising the amino acid sequence shown in SEQ ID NO: 21.

12. The isolated antibody of claim 1, wherein the antibody (1) promotes IFNγ, (2) TNF secretion from T cells, or both (1) and (2).

13. The isolated antibody of claim 1, wherein the antibody promotes proliferation of T cells.

14. The isolated antibody of claim 1, wherein the antibody inhibits tumor growth in a subject in need thereof.

15. The isolated antibody of claim 1, wherein the antibody binds human PD-1 and mouse PD-1.

16. The isolated antibody of claim 15, wherein the antibody binds human PD-1 with an affinity of about 0.73 nM at 25° C. as measured by surface plasmon resonance.

17. An isolated cell line that produces the antibody of claim 1.

18. An isolated nucleic acid encoding the antibody of claim 1.

19. A recombinant expression vector comprising the nucleic acid of claim 18.

20. A host cell comprising the expression vector of claim 19.

21. A hybridoma capable of producing the antibody of claim 1.

22. A method of producing an anti-PD-1 antagonist antibody, the method comprising: culturing a cell line that recombinantly produces the antibody of claim 1 under conditions wherein the antibody is produced; and recovering the antibody.

23. A method of producing an anti-PD-1 antagonist antibody, the method comprising: culturing a cell line comprising nucleic acid encoding an antibody comprising a heavy chain comprising the amino acid sequence shown in SEQ ID NO: 29 or 38 and a light chain comprising the amino acid sequence shown in SEQ ID NO: 39 under conditions wherein the antibody is produced; and recovering the antibody.

24. The method of claim 23, wherein the heavy and light chains of the antibody are encoded on separate vectors.

25. The method of claim 23, wherein the heavy and light chains of the antibody are encoded on the same vector.

26. A pharmaceutical composition comprising the antibody of claim 1, and a pharmaceutically acceptable carrier.

27. A kit for the treatment of cancer comprising the pharmaceutical composition of claim 26.

28. The isolated anti-PD-1 antibody of claim 11, wherein the antibody comprises a VH comprising the amino acid sequence of SEQ ID NO: 4.

29. The isolated anti-PD-1 antibody of claim 28, wherein the antibody comprises a heavy chain comprising the amino acid sequence of SEQ ID NO: 29 or 38.

30. The isolated anti-PD-1 antibody of claim 11, wherein the antibody comprises a VL comprising the amino acid sequence of SEQ ID NO: 8.

31. The isolated anti-PD-1 antibody of claim 30, wherein the antibody comprises a light chain comprising the amino acid sequence of SEQ ID NO: 39.

32. An isolated cell line that produces the antibody of claim 11.

33. A recombinant expression vector comprising a nucleic acid encoding the antibody of claim 11.

34. A hybridoma capable of producing the antibody of claim 11.

35. A pharmaceutical composition comprising the antibody of claim 11 and a pharmaceutically acceptable carrier.

36. An isolated antagonist antibody that specifically binds to PD-1, wherein the antibody comprises a heavy chain variable region (VH) comprising the amino acid sequence shown in SEQ ID NO: 4, and a light chain variable region (VL) comprising the amino acid sequence shown in SEQ ID NO: 8.

37. An isolated cell line that produces the antibody of claim 36.

38. A recombinant expression vector comprising a nucleic acid encoding the antibody of claim 36.

39. A hybridoma capable of producing the antibody of claim 36.

40. A pharmaceutical composition comprising the antibody of claim 36 and a pharmaceutically acceptable carrier.

41. An isolated antagonist antibody that specifically binds to PD-1, wherein the antibody comprises a heavy chain comprising the amino acid sequence shown in SEQ ID NO: 29 or 38 and a light chain comprising the amino acid sequence shown in SEQ ID NO: 39.

42. An isolated cell line that produces an antibody of claim 41.

43. A recombinant expression vector comprising a nucleic acid encoding an antibody of claim 41.

44. A hybridoma capable of producing an antibody of claim 41.

45. A pharmaceutical composition comprising an antibody of claim 41 and a pharmaceutically acceptable carrier.

* * * * *

UNITED STATES PATENT AND TRADEMARK OFFICE
CERTIFICATE OF CORRECTION

PATENT NO. : 10,155,037 B2
APPLICATION NO. : 14/958053
DATED : December 18, 2018
INVENTOR(S) : Yasmina Noubia Abdiche et al.

Page 1 of 1

It is certified that error appears in the above-identified patent and that said Letters Patent is hereby corrected as shown below:

In the Claims

Column 209, Claim 1, Line 25, replace "VII" with --VH--;
Column 209, Claim 1, Line 26, replace "VII" with --VH--;
Column 209, Claim 2, Line 40, replace "VII" with --VH--;
Column 210, Claim 11, Line 36, replace "VII" with --VH--;
Column 212, Claim 36, Line 9, replace "VII" with --VH--.

Signed and Sealed this
Fourteenth Day of May, 2019

Andrei Iancu
*Director of the United States Patent and Trademark Office*